(12) United States Patent
Katibah et al.

(10) Patent No.: US 10,906,930 B2
(45) Date of Patent: Feb. 2, 2021

(54) COMPOSITIONS AND METHODS FOR ACTIVATING "STIMULATOR OF INTERFERON GENE"-DEPENDENT SIGNALLING

(71) Applicants: ADURO BIOTECH, INC., Berkeley, CA (US); NOVARTIS AG, Basel (CH)

(72) Inventors: George Edwin Katibah, Fremont, CA (US); David Kanne, Corte Madera, CA (US); Leonard Sung, San Mateo, CA (US); Kelsey Gauthier, Alameda, CA (US); Laura Hix Glickman, Oakland, CA (US); Justin Leong, Union City, CA (US); Sarah M. McWhirter, Albany, CA (US); Thomas W. Dubensky, Jr., Berkeley, CA (US); Jeffrey McKenna, Carlisle, MA (US); Stephen M. Canham, Cambridge, MA (US); Chudi Obioma Ndubaku, Oakland, CA (US)

(73) Assignees: CHINOOK THERAPEUTICS, INC., Berkeley, CA (US); NOVARTIS AG, Basel (CH)

( * ) Notice: Subject to any disclaimer, the term of this patent is extended or adjusted under 35 U.S.C. 154(b) by 0 days.

(21) Appl. No.: 15/771,286

(22) PCT Filed: Oct. 28, 2016

(86) PCT No.: PCT/US2016/059506
§ 371 (c)(1),
(2) Date: Apr. 26, 2018

(87) PCT Pub. No.: WO2017/075477
PCT Pub. Date: May 4, 2017

(65) Prior Publication Data
US 2019/0062365 A1 Feb. 28, 2019

Related U.S. Application Data

(60) Provisional application No. 62/247,658, filed on Oct. 28, 2015, provisional application No. 62/379,611, filed on Aug. 25, 2016.

(51) Int. Cl.
| | | |
|---|---|---|
| C07H 21/04 | (2006.01) |
| A61K 39/39 | (2006.01) |
| C07H 21/02 | (2006.01) |
| A61K 39/12 | (2006.01) |
| A61P 35/00 | (2006.01) |
| A61K 39/395 | (2006.01) |
| A61K 45/06 | (2006.01) |
| A61K 39/00 | (2006.01) |

(52) U.S. Cl.
CPC ............ *C07H 21/04* (2013.01); *A61K 39/12* (2013.01); *A61K 39/39* (2013.01); *A61K 39/395* (2013.01); *A61K 45/06* (2013.01); *A61P 35/00* (2018.01); *C07H 21/02* (2013.01); *A61K 2039/55561* (2013.01); *A61K 2039/572* (2013.01)

(58) Field of Classification Search
CPC ..................................................... C07H 19/213
See application file for complete search history.

(56) References Cited

U.S. PATENT DOCUMENTS

| | | |
|---|---|---|
| 6,087,490 A | 7/2000 | Baxter et al. |
| 9,695,212 B2 | 7/2017 | Dubensky, Jr. et al. |
| 9,724,408 B2 | 8/2017 | Dubensky, Jr. et al. |
| 9,840,533 B2 | 12/2017 | Patel et al. |
| 10,131,686 B2 | 11/2018 | Patel et al. |
| 10,176,292 B2 | 1/2019 | Patel et al. |
| 10,385,091 B2 | 8/2019 | Patel et al. |
| 10,414,789 B2 | 9/2019 | Dubensky, Jr. et al. |
| 10,449,211 B2 | 10/2019 | Katibah et al. |
| 2014/0205653 A1 | 7/2014 | Dubensky, Jr. et al. |
| 2014/0329889 A1 | 11/2014 | Vance et al. |
| 2017/0333552 A1 | 11/2017 | Dubensky, Jr. et al. |
| 2018/0028553 A1 | 2/2018 | Gajewski et al. |
| 2019/0185511 A1 | 6/2019 | Kanne et al. |
| 2019/0292216 A1 | 9/2019 | Vance et al. |
| 2019/0330257 A1 | 10/2019 | Patel et al. |

FOREIGN PATENT DOCUMENTS

| | | |
|---|---|---|
| WO | 2016120305 A1 | 8/2016 |
| WO | 2017027646 A1 | 2/2017 |

OTHER PUBLICATIONS

Zawilska. Pharmacological Reports, 2012, 65, 1-14 (Year: 2012).*
Benjamin T. Roembke et al., "A cyclic dinucleotide containing 2-aminopurine is a general fluorescent sensor for c-di-GMP and 3', 3'-cGAMP", Molecular Biosystems, vol. 10, No. 6, Mar. 28, 2014, pp. 1568-1575.
Pu Gao et al., "Cyclic [G(2', 5')pA(3',5')p] Is the Metazoan Second Messenger Produced by DNA-Activated Cyclic GMP-AMP Synthase", Cell, vol. 153, No. 5, May 23, 2013, pp. 1094-1107.
Lingyin Li et al., "Hydrolysis of 2'3'-cGAMP by ENPP1 and design of nonhydrolyzable analogs", Nature Chemical Biology, vol. 10, No. 12, Dec. 2014, pp. 1043-1048.

* cited by examiner

*Primary Examiner* — Noble E Jarrell
(74) *Attorney, Agent, or Firm* — Acuity Law Group, PC; Michael A. Whittaker

(57) ABSTRACT

The present invention provides highly active cyclic-dinucleotide (CDN) immune stimulators that activate DCs via a recently discovered cytoplasmic receptor known as STING (Stimulator of Interferon Genes). In particular, the CDNs of the present invention are provided in the form of a composition comprising one or more cyclic purine dinucleotides induce human STING-dependent type I interferon production, wherein the cyclic purine dinucleotides present in the composition are 2'- or 3'-mono-fluoro substituted, or 2'3'-di-fluoro substituted mixed linkage 2',5'-3',5' CDNs.

12 Claims, 20 Drawing Sheets

Specification includes a Sequence Listing.

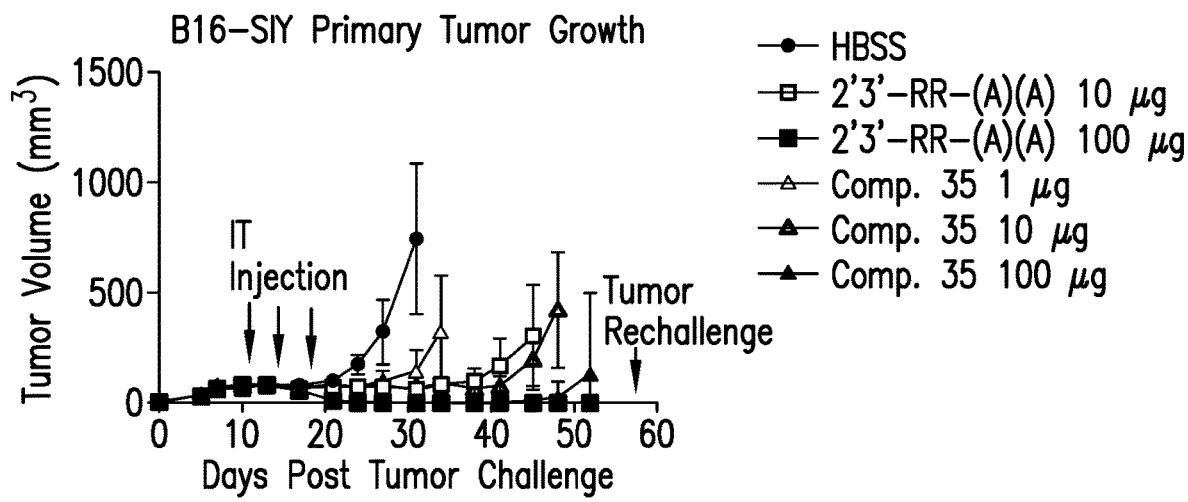
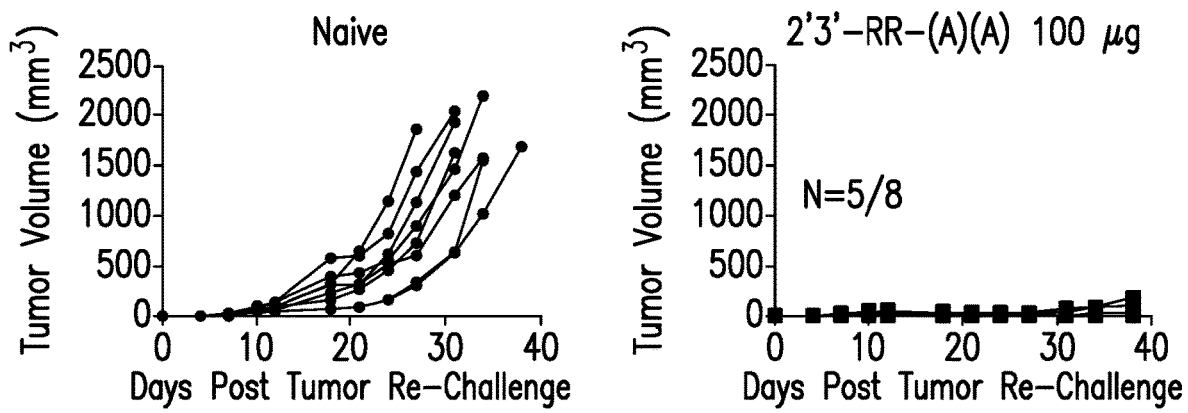
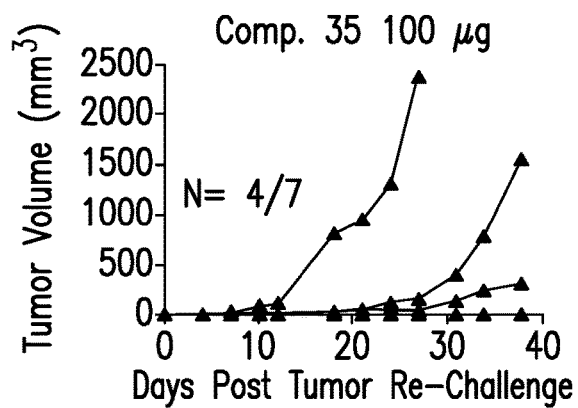
FIG.5C
FIG.5D

COMPOSITIONS AND METHODS FOR ACTIVATING "STIMULATOR OF INTERFERON GENE"-DEPENDENT SIGNALLING

The present application claims priority to U.S. Provisional Patent Application 62/247,658, filed Oct. 28, 2015, and U.S. Provisional Patent Application 62/379,611, filed Aug. 25, 2016, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

New insights into the mechanisms underlying immune-evasion, together with combination treatment regimens that potentiate the potency of therapeutic vaccination, either directly or indirectly, through combination with immune checkpoint inhibitors or other therapies, have served as a basis for the development of vaccines or immune modulators that can prime or boost an effective adaptive immune response. These modulators consist of tumor-specific CD4$^+$ and CD8$^+$ T cells specific for a targeted malignancy, resulting in an antitumor response and clinical benefit. How the innate immune system is engaged by targeted ligands shapes the development of an adaptive response and lends itself to the design of vaccines and immunomodulators (Reed et al., Trends Immunol., 30: 23-32, 2009; Dubensky and Reed, Semin. Immunol., 22: 155-61, 2010; Kastenmuller et al., J. Clin. Invest., 121: 1782-1796, 2011; Coffman et al., Immunity, 33: 492-503, 2010).

The cyclic-di-nucleotides (CDNs) cyclic-di-AMP (produced by *Listeria monocytogenes* and other bacteria) and its analogs cyclic-di-GMP and cyclic-GMP-AMP are recognized by the host cell as a pathogen associated molecular pattern (PAMP), which bind to the pathogen recognition receptor (PRR) known as Stimulator of INterferon Genes (STING). STING is an adaptor protein in the cytoplasm of host mammalian cells which activates the TANK binding kinase (TBK1)—IRF3 and the NF-κB signaling axis, resulting in the induction of IFN-β and other gene products that strongly activate innate immunity. It is now recognized that STING is a component of the host cytosolic surveillance pathway (Vance et al., 2009), that senses infection with intracellular pathogens and in response induces the production of IFN-β, leading to the development of an adaptive protective pathogen-specific immune response consisting of both antigen-specific CD4$^+$ and CD8$^+$ T cells as well as pathogen-specific antibodies. Examples of cyclic purine dinucleotides are described in some detail in, for example: U.S. Pat. Nos. 7,709,458 and 7,592,326; patent applications WO2007/054279, WO2014/093936, and WO2014/189805; and Yan et al., Bioorg. Med. Chem Lett. 18: 5631 (2008).

An uncharacterized mouse gene with significant structural homology to the catalytic domain of human oligoadenylate synthase cyclic GMP-AMP synthase was reported to be the enzyme responsible for producing STING-binding CDNs in mammalian cells (Sun et al., Science 339(6121):786-91, 2013). Termed cyclic GMP-AMP Synthase (cGAS), this enzyme catalyzes the synthesis of cyclic GMP-AMP (cGAMP) from ATP and GTP in the presence of DNA. This cGAMP then functions as a second messenger that binds to and activates STING. These cGAS-produced CDNs differed structurally from the bacterially produced CDNs in that they possess an unusual phosphodiester linkage. Thus, while the bacterially produced CDNs contain a bis-3',5' linkage between the two nucleotides, mammalian CDNs contained one 2',5' linkage and one 3',5' linkage, or a so-called "mixed linkage (ML) or non-canonical CDNs. These 2',5'-3',5' molecules bind STING with nM affinity, some 300-fold better than bacterial c-di-GMP.

Human STING (hSTING) also has known polymorphisms, including alleles encoding histidine at position 232, which are refractory to bis-3',5' (canonical) CDNs, but not 2',5'-3',5' (non-canonical, mixed linkage) CDNs (Diner et al., Cell Reports 3, 1355-61, 2013; Jin et al., Genes and Immunity, 12: 263-9, 2011). Single nucleotide polymorphisms in the hSTING gene have been reported to affect the responsiveness to bacterial-derived canonical CDNs (Diner et al., 2013; Gao et al., Cell 154, 748-762, 2013; Conlon et. al., J. Immunol. 190: 5216-5225, 2013). Five haplotypes of hSTING have been reported (WT, REF, HAQ, AQ and Q alleles), which vary at amino acid positions 71, 230, 232 and 293 (Jin et al., 2011; Yi et al., PLOS One 8: e77846, 2013). Cells expressing hSTING reportedly respond poorly to stimulation with bacterial CDNs cGAMP, c-di-AMP and c-di-GMP having bis-(3', 5') linkages, but are responsive to the endogenously produced cGAS product, ML cGAMP (Diner et al., 2013). Thus, it has been suggested that the 2',5'-3',5' molecules represent much more potent physiological ligands in terms of hSTING targeting (Zhang et al., Mol. Cell. 51:226-35, 2013; Xiao and Fitzgerald, Mol. Cell 51: 135-39, 2013).

SUMMARY OF THE INVENTION

It is an object of the present invention to provide compositions and methods which modulate immune responses to diseases. It is a further object of the invention to provide compositions and methods which provide cyclic purine dinucleotide analogs that exhibit improved characteristics when employed for activation of mammalian, and preferably human, STING. It is yet a further object of the invention to provide compositions and methods for the treatment of cancer.

In a first aspect, the present invention provides a mono- or di-fluoro substituted mixed linkage (ML) 2',5'-3',5' cyclic purine dinucleotide ("mono- or di-F-ML-CDN") Compound of Formula I:

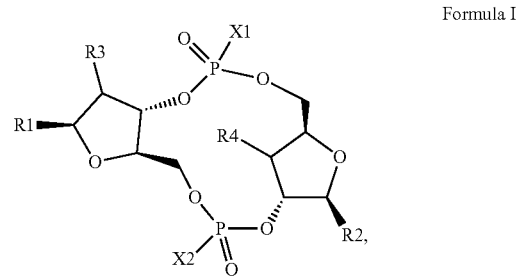

Formula I or a prodrug, pharmaceutically acceptable salt, pharmaceutically acceptable solvate or pharmaceutically acceptable hydrate thereof,
wherein:
R1 and R2 are independently a guanine or adenine bound to the structure via the N9 position, provided that R1 and R2 are not both guanine;

R3 and R4 are independently —H, —OH, —O—C(=O)—C$_{1-14}$ alkyl or —F, provided that at least one of R3 and R4 is —F; and X1 and X2 are independently —OH or —SH.

As described hereinafter, in certain embodiments, X1 and X2 are each —SH, and one or both of R3 and R4 are —F; and in certain of these embodiments, if only one of R3 and R4 is F, the other of R3 and R4 is —O—C(=O)—C$_{1-14}$ alkyl, and preferably —O—C(=O)—C$_{6-12}$ alkyl. In certain of these embodiments, R3 is F and R4 is —O—C(=O)—C$_{1-14}$ alkyl, and preferably —O—C(=O)—C$_{6-12}$. Additionally, when X1 or X2 are —SH, a chiral center is introduced into the molecule at the thiophosphate. In certain of these embodiments, the compounds are R,R diastereoisomers.

In a first embodiment of the first aspect, the Compound of Formula I is a Compound of Formula I-a:

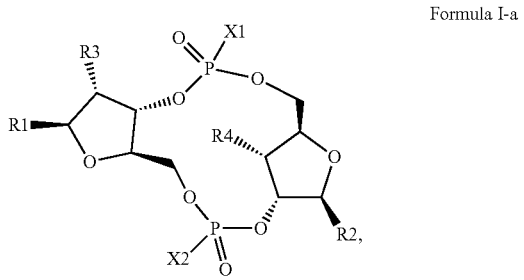

Formula I-a or a prodrug, pharmaceutically acceptable salt, pharmaceutically acceptable solvate or pharmaceutically acceptable hydrate thereof, wherein R1, R2, R3, R4, X1 and X2 are as defined for Compounds of Formula I.

In a second embodiment of the first aspect, the Compound of Formula I is a Compound of Formula I-b:

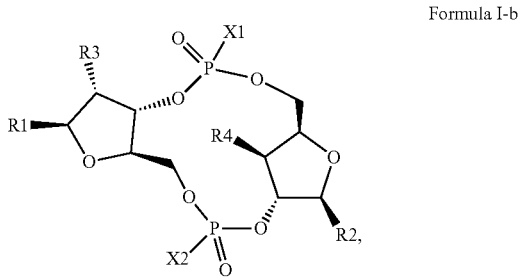

Formula I-b or a prodrug, pharmaceutically acceptable salt, pharmaceutically acceptable solvate or pharmaceutically acceptable hydrate thereof, wherein R1, R2, R3, R4, X1 and X2 are as defined for Compounds of Formula I.

In some embodiments of the first aspect and first or second embodiments thereof, X1 and X2 are —SH. In some embodiments X1 and X2 are —SH, R3 is —F and R4 is —H, —OH or —O—C(=O)—C$_{1-14}$alkyl. In some embodiments X1 and X2 are —SH, R3 is —F and R4 is —H or —OH. In some embodiments X1 and X2 are —SH, R3 is —F and R4 is —OH. In some embodiments X1 and X2 are —SH, R3 is —H, —OH or —O—C(=O)—C$_{1-14}$alkyl and R4 is —F. In some embodiments X1 and X2 are —SH, R3 is —H or —OH and R4 is —F. In some embodiments X1 and X2 are —SH, R3 is —OH and R4 is —F. In some embodiments X1 and X2 are —SH, and R3 and R4 are —F. In some embodiments X1 and X2 are —SH, and R1 and R2 are adenine. In some embodiments X1 and X2 are —SH, R3 is —F, R4 is —H, —OH or —O—C(=O)—C$_{1-14}$ alkyl, and R1 and R2 are adenine. In some embodiments X1 and X2 are —SH, R3 is —F, R4 is —H or —OH, and R1 and R2 are adenine. In some embodiments X1 and X2 are —SH, R3 is —F, R4 is —OH, and R1 and R2 are adenine. In some embodiments X1 and X2 are —SH, R3 is —H, —OH or —O—C(=O)—C$_{1-14}$ alkyl, R4 is —F, and R1 and R2 are adenine. In some embodiments X1 and X2 are —SH, R3 is —H or —OH, R4 is —F, and R1 and R2 are adenine. In some embodiments X1 and X2 are —SH, R3 —OH, R4 is —F, and R1 and R2 are adenine. In some embodiments X1 and X2 are —SH, R3 and R4 are F, and R1 and R2 are adenine. In some embodiments X1 and X2 are —SH, R1 is adenine and R2 is guanine. In some embodiments X1 and X2 are —SH, R3 is —F, R4 is —H, —OH or —O—C(=O)—C$_{1-14}$ alkyl, R1 is adenine and R2 is guanine. In some embodiments X1 and X2 are —SH, R3 is —F, R4 is —H or —OH, R1 is adenine and R2 is guanine. In some embodiments X1 and X2 are —SH, R3 is —F, R4 is —OH, R1 is adenine and R2 is guanine. In some embodiments X1 and X2 are —SH, R3 is —H, —OH or —O—C(=O)—C$_{1-14}$ alkyl, R4 is —F, R1 is adenine and R2 is guanine. In some embodiments X1 and X2 are —SH, R3 is —H or —OH, R4 is —F, R1 is adenine and R2 is guanine. In some embodiments X1 and X2 are —SH, R3 is —OH, R4 is —F, R1 is adenine and R2 is guanine. In some embodiments X1 and X2 are —SH, R3 and R4 are —F, R1 is adenine and R2 is guanine. In some embodiments X1 and X2 are —SH, R1 is guanine and R2 is adenine. In some embodiments X1 and X2 are —SH, R3 is —F, R4 is —H, —OH or —O—C(=O)—C$_{1-14}$ alkyl, R1 is guanine and R2 is adenine. In some embodiments X1 and X2 are —SH, R3 is —F, R4 is —H or —OH, R1 is guanine and R2 is adenine. In some embodiments X1 and X2 are —SH, R3 is —F, R4 is —OH, R1 is guanine and R2 is adenine. In some embodiments X1 and X2 are —SH, R3 is —H, —OH or —O—C(=O)—C$_{1-14}$ alkyl, R4 is —F, R1 is guanine and R2 is adenine. In some embodiments X1 and X2 are —SH, R3 is —H or —OH, R4 is —F, R1 is guanine and R2 is adenine. In some embodiments X1 and X2 are —SH, R3 is —OH, R4 is —F, R1 is guanine and R2 is adenine. In some embodiments X1 and X2 are —SH, R3 and R4 are —F, R1 is guanine and R2 is adenine.

In some embodiments of the first aspect and first or second embodiments thereof, X1 is —OH and X2 is —SH. In some embodiments X1 is —OH, X2 is —SH, R3 is —F and R4 is —H, —OH or —O—C(=O)—C$_{1-14}$ alkyl. In some embodiments X1 is —OH, X2 is —SH, R3 is —F and R4 is —H or —OH. In some embodiments X1 is —OH, X2 is —SH, R3 is —F and R4 is —OH. In some embodiments X1 is —OH, X2 is —SH, R3 is —H, —OH or —O—C(=O)—C$_{1-14}$ alkyl and R4 is —F. In some embodiments X1 is —OH, X2 is —SH, R3 is —H or —OH and R4 is —F. In some embodiments X1 is —OH, X2 is —SH, R3 is —OH and R4 is —F. In some embodiments X1 is —OH, X2 is —SH, and R3 and R4 are —F. In some embodiments X1 is —OH, X2 is —SH, and R1 and R2 are adenine. In some embodiments X1 is —OH, X2 is —SH, R3 is —F, R4 is —H, —OH or —O—C(=O)—C$_{1-14}$alkyl, and R1 and R2 are adenine. In some embodiments X1 is —OH, X2 is —SH, R3 is —F, R4 is —H or —OH, and R1 and R2 are adenine. In some embodiments X1 is —OH, X2 is —SH, R3 is —F, R4 is —OH, and R1 and R2 are adenine. In some embodiments X1 is —OH, X2 is —SH, R3 is —H, —OH or —O—C(=O)—C$_{1-14}$ alkyl, R4 is —F, and R1 and R2 are adenine. In some embodiments X1 is —OH, X2 is —SH, R3 is —H or —OH, R4 is —F, and R1 and R2 are adenine. In some embodiments X1 is —OH, X2 is —SH, R3 is —OH, R4 is —F, and R1 and R2 are adenine. In some embodiments X1 is —OH, X2 is —SH, R3 and R4 are —F, and R1 and R2 are adenine. In some embodiments X1 is —OH, X2 is —SH, R1 is adenine and R2 is guanine. In some embodiments X1 is —OH, X2 is —SH, R3 is —F, R4 is —H, —OH or —O—C(=O)—C$_{1-14}$ alkyl, R1 is adenine and R2 is guanine. In some embodiments X1 is —OH, X2 is —SH, R3 is —F, R4 is —H or —OH, R1 is adenine and R2 is guanine. In some embodiments X1 is —OH, X2 is —SH, R3 is —F, R4 is —OH, R1 is adenine and R2 is guanine. In some embodiments X1 is —OH, X2 is —SH, R3 is —H, —OH or —O—C(=O)—C$_{1-14}$ alkyl, R4 is —F, R1 is adenine and R2 is guanine. In some embodiments X1 is —OH, X2 is —SH, R3 is —H or —OH, R4 is —F, R1 is adenine and R2 is guanine. In some embodiments X1 is —OH, X2 is —SH, R3 is —OH, R4 is —F, R1 is adenine and R2 is guanine. In some embodiments X1 is —OH, X2 is —SH, R3 and R4 are —F, R1 is adenine and R2 is guanine. In some embodiments X1 is —OH, X2 is —SH, R1 is guanine and R2 is adenine. In some embodiments X1 is —OH, X2 is —SH, R3 is —F, R4 is —H, —OH or —O—C(=O)—C$_{1-14}$ alkyl, R1 is guanine and R2 is adenine. In some embodiments X1 is —OH, X2 is —SH, R3 is —F, R4 is —H or —OH, R1 is guanine and R2 is adenine. In some embodiments X1 is —OH, X2 is —SH, R3 is —F, R4 is —OH, R1 is guanine and R2 is adenine. In some embodiments X1 is —OH, X2 is —SH, R3 is —OH, R4 is —F, R1 is guanine and R2 is adenine. In some embodiments X1 is —OH, X2 is —SH, R3 and R4 are —F, R1 is guanine and R2 is adenine.

In some embodiments of the first aspect and first or second embodiments thereof, X1 is —SH and X2 is —OH. In some embodiments X1 is —SH, X2 is —OH, R3 is —F and R4 is —H, —OH or —O—C(=O)—C$_{1-14}$ alkyl. In some embodiments X1 is —SH, X2 is —OH, R3 is —F and R4 is —H or —OH. In some embodiments X1 is —SH, X2 is —OH, R3 is —F and R4 is —OH. In some embodiments X1 is —SH, X2 is —OH, R3 is —H, —OH or —O—C(=O)—C$_{1-14}$ alkyl and R4 is —F. In some embodiments X1 is —SH, X2 is —OH, R3 is —H or —OH and R4 is —F. In some embodiments X1 is —SH, X2 is —OH, R3 is —OH and R4 is —F. In some embodiments X1 is —SH, X2 is —OH, and R3 and R4 are —F. In some embodiments X1 is —SH, X2 is —OH, and R1 and R2 are adenine. In some embodiments X1 is —SH, X2 is —OH, R3 is —F, R4 is —H, —OH or —O—C(=O)—C$_{1-14}$ alkyl, and R1 and R2 are adenine. In some embodiments X1 is —SH, X2 is —OH, R3 is —F, R4 is —H or —OH, and R1 and R2 are adenine. In some embodiments X1 is —SH, X2 is —OH, R3 is —F, R4 is —OH, and R1 and R2 are adenine. In some embodiments X1 is —SH, X2 is —OH, R3 is —H, —OH or —O—C(=O)—C$_{1-14}$ alkyl, R4 is —F, and R1 and R2 are adenine. In some embodiments X1 is —SH, X2 is —OH, R3 is —H or —OH, R4 is —F, and R1 and R2 are adenine. In some embodiments X1 is —SH, X2 is —OH, R3 is —OH, R4 is —F, and R1 and R2 are adenine. In some embodiments X1 is —SH, X2 is —OH, R3 and R4 are —F, and R1 and R2 are adenine. In some embodiments X1 is —SH, X2 is —OH, R1 is adenine and R2 is guanine. In some embodiments X1 is —SH, X2 is —OH, R3 is —F, R4 is —H, —OH or —O—C(=O)—C$_{1-14}$ alkyl, R1 is adenine and R2 is guanine. In some embodiments X1 is —SH, X2 is —OH, R3 is —F, R4 is —H or —OH, R1 is adenine and R2 is guanine. In some embodiments X1 is —SH, X2 is —OH, R3 is —F, R4 is —OH, R1 is adenine and R2 is guanine. In some embodiments X1 is —SH, X2 is —OH, R3 is —H, —OH or —O—C(=O)—C$_{1-14}$ alkyl, R4 is —F, R1 is adenine and R2 is guanine. In some embodiments X1 is —SH, X2 is —OH, R3 is —H or —OH, R4 is —F, R1 is adenine and R2 is guanine. In some embodiments X1 is —SH, X2 is —OH, R3 is —OH, R4 is —F, R1 is adenine and R2 is guanine. In some embodiments X1 is —SH, X2 is —OH, R3 and R4 are —F, R1 is adenine and R2 is guanine. In some embodiments X1 is —SH, X2 is —OH, R1 is guanine and R2 is adenine. In some embodiments X1 is —SH, X2 is —OH, R3 is —F, R4 is —H, —OH or —O—C(=O)—C$_{1-14}$ alkyl, R1 is guanine and R2 is adenine. In some embodiments X1 is —SH, X2 is —OH, R3 is —F, R4 is —H or —OH, R1 is guanine and R2 is adenine. In some embodiments X1 is —SH, X2 is —OH, R3 is —F, R4 is —OH, R1 is guanine and R2 is adenine. In some embodiments X1 is —SH, X2 is —OH, R3 is —H, —OH or —O—C(=O)—C$_{1-14}$ alkyl, R4 is —F, R1 is guanine and R2 is adenine. In some embodiments X1 is —SH, X2 is —OH, R3 is —H or —OH, R4 is —F, R1 is guanine and R2 is adenine. In some embodiments X1 is —SH, X2 is —OH, R3 is —OH, R4 is —F, R1 is guanine and R2 is adenine. In some embodiments X1 is —SH, X2 is —OH, R3 and R4 are —F, R1 is guanine and R2 is adenine.

In some embodiments of the first aspect and first or second embodiments thereof, X1 and X2 are —OH. In some embodiments X1 and X2 are —OH, R3 is —F and R4 is —H, —OH or —O—C(=O)—C$_{1-14}$alkyl. In some embodiments X1 and X2 are —OH, R3 is —F and R4 is —H or —OH. In some embodiments X1 and X2 are —OH, R3 is —F and R4 is —OH. In some embodiments X1 and X2 are —OH, R3 is —H, —OH or —O—C(=O)—C$_{1-14}$ alkyl and R4 is —F. In some embodiments X1 and X2 are —OH, R3 is —H or —OH and R4 is —F. In some embodiments X1 and X2 are —OH, R3 is —OH and R4 is —F. In some embodiments X1 and X2 are —OH, and R3 and R4 are —F. In some embodiments X1 and X2 are —OH, and R1 and R2 are adenine. In some embodiments X1 and X2 are —OH, R3 is —F, R4 is —H, —OH or —O—C(=O)—C$_{1-14}$ alkyl, and R1 and R2 are adenine. In some embodiments X1 and X2 are —OH, R3 is —F, R4 is —H or —OH, and R1 and R2 are adenine. In some embodiments X1 and X2 are —OH, R3 is —F, R4 is —OH, and R1 and R2 are adenine. In some embodiments X1 and X2 are —OH, R3 is —H, —OH or —O—C(=O)—C$_{1-14}$ alkyl, R4 is —F, and R1 and R2 are adenine. In some embodiments X1 and X2 are —OH, R3 is —H or —OH, R4 is —F, and R1 and R2 are adenine. In some embodiments X1 and X2 are —OH, R3 is —OH, R4 is —F, and R1 and R2 are adenine. In some embodiments X1 and X2 are —OH, R3 and R4 are —F, and R1 and R2 are adenine. In some embodiments X1 and X2 are —OH, R1 is adenine and R2 is guanine. In some embodiments X1 and X2 are —OH, R3 is —F, R4 is —H, —OH or —O—C(=O)—C$_{1-14}$alkyl, R1 is adenine and R2 is guanine. In some embodiments X1 and X2 are —OH, R3 is —F, R4 is —H or —OH, R1 is adenine and R2 is guanine. In some embodiments X1 and X2 are —OH, R3 is —F, R4 is —OH, R1 is adenine and R2 is guanine. In some embodiments X1 and X2 are —OH, R3 is —H, —OH or —O—C(=O)—C$_{1-14}$ alkyl, R4 is —F, R1 is adenine and R2 is guanine. In some embodiments X1 and X2 are —OH, R3 is —H or —OH, R4 is —F, R1 is adenine and R2 is guanine. In some embodiments X1 and X2 are —OH, R3 is —OH, R4 is —F, R1 is adenine and R2 is guanine. In some embodiments X1 and X2 are —OH, R3 and R4 are —F, R1 is adenine and R2 is guanine. In some embodiments X1 and X2 are —OH, R1 is guanine and R2 is adenine. In some embodiments X1 and X2 are —OH, R3 is —F, R4 is —H, —OH or —O—C (=O)—C$_{1-14}$alkyl, R1 is guanine and R2 is adenine. In some embodiments X1 and X2 are —OH, R3 is —F, R4 is —H or —OH, R1 is guanine and R2 is adenine. In some embodiments X1 and X2 are —OH, R3 is —F, R4 is —OH, R1 is guanine and R2 is adenine. In some embodiments X1 and X2 are —OH, R3 is —H, —OH or —O—C(=O)—C$_{1-14}$alkyl, R4 is —F, R1 is guanine and R2 is adenine. In some embodiments X1 and X2 are —OH, R3 is —H or —OH, R4 is —F, R1 is guanine and R2 is adenine. In some embodiments X1 and X2 are —OH, R3 is —OH, R4 is —F, R1 is guanine and R2 is adenine. In some embodiments X1 and X2 are —OH, R3 and R4 are —F, R1 is guanine and R2 is adenine.

In some embodiments of the first aspect and first or second embodiments thereof, R1 and R2 are adenine. In some embodiments, R1 and R2 are adenine, R3 is —H, —OH or —O—C(=O)—C$_{1-14}$ alkyl and R4 is —F. In some embodiments, R1 and R2 are adenine, R3 is —H or —OH and R4 is —F. In some embodiments, R1 and R2 are adenine, R3 is —OH and R4 is —F. In some embodiments, R1 and R2 are adenine, R3 is —F and R4 is —H, —OH or —O—C(=O)—C$_{1-14}$ alkyl. In some embodiments, R1 and R2 are adenine, R3 is —F and R4 is —H or —OH. In some embodiments, R1 and R2 are adenine, R3 is —F and R4 is —OH. In some embodiments, R1 and R2 are adenine and R3 and R4 are —F.

In some embodiments of the first aspect and first or second embodiments thereof, R1 is adenine and R2 is guanine. In some embodiments R1 is adenine, R2 is guanine, R3 is —H, —OH or —O—C(=O)—C$_{1-14}$ alkyl and R4 is —F. In some embodiments R1 is adenine, R2 is guanine, R3 is —H or —OH and R4 is —F. In some embodiments R1 is adenine, R2 is guanine, R3 is —OH and R4 is —F. In some embodiments, R1 is adenine, R2 is guanine, R3 is —F and R4 is —H, —OH or —O—C(=O)—C$_{1-14}$ alkyl. In some embodiments, R1 is adenine, R2 is guanine, R3 is —F and R4 is —H or —OH. In some embodiments, R1 is adenine, R2 is guanine, R3 is —F and R4 is —OH. In some embodiments, R1 is adenine, R2 is guanine and R3 and R4 are —F.

In some embodiments of the first aspect and first or second embodiments thereof, R1 is guanine and R2 is adenine. In some embodiments R1 is guanine, R2 is adenine, R3 is —H, —OH or —O—C(=O)—C$_{1-14}$ alkyl and R4 is —F. In some embodiments R1 is guanine, R2 is adenine, R3 is —H or —OH and R4 is —F. In some embodiments R1 is guanine, R2 is adenine, R3 is —OH and R4 is —F. In some embodiments, R1 is guanine, R2 is adenine, R3 is —F and R4 is —H, —OH or —O—C(=O)—C$_{1-14}$ alkyl. In some embodiments, R1 is guanine, R2 is adenine, R3 is —F and R4 is —H or —OH. In some embodiments, R1 is guanine, R2 is adenine, R3 is —F and R4 is —OH. In some embodiments, R1 is guanine, R2 is adenine and R3 and R4 are —F.

In some embodiments of the first aspect and first or second embodiments thereof, R3 is —H, —OH or —O—C(=O)—C$_{1-14}$ alkyl and R4 is —F. In some embodiments, R3 is —H or —OH and R4 is —F. In some embodiments, R3 is —OH and R4 is —F. In some embodiments, R3 is —F and R4 is —H, —OH or —O—C(=O)—C$_{1-14}$ alkyl. In some embodiments, R3 is —F and R4 is —H or —OH. In some embodiments, R3 is —F and R4 is —OH. In some embodiments, R3 and R4 are —F.

In some embodiments of the first aspect, the compound is selected from the group consisting of:

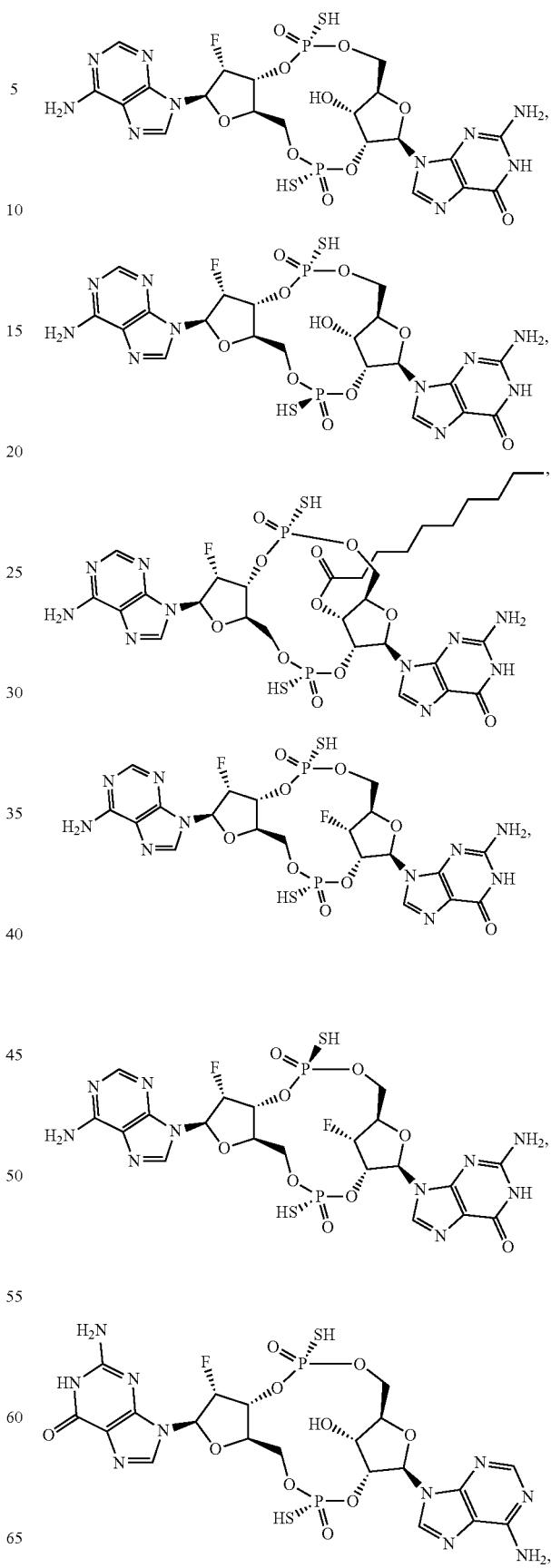

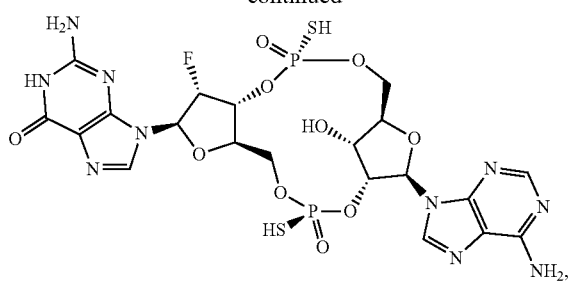
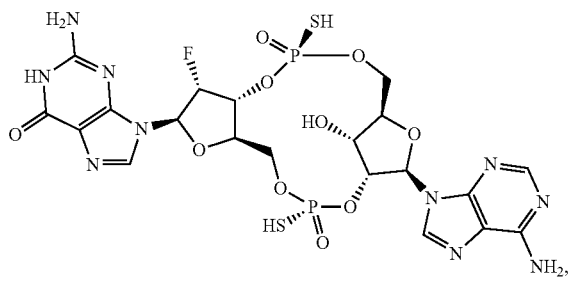
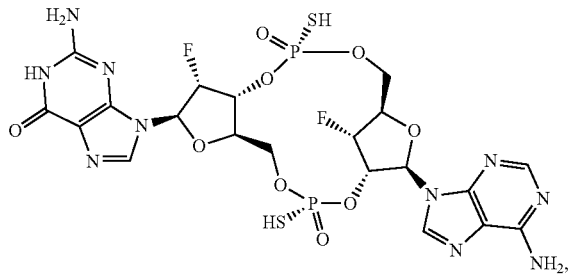
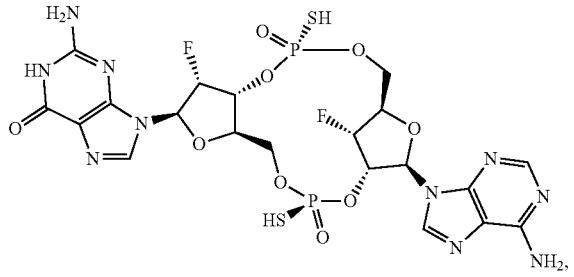
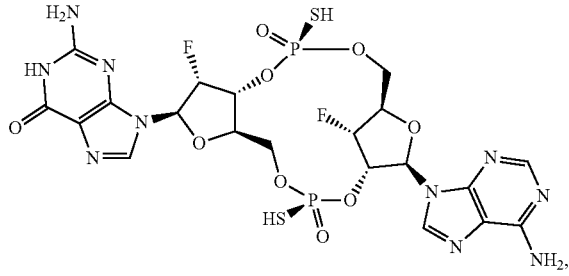
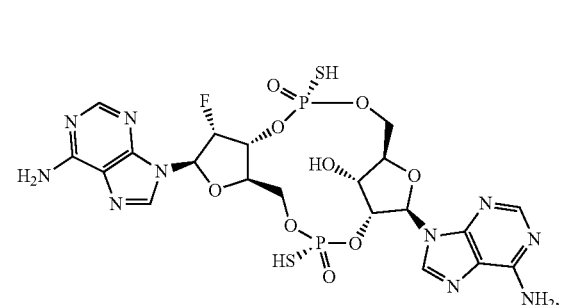
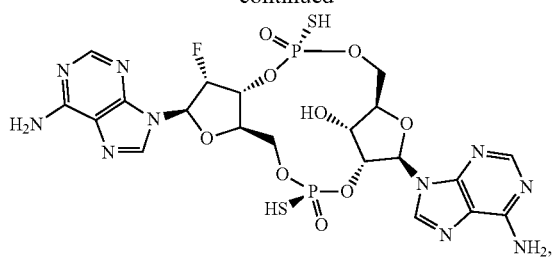
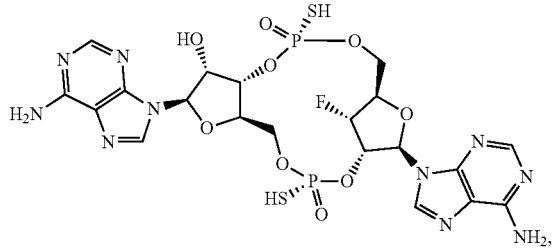
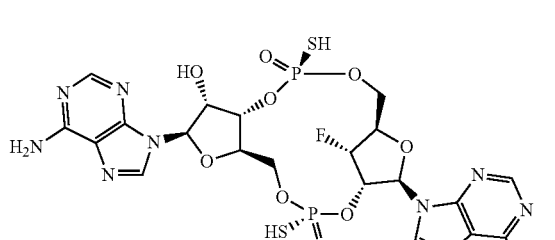
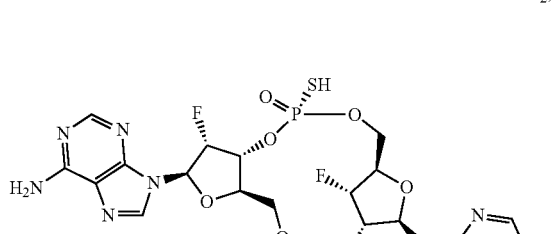
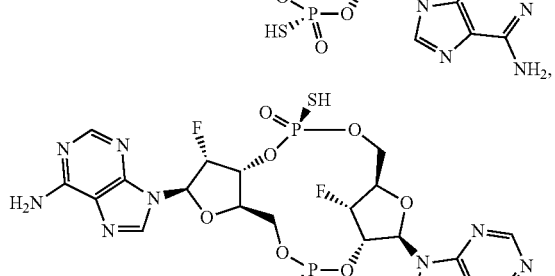
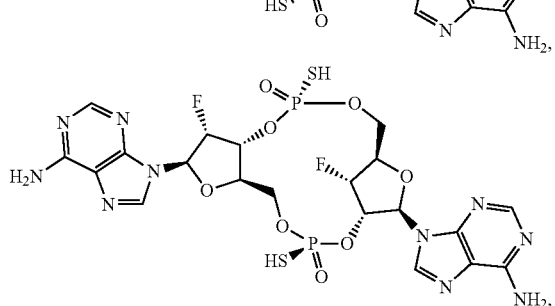

-continued
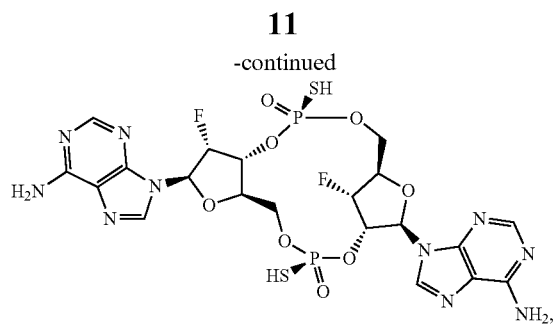
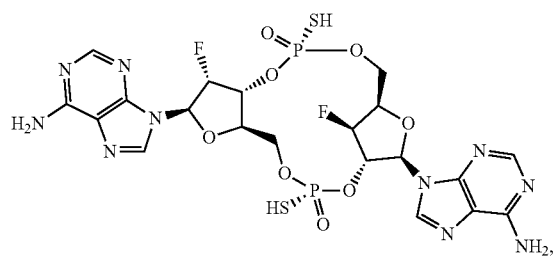
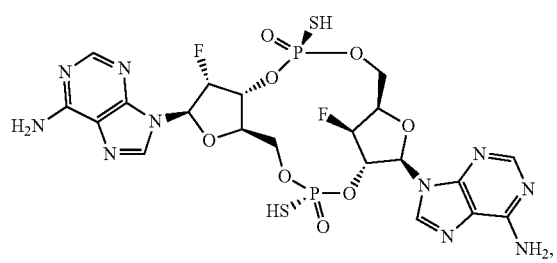
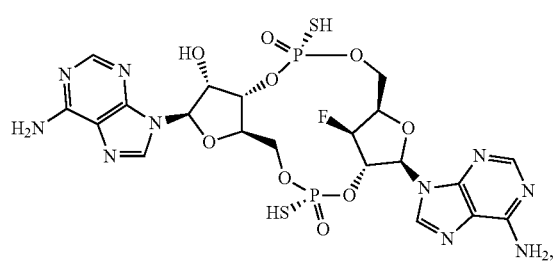
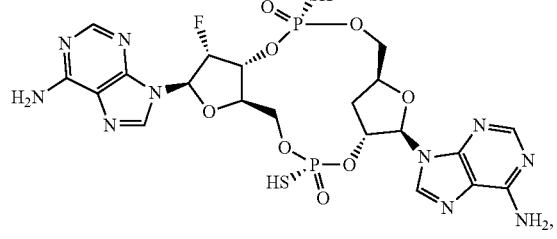
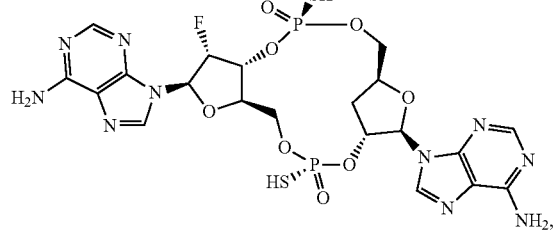
-continued
or a prodrug, pharmaceutically acceptable salt, pharmaceutically acceptable solvate or pharmaceutically acceptable hydrate thereof.
In some embodiments of the first aspect and first embodiment thereof, the compound is selected from the group consisting of:
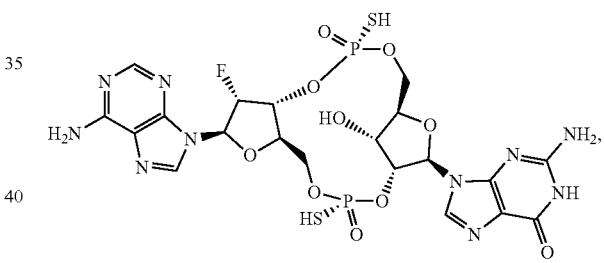
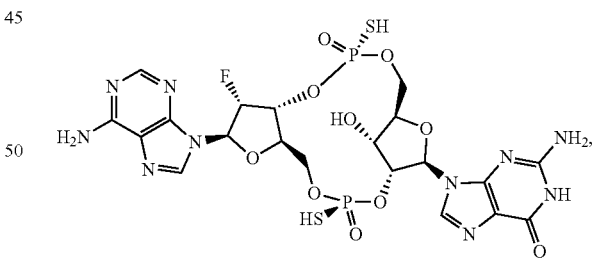
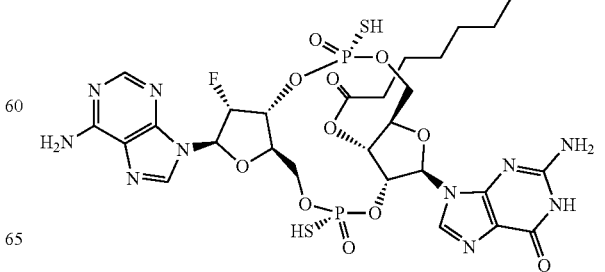

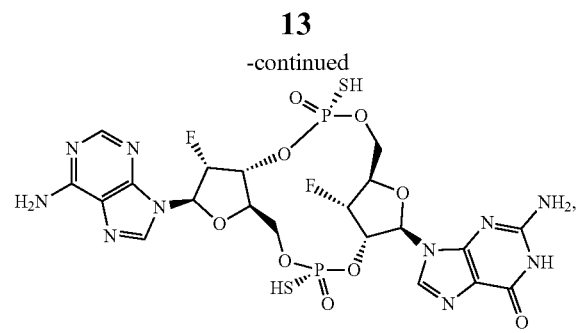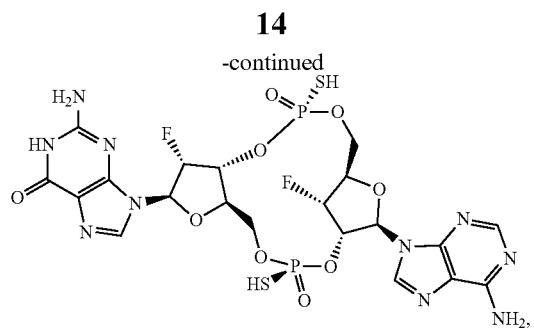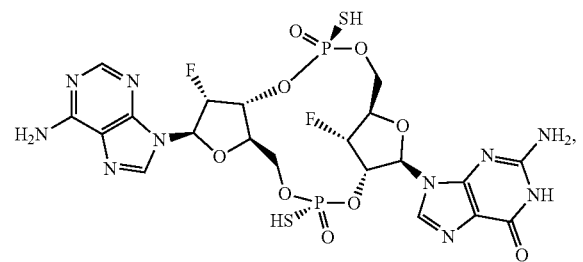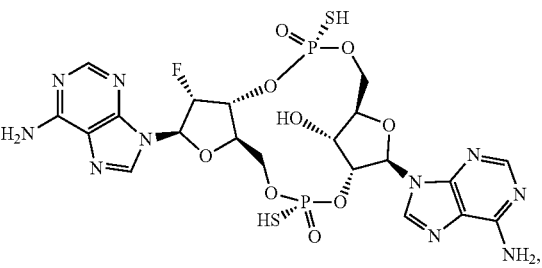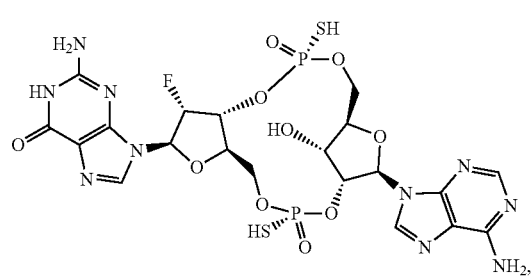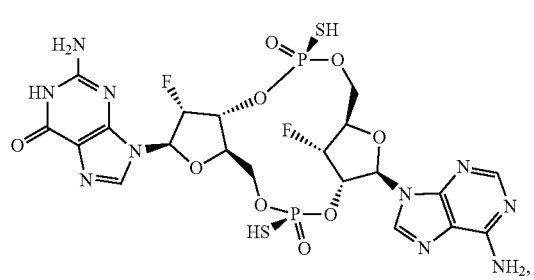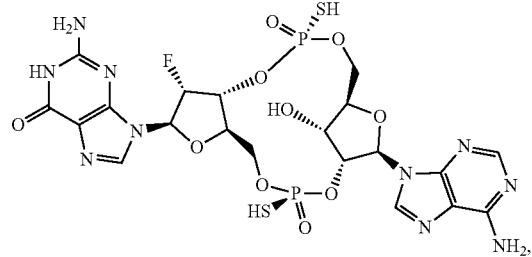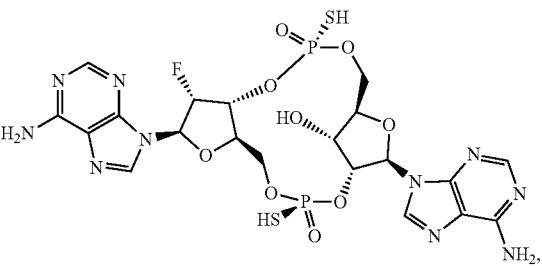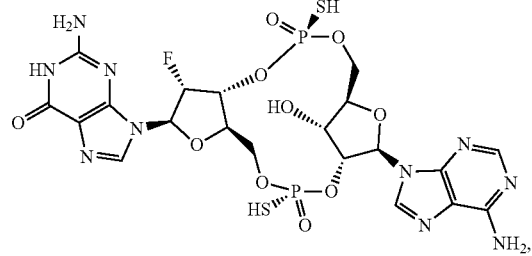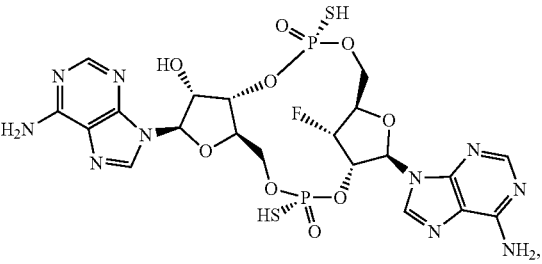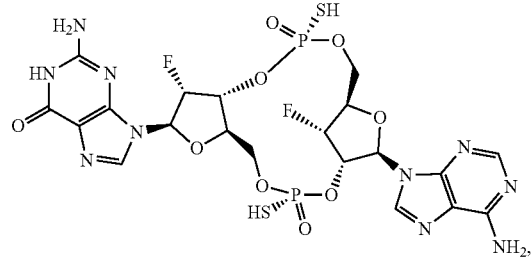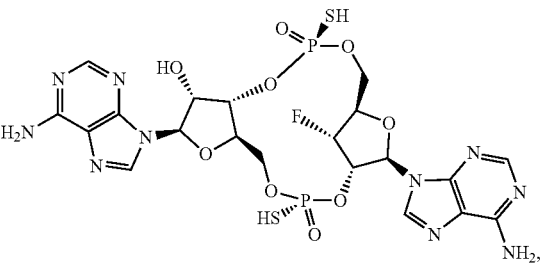

-continued

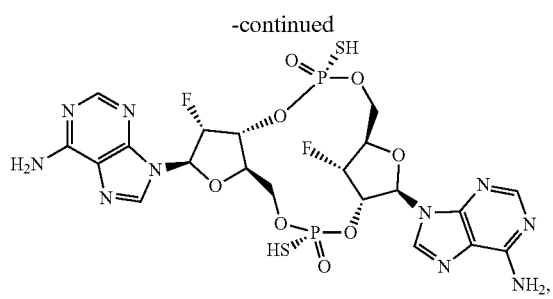

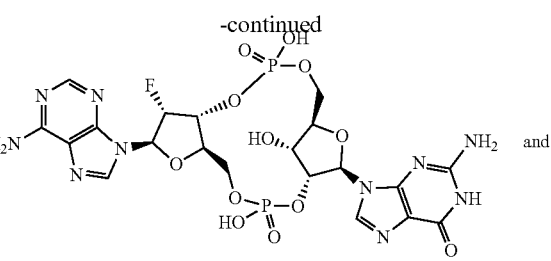

or a prodrug, pharmaceutically acceptable salt, pharmaceutically acceptable solvate or pharmaceutically acceptable hydrate thereof.

In some embodiments of the first aspect and second embodiment thereof, the Compound is selected from the group consisting of:

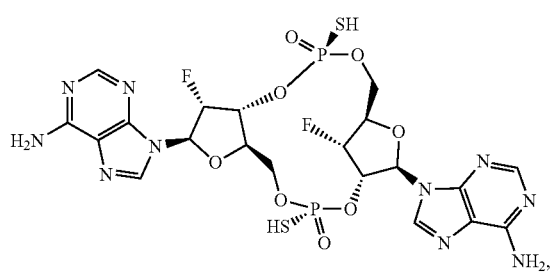

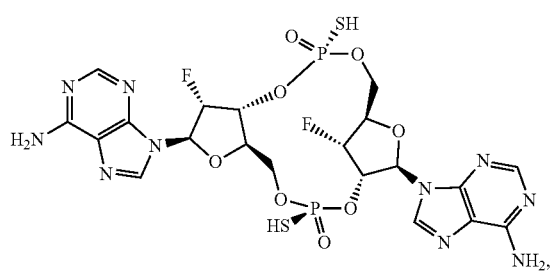

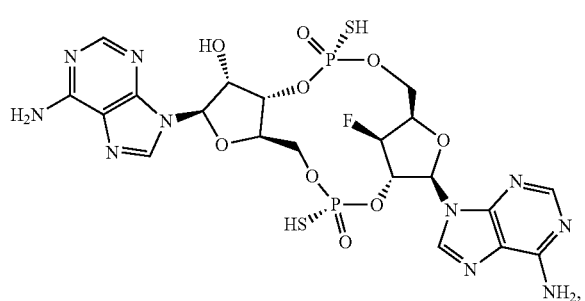

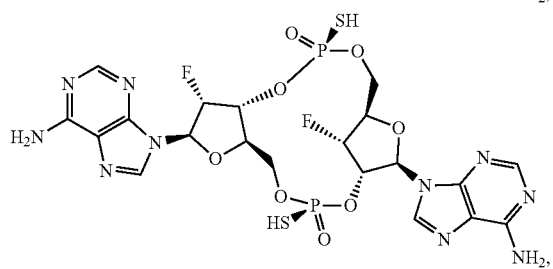

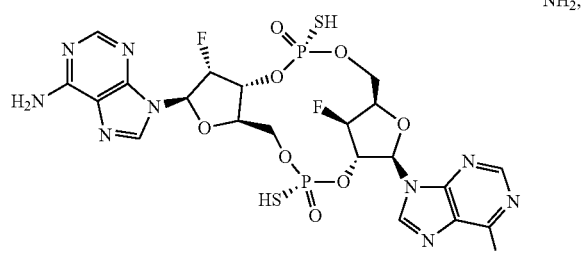

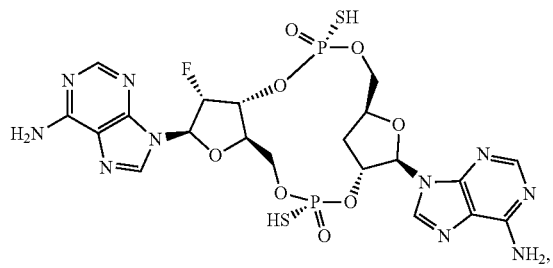

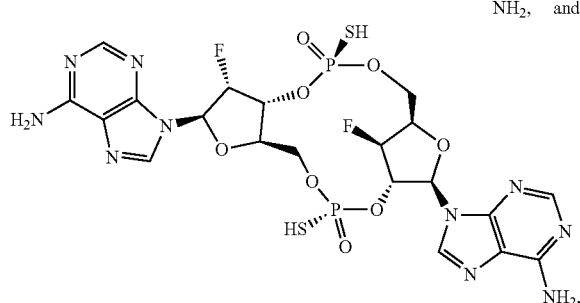

or a prodrug, pharmaceutically acceptable salt, pharmaceutically acceptable solvate or pharmaceutically acceptable hydrate thereof.

In a third embodiment of the first aspect, the Compound of Formula I is a Compound of Formula I-c:

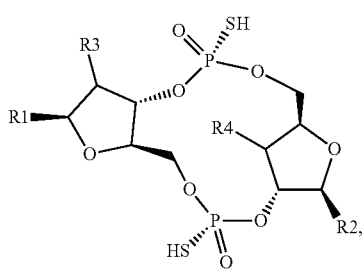

Formula I-c or a prodrug, pharmaceutically acceptable salt, pharmaceutically acceptable solvate or pharmaceutically acceptable hydrate thereof, wherein R1, R2, R3 and R4 are as defined for Compounds of Formula I.

In a fourth embodiment of the first aspect, the Compound of Formula I is a Compound of Formula I-d:

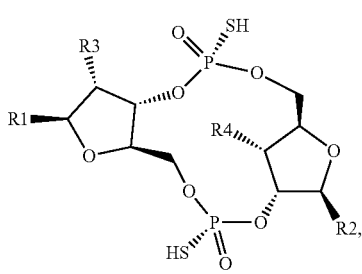

Formula I-d or a prodrug, pharmaceutically acceptable salt, pharmaceutically acceptable solvate or pharmaceutically acceptable hydrate thereof, wherein R1, R2, R3 and R4 are as defined for Compounds of Formula I.

In a fifth embodiment of the first aspect, the Compound of Formula I is a Compound of Formula I-e:

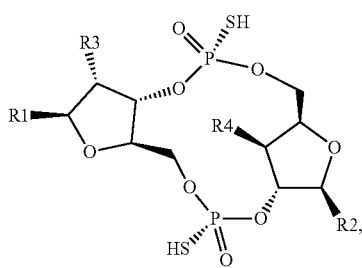

Formula I-e or a prodrug, pharmaceutically acceptable salt, pharmaceutically acceptable solvate or pharmaceutically acceptable hydrate thereof, wherein R1, R2, R3 and R4 are as defined for Compounds of Formula I.

In some embodiments of the first aspect and third, fourth or fifth embodiments thereof, R3 is —F and R4 is —H, —OH or —O—C(=O)—$C_{1-14}$ alkyl. In some embodiments R3 is —F and R4 is —H or —OH. In some embodiments R3 is —F and R4 is —OH. In some embodiments R3 is —H, —OH or —O—C(=O)—$C_{1-14}$ alkyl and R4 is —F. In some embodiments R3 is —H or —OH and R4 is —F. In some embodiments R3 is —OH and R4 is —F. In some embodiments R3 and R4 are —F. In some embodiments, R1 and R2 are adenine. In some embodiments, R1 is adenine and R2 is guanine. In some embodiments, R1 is guanine and R2 is adenine. In some embodiments, R1 and R2 are adenine, R3 is —F and R4 is —H, —OH or —O—C(=O)—$C_{1-14}$ alkyl. In some embodiments, R1 and R2 are adenine, R3 is —F and R4 is —H or —OH. In some embodiments, R1 and R2 are adenine, R3 is —F and R4 is —OH. In some embodiments, R1 and R2 are adenine, R3 is —H, —OH or —O—C(=O)—$C_{1-14}$ alkyl and R4 is —F. In some embodiments, R1 and R2 are adenine, R3 is —H or —OH and R4 is —F. In some embodiments, R1 and R2 are adenine, R3 is —OH and R4 is —F. In some embodiments, R1 and R2 are adenine, and R3 and R4 are —F. In some embodiments, R1 is adenine, R2 is guanine, R3 is —F and R4 is —H, —OH or —O—C(=O)—$C_{1-14}$ alkyl. In some embodiments, R1 is adenine, R2 is guanine, R3 is —F and R4 is —H or —OH. In some embodiments, R1 is adenine, R2 is guanine, R3 is —F and R4 is —OH. In some embodiments, R1 is adenine, R2 is guanine, R3 is —H, —OH or —O—C(=O)—$C_{1-14}$ alkyl and R4 is —F. In some embodiments, R1 is adenine, R2 is guanine, R3 is —H or —OH and R4 is —F. In some embodiments, R1 is adenine, R2 is guanine, R3 is —OH and R4 is —F. In some embodiments, R1 is adenine, R2 is guanine, and R3 and R4 are —F. In some embodiments, R1 is guanine, R2 is adenine, R3 is —F and R4 is —H, —OH or —O—C(=O)—$C_{1-14}$ alkyl. In some embodiments, R1 is guanine, R2 is adenine, R3 is —F and R4 is —H or —OH. In some embodiments, R1 is guanine, R2 is adenine, R3 is —F and R4 is —OH. In some embodiments, R1 is guanine, R2 is adenine, R3 is —H, —OH or —O—C(=O)—$C_{1-14}$ alkyl and R4 is —F. In some embodiments, R1 is guanine, R2 is adenine, R3 is —H or —OH and R4 is —F. In some embodiments, R1 is guanine, R2 is adenine, R3 is —OH and R4 is —F. In some embodiments, R1 is guanine, R2 is adenine, and R3 and R4 are —F.

In some embodiments of the first aspect and any of the above embodiments thereof, when R3 or R4 is —O—C(=O)—$C_{1-14}$ alkyl, —O—C(=O)—$C_{1-14}$ alkyl is —O—C(=O)—$C_{3-14}$ alkyl, —O—C(=O)—$C_{5-13}$ alkyl, —O—C(=O)—$C_{5-11}$ alkyl, or —O—C(=O)—$C_9$ alkyl, preferably wherein the alkyl chain is linear. In a preferred embodiment, —O—C(=O)—$C_{1-14}$ alkyl is —O—C(=O)—$(CH_2)_8$—$CH_3$.

In some embodiments of the first aspect and third embodiment thereof, the compound is selected from the group consisting of:

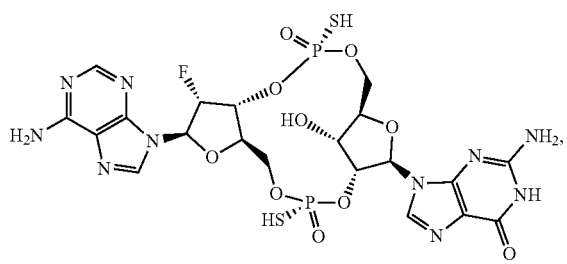

-continued
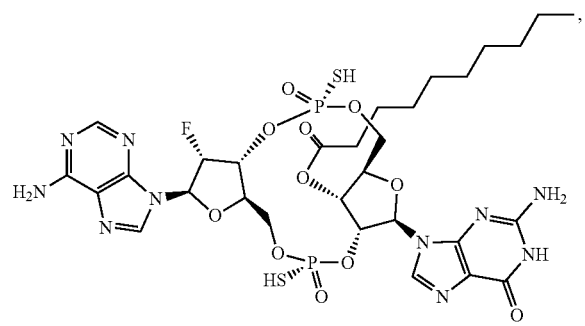
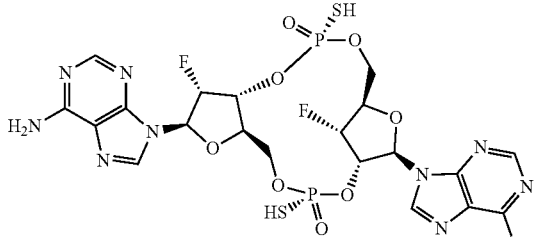
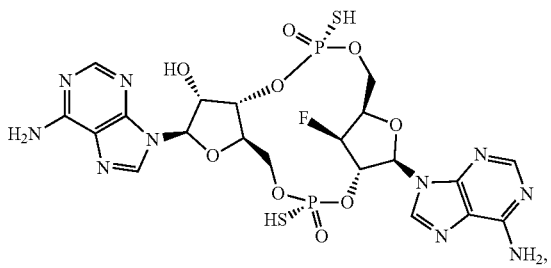
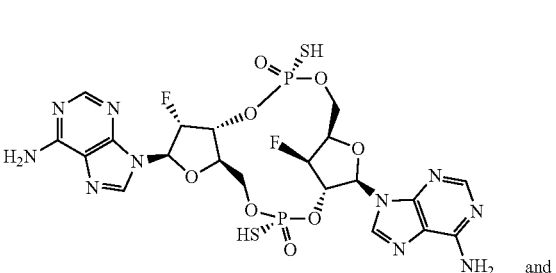
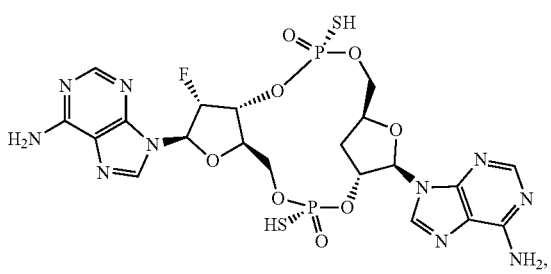
and
or a prodrug, pharmaceutically acceptable salt, pharmaceutically acceptable solvate or pharmaceutically acceptable hydrate thereof.
In some embodiments of the first aspect and first or fourth embodiments thereof, the compound is selected from the group consisting of:
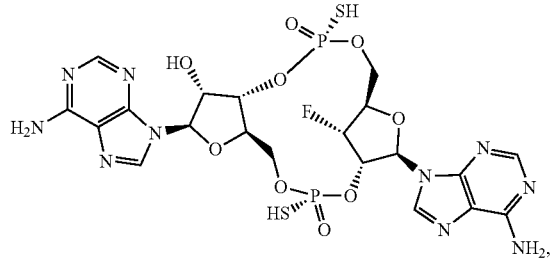
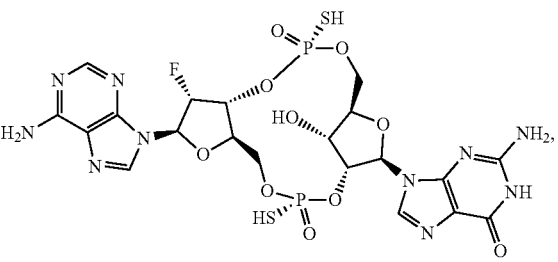

-continued

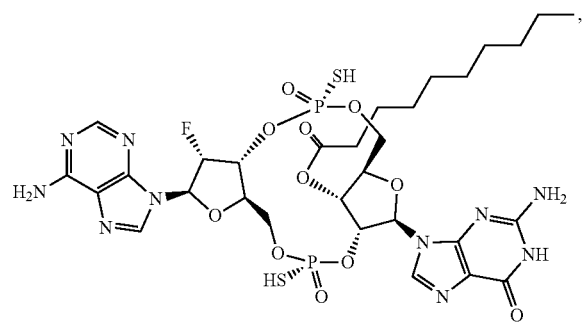

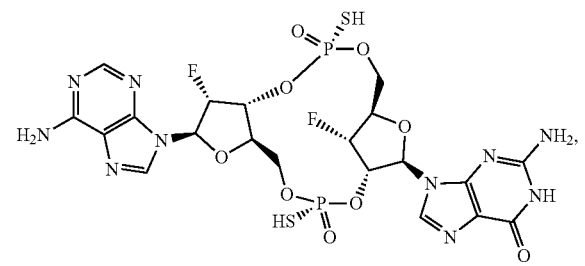

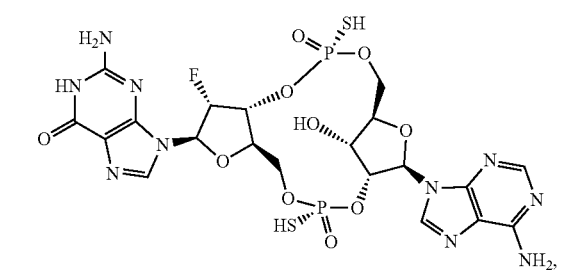

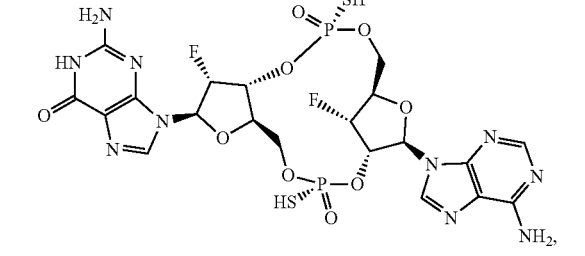

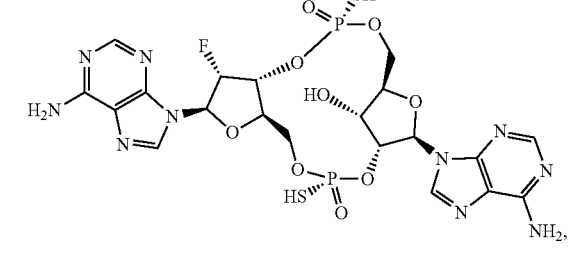

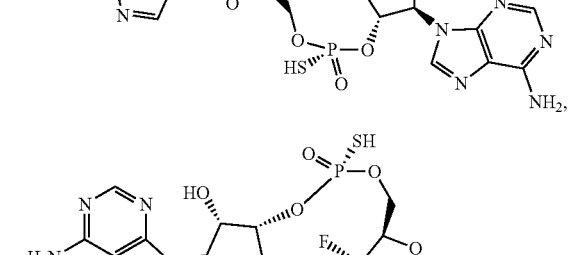

-continued

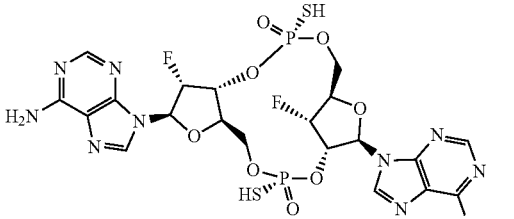

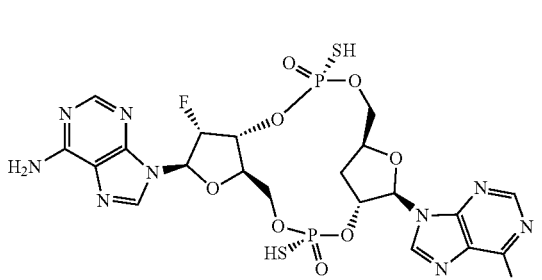

or a prodrug, pharmaceutically acceptable salt, pharmaceutically acceptable solvate or pharmaceutically acceptable hydrate thereof.

In some embodiments of the first aspect and fifth embodiment thereof, the compound is selected from the group consisting of:

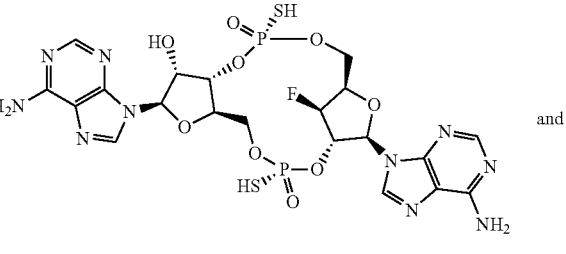

and

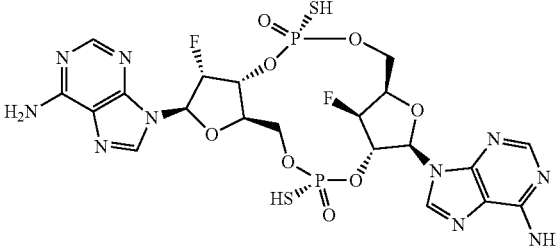

or a prodrug, pharmaceutically acceptable salt, pharmaceutically acceptable solvate or pharmaceutically acceptable hydrate thereof.

In a second aspect, the present invention provides a mono- or di-F-ML-CDN Compound of Formula IA:

Formula IA

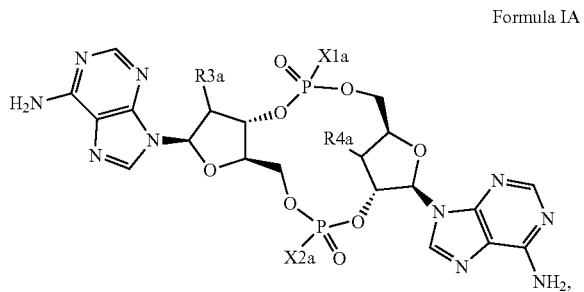

Formula IA-b

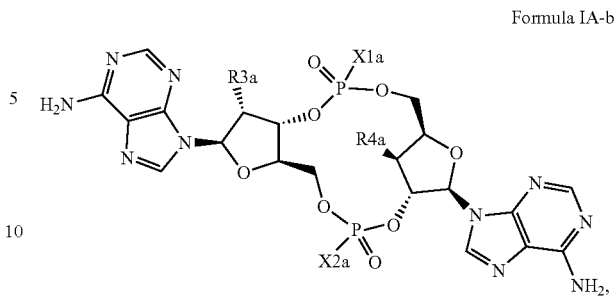

or a prodrug, pharmaceutically acceptable salt, pharmaceutically acceptable solvate or pharmaceutically acceptable hydrate thereof, wherein:

R3a and R4a are independently —H, —OH, —O—C(=O)—$C_{1-14}$ alkyl or —F, provided that at least one of R3a and R4a is —F; and X1a and X2a are independently —OH or —SH.

As described hereinafter, in certain embodiments, X1a and X2a are each —SH, and one or both of R3a and R4a are —F; and in certain of these embodiments, if only one of R3a and R4a is F, the other of R3a and R4a is —O—C(=O)—$C_{1-14}$ alkyl, and preferably —O—C(=O)—$C_{6-12}$ alkyl. In certain of these embodiments, R3a is F and R4a is —O—C(=O)—$C_{1-14}$ alkyl, and preferably —O—C(=O)—$C_{6-12}$. Additionally, when X1a or X2a are —SH, a chiral center is introduced into the molecule at the thiophosphate. In certain of these embodiments, the compounds are R,R diastereoisomers.

In a first embodiment of the second aspect, the Compound of Formula IA is a Compound of Formula IA-a:

Formula IA-a

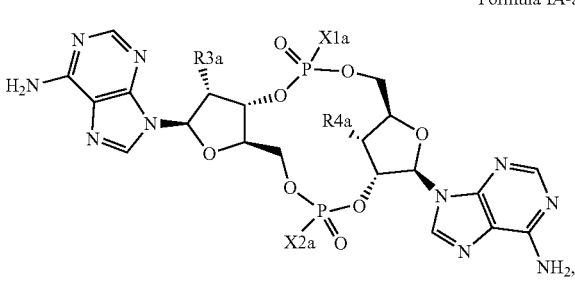

or a prodrug, pharmaceutically acceptable salt, pharmaceutically acceptable solvate or pharmaceutically acceptable hydrate thereof, wherein R3a, R4a, X1a and X2a are as defined for Compounds of Formula IA.

In a second embodiment of the second aspect, the Compound of Formula IA is a Compound of Formula IA-b:

or a prodrug, pharmaceutically acceptable salt, pharmaceutically acceptable solvate or pharmaceutically acceptable hydrate thereof, wherein R3a, R4a, X1a and X2a are as defined for Compounds of Formula IA.

In some embodiments of the second aspect and first or second embodiments thereof, X1a and X2a are —SH. In some embodiments X1a and X2a are —SH, R3a is —F and R4a is —H, —OH or —O—C(=O)—$C_{1-14}$ alkyl. In some embodiments X1a and X2a are —SH, R3a is —F and R4a is —H or —OH. In some embodiments X1a and X2a are —SH, R3a is —F and R4a is —OH. In some embodiments X1a and X2a are —SH, R3a is —H, —OH or —O—C(=O)—$C_{1-14}$ alkyl and R4a is —F. In some embodiments X1a and X2a are —SH, R3a is —H or —OH and R4a is —F. In some embodiments X1a and X2a are —SH, R3a is —OH and R4a is —F. In some embodiments X1a and X2a are —SH, and R3a and R4a are —F.

In some embodiments of the second aspect and first or second embodiments thereof, X1a is —OH and X2a is —SH. In some embodiments X1a is —OH, X2a is —SH, R3a is —F and R4a is —H, —OH or —O—C(=O)—$C_{1-14}$ alkyl. In some embodiments X1a is —OH, X2a is —SH, R3a is —F and R4a is —H or —OH. In some embodiments X1a is —OH, X2a is —SH, R3a is —F and R4a is —OH. In some embodiments X1a is —OH, X2a is —SH, R3a is —H, —OH or —O—C(=O)—$C_{1-14}$alkyl and R4a is —F. In some embodiments X1a is —OH, X2a is —SH, R3a is —H or —OH and R4a is —F. In some embodiments X1a is —OH, X2a is —SH, R3a is —OH and R4a is —F. In some embodiments X1a is —OH, X2a is —SH, and R3a and R4a are —F.

In some embodiments of the second aspect and first or second embodiments thereof, X1a is —SH and X2a is —OH. In some embodiments X1a is —SH, X2a is —OH, R3a is —F and R4a is —H, —OH or —O—C(=O)—$C_{1-14}$ alkyl. In some embodiments X1a is —SH, X2a is —OH, R3a is —F and R4a is —H or —OH. In some embodiments X1a is —SH, X2a is —OH, R3a is —F and R4a is —OH. In some embodiments X1a is —SH, X2a is —OH, R3a is —H, —OH or —O—C(=O)—$C_{1-14}$ alkyl and R4a is —F. In some embodiments X1a is —SH, X2a is —OH, R3a is —H or —OH and R4a is —F. In some embodiments X1a is —SH, X2a is —OH, R3a is —OH and R4a is —F. In some embodiments X1a is —SH, X2a is —OH, and R3a and R4a are —F.

In some embodiments of the second aspect and first or second embodiments thereof, X1a and X2a are —OH. In some embodiments X1a and X2a are —OH, R3a is —F and R4a is —H, —OH or —O—C(=O)—$C_{1-14}$ alkyl. In some embodiments X1a and X2a are —OH, R3a is —F and R4a is —H or —OH. In some embodiments X1a and X2a are —OH, R3a is —F and R4a is —OH. In some embodiments X1a and X2a are —OH, R3a is —H, —OH or —O—C (=O)—C$_{1-14}$ alkyl and R4a is —F. In some embodiments X1a and X2a are —OH, R3a is —H or —OH and R4a is —F. In some embodiments X1a and X2a are —OH, R3a is —OH and R4a is —F. In some embodiments X1a and X2a are —OH, and R3a and R4a are —F.

In some embodiments of the second aspect and first or second embodiments thereof, R3a is —H, —OH or —O—C(=O)—C$_{1-14}$ alkyl and R4a is —F. In some embodiments, R3a is —H or —OH and R4a is —F. In some embodiments, R3a is —OH and R4a is —F. In some embodiments, R3a is —F and R4a is —H, —OH or —O—C(=O)—C$_{1-14}$ alkyl. In some embodiments, R3a is —F and R4a is —H or —OH. In some embodiments, R3a is —F and R4a is —OH. In some embodiments, R3a and R4a are —F.

In some embodiments of the second aspect and any of the above embodiments thereof, when R3a or R4a is —O—C(=O)—C$_{1-14}$ alkyl, —O—C(=O)—C$_{1-14}$ alkyl is —O—C(=O)—C$_{3-14}$ alkyl, —O—C(=O)—C$_{5-13}$ alkyl, —O—C(=O)—C$_{5-11}$ alkyl, or —O—C(=O)—C$_9$ alkyl, preferably wherein the alkyl chain is linear. In a preferred embodiment, —O—C(=O)—C$_{1-14}$ alkyl is —O—C(=O)—(CH$_2$)$_8$—CH$_3$.

In a third embodiment of the second aspect, the Compound of Formula IA is a Compound of Formula IA-c:

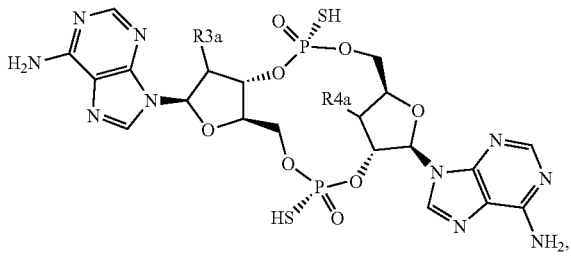

Formula IA-c or a prodrug, pharmaceutically acceptable salt, pharmaceutically acceptable solvate or pharmaceutically acceptable hydrate thereof, wherein R3a and R4a are independently —H, —OH, —O—C(=O)—C$_{1-14}$ alkyl or —F, provided that at least one of R3a and R4a is —F. In some embodiments R3a is —H, —OH or —O—C(=O)—C$_{1-14}$ alkyl and R4a is —F. In some embodiments R3a is —H or —OH and R4a is —F. In some embodiments R3a is —OH and R4a is —F. In some embodiments, R3a is —F and R4a is —H, —OH, —O—C(=O)—C$_{1-14}$ alkyl. In some embodiments, R3a is —F and R4a is —H or —OH. In some embodiments, R3a is —F and R4a is —OH. In some embodiments, R3a and R4a are —F. In some embodiments, when R3a or R4a is —O—C(=O)—C$_{1-14}$ alkyl, —O—C(=O)—C$_{1-14}$ alkyl is —O—C(=O)—C$_{3-14}$ alkyl, —O—C(=O)—C$_{5-13}$ alkyl, —O—C(=O)—C$_{5-11}$ alkyl, or —O—C(=O)—C$_9$ alkyl, preferably wherein the alkyl chain is linear. In a preferred embodiment, —O—C(=O)—C$_{1-14}$ alkyl is —O—C(=O)—(CH$_2$)$_8$—CH$_3$.

In a fourth embodiment of the second aspect, the Compound of Formula IA is a Compound of Formula IA-d:

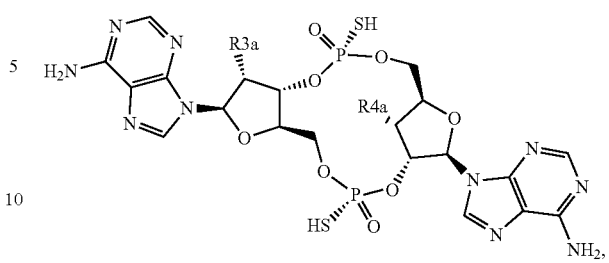

Formula IA-d or a prodrug, pharmaceutically acceptable salt, pharmaceutically acceptable solvate or pharmaceutically acceptable hydrate thereof, wherein R3a and R4a are independently —H, —OH, —O—C(=O)—C$_{1-14}$ alkyl or —F, provided that at least one of R3a and R4a is —F. In some embodiments R3a is —H, —OH or —O—C(=O)—C$_{1-14}$ alkyl and R4a is —F. In some embodiments R3a is —H or —OH and R4a is —F. In some embodiments R3a is —OH and R4a is —F. In some embodiments, R3a is —F and R4a is —H, —OH, —O—C(=O)—C$_{1-14}$ alkyl. In some embodiments, R3a is —F and R4a is —H or —OH. In some embodiments, R3a is —F and R4a is —OH. In some embodiments, R3a and R4a are —F. In some embodiments, when R3a or R4a is —O—C(=O)—C$_{1-14}$ alkyl, —O—C(=O)—C$_{1-14}$ alkyl is —O—C(=O)—C$_{3-14}$ alkyl, —O—C(=O)—C$_{5-13}$ alkyl, —O—C(=O)—C$_{5-11}$ alkyl, or —O—C(=O)—C$_9$ alkyl, preferably wherein the alkyl chain is linear. In a preferred embodiment, —O—C(=O)—C$_{1-14}$ alkyl is —O—C(=O)—(CH$_2$)$_8$—CH$_3$.

In a fifth embodiment of the second aspect, the Compound of Formula IA is a Compound of Formula IA-e:

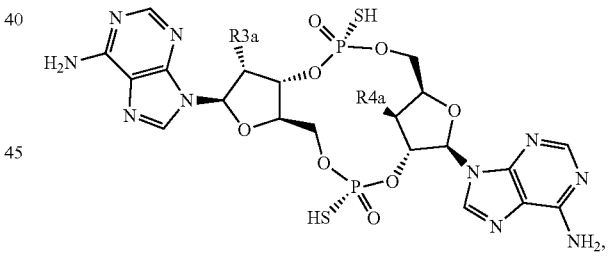

Formula IA-e or a prodrug, pharmaceutically acceptable salt, pharmaceutically acceptable solvate or pharmaceutically acceptable hydrate thereof, wherein R3a and R4a are independently —H, —OH, —O—C(=O)—C$_{1-14}$ alkyl or —F, provided that at least one of R3a and R4a is —F. In some embodiments R3a is —H, —OH or —O—C(=O)—C$_{1-14}$ alkyl and R4a is —F. In some embodiments R3a is —H or —OH and R4a is —F. In some embodiments R3a is —OH and R4a is —F. In some embodiments, R3a is —F and R4a is —H, —OH, —O—C(=O)—C$_{1-14}$ alkyl. In some embodiments, R3a is —F and R4a is —H or —OH. In some embodiments, R3a is —F and R4a is —OH. In some embodiments, R3a and R4a are —F. In some embodiments, when R3a or R4a is —O—C(=O)—C$_{1-14}$ alkyl, —O—C(=O)—C$_{1-14}$ alkyl is —O—C(=O)—C$_{3-14}$ alkyl, —O—C(=O)—C$_{5-13}$ alkyl, —O—C(=O)—C$_{5-11}$ alkyl, or —O—C(=O)—C$_9$ alkyl, preferably wherein the alkyl chain is linear. In a preferred embodiment, —O—C(=O)—C$_{1-14}$ alkyl is —O—C(=O)—(CH$_2$)$_8$—CH$_3$.

In some embodiments of the second aspect and third embodiment thereof, the compound is selected from the group consisting of:

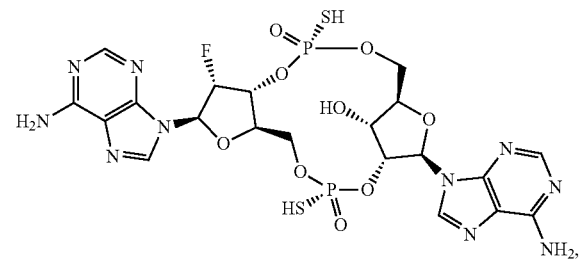

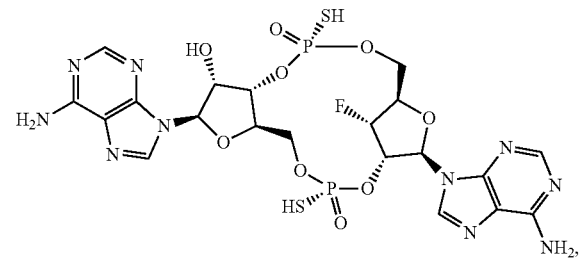

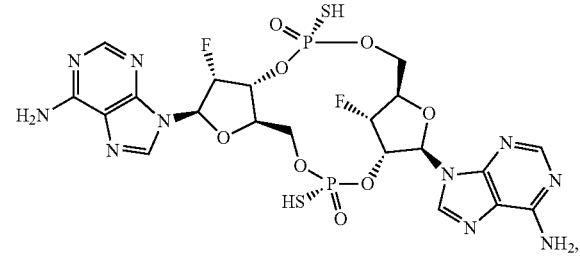

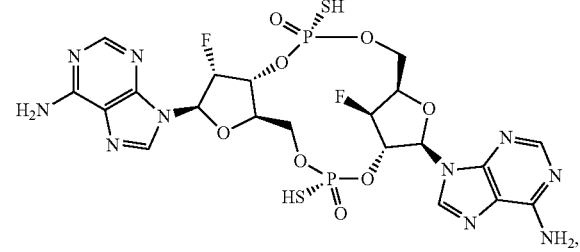

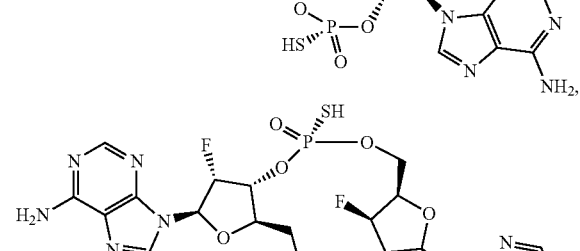

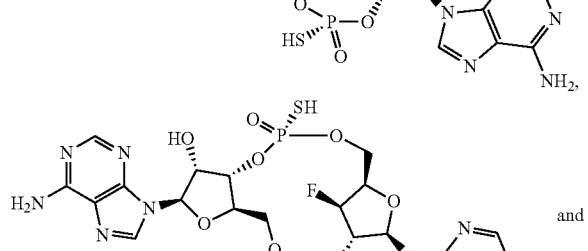

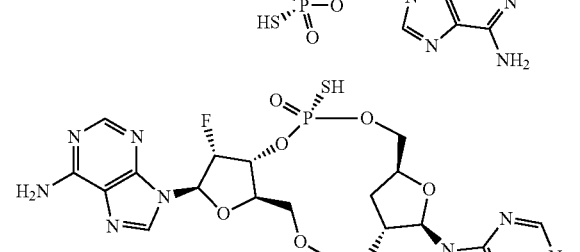

or a prodrug, pharmaceutically acceptable salt, pharmaceutically acceptable solvate or pharmaceutically acceptable hydrate thereof.

In some embodiments of the second aspect and first or fourth embodiments thereof, the compound is selected from the group consisting of:

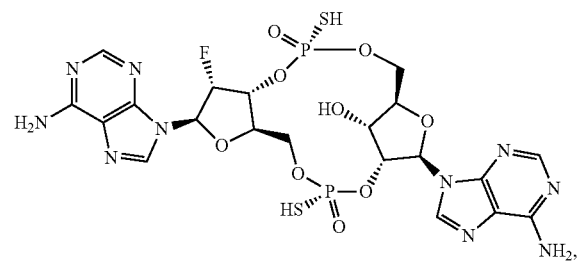

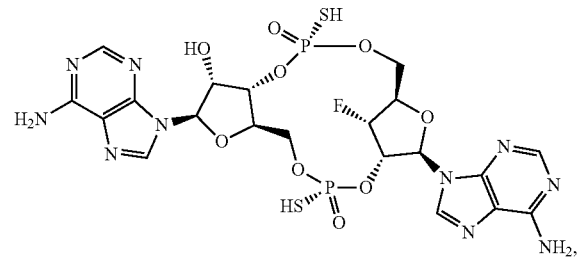

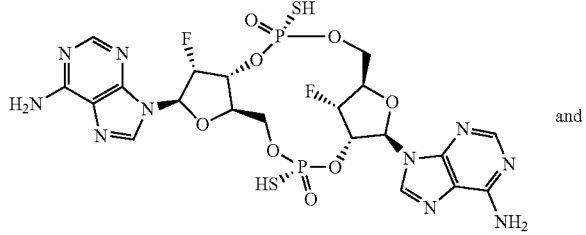

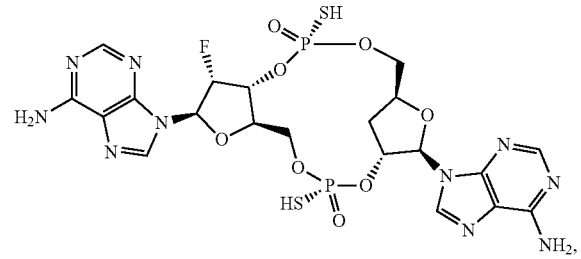

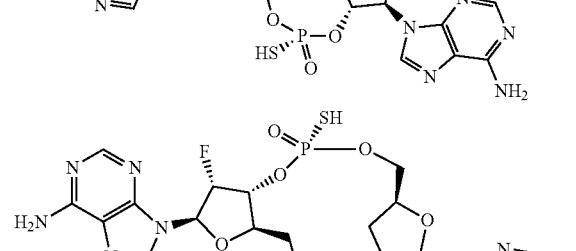

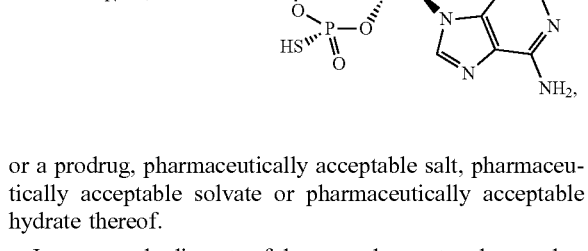

or a prodrug, pharmaceutically acceptable salt, pharmaceutically acceptable solvate or pharmaceutically acceptable hydrate thereof.

In some embodiments of the second aspect and second or fifth embodiments thereof, the compound is selected from the group consisting of:

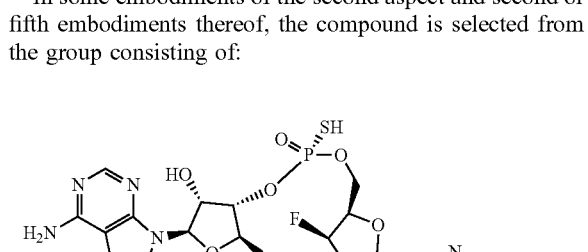

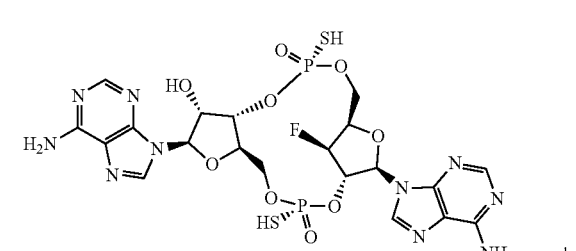

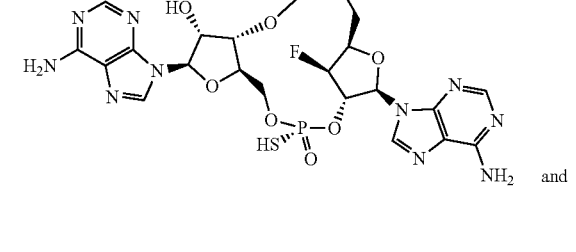

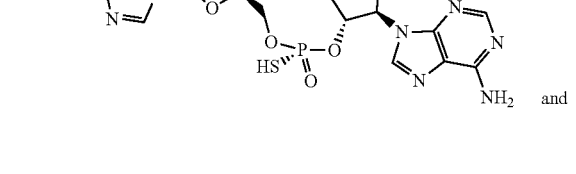

and

-continued

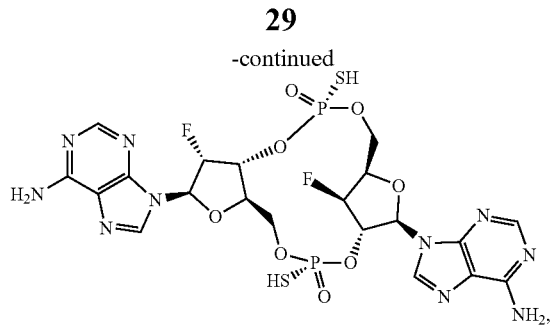

or a prodrug, pharmaceutically acceptable salt, pharmaceutically acceptable solvate or pharmaceutically acceptable hydrate thereof.

In a third aspect, the present invention provides a mono- or di-F-ML-CDN Compound of Formula IB:

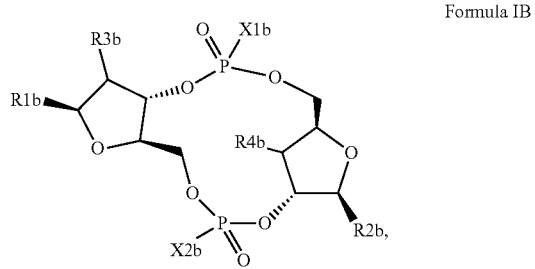

Formula IB or a prodrug, pharmaceutically acceptable salt, pharmaceutically acceptable solvate or pharmaceutically acceptable hydrate thereof, wherein:

one of R1b and R2b is a guanine bound to the structure via the N9 position, and the other of R1b and R2b is an adenine bound to the structure via the N9 position;

R3b and R4b are independently —H, —OH, —O—C(=O)—$C_{1-14}$ alkyl or —F, provided that at least one of R3b and R4b is —F; and X1b and X2b are independently —OH or —SH.

As described hereinafter, in certain embodiments, X1b and X2b are each —SH, and one or both of R3b and R4b are —F; and in certain of these embodiments, if only one of R3b and R4b is F, the other of R3b and R4b is —O—C(=O)—$C_{1-14}$ alkyl, and preferably —O—C(=O)—$C_{6-12}$ alkyl. In certain of these embodiments, R3b is F and R4b is —O—C(=O)—$C_{1-14}$ alkyl, and preferably —O—C(=O)—$C_{6-12}$. Additionally, when X1b or X2b are —SH, a chiral center is introduced into the molecule at the thiophosphate. In certain of these embodiments, the compounds are R,R diastereoisomers.

In a first embodiment of the third aspect, the Compound of Formula IB is a Compound of Formula IB-a:

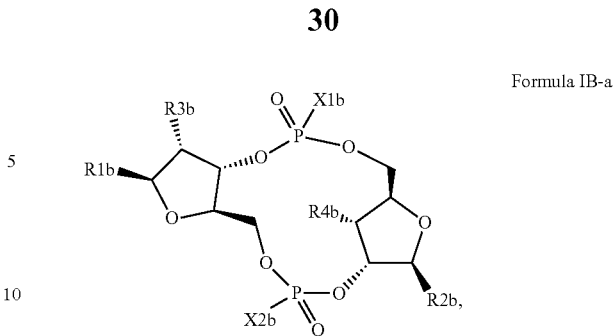

Formula IB-a or a prodrug, pharmaceutically acceptable salt, pharmaceutically acceptable solvate or pharmaceutically acceptable hydrate thereof, wherein R1b, R2b, R3b, R4b, X1b and X2b are as defined for Compounds of Formula IB.

In some embodiments of the third aspect and first embodiment thereof, X1b and X2b are —SH. In some embodiments X1b and X2b are —SH, R3b is —F and R4b is —H, —OH or —O—C(=O)—$C_{1-14}$alkyl. In some embodiments X1b and X2b are —SH, R3b is —F and R4b is —H or —OH. In some embodiments X1b and X2b are —SH, R3b is —F and R4b is —OH. In some embodiments X1b and X2b are —SH, R3b is —H, —OH or —O—C(=O)—$C_{1-14}$ alkyl and R4b is —F. In some embodiments X1b and X2b are —SH, R3b is —H or —OH and R4b is —F. In some embodiments X1b and X2b are —SH, R3b is —OH and R4b is —F. In some embodiments X1b and X2b are —SH, and R3b and R4b are —F. In some embodiments X1b and X2b are —SH, R1b is adenine and R2b is guanine. In some embodiments X1b and X2b are —SH, R3b is —F, R4b is —H, —OH or —O—C(=O)—$C_{1-14}$ alkyl, R1b is adenine and R2b is guanine. In some embodiments X1b and X2b are —SH, R3b is —F, R4b is —H or —OH, R1b is adenine and R2b is guanine. In some embodiments X1b and X2b are —SH, R3b is —F, R4b is —OH, R1b is adenine and R2b is guanine. In some embodiments X1b and X2b are —SH, R3b is —H, —OH or —O—C(=O)—$C_{1-14}$ alkyl, R4b is —F, R1b is adenine and R2b is guanine. In some embodiments X1b and X2b are —SH, R3b is —H or —OH, R4b is —F, Rib is adenine and R2b is guanine. In some embodiments X1b and X2b are —SH, R3b is —OH, R4b is —F, R1b is adenine and R2b is guanine. In some embodiments X1b and X2b are —SH, R3b and R4b are —F, R1b is adenine and R2b is guanine. In some embodiments X1b and X2b are —SH, R1b is guanine and R2b is adenine. In some embodiments X1b and X2b are —SH, R3b is —F, R4b is —H, —OH or —O—C(=O)—$C_{1-14}$ alkyl, R1b is guanine and R2b is adenine. In some embodiments X1b and X2b are —SH, R3b is —F, R4b is —H or —OH, R1b is guanine and R2b is adenine. In some embodiments X1b and X2b are —SH, R3b is —F, R4b is —OH, R1b is guanine and R2b is adenine. In some embodiments X1b and X2b are —SH, R3b is —H, —OH or —O—C(=O)—$C_{1-14}$ alkyl, R4b is —F, R1b is guanine and R2b is adenine. In some embodiments X1b and X2b are —SH, R3b is —H or —OH, R4b is —F, Rib is guanine and R2b is adenine. In some embodiments X1b and X2b are —SH, R3b is —OH, R4b is —F, R1b is guanine and R2b is adenine. In some embodiments X1b and X2b are —SH, R3b and R4b are —F, R1b is guanine and R2b is adenine.

In some embodiments of the third aspect and first embodiment thereof, X1b is —OH and X2b is —SH. In some embodiments X1b is —OH, X2b is —SH, R3b is —F and R4b is —H, —OH or —O—C(=O)—$C_{1-14}$ alkyl. In some embodiments X1b is —OH, X2b is —SH, R3b is —F and R4b is —H or —OH. In some embodiments X1b is —OH, X2b is —SH, R3b is —F and R4b is —OH. In some embodiments X1b is —OH, X2b is —SH, R3b is —H, —OH or —O—C(=O)—C$_{1-14}$ alkyl and R4b is —F. In some embodiments X1b is —OH, X2b is —SH, R3b is —H or —OH and R4b is —F. In some embodiments X1b is —OH, X2b is —SH, R3b is —OH and R4b is —F. In some embodiments X1b is —OH, X2b is —SH, and R3b and R4b are —F. In some embodiments X1b is —OH, X2b is —SH, R1b is adenine and R2b is guanine. In some embodiments X1b is —OH, X2b is —SH, R3b is —F, R4b is —H, —OH or —O—C(=O)—C$_{1-14}$ alkyl, R1b is adenine and R2b is guanine. In some embodiments X1b is —OH, X2b is —SH, R3b is —F, R4b is —H or —OH, R1b is adenine and R2b is guanine. In some embodiments X1b is —OH, X2b is —SH, R3b is —F, R4b is —OH, R1b is adenine and R2b is guanine. In some embodiments X1b is —OH, X2b is —SH, R3b is —H, —OH or —O—C(=O)—C$_{1-14}$ alkyl, R4b is —F, R1b is adenine and R2b is guanine. In some embodiments X1b is —OH, X2b is —SH, R3b is —H or —OH, R4b is —F, R1b is adenine and R2b is guanine. In some embodiments X1b is —OH, X2b is —SH, R3b is —OH, R4b is —F, R1b is adenine and R2b is guanine. In some embodiments X1b is —OH, X2b is —SH, R3b and R4b are —F, R1b is adenine and R2b is guanine. In some embodiments X1b is —OH, X2b is —SH, R1b is guanine and R2b is adenine. In some embodiments X1b is —OH, X2b is —SH, R3b is —F, R4b is —H, —OH or —O—C(=O)—C$_{1-14}$ alkyl, R1b is guanine and R2b is adenine. In some embodiments X1b is —OH, X2b is —SH, R3b is —F, R4b is —H or —OH, R1b is guanine and R2b is adenine. In some embodiments X1b is —OH, X2b is —SH, R3b is —F, R4b is —OH, R1b is guanine and R2b is adenine. In some embodiments X1b is —OH, X2b is —SH, R3b is —H, —OH or —O—C(=O)—C$_{1-14}$ alkyl, R4b is —F, R1b is guanine and R2b is adenine. In some embodiments X1b is —OH, X2b is —SH, R3b is —H or —OH, R4b is —F, R1b is guanine and R2b is adenine. In some embodiments X1b is —OH, X2b is —SH, R3b is —OH, R4b is —F, R1b is guanine and R2b is adenine. In some embodiments X1b is —OH, X2b is —SH, R3b and R4b are —F, R1b is guanine and R2b is adenine.

In some embodiments of the third aspect and first embodiment thereof, X1b is —SH and X2b is —OH. In some embodiments X1b is —SH, X2b is —OH, R3b is —F and R4b is —H, —OH or —O—C(=O)—C$_{1-14}$ alkyl. In some embodiments X1b is —SH, X2b is —OH, R3b is —F and R4b is —H or —OH. In some embodiments X1b is —SH, X2b is —OH, R3b is —F and R4b is —OH. In some embodiments X1b is —SH, X2b is —OH, R3b is —H, —OH or —O—C(=O)—C$_{1-14}$ alkyl and R4b is —F. In some embodiments X1b is —SH, X2b is —OH, R3b is —H or —OH and R4b is —F. In some embodiments X1b is —SH, X2b is —OH, R3b is —OH and R4b is —F. In some embodiments X1b is —SH, X2b is —OH, and R3b and R4b are —F. In some embodiments X1b is —SH, X2b is —OH, R1b is adenine and R2b is guanine. In some embodiments X1b is —SH, X2b is —OH, R3b is —F, R4b is —H, —OH or —O—C(=O)—C$_{1-14}$ alkyl, R1b is adenine and R2b is guanine. In some embodiments X1b is —SH, X2b is —OH, R3b is —F, R4b is —H or —OH, R1b is adenine and R2b is guanine. In some embodiments X1b is —SH, X2b is —OH, R3b is —F, R4b is —OH, R1b is adenine and R2b is guanine. In some embodiments X1b is —SH, X2b is —OH, R3b is —H, —OH or —O—C(=O)—C$_{1-14}$ alkyl, R4b is —F, R1b is adenine and R2b is guanine. In some embodiments X1b is —SH, X2b is —OH, R3b is —H or —OH, R4b is —F, R1b is adenine and R2b is guanine. In some embodiments X1b is —SH, X2b is —OH, R3b is —OH, R4b is —F, R1b is adenine and R2b is guanine. In some embodiments X1b is —SH, X2b is —OH, R3b and R4b are —F, R1b is adenine and R2b is guanine. In some embodiments X1b is —SH, X2b is —OH, R1b is guanine and R2b is adenine. In some embodiments X1b is —SH, X2b is —OH, R3b is —F, R4b is —H, —OH or —O—C(=O)—C$_{1-14}$ alkyl, R1b is guanine and R2b is adenine. In some embodiments X1b is —SH, X2b is —OH, R3b is —F, R4b is —H or —OH, R1b is guanine and R2b is adenine. In some embodiments X1b is —SH, X2b is —OH, R3b is —F, R4b is —OH, R1b is guanine and R2b is adenine. In some embodiments X1b is —SH, X2b is —OH, R3b is —H, —OH or —O—C(=O)—C$_{1-14}$ alkyl, R4b is —F, R1b is guanine and R2b is adenine. In some embodiments X1b is —SH, X2b is —OH, R3b is —H or —OH, R4b is —F, R1b is guanine and R2b is adenine. In some embodiments X1b is —SH, X2b is —OH, R3b is —OH, R4b is —F, R1b is guanine and R2b is adenine. In some embodiments X1b is —SH, X2b is —OH, R3b and R4b are —F, R1b is guanine and R2b is adenine.

In some embodiments of the third aspect and first embodiment thereof, X1b and X2b are —OH. In some embodiments X1b and X2b are —OH, R3b is —F and R4b is —H, —OH or —O—C(=O)—C$_{1-14}$alkyl. In some embodiments X1b and X2b are —OH, R3b is —F and R4b is —H or —OH. In some embodiments X1b and X2b are —OH, R3b is —F and R4b is —OH. In some embodiments X1b and X2b are —OH, R3b is —H, —OH or —O—C(=O)—C$_{1-14}$ alkyl and R4b is —F. In some embodiments X1b and X2b are —OH, R3b is —H or —OH and R4b is —F. In some embodiments X1b and X2b are —OH, R3b is —OH and R4b is —F. In some embodiments X1b and X2b are —OH, and R3b and R4b are —F. In some embodiments X1b and X2b are —OH, R1b is adenine and R2b is guanine. In some embodiments X1b and X2b are —OH, R3b is —F, R4b is —H, —OH or —O—C(=O)—C$_{1-14}$ alkyl, R1b is adenine and R2b is guanine. In some embodiments X1b and X2b are —OH, R3b is —F, R4b is —H or —OH, R1b is adenine and R2b is guanine. In some embodiments X1b and X2b are —OH, R3b is —F, R4b is —OH, R1b is adenine and R2b is guanine. In some embodiments X1b and X2b are —OH, R3b is —H, —OH or —O—C(=O)—C$_{1-14}$ alkyl, R4b is —F, R1b is adenine and R2b is guanine. In some embodiments X1b and X2b are —OH, R3b is —H or —OH, R4b is —F, R1b is adenine and R2b is guanine. In some embodiments X1b and X2b are —OH, R3b is —OH, R4b is —F, R1b is adenine and R2b is guanine. In some embodiments X1b and X2b are —OH, R3b and R4b are —F, R1b is adenine and R2b is guanine. In some embodiments X1b and X2b are —OH, R1b is guanine and R2b is adenine. In some embodiments X1b and X2b are —OH, R3b is —F, R4b is —H, —OH or —O—C(=O)—C$_{1-14}$ alkyl, R1b is guanine and R2b is adenine. In some embodiments X1b and X2b are —OH, R3b is —F, R4b is —H or —OH, R1b is guanine and R2b is adenine. In some embodiments X1b and X2b are —OH, R3b is —F, R4b is —OH, R1b is guanine and R2b is adenine. In some embodiments X1b and X2b are —OH, R3b is —H, —OH or —O—C(=O)—C$_{1-14}$ alkyl, R4b is —F, R1b is guanine and R2b is adenine. In some embodiments X1b and X2b are —OH, R3b is —H or —OH, R4b is —F, R1b is guanine and R2b is adenine. In some embodiments X1b and X2b are —OH, R3b is —OH, R4b is —F, R1b is guanine and R2b is adenine. In some embodiments X1b and X2b are —OH, R3b and R4b are —F, R1b is guanine and R2b is adenine.

In some embodiments of the third aspect and first embodiment thereof, R1b is adenine and R2b is guanine. In some embodiments R1b is adenine, R2b is guanine, R3b is —H, —OH or —O—C(=O)—C$_{1-14}$ alkyl and R4b is —F. In some embodiments R1b is adenine, R2b is guanine, R3b is —H or —OH and R4b is —F. In some embodiments R1b is adenine, R2b is guanine, R3b is —OH and R4b is —F. In some embodiments, R1b is adenine, R2b is guanine, R3b is —F and R4b is —H, —OH or —O—C(=O)—C$_{1-14}$ alkyl. In some embodiments, R1b is adenine, R2b is guanine, R3b is —F and R4b is —H or —OH. In some embodiments, R1b is adenine, R2b is guanine, R3b is —F and R4b is —OH. In some embodiments, R1b is adenine, R2b is guanine and R3b and R4b are —F.

In some embodiments of the third aspect and first embodiment thereof, R1b is guanine and R2b is adenine. In some embodiments R1b is guanine, R2b is adenine, R3b is —H, —OH or —O—C(=O)—C$_{1-14}$ alkyl and R4b is —F. In some embodiments R1b is guanine, R2b is adenine, R3b is —H or —OH and R4b is —F. In some embodiments R1b is guanine, R2b is adenine, R3b is —OH and R4b is —F. In some embodiments, R1b is guanine, R2b is adenine, R3b is —F and R4b is —H, —OH or —O—C(=O)—C$_{1-14}$ alkyl. In some embodiments, R1b is guanine, R2b is adenine, R3b is —F and R4b is —H or —OH. In some embodiments, R1b is guanine, R2b is adenine, R3b is —F and R4b is —OH. In some embodiments, R1b is guanine, R2b is adenine and R3b and R4b are —F.

In some embodiments of the third aspect and first embodiment thereof, R3b is —H, —OH or —O—C(=O)—C$_{1-14}$ alkyl and R4b is —F. In some embodiments, R3b is —H or —OH and R4b is —F. In some embodiments, R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In some embodiments of the third aspect and first embodiment thereof, the compound is selected from the group consisting of:

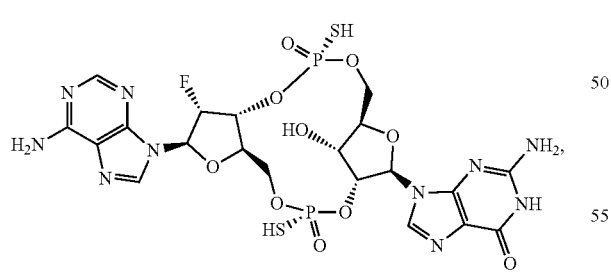

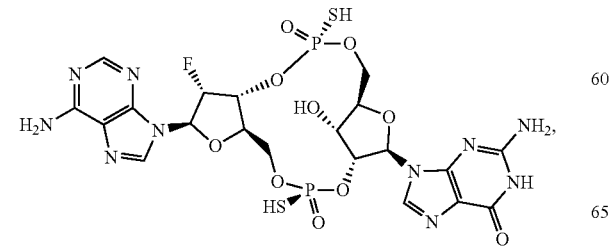

-continued

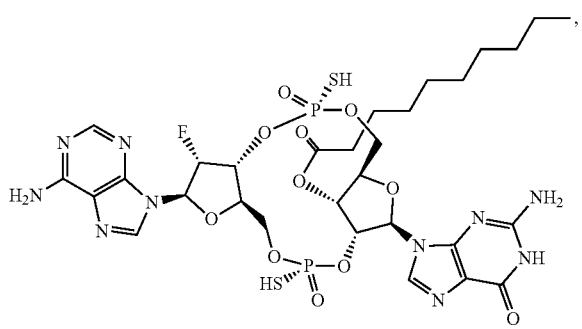

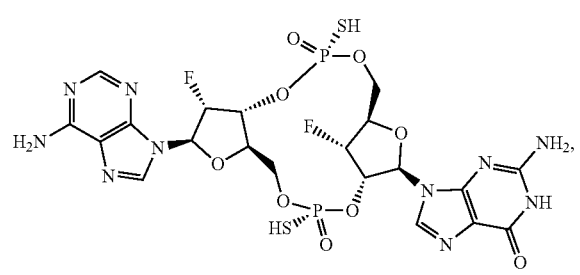

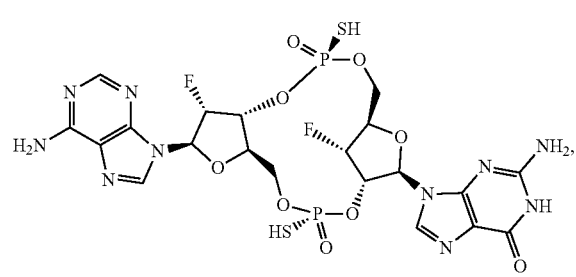

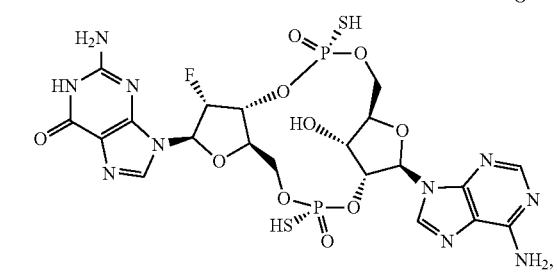

-continued

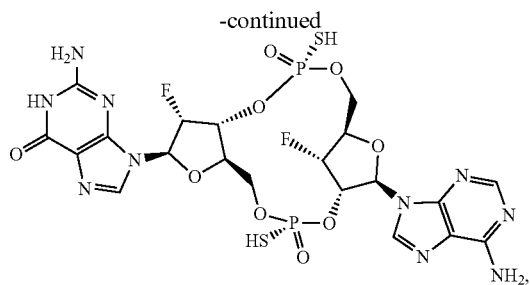

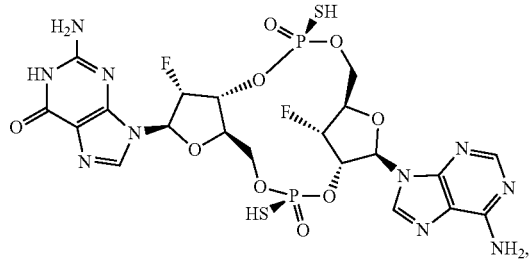

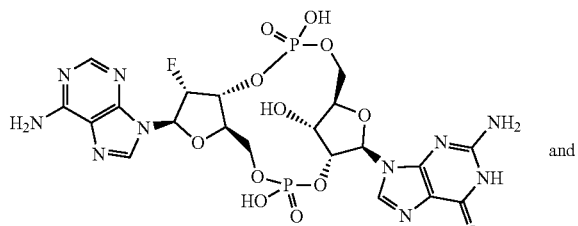

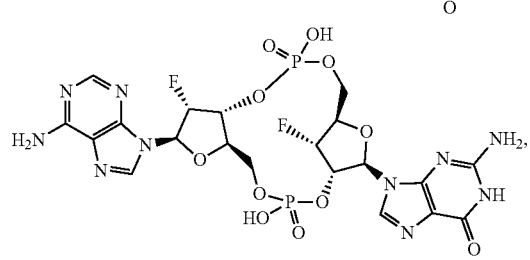

or a prodrug, pharmaceutically acceptable salt, pharmaceutically acceptable solvate or pharmaceutically acceptable hydrate thereof.

In a second embodiment of the third aspect, the Compound of Formula IB is a Compound of Formula IB-b:

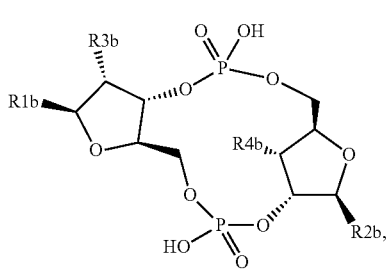

Formula IB-b or a prodrug, pharmaceutically acceptable salt, pharmaceutically acceptable solvate or pharmaceutically acceptable hydrate thereof, wherein R1b, R2b, R3b and R4b are as defined for Compounds of Formula IB.

In a third embodiment of the third aspect, the Compound of Formula IB is a Compound of Formula IB-c:

Formula IB-c or a prodrug, pharmaceutically acceptable salt, pharmaceutically acceptable solvate or pharmaceutically acceptable hydrate thereof, wherein R1b, R2b, R3b and R4b are as defined for Compounds of Formula IB.

In some embodiments of the third aspect and second or third embodiments thereof, R3b is —F and R4b is —H, —OH or —O—C(=O)—$C_{1-14}$ alkyl. In some embodiments R3b is —F and R4b is —H or —OH. In some embodiments R3b is —F and R4b is —OH. In some embodiments R3b is —H, —OH or —O—C(=O)—$C_{1-14}$ alkyl and R4b is —F. In some embodiments R3b is —H or —OH and R4b is —F. In some embodiments R3b is —OH and R4b is —F. In some embodiments R3b and R4b are —F. In some embodiments R3b is —F, R4b is —H, —OH or —O—C(=O)—$C_{1-14}$ alkyl, R1b is adenine and R2b is guanine. In some embodiments R3b is —F, R4b is —H or —OH, R1b is adenine and R2b is guanine. In some embodiments R3b is —F, R4b is —OH, R1b is adenine and R2b is guanine. In some embodiments R3b is —H, —OH or —O—C(=O)—$C_{1-14}$ alkyl, R4b is —F, R1b is adenine and R2b is guanine. In some embodiments R3b is —H or —OH, R4b is —F, R1b is adenine and R2b is guanine. In some embodiments R3b is —OH, R4b is —F, R1b is adenine and R2b is guanine. In some embodiments R3b and R4b are —F, R1b is adenine and R2b is guanine. In some embodiments R3b is —F, R4b is —H, —OH or —O—C(=O)—$C_{1-14}$ alkyl, R1b is guanine and R2b is adenine. In some embodiments R3b is —F, R4b is —H or —OH, R1b is guanine and R2b is adenine. In some embodiments R3b is —F, R4b is —OH, R1b is guanine and R2b is adenine. In some embodiments R3b is —H, —OH or —O—C(=O)—$C_{1-14}$ alkyl, R4b is —F, R1b is guanine and R2b is adenine. In some embodiments R3b is —H or —OH, R4b is —F, R1b is guanine and R2b is adenine. In some embodiments R3b is —OH, R4b is —F, R1b is guanine and R2b is adenine. In some embodiments R3b and R4b are —F, R1b is guanine and R2b is adenine.

In some embodiments of the third aspect and second or third embodiments thereof, R1b is adenine and R2b is guanine. In some embodiments R1b is guanine and R2b is adenine.

In some embodiments of the third aspect and first or second embodiment thereof, the compound is selected from the group consisting of:

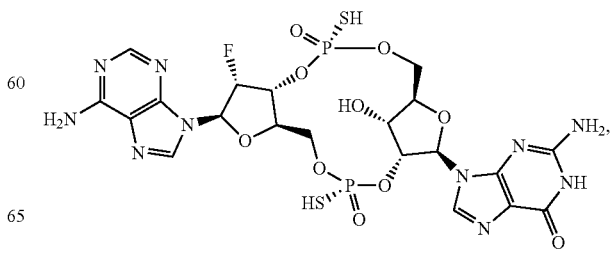

37

-continued

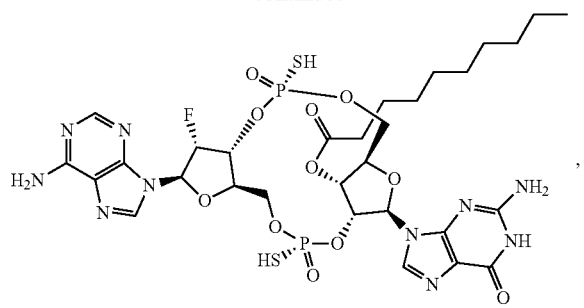

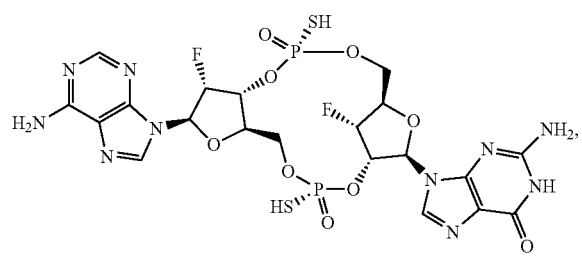

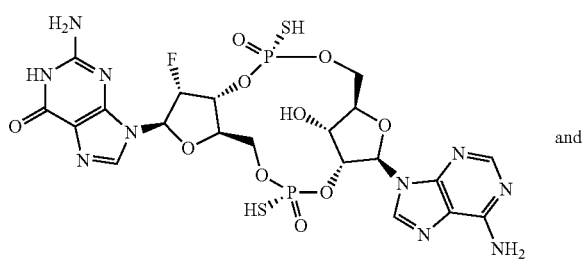

and

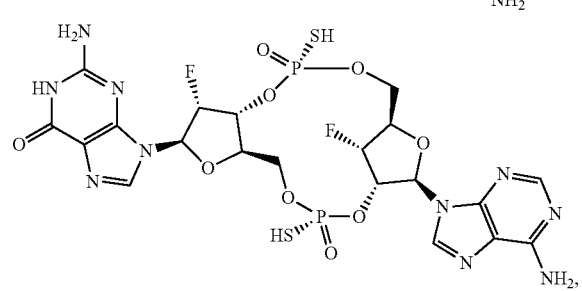

or a prodrug, pharmaceutically acceptable salt, pharmaceutically acceptable solvate or pharmaceutically acceptable hydrate thereof.

In some embodiments of the third aspect and first or third embodiment thereof, the compound is selected from the group consisting of:

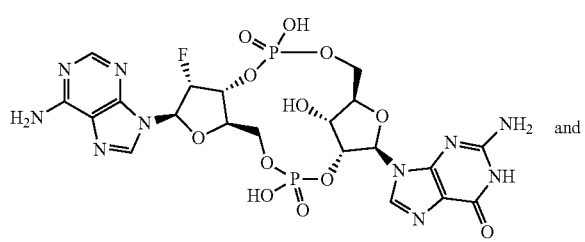

and

38

-continued

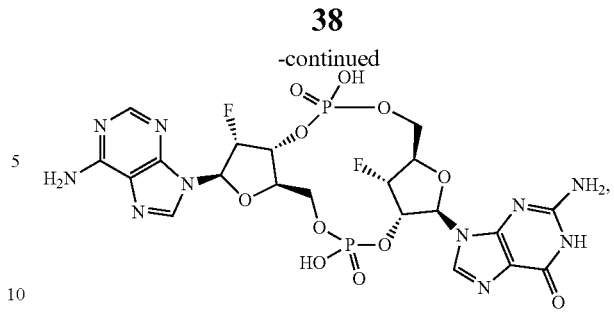

or a prodrug, pharmaceutically acceptable salt, pharmaceutically acceptable solvate or pharmaceutically acceptable hydrate thereof.

In a fourth embodiment of the third aspect, the Compound of Formula IB is a Compound of Formula IB-d:

Formula IB-d

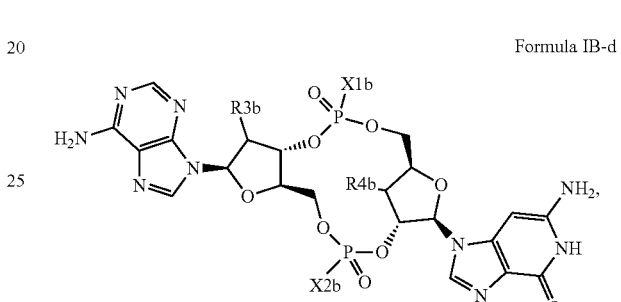

or a prodrug, pharmaceutically acceptable salt, pharmaceutically acceptable solvate or pharmaceutically acceptable hydrate thereof, wherein R3b, R4b, X1b and X2b are as defined for Compounds of Formula IB.

In a fifth embodiment of the third aspect, the Compound of Formula IB is a Compound of Formula IB-e:

Formula IB-e

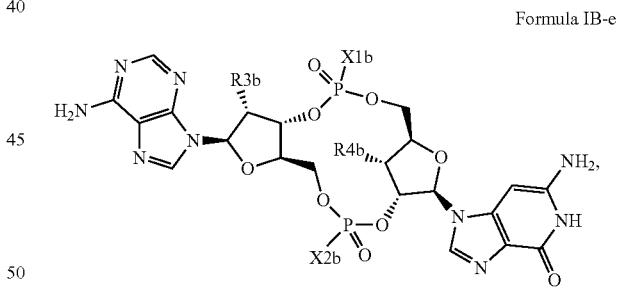

or a prodrug, pharmaceutically acceptable salt, pharmaceutically acceptable solvate or pharmaceutically acceptable hydrate thereof, wherein R3b, R4b, X1b and X2b are as defined for Compounds of Formula IB.

In some embodiments of the third aspect and fourth or fifth embodiments thereof, X1b and X2b are —SH. In some embodiments X1b and X2b are —SH, R3b is —F and R4b is —H, —OH or —O—C(═O)—$C_{1-14}$ alkyl. In some embodiments X1b and X2b are —SH, R3b is —F and R4b is —H or —OH. In some embodiments X1b and X2b are —SH, R3b is —F and R4b is —OH. In some embodiments X1b and X2b are —SH, R3b is —H, —OH or —O—C(═O)—$C_{1-14}$ alkyl and R4b is —F. In some embodiments X1b and X2b are —SH, R3b is —H or —OH and R4b is —F. In some embodiments X1b and X2b are —SH, R3b is —OH and R4b is —F. In some embodiments X1b and X2b are —SH, and R3b and R4b are —F.

In some embodiments of the third aspect and fourth or fifth embodiments thereof, X1b is —SH and X2b is —OH. In some embodiments X1b is —SH, X2b is —OH, R3b is —F and R4b is —H, —OH or —O—C(=O)—$C_{1-14}$ alkyl. In some embodiments X1b is —SH, X2b is —OH, R3b is —F and R4b is —H or —OH. In some embodiments X1b is —SH, X2b is —OH, R3b is —F and R4b is —OH. In some embodiments X1b is —SH, X2b is —OH, R3b is —H, —OH or —O—C(=O)—$C_{1-14}$alkyl and R4b is —F. In some embodiments X1b is —SH, X2b is —OH, R3b is —H or —OH and R4b is —F. In some embodiments X1b is —SH, X2b is —OH, R3b is —OH and R4b is —F. In some embodiments X1b is —SH, X2b is —OH, and R3b and R4b are —F.

In some embodiments of the third aspect and fourth or fifth embodiments thereof, X1b is —OH, X2b is —SH. In some embodiments X1b is —OH, X2b is —SH, R3b is —F and R4b is —H, —OH or —O—C(=O)—$C_{1-14}$alkyl. In some embodiments X1b is —OH, X2b is —SH, R3b is —F and R4b is —H or —OH. In some embodiments X1b is —OH, X2b is —SH, R3b is —F and R4b is —OH. In some embodiments X1b is —OH, X2b is —SH, R3b is —H, —OH or —O—C(=O)—$C_{1-14}$ alkyl and R4b is —F. In some embodiments X1b is —OH, X2b is —SH, R3b is —H or —OH and R4b is —F. In some embodiments X1b is —OH, X2b is —SH, R3b is —OH and R4b is —F. In some embodiments X1b is —OH, X2b is —SH, and R3b and R4b are —F.

In some embodiments of the third aspect and fourth or fifth embodiments thereof, X1b and X2b are —OH. In some embodiments X1b and X2b are —OH, R3b is —F and R4b is —H, —OH or —O—C(=O)—$C_{1-14}$ alkyl. In some embodiments X1b and X2b are —OH, R3b is —F and R4b is —H or —OH. In some embodiments X1b and X2b are —OH, R3b is —F and R4b is —OH. In some embodiments X1b and X2b are —OH, R3b is —H, —OH or —O—C(=O)—$C_{1-14}$ alkyl and R4b is —F. In some embodiments X1b and X2b are —OH, R3b is —H or —OH and R4b is —F. In some embodiments X1b and X2b are —OH, R3b is —OH and R4b is —F. In some embodiments X1b and X2b are —OH, and R3b and R4b are —F.

In some embodiments of the third aspect and fourth or fifth embodiments thereof, R3b is —F and R4b is —H, —OH or —O—C(=O)—$C_{1-14}$ alkyl. In some embodiments R3b is —F and R4b is —H or —OH. In some embodiments R3b is —F and R4b is —OH. In some embodiments R3b is —H, —OH or —O—C(=O)—$C_{1-14}$ alkyl and R4b is —F. In some embodiments R3b is —H or —OH and R4b is —F. In some embodiments R3b is —OH and R4b is —F. In some embodiments R3b and R4b are —F.

In some embodiments of the third aspect and first, fourth or fifth embodiments thereof, the compound is selected from the group consisting of:

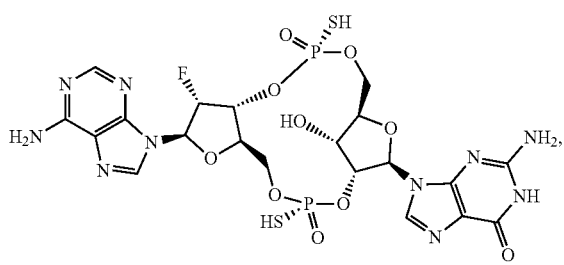

-continued

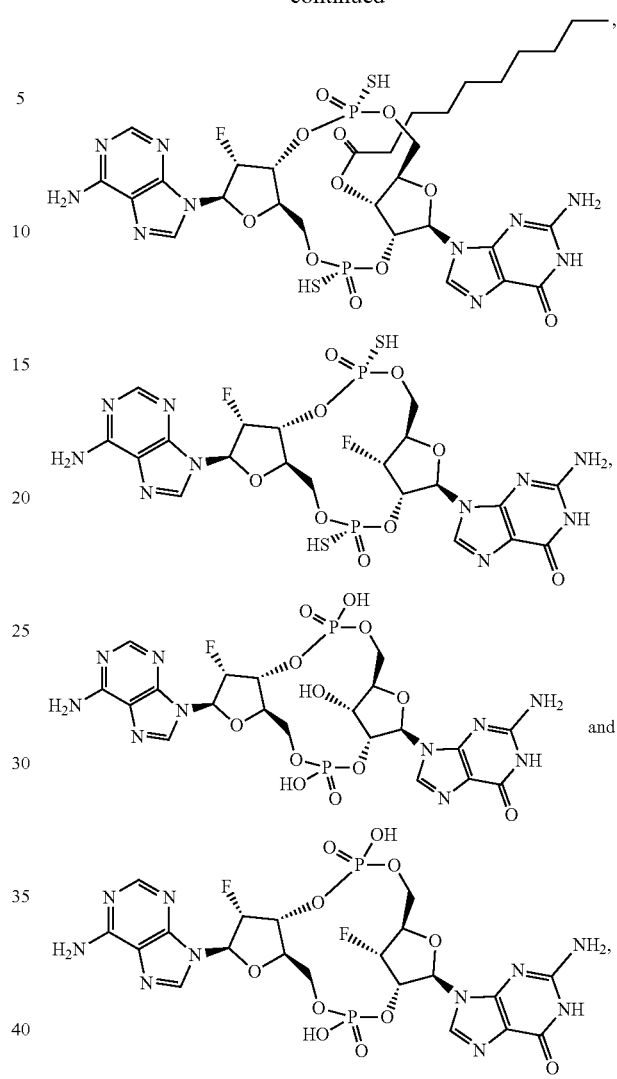

or a prodrug, pharmaceutically acceptable salt, pharmaceutically acceptable solvate or pharmaceutically acceptable hydrate thereof.

In a sixth embodiment of the third aspect, the Compound of Formula IB is a Compound of Formula IB-f:

Formula IB-f

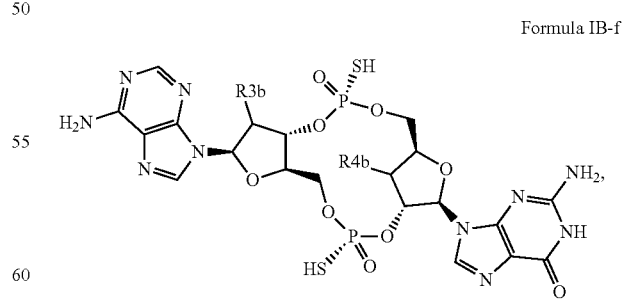

or a prodrug, pharmaceutically acceptable salt, pharmaceutically acceptable solvate or pharmaceutically acceptable hydrate thereof, wherein R3b and R4b are independently —H, —OH, —O—C(=O)—$C_{1-14}$ alkyl or —F, provided that at least one of R3b and R4b is —F. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In a seventh embodiment of the third aspect, the Compound of Formula IB is a Compound of Formula IB-g:

Formula IB-g

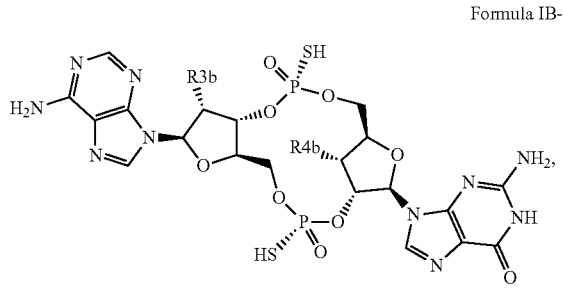

or a prodrug, pharmaceutically acceptable salt, pharmaceutically acceptable solvate or pharmaceutically acceptable hydrate thereof, wherein R3b and R4b are independently —H, —OH, —O—C(=O)—C$_{1-14}$ alkyl or —F, provided that at least one of R3b and R4b is —F. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In some embodiments of the third aspect and first, second, fourth, fifth, sixth or seventh embodiments thereof, the compound is selected from the group consisting of:

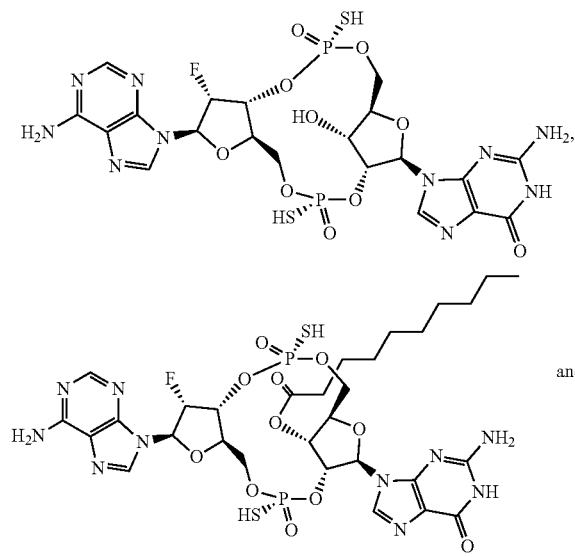

-continued

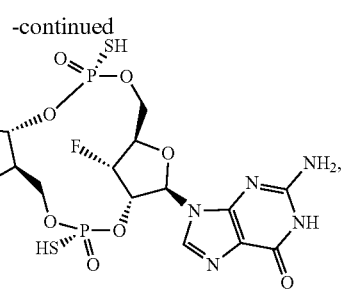

or a prodrug, pharmaceutically acceptable salt, pharmaceutically acceptable solvate or pharmaceutically acceptable hydrate thereof.

In an eighth embodiment of the third aspect, the Compound of Formula IB is a Compound of Formula IB-h:

Formula IB-h

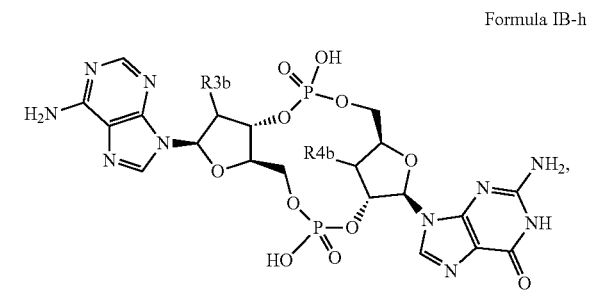

or a prodrug, pharmaceutically acceptable salt, pharmaceutically acceptable solvate or pharmaceutically acceptable hydrate thereof, wherein R3b and R4b are independently —H, —OH, —O—C(=O)—C$_{1-14}$ alkyl or —F, provided that at least one of R3b and R4b is —F. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In a ninth embodiment of the third aspect, the Compound of Formula IB is a Compound of Formula IB-i:

Formula IB-i

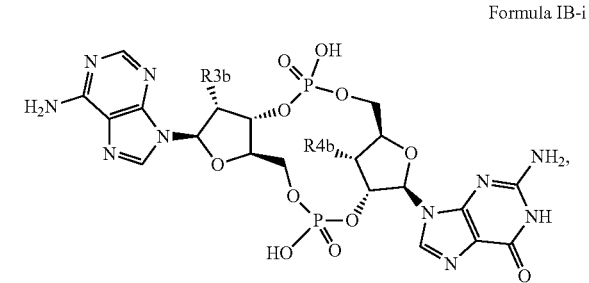

or a prodrug, pharmaceutically acceptable salt, pharmaceutically acceptable solvate or pharmaceutically acceptable hydrate thereof, wherein R3b and R4b are independently —H, —OH, —O—C(=O)—C$_{1-14}$ alkyl or —F, provided that at least one of R3b and R4b is —F. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In some embodiments of the third aspect and first, second, fourth, fifth, eighth or ninth embodiments thereof, the compound is selected from the group consisting of:

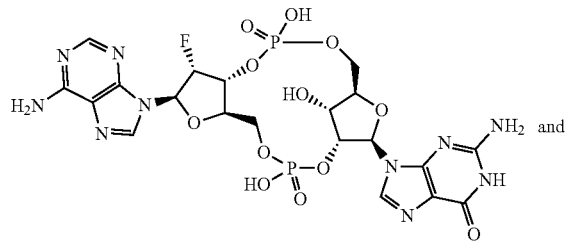

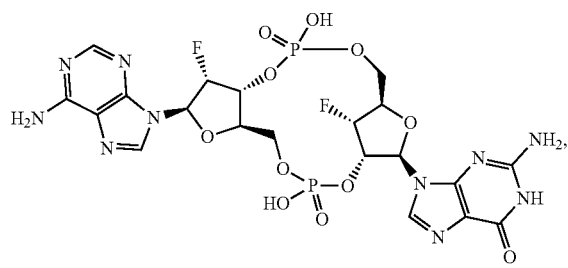

or a prodrug, pharmaceutically acceptable salt, pharmaceutically acceptable solvate or pharmaceutically acceptable hydrate thereof.

In a tenth embodiment of the third aspect, the Compound of Formula IB is a Compound of Formula IB-j:

Formula IB-j

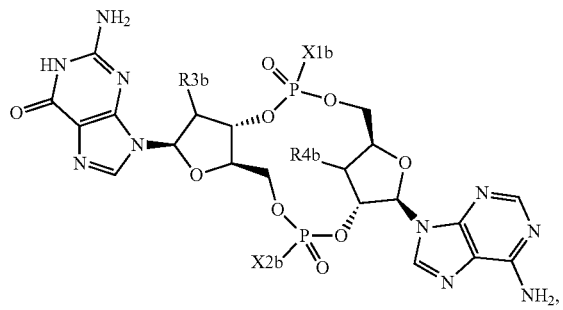

or a prodrug, pharmaceutically acceptable salt, pharmaceutically acceptable solvate or pharmaceutically acceptable hydrate thereof, wherein R3b, R4b, X1b and X2b are as defined for Compounds of Formula IB.

In an eleventh embodiment of the third aspect, the Compound of Formula IB is a Compound of Formula IB-k:

Formula IB-k

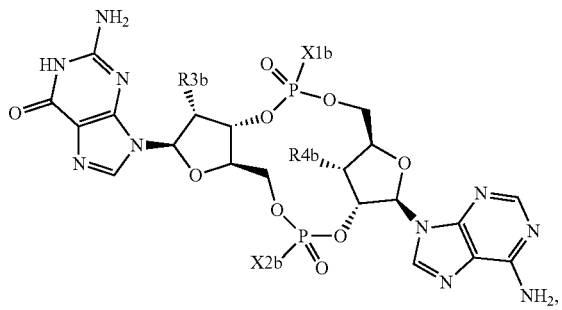

or a prodrug, pharmaceutically acceptable salt, pharmaceutically acceptable solvate or pharmaceutically acceptable hydrate thereof, wherein R3b, R4b, X1b and X2b are as defined for Compounds of Formula IB.

In some embodiments of the third aspect and tenth or eleventh embodiments thereof, X1b and X2b are —SH. In some embodiments X1b and X2b are —SH, R3b is —F and R4b is —H, —OH or —O—C(=O)—C$_{1-14}$ alkyl. In some embodiments X1b and X2b are —SH, R3b is —F and R4b is —H or —OH. In some embodiments X1b and X2b are —SH, R3b is —F and R4b is —OH. In some embodiments X1b and X2b are —SH, R3b is —H, —OH or —O—C(=O)—C$_{1-14}$ alkyl and R4b is —F. In some embodiments X1b and X2b are —SH, R3b is —H or —OH and R4b is —F. In some embodiments X1b and X2b are —SH, R3b is —OH and R4b is —F. In some embodiments X1b and X2b are —SH, and R3b and R4b are —F.

In some embodiments of the third aspect and tenth or eleventh embodiments thereof, X1b is —SH and X2b is —OH. In some embodiments X1b is —SH, X2b is —OH, R3b is —F and R4b is —H, —OH or —O—C(=O)—C$_{1-14}$ alkyl. In some embodiments X1b is —SH, X2b is —OH, R3b is —F and R4b is —H or —OH. In some embodiments X1b is —SH, X2b is —OH, R3b is —F and R4b is —OH. In some embodiments X1b is —SH, X2b is —OH, R3b is —H, —OH or —O—C(=O)—C$_{1-14}$alkyl and R4b is —F. In some embodiments X1b is —SH, X2b is —OH, R3b is —H or —OH and R4b is —F. In some embodiments X1b is —SH, X2b is —OH, R3b is —OH and R4b is —F. In some embodiments X1b is —SH, X2b is —OH, and R3b and R4b are —F.

In some embodiments of the third aspect and tenth or eleventh embodiments thereof, X1b is —OH, X2b is —SH. In some embodiments X1b is —OH, X2b is —SH, R3b is —F and R4b is —H, —OH or —O—C(=O)—C$_{1-14}$ alkyl. In some embodiments X1b is —OH, X2b is —SH, R3b is —F and R4b is —H or —OH. In some embodiments X1b is —OH, X2b is —SH, R3b is —F and R4b is —OH. In some embodiments X1b is —OH, X2b is —SH, R3b is —H, —OH or —O—C(=O)—C$_{1-14}$alkyl and R4b is —F. In some embodiments X1b is —OH, X2b is —SH, R3b is —H or —OH and R4b is —F. In some embodiments X1b is —OH, X2b is —SH, R3b is —OH and R4b is —F. In some embodiments X1b is —OH, X2b is —SH, and R3b and R4b are —F.

In some embodiments of the third aspect and tenth or eleventh embodiments thereof, X1b and X2b are —OH. In some embodiments X1b and X2b are —OH, R3b is —F and R4b is —H, —OH or —O—C(=O)—C$_{1-14}$alkyl. In some embodiments X1b and X2b are —OH, R3b is —F and R4b is —H or —OH. In some embodiments X1b and X2b are —OH, R3b is —F and R4b is —OH. In some embodiments X1b and X2b are —OH, R3b is —H, —OH or —O—C(=O)—C$_{1-14}$ alkyl and R4b is —F. In some embodiments X1b and X2b are —OH, R3b is —H or —OH and R4b is —F. In some embodiments X1b and X2b are —OH, R3b is —OH and R4b is —F. In some embodiments X1b and X2b are —OH, and R3b and R4b are —F.

In some embodiments of the third aspect and tenth or eleventh embodiments thereof, R3b is —F and R4b is —H, —OH or —O—C(=O)—C$_{1-14}$ alkyl. In some embodiments R3b is —F and R4b is —H or —OH. In some embodiments R3b is —F and R4b is —OH. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments R3b and R4b are —F.

In a twelfth embodiment of the third aspect, the Compound of Formula IB is a Compound of Formula IB-m:

Formula IB-m

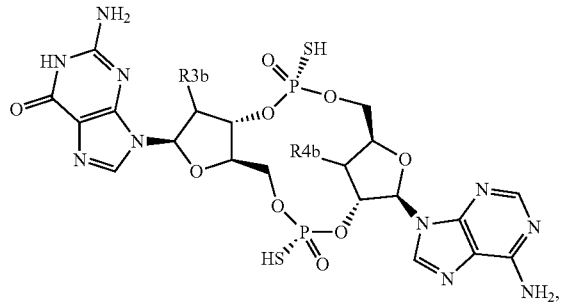

or a prodrug, pharmaceutically acceptable salt, pharmaceutically acceptable solvate or pharmaceutically acceptable hydrate thereof, wherein R3b and R4b are independently —H, —OH, —O—C(=O)—C$_{1-14}$ alkyl or —F, provided that at least one of R3b and R4b is —F. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In a thirteenth embodiment of the third aspect, the Compound of Formula IB is a Compound of Formula IB-n:

Formula IB-n

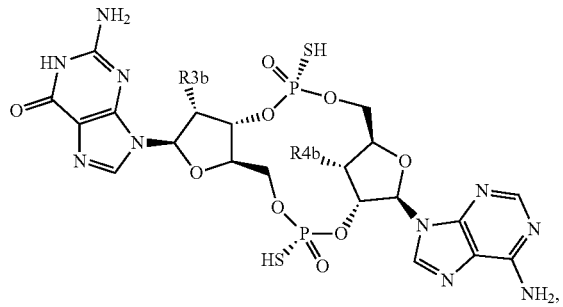

or a prodrug, pharmaceutically acceptable salt, pharmaceutically acceptable solvate or pharmaceutically acceptable hydrate thereof, wherein R3b and R4b are independently —H, —OH, —O—C(=O)—C$_{1-14}$ alkyl or —F, provided that at least one of R3b and R4b is —F. In some embodiments R3b is —H, —OH or —O—C(=O)—C$_{1-14}$ alkyl and R4b is —F. In some embodiments R3b is —H or —OH and R4b is —F. In some embodiments R3b is —OH and R4b is —F. In some embodiments, R3b is —F and R4b is —H, —OH or —O—C(=O)—C$_{1-14}$ alkyl. In some embodiments, R3b is —F and R4b is —H or —OH. In some embodiments, R3b is —F and R4b is —OH. In some embodiments, R3b and R4b are —F.

In some embodiments of the third aspect and any of the above embodiments thereof, when R3b or R4b is —O—C(=O)—C$_{1-14}$ alkyl, —O—C(=O)—C$_{1-14}$ alkyl is —O—C(=O)—C$_{3-14}$ alkyl, —O—C(=O)—C$_{5-13}$ alkyl, —O—C(=O)—C$_{5-11}$ alkyl, or —O—C(=O)—C$_9$ alkyl, preferably wherein the alkyl chain is linear. In a preferred embodiment, —O—C(=O)—C$_{1-14}$ alkyl is —O—C(=O)—(CH$_2$)$_8$—CH$_3$.

In one embodiment of the third aspect and first, second, tenth, eleventh, twelfth or thirteenth embodiments thereof, the compound is selected from the group consisting of:

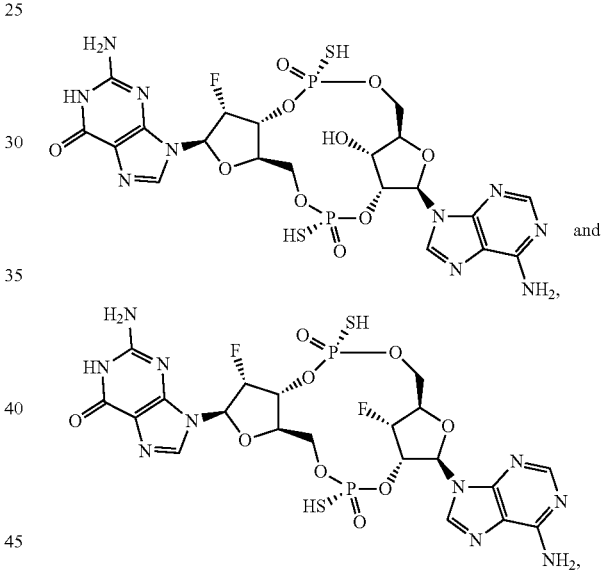

and

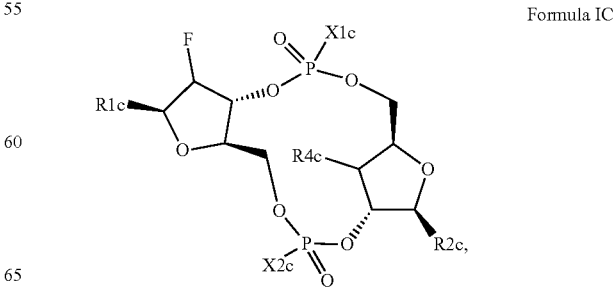

or a prodrug, pharmaceutically acceptable salt, pharmaceutically acceptable solvate or pharmaceutically acceptable hydrate thereof.

In a fourth aspect, the present invention provides a mono-F-ML-CDN Compound of Formula IC:

Formula IC or a prodrug, pharmaceutically acceptable salt, pharmaceutically acceptable solvate or pharmaceutically acceptable hydrate thereof,
wherein:
R1c and R2c are independently a guanine or adenine bound to the structure via the N9 position, provided that R1c and R2c are not both guanine;
R4c is —H, —OH or —O—C(=O)—$C_{1-14}$ alkyl; and
X1c and X2c are independently —OH or —SH.

As described hereinafter, in certain embodiments, X1c and X2c are each —SH, and one or both of R3c and R4c are —F; and in certain of these embodiments, if only one of R3c and R4c is F, the other of R3c and R4c is —O—C(=O)—$C_{1-14}$ alkyl, and preferably —O—C(=O)—$C_{6-12}$ alkyl. In certain of these embodiments, R3c is F and R4c is —O—C(=O)—$C_{1-14}$ alkyl, and preferably —O—C(=O)—$C_{6-12}$. Additionally, when X1c or X2c are —SH, a chiral center is introduced into the molecule at the thiophosphate. In certain of these embodiments, the compounds are R,R diastereoisomers.

In a first embodiment of the fourth aspect, the Compound of Formula IC is a Compound of Formula IC-a:

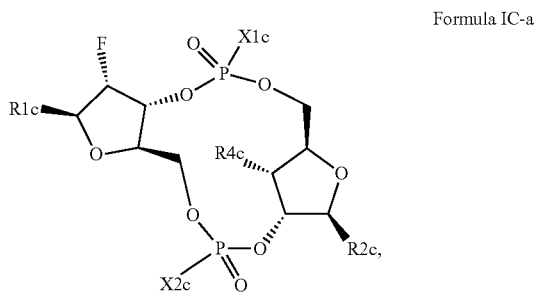

Formula IC-a or a prodrug, pharmaceutically acceptable salt, pharmaceutically acceptable solvate or pharmaceutically acceptable hydrate thereof, wherein R1c, R2c, R4c, X1c and X2c are as defined for Compounds of Formula IC.

In some embodiments of the fourth aspect and first embodiment thereof, X1c and X2c are —SH. In some embodiments X1c and X2c are —SH, R1c is adenine and R2c is guanine. In some embodiments X1c and X2c are —SH, R1c is guanine and R2c is adenine. In some embodiments X1c and X2c are —SH, and R1c and R2c are adenine. In some embodiments X1c and X2c are —SH, R1c is adenine, R2c is guanine and R4c is —H or —OH. In some embodiments X1c and X2c are —SH, R1c is adenine, R2c is guanine and R4c is —OH or —O—C(=O)—$C_{1-14}$alkyl. In some embodiments X1c and X2c are —SH, R1c is adenine, R2c is guanine and R4c is —OH. In some embodiments X1c and X2c are —SH, R1c is adenine, R2c is guanine and R4c is —H. In some embodiments X1c and X2c are —SH, R1c is adenine, R2c is guanine and R4c is —O—C(=O)—$C_{1-14}$ alkyl. In some embodiments X1c and X2c are —SH, R1c is guanine, R2c is adenine and R4c is —H or —OH. In some embodiments X1c and X2c are —SH, R1c is guanine, R2c is adenine and R4c is —OH or —O—C(=O)—$C_{1-14}$ alkyl. In some embodiments X1c and X2c are —SH, R1c is guanine, R2c is adenine and R4c is —OH. In some embodiments X1c and X2c are —SH, R1c is guanine, R2c is adenine and R4c is —H. In some embodiments X1c and X2c are —SH, R1c is guanine, R2c is adenine and R4c is —O—C(=O)—$C_{1-14}$ alkyl. In some embodiments X1c and X2c are —SH, R1c and R2c are adenine and R4c is —H or —OH. In some embodiments X1c and X2c are —SH, R1c and R2c are adenine and R4c is —OH or —O—C(=O)—$C_{1-14}$ alkyl. In some embodiments X1c and X2c are —SH, R1c and R2c are adenine and R4c is —OH. In some embodiments X1c and X2c are —SH, R1c and R2c are adenine and R4c is —H. In some embodiments X1c and X2c are —SH, R1c and R2c are adenine and R4c is —O—C(=O)—$C_{1-14}$ alkyl.

In some embodiments of the fourth aspect and first embodiment thereof, X1c is —SH and X2c is —OH. In some embodiments X1c is —SH, X2c is —OH, R1c is adenine and R2c is guanine. In some embodiments X1c is —SH, X2c is —OH, R1c is guanine and R2c is adenine. In some embodiments X1c is —SH, X2c is —OH and R1c and R2c are adenine. In some embodiments X1c is —SH, X2c is —OH, R1c is adenine, R2c is guanine and R4c is —H or —OH. In some embodiments X1c is —SH, X2c is —OH, R1c is adenine, R2c is guanine and R4c is —OH or —O—C(=O)—$C_{1-14}$ alkyl. In some embodiments X1c is —SH, X2c is —OH, R1c is adenine, R2c is guanine and R4c is —OH. In some embodiments X1c is —SH, X2c is —OH, R1c is adenine, R2c is guanine and R4c is —H. In some embodiments X1c is —SH, X2c is —OH, R1c is adenine, R2c is guanine and R4c is —O—C(=O)—$C_{1-14}$ alkyl. In some embodiments X1c is —SH, X2c is —OH, R1c is guanine, R2c is adenine and R4c is —H or —OH. In some embodiments X1c is —SH, X2c is —OH, R1c is guanine, R2c is adenine and R4c is —OH or —O—C(=O)—$C_{1-14}$ alkyl. In some embodiments X1c is —SH, X2c is —OH, R1c is guanine, R2c is adenine and R4c is —OH. In some embodiments X1c is —SH, X2c is —OH, R1c is guanine, R2c is adenine and R4c is —H. In some embodiments X1c is —SH, X2c is —OH, R1c is guanine, R2c is adenine and R4c is —O—C(=O)—$C_{1-14}$ alkyl. In some embodiments X1c is —SH, X2c is —OH, R1c and R2c are adenine and R4c is —H or —OH. In some embodiments X1c is —SH, X2c is —OH, R1c and R2c are adenine and R4c is —OH or —O—C(=O)—$C_{1-14}$ alkyl. In some embodiments X1c is —SH, X2c is —OH, R1c and R2c are adenine and R4c is —OH. In some embodiments X1c is —SH, X2c is —OH, R1c and R2c are adenine and R4c is —H. In some embodiments X1c is —SH, X2c is —OH, R1c and R2c are adenine and R4c is —O—C(=O)—$C_{1-14}$ alkyl.

In some embodiments of the fourth aspect and first embodiment thereof, X1c is —OH and X2c is —SH. In some embodiments X1c is —OH, X2c is —SH, R1c is adenine and R2c is guanine. In some embodiments X1c is —OH, X2c is —SH, R1c is guanine and R2c is adenine. In some embodiments X1c is —OH, X2c is —SH and R1c and R2c are adenine. In some embodiments X1c is —OH, X2c is —SH, R1c is adenine, R2c is guanine and R4c is —H or —OH. In some embodiments X1c is —OH, X2c is —SH, R1c is adenine, R2c is guanine and R4c is —OH or —O—C(=O)—$C_{1-14}$ alkyl. In some embodiments X1c is —OH, X2c is —SH, R1c is adenine, R2c is guanine and R4c is —OH. In some embodiments X1c is —OH, X2c is —SH, R1c is adenine, R2c is guanine and R4c is —H. In some embodiments X1c is —OH, X2c is —SH, R1c is adenine, R2c is guanine and R4c is —O—C(=O)—$C_{1-14}$ alkyl. In some embodiments X1c is —OH, X2c is —SH, R1c is guanine, R2c is adenine and R4c is —H or —OH. In some embodiments X1c is —OH, X2c is —SH, R1c is guanine, R2c is adenine and R4c is —OH or —O—C(=O)—$C_{1-14}$ alkyl. In some embodiments X1c is —OH, X2c is —SH, R1c is guanine, R2c is adenine and R4c is —OH. In some embodiments X1c is —OH, X2c is —SH, R1c is guanine, R2c is adenine and R4c is —H. In some embodiments X1c is —OH, X2c is —SH, R1c is guanine, R2c is adenine and R4c is —O—C(=O)—C$_{1-14}$ alkyl. In some embodiments X1c is —OH, X2c is —SH, R1c and R2c are adenine and R4c is —H or —OH. In some embodiments X1c is —OH, X2c is —SH, R1c and R2c are adenine and R4c is —OH or —O—C(=O)—C$_{1-14}$ alkyl. In some embodiments X1c is —OH, X2c is —SH, R1c and R2c are adenine and R4c is —OH. In some embodiments X1c is —OH, X2c is —SH, R1c and R2c are adenine and R4c is —H. In some embodiments X1c is —OH, X2c is —SH, R1c and R2c are adenine and R4c is —O—C(=O)—C$_{1-14}$ alkyl.

In some embodiments of the fourth aspect and first embodiment thereof, X1c and X2c are —OH. In some embodiments X1c and X2c are —OH, R1c is adenine and R2c is guanine. In some embodiments X1c and X2c are —OH, R1c is guanine and R2c is adenine. In some embodiments X1c and X2c are —OH and R1c and R2c are adenine. In some embodiments X1c and X2c are —OH, R1c is adenine, R2c is guanine and R4c is —H or —OH. In some embodiments X1c and X2c are —OH, R1c is adenine, R2c is guanine and R4c is —OH or —O—C(=O)—C$_{1-14}$ alkyl. In some embodiments X1c and X2c are —OH, R1c is adenine, R2c is guanine and R4c is —OH. In some embodiments X1c and X2c are —OH, R1c is adenine, R2c is guanine and R4c is —H. In some embodiments X1c and X2c are —OH, R1c is adenine, R2c is guanine and R4c is —O—C(=O)—C$_{1-14}$ alkyl. In some embodiments X1c and X2c are —OH, R1c is guanine, R2c is adenine and R4c is —H or —OH. In some embodiments X1c and X2c are —OH, R1c is guanine, R2c is adenine and R4c is —OH or —O—C(=O)—C$_{1-14}$ alkyl. In some embodiments X1c and X2c are —OH, R1c is guanine, R2c is adenine and R4c is —OH. In some embodiments X1c and X2c are —OH, R1c is guanine, R2c is adenine and R4c is —H. In some embodiments X1c and X2c are —OH, R1c is guanine, R2c is adenine and R4c is —O—C(=O)—C$_{1-14}$ alkyl. In some embodiments X1c and X2c are —OH, R1c and R2c are adenine and R4c is —H or —OH. In some embodiments X1c and X2c are —OH, R1c and R2c are adenine and R4c is —OH or —O—C(=O)—C$_{1-14}$ alkyl. In some embodiments X1c and X2c are —OH, R1c and R2c are adenine and R4c is —OH. In some embodiments X1c and X2c are —OH, R1c and R2c are adenine and R4c is —H. In some embodiments X1c and X2c are —OH, R1c and R2c are adenine and R4c is —O—C(=O)—C$_{1-14}$ alkyl.

In some embodiments of the fourth aspect and first embodiment thereof, R1c is adenine and R2c is guanine. In some embodiments, R1c is guanine and R2c is adenine. In some embodiments, R1c and R2c are adenine.

In some embodiments of the fourth aspect and first embodiment thereof, the compound is selected from the group consisting of:

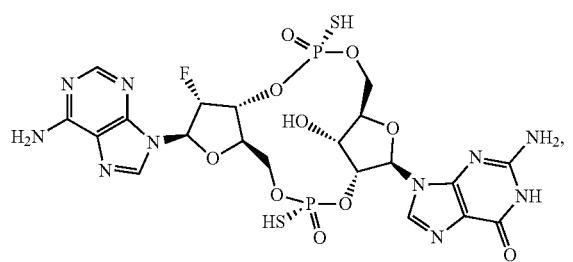

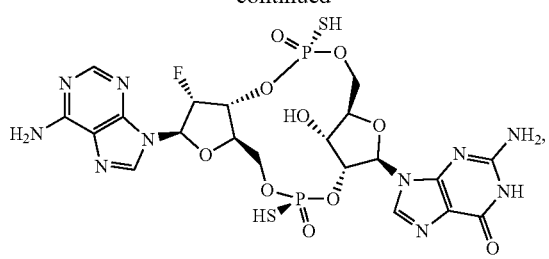

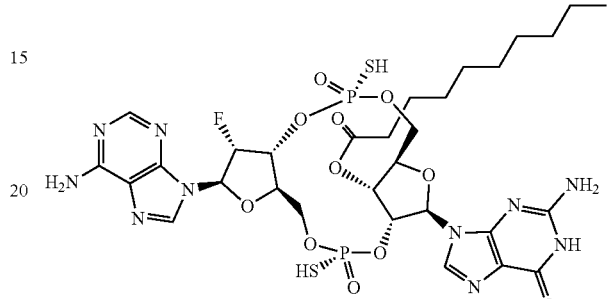

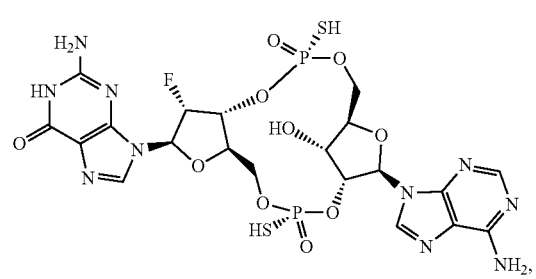

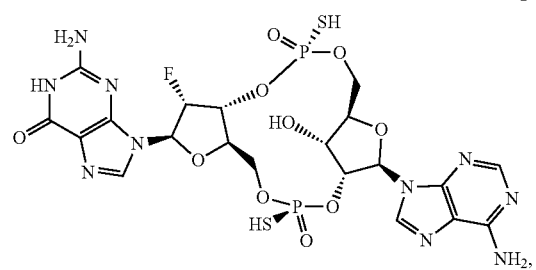

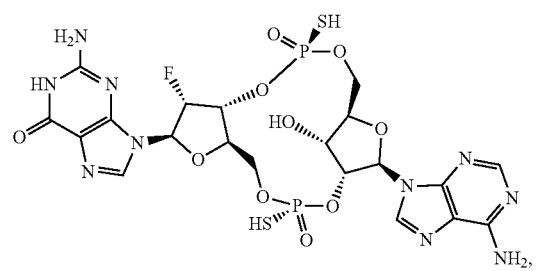

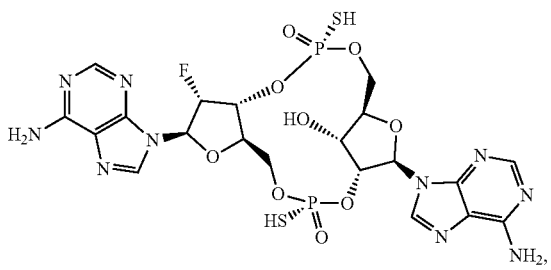

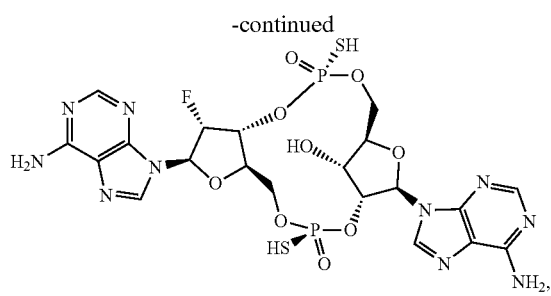

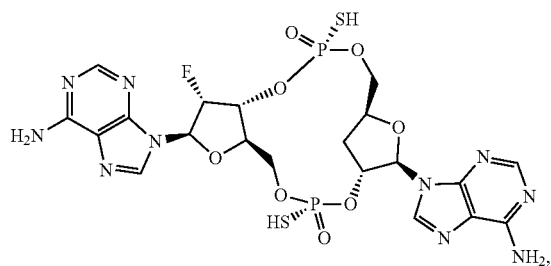

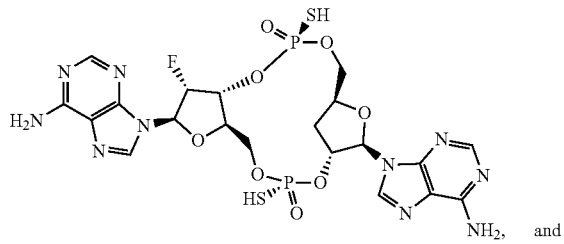

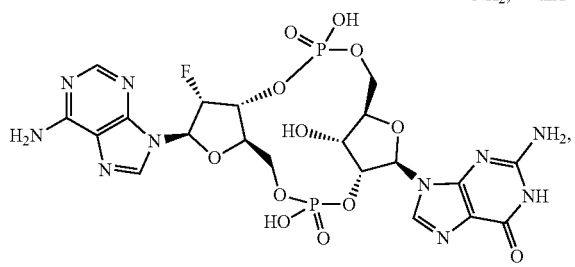

or a prodrug, pharmaceutically acceptable salt, pharmaceutically acceptable solvate or pharmaceutically acceptable hydrate thereof.

In a second embodiment of the fourth aspect, the Compound of Formula IC is a Compound of Formula IC-b:

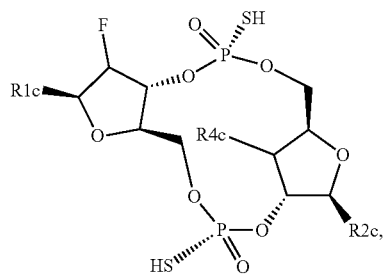

Formula IC-b or a prodrug, pharmaceutically acceptable salt, pharmaceutically acceptable solvate or pharmaceutically acceptable hydrate thereof, wherein R1c, R2c and R4c are as defined for Compounds of Formula IC.

In a third embodiment of the fourth aspect, the Compound of Formula IC is a Compound of Formula IC-c:

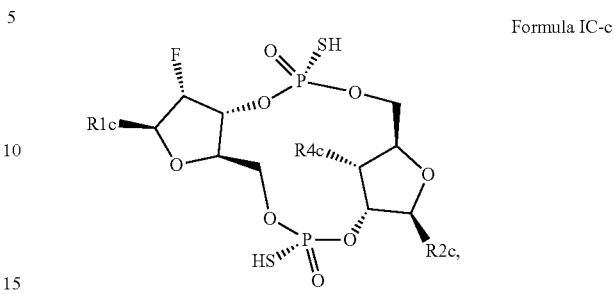

Formula IC-c or a prodrug, pharmaceutically acceptable salt, pharmaceutically acceptable solvate or pharmaceutically acceptable hydrate thereof, wherein R1c, R2c and R4c are as defined for Compounds of Formula IC.

In some embodiments of the fourth aspect and second or third embodiment thereof, R1c is adenine and R2c is guanine. In some embodiments R1c is guanine and R2c is adenine. In some embodiments R1c and R2c are adenine. In some embodiments R1c is adenine, R2c is guanine and R4c is —H or —OH. In some embodiments R1c is adenine, R2c is guanine and R4c is —OH or —O—C(=O)—$C_{1-14}$ alkyl. In some embodiments R1c is adenine, R2c is guanine and R4c is —OH. In some embodiments R1c is adenine, R2c is guanine and R4c is —H. In some embodiments R1c is adenine, R2c is guanine and R4c is —O—C(=O)—$C_{1-14}$alkyl. In some embodiments R1c is guanine, R2c is adenine and R4c is —H or —OH. In some embodiments R1c is guanine, R2c is adenine and R4c is —OH or —O—C(=O)—$C_{1-14}$ alkyl. In some embodiments R1c is guanine, R2c is adenine and R4c is —OH. In some embodiments R1c is guanine, R2c is adenine and R4c is —H. In some embodiments R1c is guanine, R2c is adenine and R4c is —O—C(=O)—$C_{1-14}$ alkyl. In some embodiments R1c and R2c are adenine and R4c is —H or —OH. In some embodiments R1c and R2c are adenine and R4c is —OH or —O—C(=O)—$C_{1-14}$ alkyl. In some embodiments R1c and R2c are adenine and R4c is —OH. In some embodiments R1c and R2c are adenine and R4c is —H. In some embodiments R1c and R2c are adenine and R4c is —O—C(=O)—$C_{1-14}$ alkyl.

In some embodiments of the fourth aspect and first, second or third embodiments thereof, the compound is selected from the group consisting of:

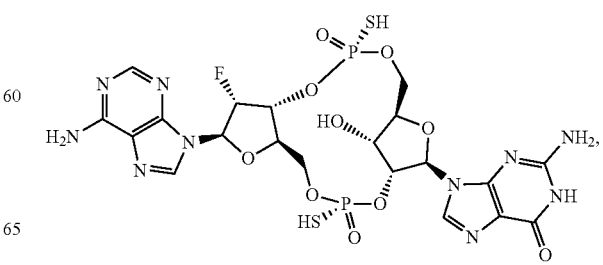

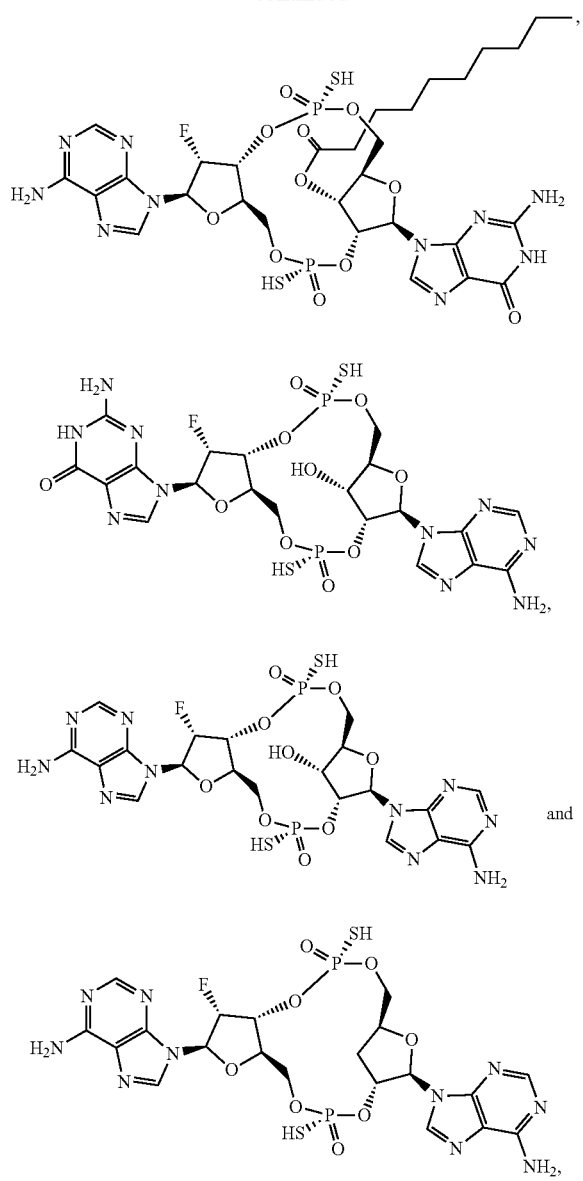
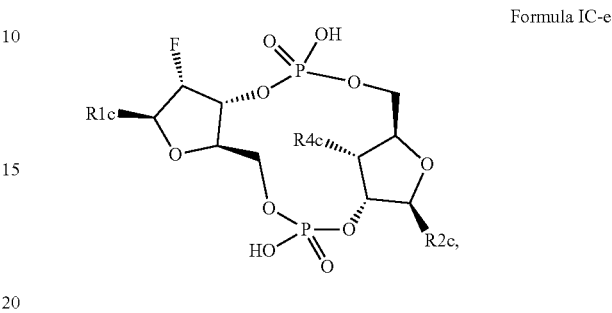

or a prodrug, pharmaceutically acceptable salt, pharmaceutically acceptable solvate or pharmaceutically acceptable hydrate thereof.

In a fourth embodiment of the fourth aspect, the Compound of Formula IC is a Compound of Formula IC-d:

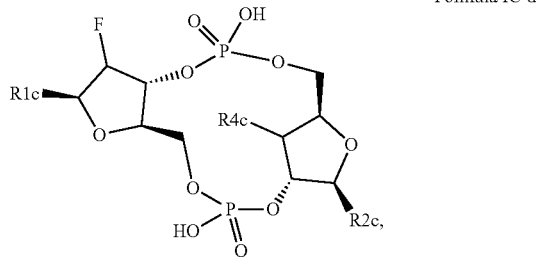

Formula IC-d or a prodrug, pharmaceutically acceptable salt, pharmaceutically acceptable solvate or pharmaceutically acceptable hydrate thereof, wherein R1c, R2c and R4c are as defined for Compounds of Formula IC.

In a fifth embodiment of the fourth aspect, the Compound of Formula IC is a Compound of Formula IC-e:

Formula IC-e or a prodrug, pharmaceutically acceptable salt, pharmaceutically acceptable solvate or pharmaceutically acceptable hydrate thereof, wherein R1c, R2c and R4c are as defined for Compounds of Formula IC.

In some embodiments of the fourth aspect and fourth or fifth embodiment thereof, R1c is adenine and R2c is guanine. In some embodiments R1c is guanine and R2c is adenine. In some embodiments R1c and R2c are adenine. In some embodiments R1c is adenine, R2c is guanine and R4c is —H or —OH. In some embodiments R1c is adenine, R2c is guanine and R4c is —OH or —O—C(=O)—$C_{1-14}$ alkyl. In some embodiments R1c is adenine, R2c is guanine and R4c is —OH. In some embodiments R1c is adenine, R2c is guanine and R4c is —H. In some embodiments R1c is adenine, R2c is guanine and R4c is —O—C(=O)—$C_{1-14}$ alkyl. In some embodiments R1c is guanine, R2c is adenine and R4c is —H or —OH. In some embodiments R1c is guanine, R2c is adenine and R4c is —OH or —O—C(=O)—$C_{1-14}$ alkyl. In some embodiments R1c is guanine, R2c is adenine and R4c is —OH. In some embodiments R1c is guanine, R2c is adenine and R4c is —H. In some embodiments R1c is guanine, R2c is adenine and R4c is —O—C(=O)—$C_{1-14}$ alkyl. In some embodiments R1c and R2c are adenine and R4c is —H or —OH. In some embodiments R1c and R2c are adenine and R4c is —OH or —O—C(=O)—$C_{1-14}$ alkyl. In some embodiments R1c and R2c are adenine and R4c is —OH. In some embodiments R1c and R2c are adenine and R4c is —H. In some embodiments R1c and R2c are adenine and R4c is —O—C(=O)—$C_{1-14}$ alkyl.

In some embodiments of the fourth aspect and any of the above embodiments thereof, when R3c or R4c is —O—C(=O)—$C_{1-14}$ alkyl, —O—C(=O)—$C_{1-14}$ alkyl is —O—C(=O)—$C_{3-14}$ alkyl, —O—C(=O)—$C_{5-13}$ alkyl, —O—C(=O)—$C_{5-11}$ alkyl, or —O—C(=O)—$C_9$ alkyl, preferably wherein the alkyl chain is linear. In a preferred embodiment, —O—C(=O)—$C_{1-14}$ alkyl is —O—C(=O)—$(CH_2)_8$—$CH_3$.

In some embodiments of the fourth aspect and first, fourth and fifth embodiments thereof, the compound is

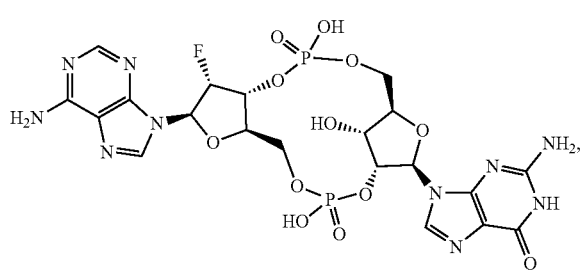 [SMILES: Nc1nc2c(ncn2[C@@H]2O[C@@H]3COP(=O)(O)O[C@H]4[C@@H](F)[C@H](n5cnc6c(N)ncnc65)O[C@@H]4COP(=O)(O)O[C@@H]2[C@@H]3O)c(=O)[nH]1]

or a prodrug, pharmaceutically acceptable salt, pharmaceutically acceptable solvate or pharmaceutically acceptable hydrate thereof.

In a fifth aspect, the present invention provides a mono-F-ML-CDN Compound of Formula ID:

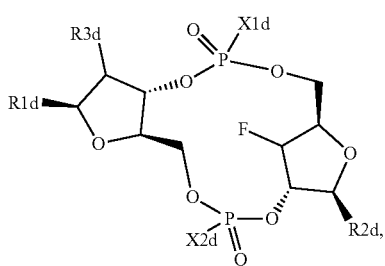

Formula ID or a prodrug, pharmaceutically acceptable salt, pharmaceutically acceptable solvate or pharmaceutically acceptable hydrate thereof,
wherein:
R1d and R2d are independently a guanine or adenine bound to the structure via the N9 position, provided that R1d and R2d are not both guanine;
R3d is —H, —OH or —O—C(=O)—$C_{1-14}$ alkyl; and
X1d and X2d are independently —OH or —SH.

As described hereinafter, in certain embodiments, X1d and X2d are each —SH, and one or both of R3d and R4d are —F; and in certain of these embodiments, if only one of R3d and R4d is F, the other of R3d and R4d is —O—C(=O)—$C_{1-14}$ alkyl, and preferably —O—C(=O)—$C_{6-12}$ alkyl. In certain of these embodiments, R3d is F and R4d is —O—C(=O)—$C_{1-14}$ alkyl, and preferably —O—C(=O)—$C_{6-12}$. Additionally, when X1d or X2d are —SH, a chiral center is introduced into the molecule at the thiophosphate. In certain of these embodiments, the compounds are R,R diastereoisomers.

In a first embodiment of the fifth aspect, the Compound of Formula ID is a Compound of Formula ID-a:

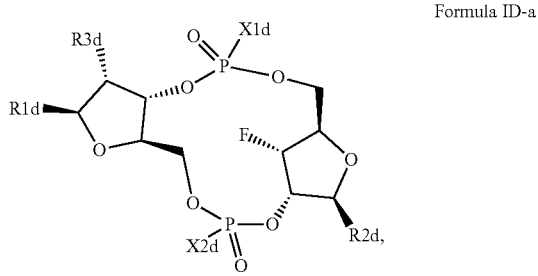

Formula ID-a or a prodrug, pharmaceutically acceptable salt, pharmaceutically acceptable solvate or pharmaceutically acceptable hydrate thereof, wherein R1d, R2d, R3d, X1d and X2d are as defined for Compounds of Formula ID.

In some embodiments of the fifth aspect and first embodiment thereof, X1d and X2d are —SH. In some embodiments X1d and X2d are —SH, R1d is adenine and R2d is guanine. In some embodiments X1d and X2d are —SH, R1d is guanine and R2d is adenine. In some embodiments X1d and X2d are —SH, and R1d and R2d are adenine. In some embodiments X1d and X2d are —SH, R1d is adenine, R2d is guanine and R3d is —H or —OH. In some embodiments X1d and X2d are —SH, R1d is adenine, R2d is guanine and R3d is —OH or —O—C(=O)—$C_{1-14}$ alkyl. In some embodiments X1d and X2d are —SH, R1d is adenine, R2d is guanine and R3d is —OH. In some embodiments X1d and X2d are —SH, R1d is adenine, R2d is guanine and R3d is —H. In some embodiments X1d and X2d are —SH, R1d is adenine, R2d is guanine and R3d is —O—C(=O)—$C_{1-14}$ alkyl. In some embodiments X1d and X2d are —SH, R1d is guanine, R2d is adenine and R3d is —H or —OH. In some embodiments X1d and X2d are —SH, R1d is guanine, R2d is adenine and R3d is —OH or —O—C(=O)—$C_{1-14}$ alkyl. In some embodiments X1d and X2d are —SH, R1d is guanine, R2d is adenine and R3d is —OH. In some embodiments X1d and X2d are —SH, R1d is guanine, R2d is adenine and R3d is —H. In some embodiments X1d and X2d are —SH, R1d is guanine, R2d is adenine and R3d is —O—C(=O)—$C_{1-14}$ alkyl. In some embodiments X1d and X2d are —SH, R1d and R2d are adenine and R3d is —H or —OH. In some embodiments X1d and X2d are —SH, R1d and R2d are adenine and R3d is —OH or —O—C(=O)—$C_{1-14}$ alkyl. In some embodiments X1d and X2d are —SH, R1d and R2d are adenine and R3d is —OH. In some embodiments X1d and X2d are —SH, R1d and R2d are adenine and R3d is —H. In some embodiments X1d and X2d are —SH, R1d and R2d are adenine and R3d is —O—C(=O)—$C_{1-14}$ alkyl.

In some embodiments of the fifth aspect and first embodiment thereof, X1d is —SH and X2d is —OH. In some embodiments X1d is —SH, X2d is —OH, R1d is adenine and R2d is guanine. In some embodiments X1d is —SH, X2d is —OH, R1d is guanine and R2d is adenine. In some embodiments X1d is —SH, X2d is —OH and R1d and R2d are adenine. In some embodiments X1d is —SH, X2d is —OH, R1d is adenine, R2d is guanine and R3d is —H or —OH. In some embodiments X1d is —SH, X2d is —OH, R1d is adenine, R2d is guanine and R3d is —OH or —O—C(=O)—$C_{1-14}$alkyl. In some embodiments X1d is —SH, X2d is —OH, R1d is adenine, R2d is guanine and R3d is —OH. In some embodiments X1d is —SH, X2d is —OH, R1d is adenine, R2d is guanine and R3d is —H. In some embodiments X1d is —SH, X2d is —OH, R1d is adenine, R2d is guanine and R3d is —O—C(=O)—$C_{1-14}$ alkyl. In some embodiments X1d is —SH, X2d is —OH, R1d is guanine, R2d is adenine and R3d is —H or —OH. In some embodiments X1d is —SH, X2d is —OH, R1d is guanine, R2d is adenine and R3d is —OH or —O—C(=O)—$C_{1-14}$alkyl. In some embodiments X1d is —SH, X2d is —OH, R1d is guanine, R2d is adenine and R3d is —OH. In some embodiments X1d is —SH, X2d is —OH, R1d is guanine, R2d is adenine and R3d is —H. In some embodiments X1d is —SH, X2d is —OH, R1d is guanine, R2d is adenine and R3d is —O—C(=O)—$C_{1-14}$ alkyl. In some embodiments X1d is —SH, X2d is —OH, R1d and R2d are adenine and R3d is —H or —OH. In some embodiments X1d is —SH, X2d is —OH, R1d and R2d are adenine and R3d is —OH or —O—C(=O)—C$_{1-14}$alkyl. In some embodiments X1d is —SH, X2d is —OH, R1d and R2d are adenine and R3d is —OH. In some embodiments X1d is —SH, X2d is —OH, R1d and R2d are adenine and R3d is —H. In some embodiments X1d is —SH, X2d is —OH, R1d and R2d are adenine and R3d is —O—C(=O)—C$_{1-14}$ alkyl.

In some embodiments of the fifth aspect and first embodiment thereof, X1d is —OH and X2d is —SH. In some embodiments X1d is —OH, X2d is —SH, R1d is adenine and R2d is guanine. In some embodiments X1d is —OH, X2d is —SH, R1d is guanine and R2d is adenine. In some embodiments X1d is —OH, X2d is —SH and R1d and R2d are adenine. In some embodiments X1d is —OH, X2d is —SH, R1d is adenine, R2d is guanine and R3d is —H or —OH. In some embodiments X1d is —OH, X2d is —SH, R1d is adenine, R2d is guanine and R3d is —OH or —O—C(=O)—C$_{1-14}$alkyl. In some embodiments X1d is —OH, X2d is —SH, R1d is adenine, R2d is guanine and R3d is —OH. In some embodiments X1d is —OH, X2d is —SH, R1d is adenine, R2d is guanine and R3d is —H. In some embodiments X1d is —OH, X2d is —SH, R1d is adenine, R2d is guanine and R3d is —O—C(=O)—C$_{1-14}$ alkyl. In some embodiments X1d is —OH, X2d is —SH, R1d is guanine, R2d is adenine and R3d is —H or —OH. In some embodiments X1d is —OH, X2d is —SH, R1d is guanine, R2d is adenine and R3d is —OH or —O—C(=O)—C$_{1-14}$alkyl. In some embodiments X1d is —OH, X2d is —SH, R1d is guanine, R2d is adenine and R3d is —OH. In some embodiments X1d is —OH, X2d is —SH, R1d is guanine, R2d is adenine and R3d is —H. In some embodiments X1d is —OH, X2d is —SH, R1d is guanine, R2d is adenine and R3d is —O—C(=O)—C$_{1-14}$ alkyl. In some embodiments X1d is —OH, X2d is —SH, R1d and R2d are adenine and R3d is —H or —OH. In some embodiments X1d is —OH, X2d is —SH, R1d and R2d are adenine and R3d is —OH or —O—C(=O)—C$_{1-14}$alkyl. In some embodiments X1d is —OH, X2d is —SH, R1d and R2d are adenine and R3d is —OH. In some embodiments X1d is —OH, X2d is —SH, R1d and R2d are adenine and R3d is —H. In some embodiments X1d is —OH, X2d is —SH, R1d and R2d are adenine and R3d is —O—C(=O)—C$_{1-14}$ alkyl.

In some embodiments of the fifth aspect and first embodiment thereof, X1d and X2d are —OH. In some embodiments X1d and X2d are —OH, R1d is adenine and R2d is guanine. In some embodiments X1d and X2d are —OH, R1d is guanine and R2d is adenine. In some embodiments X1d and X2d are —OH and R1d and R2d are adenine. In some embodiments X1d and X2d are —OH, R1d is adenine, R2d is guanine and R3d is —H or —OH. In some embodiments X1d and X2d are —OH, R1d is adenine, R2d is guanine and R3d is —OH or —O—C(=O)—C$_{1-14}$ alkyl. In some embodiments X1d and X2d are —OH, R1d is adenine, R2d is guanine and R3d is —OH. In some embodiments X1d and X2d are —OH, R1d is adenine, R2d is guanine and R3d is —H. In some embodiments X1d and X2d are —OH, R1d is adenine, R2d is guanine and R3d is —O—C(=O)—C$_{1-14}$ alkyl. In some embodiments X1d and X2d are —OH, R1d is guanine, R2d is adenine and R3d is —H or —OH. In some embodiments X1d and X2d are —OH, R1d is guanine, R2d is adenine and R3d is —OH or —O—C(=O)—C$_{1-14}$ alkyl. In some embodiments X1d and X2d are —OH, R1d is guanine, R2d is adenine and R3d is —OH. In some embodiments X1d and X2d are —OH, R1d is guanine, R2d is adenine and R3d is —H. In some embodiments X1d and X2d are —OH, R1d is guanine, R2d is adenine and R3d is —O—C(=O)—C$_{1-14}$ alkyl. In some embodiments X1d and X2d are —OH, R1d and R2d are adenine and R3d is —H or —OH. In some embodiments X1d and X2d are —OH, R1d and R2d are adenine and R3d is —OH or —O—C(=O)—C$_{1-14}$ alkyl. In some embodiments X1d and X2d are —OH, R1d and R2d are adenine and R3d is —OH. In some embodiments X1d and X2d are —OH, R1d and R2d are adenine and R3d is —H. In some embodiments X1d and X2d are —OH, R1d and R2d are adenine and R3d is —O—C(=O)—C$_{1-14}$ alkyl.

In some embodiments of the fifth aspect and first embodiment thereof, R1d is adenine and R2d is guanine. In some embodiments, R1d is guanine and R2d is adenine. In some embodiments, R1d and R2d are adenine.

In a second embodiment of the fifth aspect, the Compound of Formula ID is a Compound of Formula ID-b:

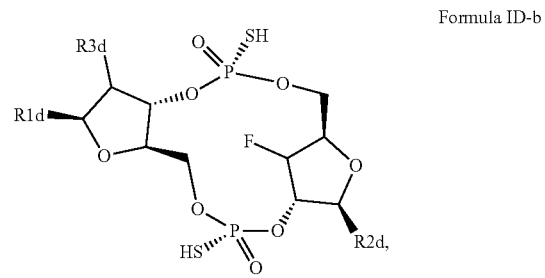

Formula ID-b or a prodrug, pharmaceutically acceptable salt, pharmaceutically acceptable solvate or pharmaceutically acceptable hydrate thereof, wherein R1d, R2d and R3d are as defined for Compounds of Formula ID.

In a third embodiment of the fifth aspect, the Compound of Formula ID is a Compound of Formula ID-c:

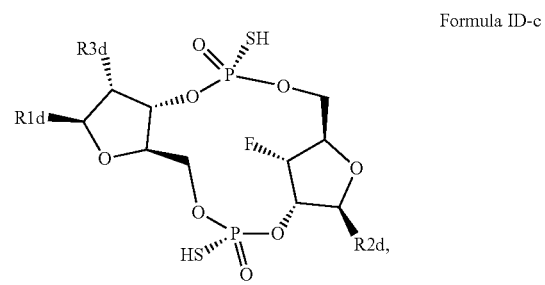

Formula ID-c or a prodrug, pharmaceutically acceptable salt, pharmaceutically acceptable solvate or pharmaceutically acceptable hydrate thereof, wherein R1d, R2d and R3d are as defined for Compounds of Formula ID.

In some embodiments of the fifth aspect and second or third embodiment thereof, R1d is adenine and R2d is guanine. In some embodiments R1d is guanine and R2d is adenine. In some embodiments R1d and R2d are adenine. In some embodiments R1d is adenine, R2d is guanine and R3d is —H or —OH. In some embodiments R1d is adenine, R2d is guanine and R3d is —OH or —O—C(=O)—C$_{1-14}$ alkyl. In some embodiments R1d is adenine, R2d is guanine and R3d is —OH. In some embodiments R1d is adenine, R2d is guanine and R3d is —H. In some embodiments R1d is adenine, R2d is guanine and R3d is —O—C(=O)—C$_{1-14}$ alkyl. In some embodiments R1d is guanine, R2d is adenine and R3d is —H or —OH. In some embodiments R1d is guanine, R2d is adenine and R3d is —OH or —O—C(=O)—C$_{1-14}$ alkyl. In some embodiments R1d is guanine, R2d is adenine and R3d is —OH. In some embodiments R1d is guanine, R2d is adenine and R3d is —H. In some embodiments R1d is guanine, R2d is adenine and R3d is —O—C(=O)—$C_{1-14}$alkyl. In some embodiments R1d and R2d are adenine and R3d is —H or —OH. In some embodiments R1d and R2d are adenine and R3d is —OH or —O—C(=O)—$C_{1-14}$ alkyl. In some embodiments R1d and R2d are adenine and R3d is —OH. In some embodiments R1d and R2d are adenine and R3d is —H. In some embodiments R1d and R2d are adenine and R3d is —O—C(=O)—$C_{1-14}$ alkyl.

In some embodiments of the third aspect and any of the above embodiments thereof, when R3d or R4d is —O—C(=O)—$C_{1-14}$ alkyl, —O—C(=O)—$C_{1-14}$ alkyl is —O—C(=O)—$C_{3-14}$ alkyl, —O—C(=O)—$C_{5-13}$ alkyl, —O—C(=O)—$C_{5-11}$ alkyl, or —O—C(=O)—$C_9$ alkyl, preferably wherein the alkyl chain is linear. In a preferred embodiment, —O—C(=O)—$C_{1-14}$ alkyl is —O—C(=O)—$(CH_2)_8$—$CH_3$.

In one embodiment of the fifth aspect and second embodiment thereof, the compound is selected from the group consisting of:

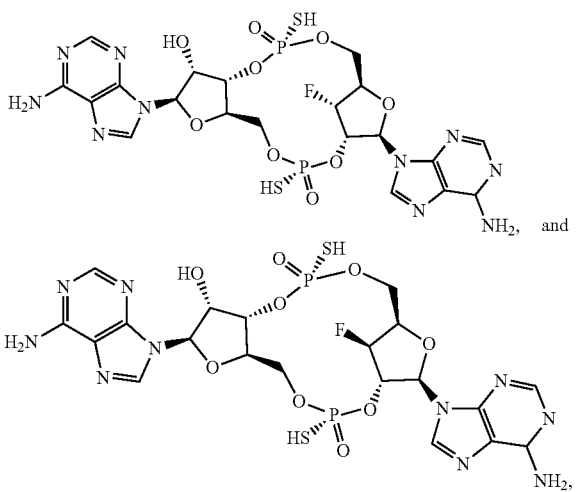

or a prodrug, pharmaceutically acceptable salt, pharmaceutically acceptable solvate or pharmaceutically acceptable hydrate thereof.

In one embodiment of the fifth aspect and first, second or third embodiments thereof, the compound is

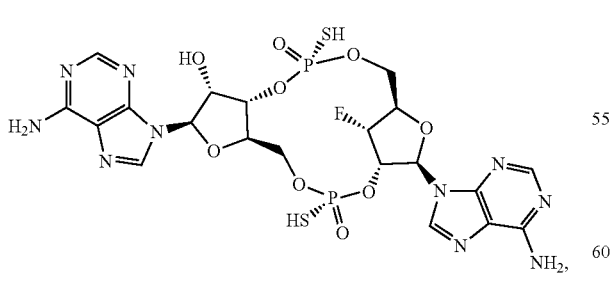

or a prodrug, pharmaceutically acceptable salt, pharmaceutically acceptable solvate or pharmaceutically acceptable hydrate thereof.

In a sixth aspect, the present invention provides a di-F-ML-CDN Compound of Formula IE:

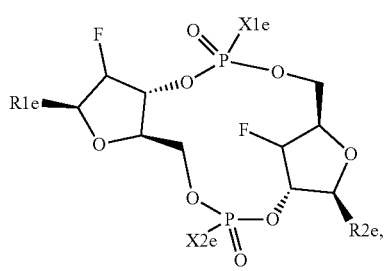

Formula IE or a prodrug, pharmaceutically acceptable salt, pharmaceutically acceptable solvate or pharmaceutically acceptable hydrate thereof,
wherein:
R1e and R2e are independently a guanine or adenine bound to the structure via the N9 position, provided that R1e and R2e are not both guanine; and
X1e and X2e are independently —OH or —SH.

As described hereinafter, in certain embodiments, X1e and X2e are each —SH, and one or both of R3e and R4e are —F; and in certain of these embodiments, if only one of R3e and R4e is F, the other of R3e and R4e is —O—C(=O)—$C_{1-14}$ alkyl, and preferably —O—C(=O)—$C_{6-12}$ alkyl. In certain of these embodiments, R3e is F and R4e is —O—C(=O)—$C_{1-14}$ alkyl, and preferably —O—C(=O)—$C_{6-12}$. Additionally, when X1e or X2e are —SH, a chiral center is introduced into the molecule at the thiophosphate. In certain of these embodiments, the compounds are R,R diastereoisomers.

In a first embodiment of the sixth aspect, the Compound of Formula IE is a Compound of Formula IE-a:

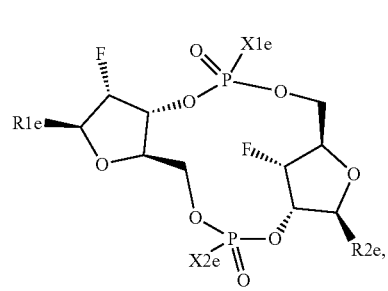

Formula IE-a or a prodrug, pharmaceutically acceptable salt, pharmaceutically acceptable solvate or pharmaceutically acceptable hydrate thereof, wherein R1e, R2e, X1e and X2e are as defined for Compounds of Formula IE.

In a second embodiment of the sixth aspect, the Compound of Formula IE is a Compound of Formula IE-b:

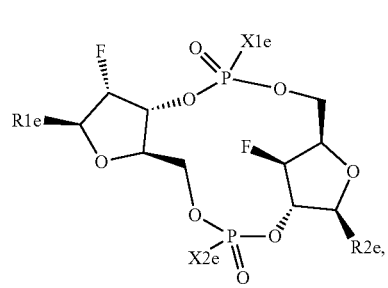

Formula IE-b or a prodrug, pharmaceutically acceptable salt, pharmaceutically acceptable solvate or pharmaceutically acceptable hydrate thereof, wherein R1e, R2e, X1e and X2e are as defined for Compounds of Formula IE.

In some embodiments of the sixth aspect and first or second embodiments thereof, X1e and X2e are —SH. In some embodiments X1e and X2e are —SH, R1e is adenine and R2e is guanine. In some embodiments X1e and X2e are —SH, R1e is guanine and R2e is adenine. In some embodiments X1e and X2e are —SH, and R1e and R2e are adenine.

In some embodiments of the sixth aspect, X1e is —SH and X2e is —OH. In some embodiments X1e is —SH, X2e is —OH, R1e is adenine and R2e is guanine. In some embodiments X1e is —SH, X2e is —OH, R1e is guanine and R2e is adenine. In some embodiments X1e is —SH, X2e is —OH and R1e and R2e are adenine.

In some embodiments of the sixth aspect, X1e is —OH and X2e is —SH. In some embodiments X1e is —OH, X2e is —SH, R1e is adenine and R2e is guanine. In some embodiments X1e is —OH, X2e is —SH, R1e is guanine and R2e is adenine. In some embodiments X1e is —OH, X2e is —SH and R1e and R2e are adenine.

In some embodiments of the sixth aspect, X1e and X2e are —OH. In some embodiments X1e and X2e are —OH, R1e is adenine and R2e is guanine. In some embodiments X1e and X2e are —OH, R1e is guanine and R2e is adenine. In some embodiments X1e and X2e are —OH and R1e and R2e are adenine.

In some embodiments of the sixth aspect and first or second embodiments thereof, R1e is adenine and R2e is guanine. In some embodiments, R1e is guanine and R2e is adenine. In some embodiments, R1e and R2e are adenine.

In some embodiments of the sixth aspect and embodiments thereof, the compound is selected from the group consisting of:

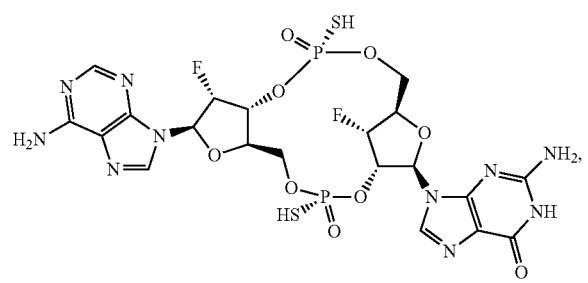

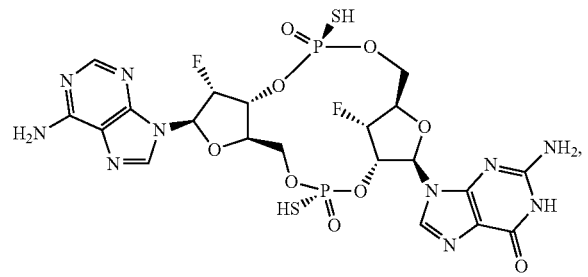

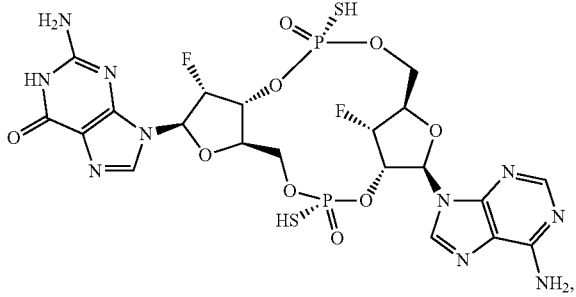

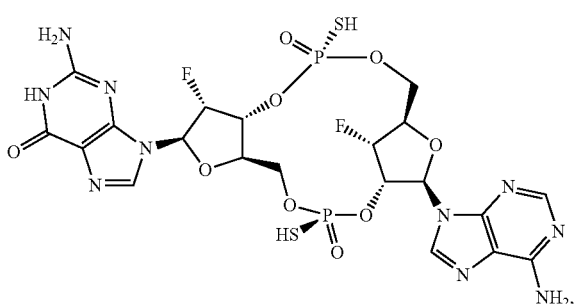

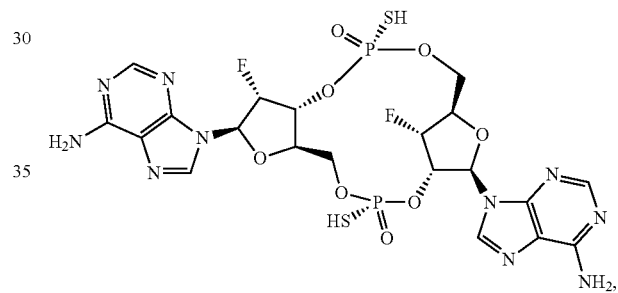

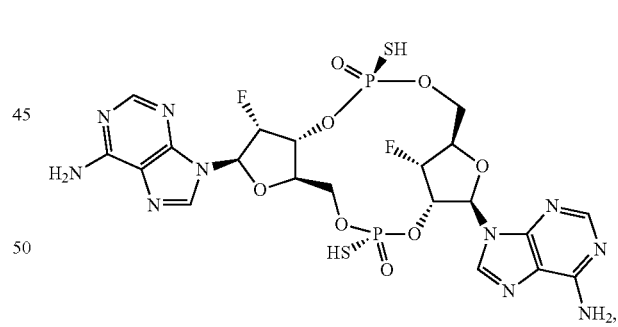

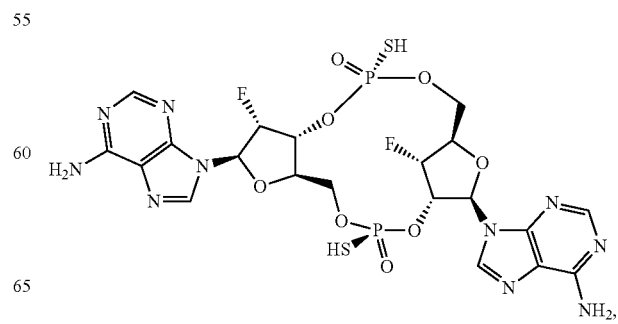

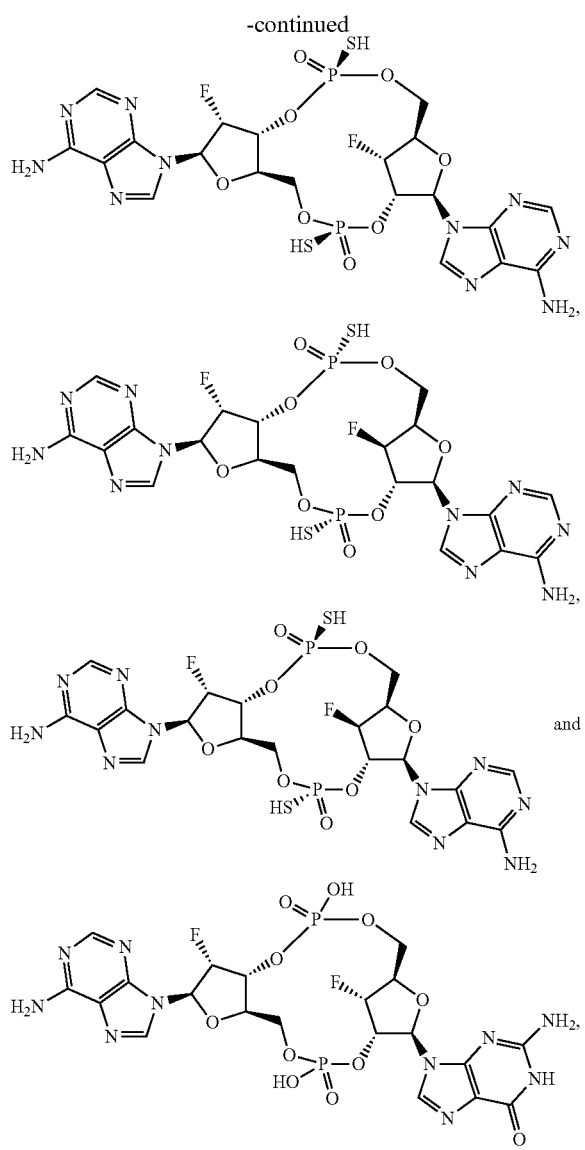

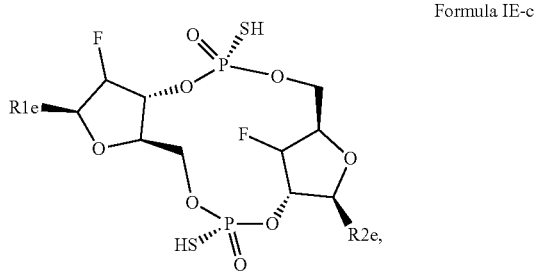

or a prodrug, pharmaceutically acceptable salt, pharmaceutically acceptable solvate or pharmaceutically acceptable hydrate thereof.

In a third embodiment of the sixth aspect, the Compound of Formula IE is a Compound of Formula IE-c:

Formula IE-c

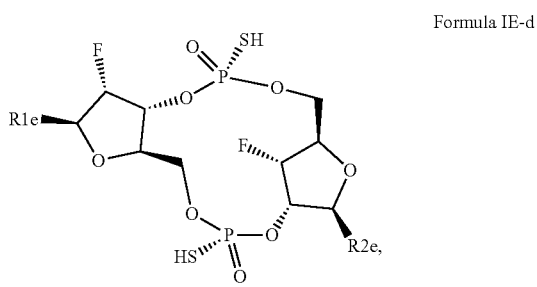

or a prodrug, pharmaceutically acceptable salt, pharmaceutically acceptable solvate or pharmaceutically acceptable hydrate thereof, wherein R1e and R2e are independently a guanine or adenine bound to the structure via the N9 position, provided that R1e and R2e are not both guanine. In some embodiments, R1e is adenine and R2e is guanine. In some embodiments, R1e is guanine and R2e is adenine. In some embodiments, R1e and R2e are adenine.

In a fourth embodiment of the sixth aspect, the Compound of Formula IE is a Compound of Formula IE-d:

Formula IE-d

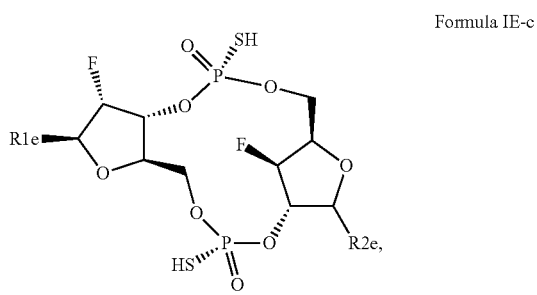

or a prodrug, pharmaceutically acceptable salt, pharmaceutically acceptable solvate or pharmaceutically acceptable hydrate thereof, wherein R1e and R2e are independently a guanine or adenine bound to the structure via the N9 position, provided that R1e and R2e are not both guanine. In some embodiments, R1e is adenine and R2e is guanine. In some embodiments, R1e is guanine and R2e is adenine. In some embodiments, R1e and R2e are adenine.

In a fifth embodiment of the sixth aspect, the Compound of Formula IE is a Compound of Formula IE-e:

Formula IE-e

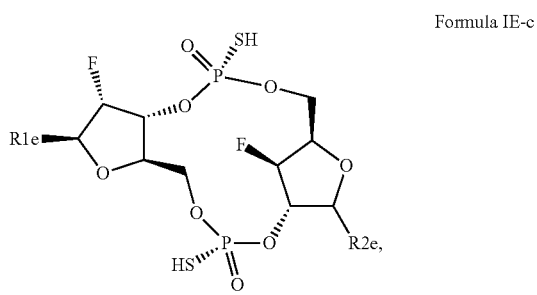

or a prodrug, pharmaceutically acceptable salt, pharmaceutically acceptable solvate or pharmaceutically acceptable hydrate thereof, wherein R1f and R2f are independently a guanine or adenine bound to the structure via the N9 position, provided that R1f and R2f are not both guanine. In some embodiments, R1f is adenine and R2f is guanine. In some embodiments, R1f is guanine and R2f is adenine. In some embodiments, R1f and R2f are adenine.

In one embodiment of the sixth aspect and third embodiment thereof, the compound is selected from the group consisting of:

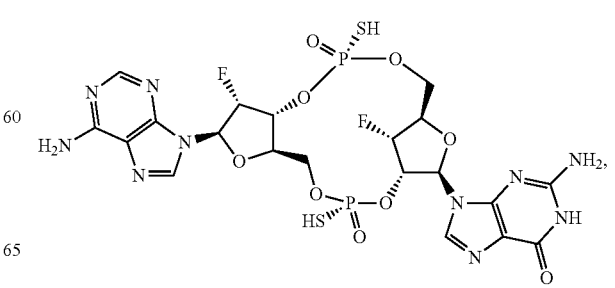

-continued

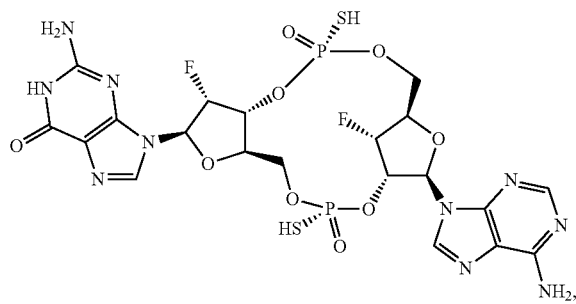

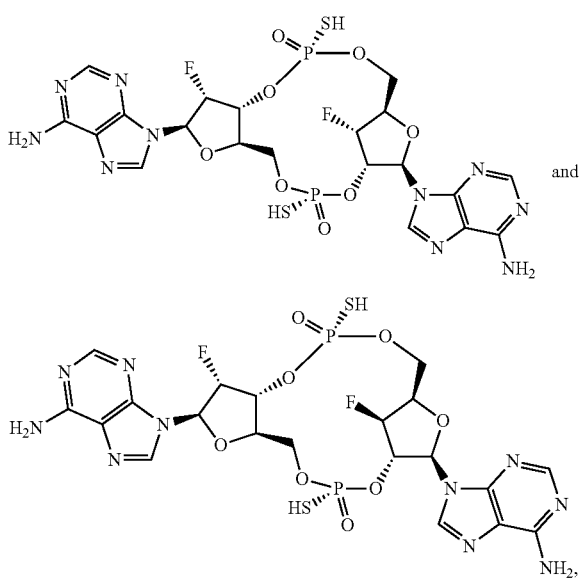

and or a prodrug, pharmaceutically acceptable salt, pharmaceutically acceptable solvate or pharmaceutically acceptable hydrate thereof.

In one embodiment of the sixth aspect and first, third or fourth embodiments thereof, the compound is selected from the group consisting of:

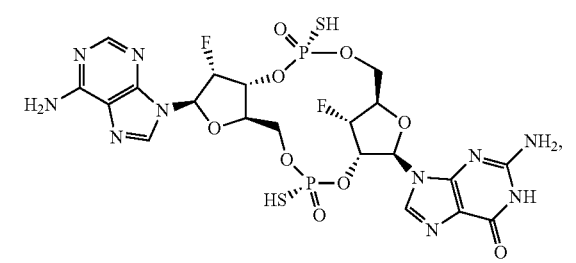

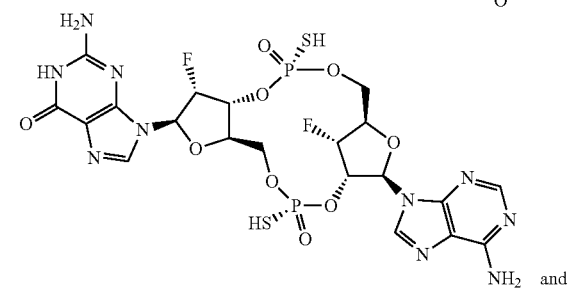

and

-continued

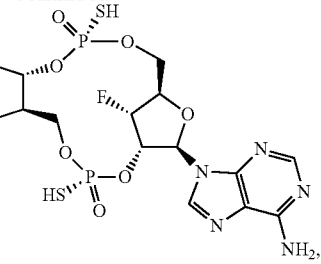

or a prodrug, pharmaceutically acceptable salt, pharmaceutically acceptable solvate or pharmaceutically acceptable hydrate thereof.

In one embodiment of the sixth aspect and second or fifth embodiments thereof, the compound is

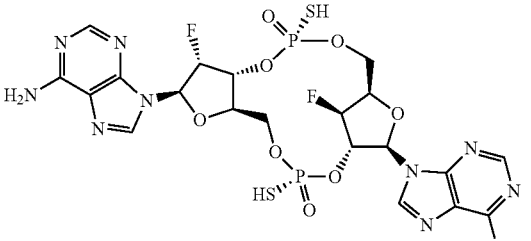

or a prodrug, pharmaceutically acceptable salt, pharmaceutically acceptable solvate or pharmaceutically acceptable hydrate thereof.

In a sixth embodiment of the sixth aspect, the Compound of Formula IE is a Compound of Formula IE-f:

Formula IE-f

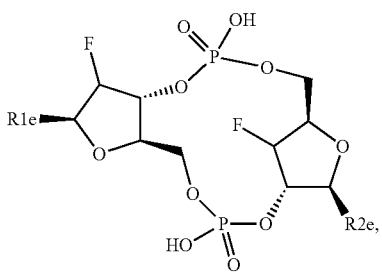

or a prodrug, pharmaceutically acceptable salt, pharmaceutically acceptable solvate or pharmaceutically acceptable hydrate thereof, wherein R1e and R2e are independently a guanine or adenine bound to the structure via the N9 position, provided that R1e and R2e are not both guanine. In some embodiments, R1e is adenine and R2e is guanine. In some embodiments, R1e is guanine and R2e is adenine. In some embodiments, R1e and R2e are adenine.

In a seventh embodiment of the sixth aspect, the Compound of Formula IE is a Compound of Formula IE-g:

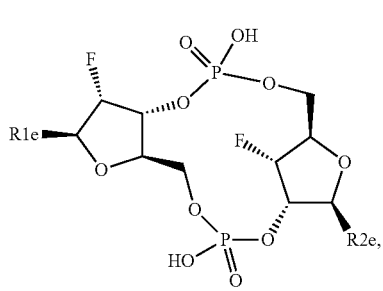

Formula IE-g or a prodrug, pharmaceutically acceptable salt, pharmaceutically acceptable solvate or pharmaceutically acceptable hydrate thereof, wherein R1e and R2e are independently a guanine or adenine bound to the structure via the N9 position, provided that R1e and R2e are not both guanine. In some embodiments, R1e is adenine and R2e is guanine. In some embodiments, R1e is guanine and R2e is adenine. In some embodiments, R1e and R2e are adenine.

In one embodiment of the sixth aspect and first, sixth or seventh embodiments thereof, the compound is

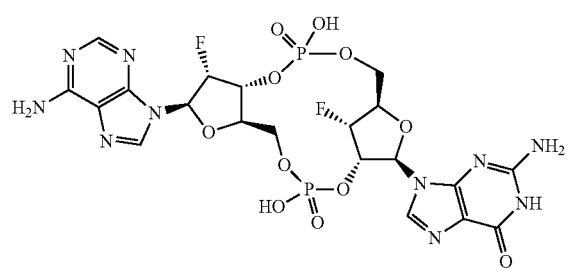 [SMILES: Nc1nc2c(ncn2[C@@H]2O[C@@H]3COP(=O)(O)O[C@H]4[C@@H](F)[C@H](n5cnc6c(N)ncnc65)O[C@@H]4COP(=O)(O)O[C@@H]2[C@@H]3F)c(=O)[nH]1]

or a prodrug, pharmaceutically acceptable salt, pharmaceutically acceptable solvate or pharmaceutically acceptable hydrate thereof.

In a seventh aspect, a compound 2'3'-RR-(3'F-A)(2'F-A) is provided, having the structure:

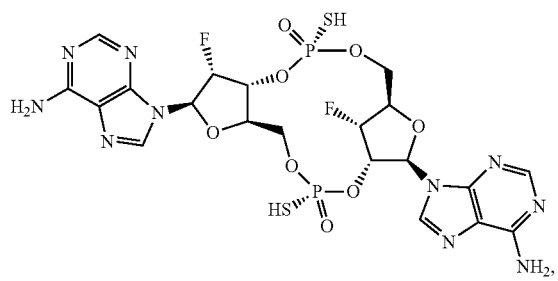 [SMILES: Nc1ncnc2c1ncn2[C@@H]1O[C@@H]2CO[P@@](=O)(S)O[C@@H]3[C@H](F)[C@@H](CO[P@@](=O)(S)O[C@H]2[C@H]1F)O[C@H]3n1cnc2c(N)ncnc21]

or a prodrug, pharmaceutically acceptable salt, pharmaceutically acceptable solvate or pharmaceutically acceptable hydrate thereof.

In an eighth aspect, a compound 2'3'-RR-(3'βF-A)(2'F-A) is provided, having the structure:

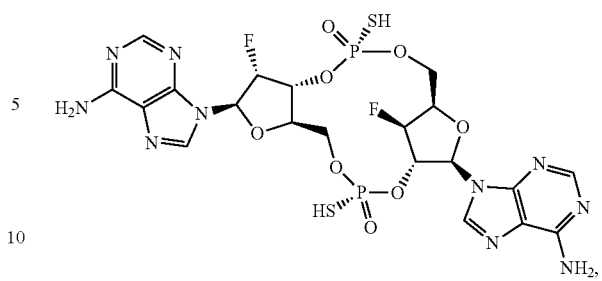

or a prodrug, pharmaceutically acceptable salt, pharmaceutically acceptable solvate or pharmaceutically acceptable hydrate thereof.

In a ninth aspect, a compound 2'3'-RR-(A)(2'F-A) is provided, having the structure:

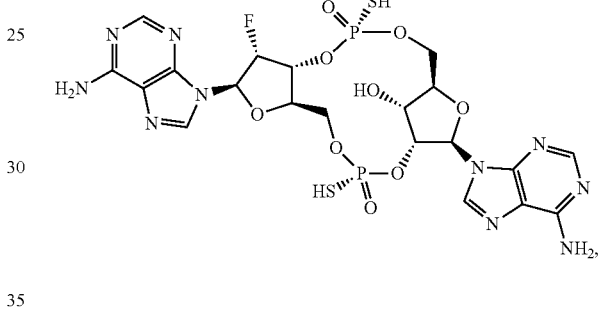

or a prodrug, pharmaceutically acceptable salt, pharmaceutically acceptable solvate or pharmaceutically acceptable hydrate thereof.

In a tenth aspect, a compound 2'3'-RR-(3'F-A)(A) is provided, having the structure:

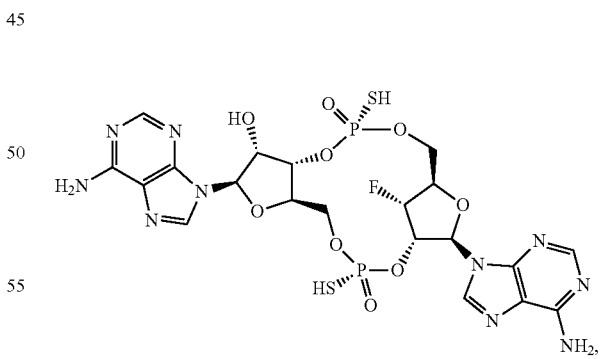

or a prodrug, pharmaceutically acceptable salt, pharmaceutically acceptable solvate or pharmaceutically acceptable hydrate thereof.

In an eleventh aspect, a compound 2'3'-RR-(3'H-A)(2'F-A) is provided, having the structure:

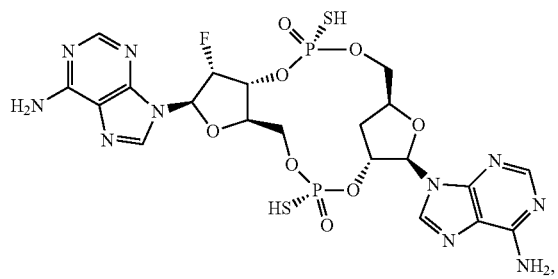 [SMILES: Nc1ncnc2c1ncn2[C@@H]1O[C@@H]2CO[P@@](=O)(S)O[C@@H]3C[C@@H](CO[P@@](=O)(S)O[C@H]2[C@H]1F)O[C@H]3n1cnc2c(N)ncnc21]

or a prodrug, pharmaceutically acceptable salt, pharmaceutically acceptable solvate or pharmaceutically acceptable hydrate thereof.

In a twelfth aspect, a compound 2'3'-RR-(G)(2'F-A) is provided, having the structure:

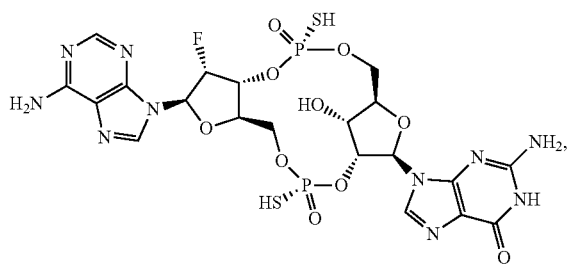 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@@H]2[C@@H]3O)c(=O)[nH]1]

or a prodrug, pharmaceutically acceptable salt, pharmaceutically acceptable solvate or pharmaceutically acceptable hydrate thereof.

In a thirteenth aspect, a compound 2'3'-RR-(3'decanoyl-O-G)(2'F-A) is provided, having the structure:

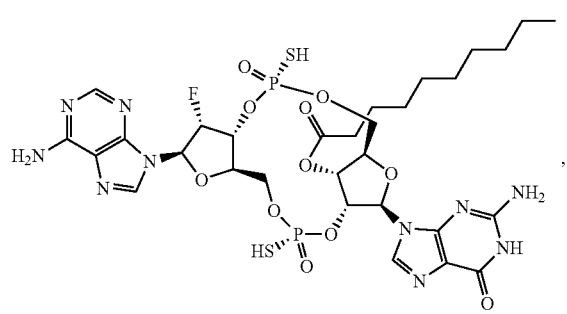 [SMILES: CCCCCCCCCC(=O)O[C@H]1[C@H]2O[P@](=O)(S)OC[C@H]3O[C@@H](n4cnc5c(N)ncnc54)[C@H](F)[C@@H]3O[P@](=O)(S)OC[C@H]1O[C@H]2n1cnc2c(=O)[nH]c(N)nc21]

or a prodrug, pharmaceutically acceptable salt, pharmaceutically acceptable solvate or pharmaceutically acceptable hydrate thereof.

In a fourteenth aspect, a compound 2'3'-RR-(3'F-G)(2'F-A) is provided, having the structure:

or a prodrug, pharmaceutically acceptable salt, pharmaceutically acceptable solvate or pharmaceutically acceptable hydrate thereof.

In a fifteenth aspect, a compound 3'2'-RR-(2'F-G)(3'F-A) is provided, having the structure:

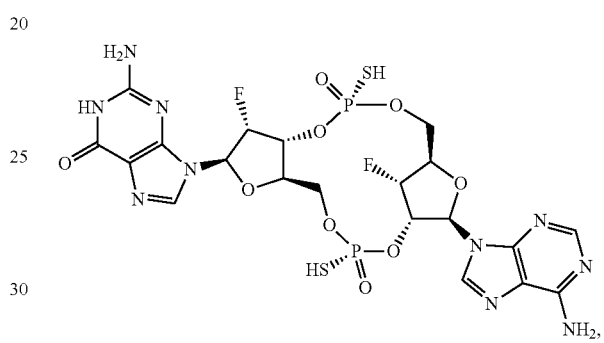

or a prodrug, pharmaceutically acceptable salt, pharmaceutically acceptable solvate or pharmaceutically acceptable hydrate thereof.

In a sixteenth aspect, a compound 3'2'-RR-(2'F-G)(A) is provided, having the structure:

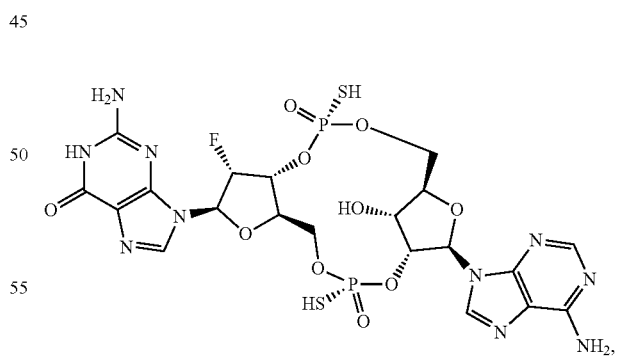

or a prodrug, pharmaceutically acceptable salt, pharmaceutically acceptable solvate or pharmaceutically acceptable hydrate thereof.

In a seventeenth aspect, a compound 2'3'-(G)(2'F-A) is provided, having the structure:

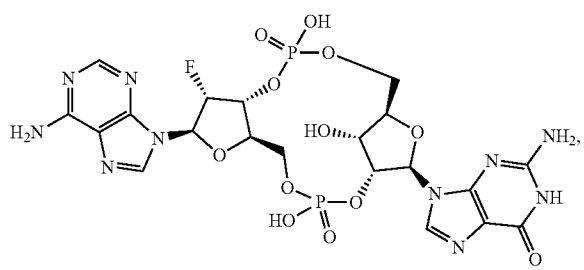 [SMILES: Nc1nc2c(ncn2[C@@H]2O[C@@H]3COP(=O)(O)O[C@H]4[C@@H](F)[C@H](n5cnc6c(N)ncnc65)O[C@@H]4COP(=O)(O)O[C@@H]2[C@@H]3O)c(=O)[nH]1]

or a prodrug, pharmaceutically acceptable salt, pharmaceutically acceptable solvate or pharmaceutically acceptable hydrate thereof.

In an eighteenth aspect, a compound 2'3'-(3'F-G)(2'F-A) is provided, having the structure:

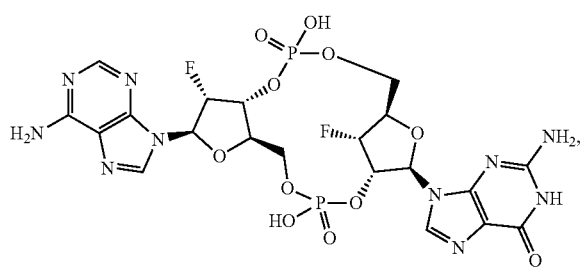 [SMILES: Nc1nc2c(ncn2[C@@H]2O[C@@H]3COP(=O)(O)O[C@H]4[C@@H](F)[C@H](n5cnc6c(N)ncnc65)O[C@@H]4COP(=O)(O)O[C@@H]2[C@@H]3F)c(=O)[nH]1]

or a prodrug, pharmaceutically acceptable salt, pharmaceutically acceptable solvate or pharmaceutically acceptable hydrate thereof.

In a nineteenth aspect, a compound 2'3'-RR-(3'βF-A)(A) is provided, having the structure:

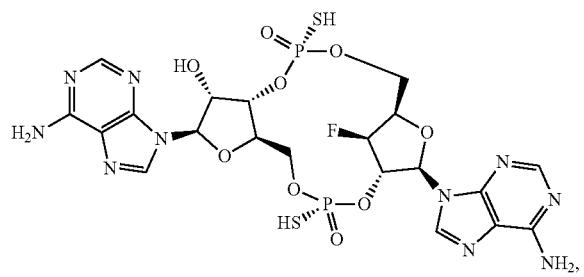 [SMILES: Nc1ncnc2c1ncn2[C@@H]1O[C@@H]2CO[P@@](=O)(S)O[C@@H]3[C@@H](F)[C@@H](CO[P@@](=O)(S)O[C@H]2[C@H]1O)O[C@H]3n1cnc2c(N)ncnc21]

or a prodrug, pharmaceutically acceptable salt, pharmaceutically acceptable solvate or pharmaceutically acceptable hydrate thereof.

In any of the mono- or di-F-ML-CDN compounds of any of the above aspects and embodiments thereof, when X1 and X2 (including X1a, X2a, X1b, X2b, etc.) are within a structure, and X1 and X2 are —SH, or X1 is —SH and X2 is —OH, or X1 is —SH and X2 is —OH, the stereochemistry at each thio substituted phosphorus is R. In some embodiments, when a thiophosphate stereochemistry is defined within a structure (e.g. the third embodiment of the first aspect), or when X1 and X2 are within a structure and X1 and X2 are —SH, or X1 is —SH and X2 is —OH, or X1 is —SH and X2 is —OH, the stereochemistry at each thio substituted phosphorus is R, and the compound is substantially pure. In a preferred embodiment the mono- or di-F-ML-CDN compound is a structure having the thiophosphate stereochemistry defined as R in the structure (e.g. the third embodiment of the first aspect), or X1 and X2 are within a structure and both X1 and X2 are —SH, the stereochemistry at each phosphorus is R, and the compound is substantially pure.

In some embodiments of any of the above aspects and embodiments thereof, the mono- or di-F-ML-CDN compounds include prodrugs, pharmaceutically acceptable salts, pharmaceutically acceptable solvates or pharmaceutically acceptable hydrates thereof, including pharmaceutically acceptable salts, pharmaceutically acceptable solvates or pharmaceutically acceptable hydrates of any prodrugs thereof, and including any pharmaceutically acceptable solvates or pharmaceutically acceptable hydrates of any pharmaceutically acceptable salts thereof. In some embodiments, the mono- or di-F-ML-CDN compounds include pharmaceutically acceptable solvates, pharmaceutically acceptable hydrates or pharmaceutically acceptable salts thereof. In some embodiments, the mono- or di-F-ML-CDN compound is a pharmaceutically acceptable salt, or a pharmaceutically acceptable solvate or pharmaceutically acceptable hydrate thereof. In some embodiments, the mono- or di-F-ML-CDN compound is a pharmaceutically acceptable salt.

In some embodiments of any of the above aspects and embodiments thereof, the mono- or di-F-ML-CDN compounds include pharmaceutically acceptable salts thereof. In some embodiments, the pharmaceutically acceptable salt is selected from the group consisting of the sodium, potassium, calcium, magnesium, zinc, aluminum, ammonium, diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine, lysine and arginine salt.

In one embodiment of any of the above aspects or embodiments thereof, the mono- or di-F-ML-CDN compounds are provided as the disodium salt thereof. In some embodiments, the mono- or di-F-ML-CDN compounds are provided as the disodium salt thereof, or a pharmaceutically acceptable solvate or pharmaceutically acceptable hydrate thereof.

In some embodiments of any of the above aspects and embodiments thereof, the mono- or di-F-ML-CDN compound is more active in a cellular assay that measures the induction of human STING dependent IFN-β production as compared to one or more reference compounds. In some embodiments, the one or more reference compounds are selected from the group consisting of 2'3'-(A)(A), 2'3'-(G)(A), 3'2'-(G)(A), 2'3'-RR-(A)(A) and 2'3'-RR-(G)(A). In some embodiments, the mono- or di-F-ML-CDN compound is a mono- or di-F-ML-RR-CDN compound and the one or more reference compounds are selected from the group consisting of 2'3'-RR-(A)(A) and 2'3'-RR-(G)(A). In some embodiments, the reference compound is the di-OH reference compound. In some embodiments, the cellular assay is an hPBMC assay, for example the assay as described in Example 15. In some embodiments, the cellular assay is a THP1 assay, for example the assay as described in Example 16. In a preferred embodiment, the cellular assay is performed without the addition of an agent that enhances uptake of the mono- or di-F-ML-CDN compound or reference compound by the assay cells or an agent that enhances the permeability of the mono- or di-F-ML-CDN compound or reference compound to the assay cells. In some embodiments, the cellular assay is a THP1 cellular assay performed without the addition of an agent that enhances uptake of the mono- or di-F-ML-CDN compound or reference compound by the assay cells or an agent that enhances the permeability of the mono- or di-F-ML-CDN compound or reference compound to the assay cells, in which the mono- or di-F-ML-CDN compound has an EC50 of less than 40 µM, less than 30 µM, less than 20 µM, less than 15 µM, or less than 10 µM. In some embodiments the mono- or di-F-ML-CDN compound has an EC50 of less than 40 µM, less than 30 µM, less than 20 µM, less than 15 µM, or less than 10 µM in a cellular assay that measures induction of human STING dependent IFN-β production, wherein the cellular assay is performed without the addition of an agent that enhances uptake of the mono- or di-F-ML-CDN compound by the assay cells or an agent that enhances the permeability of the mono- or di-F-ML-CDN compound to the assay cells. In one embodiment the cellular assay is a THP1 cellular assay as described in Example 16, wherein the assay is performed without addition of digitonin. In some embodiments, the mono- or di-F-ML-CDN compound has an EC50 that is less than the EC50 of one or more reference compounds selected from the group consisting of 2'3'-(A)(A), 2'3'-(G)(A), 3'2'-(G)(A), 2'3'-RR-(A)(A), and 2'3'-RR-(G)(A) in a cellular assay that measures induction of human STING dependent IFN-β production, preferably wherein the cellular assay is performed without the addition of an agent that enhances uptake of the mono- or di-F-ML-CDN compound or reference compound by the assay cells or an agent that enhances the permeability of the mono- or di-F-ML-CDN compound or reference compound to the assay cells. In some embodiments, the mono- or di-F-ML-CDN compound has an EC50 that is less than the EC50 of a di-OH reference compound in a THP1 cellular assay as described in Example 16, preferably wherein the assay is performed without addition of digitonin. In some embodiments, the mono- or di-F-ML-CDN compound has an EC50 that is at least 2-fold, at least 3-fold, at least 4-fold, at least 5-fold, at least 6-fold, at least 7-fold, or at least 8-fold lower than the EC50 of the di-OH reference compound in the THP1 cellular assay as described in Example 16, wherein the assay is performed without addition of digitonin.

In some embodiments of any of the above aspects and embodiments thereof, the mono- or di-F-ML-CDN compound binds at least one human STING allelic protein product (including any one of WT, REF, HAQ, AQ and Q alleles) with a greater affinity than one or more reference compounds selected from the group consisting of 2'3'-(A)(A), 2'3'-(G)(A), 3'2'-(G)(A), 2'3'-RR-(A)(A), and 2'3'-RR-(G)(A) when measured using at least one human STING protein. In some embodiments of any of the above aspects and embodiments thereof, the mono- or di-F-ML-CDN compound binds at least one human STING allelic protein product with an affinity greater than a di-OH reference compound. Preferably, this is measured using the isolated protein encoded by the hSTING (WT), hSTING (HAQ) or hSTING (REF) allele (Ishikawa, H., and Barber, G. N. (2008). *Nature* 455, 674-678; Yi et al., 2013, PLos One 2013 Oct. 21, 8(10):e77846; the protein sequence of the REF allele is NCBI Reference Sequence NP_938023) using a method such as differential scanning fluorometry (DSF) as described hereinafter and in Example 14.

In a twentieth aspect, the present invention provides pharmaceutical compositions comprising one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, and a delivery vehicle which enhances cellular uptake and/or stability of the compound. In some embodiments, the delivery vehicle comprises one or more agents selected from the group consisting of adjuvants, lipids, liposomes, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

In a twenty-first aspect, the present invention provides pharmaceutical compositions comprising one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, and a pharmaceutically acceptable excipient.

In a first embodiment of the twenty-first aspect, the pharmaceutical composition does not include an agent that enhances cellular permeability of the one or more mono- or di-F-ML-CDN compounds.

In a second embodiment of the twenty-first aspect, the pharmaceutical composition does not include an agent that enhances cellular uptake of the one or more mono- or di-F-ML-CDN compounds.

In a third embodiment of the twenty-first aspect, the pharmaceutical composition further comprises a delivery vehicle which enhances cellular uptake and/or stability of the compound. In some embodiments, the delivery vehicle comprises one or more agents selected from the group consisting of adjuvants, lipids, liposomes, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

In some embodiments of the twentieth aspect and embodiments thereof or twenty-first aspect and first, second or third embodiments thereof, the pharmaceutical composition further comprises one or more additional pharmaceutically active components selected from the group consisting of an immune checkpoint inhibitor (e.g. CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL3280A, MEDI4736, or avelumab; antibodies targeting CD47 or its principal ligand Signal-regulatory protein alpha (SIRPα) expressed on macrophages); antibodies targeting A proliferation-inducing ligand (APRIL); a TLR agonist (e.g. CpG or monophosphoryl lipid A); an inactivated or attenuated bacteria which induce innate immunity (e.g., inactivated or attenuated *Listeria monocytogenes*); a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent. In some embodiments, the immune checkpoint inhibitor is selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, and a TIGIT pathway antagonist. In some embodiments, the immune checkpoint inhibitor is an anti-PD-1 antibody, an anti-PD-L1 antibody, an anti-CTLA-4 antibody, an anti-TIM-3 antibody, an anti-Vista antibody, an anti-BTLA antibody, an anti-TIGIT antibody, an anti-CD47 antibody, an anti-SIRPα antibody, or an anti-LAG-3 antibody. In some embodiments, the immune checkpoint inhibitor is selected from the group consisting of nivolumab, pembrolizumab, pidilizumab, AMP-224, ipilimumab, BMS-936559, MPDL3280A, MEDI4736, and avelumab. In some embodiments, the TLR agonist is CpG or monophosphoryl lipid A.

In some embodiments of the twentieth aspect or twenty-first aspect and any of the above embodiments thereof, the pharmaceutical composition further comprises an inactivated tumor cell which expresses and secretes one or more cytokines which stimulate dendritic cell induction, recruitment and/or maturation, or which expresses and secretes one or more heat shock proteins, including gp96-Ig fusion proteins. In some embodiments, the one or more cytokines is selected from the group consisting of GM-CSF, CCL20, CCL3, IL-12p70 and FLT-3 ligand. In some embodiments, the tumor cell is inactivated by treatment with radiation. In some embodiments, the one or more cytokines is selected from the group consisting of GM-CSF, CCL20, CCL3, IL-12p70 and FLT-3 ligand, and the tumor cell is inactivated by treatment with radiation. In some embodiments, the inactivated tumor cell expresses and secretes a gp96-Ig fusion protein.

In some embodiments of the twentieth aspect or twenty-first aspect and any of the above embodiments thereof, the pharmaceutical composition further comprises one or more antigens selected for the purposes of inducing an immune response against said one or more antigen(s) when the composition is administered to an individual. In some embodiments, the antigen is a recombinant protein antigen. In some embodiments, the antigen is a recombinant protein antigen related to an infectious disease, a malignancy, or an allergan. In some embodiments, the one or more antigens is one or more antigens in Table 1.

In some embodiments of the twentieth aspect or twenty-first aspect and any of the above embodiments thereof, the pharmaceutical compositions are formulated as aqueous or oil-in-water emulsions.

In a twenty-second aspect, the invention provides a method for treating an individual suffering from a cancer, wherein the method comprises administering to the individual in need thereof an effective amount of one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above. In some embodiments, the one or more mono- or di-F-ML-CDN compounds or composition thereof is administered non-parenterally or parenterally. In some embodiments, the administration is intravenous, subcutaneous, intramuscular, intradermal, oral, mucosal, vaginal, cervical, peri-tumoral, intra-tumoral, or directly into the tumor-draining lymph node(s). In some embodiments, the administration is mucosal or oral, preferably oral.

In a first embodiment of the twenty-second aspect, the individual receiving such treatment may be suffering from a cancer selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In a second embodiment of the twenty-second aspect and of the first embodiment thereof, the method for treating an individual suffering from a cancer further comprises administering one or more additional cancer therapies. In some embodiments, the one or more additional cancer therapies comprises radiation therapy, surgery, a chemotherapy, or an immunotherapy (for example, without limitation, an immunomodulator, an immune checkpoint inhibitor, a cellular immunotherapy, or a cancer vaccine). In some embodiments, the one or more additional cancer therapies comprises an inactivated tumor cell that expresses and secretes one or more cytokines or one or more heat shock proteins. In some embodiments, the cytokine is selected from the group consisting of GM-CSF, CCL20, CCL3, IL-12p70, and FLT-3 ligand. In some embodiments the heat shock protein is a gp96-Ig protein. In some embodiments, the method comprises administering one or more additional cancer therapies selected from the group consisting of a chemotherapeutic agent; an immune checkpoint inhibitor; a TLR agonist; a vaccine selected to stimulate an immune response to one or more cancer antigens, a therapeutic antibody that induces antibody-dependent cellular cytotoxicity; an immunomodulatory cell line; an inactivated or attenuated bacteria that induces innate immunity; an antigen selected for the purpose of inducing an immune response, and a composition that mediates innate immune activation via Toll-like Receptors (TLRs), (NOD)-like receptors (NLRs), Retinoic acid inducible gene-based (RIG)-I-like receptors (RLRs), C-type lectin receptors (CLRs) or pathogen-associated molecular patterns ("PAMPs"). In some embodiments, the immune checkpoint inhibitor is an anti-PD-1 antibody, an anti-PD-L1 antibody, an anti-CTLA-4 antibody, an anti-TIM-3 antibody, an anti-Vista antibody, an anti-BTLA antibody, an anti-TIGIT antibody, an anti-CD47 antibody, an anti-SIRPα antibody, or an anti-LAG-3 antibody. In some embodiments, the TLR agonist is CpG or monophosphoryl lipid A. In some embodiments, the therapeutic antibody that induces antibody-dependent cellular cytotoxicity is rituximab, ibritumomab, tositumomab, cetuximab, trastuzumab, brentuximab vedotin, alemtuzumab, oncolym, ibilimumab, vitaxin, or bevacizumab.

In some embodiments of the twenty-second aspect and first and second embodiments thereof, the individual suffers from a cancer expressing a cancer antigen, and the method for treating said individual further comprises administering to the individual a primary therapy to remove or kill cancer cells expressing the cancer antigen, wherein the administration of the primary therapy is simultaneously with, prior to or following administration of the mono- or di-F-ML-CDN compound or composition thereof. In some embodiments, the mono- or di-F-ML-CDN compound or composition thereof is administered as a neoadjuvant therapy to the primary therapy. In preferred embodiments, the mono- or di-F-ML-CDN compound or composition thereof is administered following the primary therapy. In some embodiments, the primary therapy comprises surgery to remove the cancer cells from the mammal, radiation therapy to kill the cancer cells in the mammal, or both surgery and radiation therapy.

In a twenty-third aspect, the invention provides a method of treating a disease in an individual, comprising administering to the individual in need thereof i) an effective amount of one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above; and ii) an effective amount of one or more therapeutic antibodies that induce antibody-dependent cellular cytotoxicity, wherein the disease is selected from the group consisting of a cancer, acute rejection of an organ transplant, Type I diabetes mellitus, rheumatoid arthritis, psoriasis, Crohn's disease, restenosis and allergic asthma. In some embodiments, the cancer is selected from the group consisting of lymphoma (e.g. B-cell lymphoma), breasts cancer, chronic lymphocytic leukemia, colorectal cancer, melanoma, non-small cell lung carcinoma, small cell lung cancer, bladder cancer, prostate cancer and other solid tumors. In some embodiments, the therapeutic antibody is selected from the group consisting of muromonab-CD3, infliximab, daclizumab, omalizumab, abciximab, rituximab, ibritumomab, tositumomab, cetuximab, trastuzumab, brentuximab vedotin, alemtuzumab, oncolym, ibilimumab, vitaxin, and bevacizumab.

In a twenty-fourth aspect, the invention provides a method for the treatment of disorders in which shifting of Th1 to Th2 immunity confers clinical benefit, wherein the method comprises administering to the individual in need thereof one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4$^+$ T lymphocytes producing IL-4, IL-6 and IL-10. Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

In a twenty-fifth aspect, the invention provides a method for treating an individual suffering from a chronic infectious disease, wherein the method comprises administering to the individual in need thereof an effective amount of mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above. In some embodiments, the one or more mono- or di-F-ML-CDN compounds or composition thereof is administered in combination with another agent for use in treating the chronic infectious disease. In some embodiments, the chronic infectious disease is selected from the group consisting of HBV infection, HCV infection, HPV infection, HSV infection and hepatocellular cancer.

The mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above, may be administered to individuals in need thereof, as described in the methods of the twenty-second through twenty-fifth aspects and any embodiments thereof as described herein above, by a variety of parenteral and non-parenteral routes in formulations containing pharmaceutically acceptable excipients (e.g. carriers, adjuvants, vehicles and the like). Preferred non-parenteral routes include oral, mucosal, vaginal, nasal, and cervical routes. Preferred parenteral routes include but, are not limited to, one or more of subcutaneous, intravenous, intramuscular, intraarterial, intradermal, intrathecal and epidural administrations. Preferably administration is by subcutaneous, intratumoral or peri-tumoral routes.

The mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein may be co-administered to individuals in need thereof, as described in the methods of the twenty-second through twenty-fifth aspects and any embodiments thereof as described herein above, with one or more additional pharmaceutically active components such as adjuvants, lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers, immune checkpoint inhibitors (e.g. CTLA-4, PD-1, Tim-3, Vista, BTLA, LAG-3 and TIGIT pathway antagonists; PD-1 pathway blocking agents; PD-L1 inhibitors; including without limitation anti-PD-1 antibodies nivolumab, pembrolizumab or pidilizumab; PD-1 inhibitor AMP-224; anti-CTLA-4 antibody ipilimumab; and anti-PD-L1 antibodies BMS-936559, MPDL3280A, MEDI4736, or avelumab), inactivated or attenuated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), or pathogen-associated molecular patterns ("PAMPs"), or chemotherapeutic agents.

In a twenty-sixth aspect, the invention provides one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above, for use as adjuvants in combination with a therapeutic or prophylactic vaccine. In some embodiments, the vaccine is selected to stimulate an immune response to one or more predetermined antigens. In some embodiments, the vaccine comprises one or more antigens, including a recombinant protein antigen related to an infectious disease, a malignancy, or an allergan. In some embodiments, the one or more mono- or di-F-ML-CDN compound or composition thereof is used simultaneously with, prior to or following the vaccine. In some embodiments, the one or more mono- or di-F-ML-CDN compound or composition thereof is formulated in the same composition as the vaccine.

In a first embodiment of the twenty-sixth aspect, the vaccine comprises an inactivated or attenuated bacteria or virus comprising the one or more antigens of interest, one or more purified antigens, live viral or bacterial delivery vectors recombinantly engineered to express and/or secrete the one or more antigens, antigen presenting cell (APC) vectors comprising cells that are loaded with the one or more antigens or transfected with a composition comprising a nucleic acid encoding the one or more antigens, liposomal antigen delivery vehicles, or naked nucleic acid vectors encoding the one or more antigens. In some embodiments, the vaccine is an anti-bacterial, anti-viral, or anti-cancer therapeutic or prophylactic vaccine. In some embodiments, the one or more antigens is one or more antigens selected from the group consisting of a viral antigen, a bacterial antigen and a cancer antigen.

In some embodiments of the twenty-sixth aspect and first embodiment thereof, the vaccine comprises an inactivated tumor cell that expresses and secretes one or more cytokines. In some embodiments, the cytokine is selected from the group consisting of GM-CSF, CCL20, CCL3, IL-12p70, and FLT-3 ligand.

In some embodiments of the twenty-sixth aspect and first embodiment thereof, the vaccine comprises an inactivated tumor cell that expresses and secretes one or more heat shock proteins. In some embodiments, the heat shock protein is gp96-Ig fusion protein.

In a twenty-seventh aspect, the invention provides one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above, for use in treating a disease or indication as described in any of the twenty-second through twenty-sixth aspects and any embodiments thereof as described herein above. In a preferred embodiment, the one or more mono- or di-F-ML-CDN compounds are for use in treating a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In a twenty-eighth aspect, the invention provides one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above, for use the preparation of a medicament for the treatment of a disease or indication as described in any of the twenty-second through twenty-sixth aspects and any embodiments thereof as described herein above. In a preferred embodiment, the one or more mono- or di-F-ML-CDN compounds are for use in preparation of a medicament for the treatment of a cancer. In some embodiments, the cancer is selected from the group consisting of a colorectal cancer, an aero-digestive squamous cancer, a lung cancer, a brain cancer, a liver cancer, a stomach cancer, a bladder cancer, a thyroid cancer, an adrenal cancer, a gastrointestinal cancer, an oropharyngeal cancer, an esophageal cancer, a head and neck cancer, an ovarian cancer, a uterine cancer, a cervical cancer, an endometrial cancer, a breast cancer, a melanoma, a prostate cancer, a pancreatic carcinoma, a renal carcinoma, a sarcoma, a leukemia, a lymphoma and a multiple myeloma.

In a twenty-ninth aspect, the invention provides a kit that includes one or more mono- or di-F-ML-CDN compounds, as described in the first through nineteenth aspects and any embodiments thereof as described herein above, including any prodrugs, pharmaceutically acceptable salts, pharmaceutically acceptable solvates, or pharmaceutically acceptable hydrates thereof, or compositions thereof as described in the twentieth and twenty-first aspects and any embodiments thereof as described herein above. In some embodiments, one or more mono- or di-F-ML-CDN compounds or compositions thereof is packaged, e.g., in a vial, bottle or similar container, which may be further packaged, e.g., within a box, envelope, or similar container. In some embodiments, one or more mono- or di-F-ML-CDN compounds or compositions thereof is approved by the U.S. Food and Drug Administration or similar regulatory agency for administration to a mammal, e.g., a human. In one embodiment, such a kit includes written instructions for use and/or other indication that the one or more mono- or di-F-ML-CDN compounds or compositions thereof is suitable or approved for administration to a mammal, e.g., a human, for a suitable disease or condition. In some embodiments, the compound or composition is packaged in unit dose or single dose form, e.g., single dose pills, capsules, or the like.

BRIEF DESCRIPTION OF THE FIGURES

FIG. 5A-D depicts the tumor volume in a B16.SIY melanoma mouse model, following three intra-tumoral injections of Compound 26 (5A,B) and Compound 35 (5C,D), at 1 μg, 10 μg or 100 μg and reference compound 2'3'-RR-(A)(A) at 10 µg or 100 µg, where tumor volumes were measured for primary growth (5A,C) or after re-challenge (5B,D).

DETAILED DESCRIPTION OF THE INVENTION

Figure 1A:
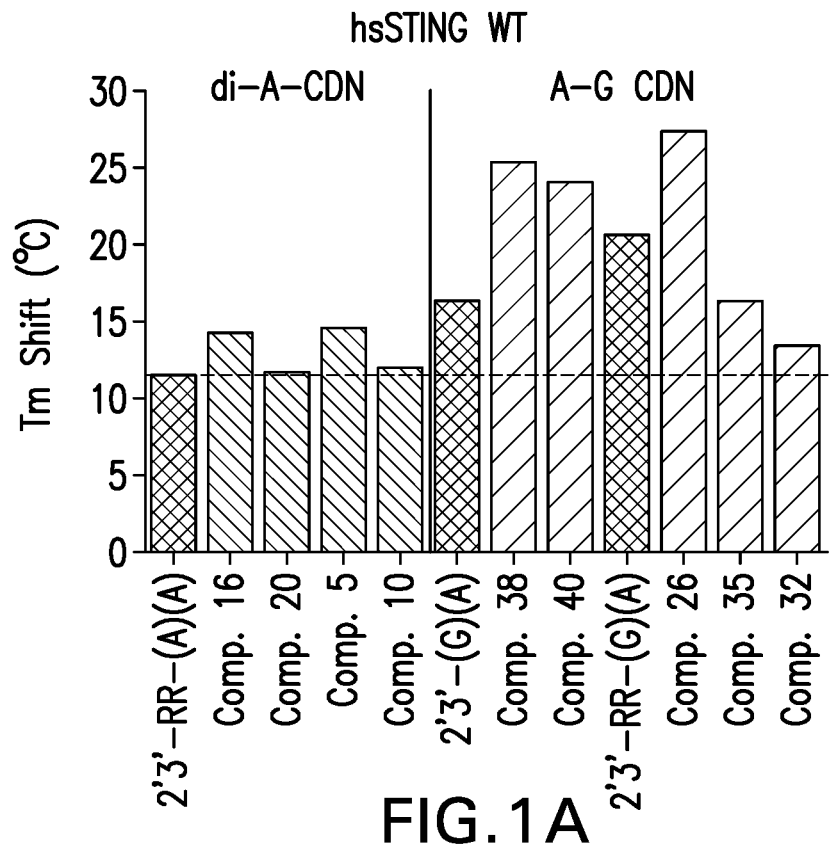
FIG. 1A-C depicts $T_m$ shift in a DSF assay of mono- or di-F-ML-CDN compounds to human STING WT (FIG. 1A), HAQ allele (FIG. 1B) and REF allele (FIG. 1C) protein.

The present invention relates to the production and use of mono- or di-fluoro substituted mixed linkage cyclic-di-nucleotide (mono- or di-F-ML-CDN) immune stimulators that activate DCs via a cytoplasmic receptor known as STING (Stimulator of Interferon Genes).

Conserved microbial structures known as Pathogen-Associated Molecular Patterns (PAMPs) are sensed by host cell Pattern Recognition Receptors (PRRs with germ-line encoded specificity), triggering a downstream signaling cascade resulting in the induction of cytokines and chemokines, and initiation of a specific adaptive immune response (Iwasaki and Medzhitov, Science 327, 291-5, 2010). How the innate immune system is engaged by PAMPs presented from an infectious agent shapes the development of an adaptive response appropriate to combat the invading pathogen from causing disease.

One objective in the design of immune modulators and adjuvants is to select defined PAMPs or synthetic molecules which activate designated PRRs and initiate a desired response. Adjuvants such as monophosphoryl lipid A (MPL) and CpG are microbial-derived PAMPs recognized by Toll-like receptors (TLRs), a class of PRRs that signal through MyD88 and TRIF adaptor molecules and mediate induction of NF-kB dependent proinflammatory cytokines (Pandey et. al., Cold Spring Harb Perspect Biol 2015; 7: a016246). MPL (TLR-4 agonist) and CpG (TLR-9 agonist) are the most clinically advanced adjuvants, and are components of vaccines that are approved or pending approval by the FDA (Einstein et al., Human Vaccines, 5: 705-19, 2009; Ahmed et al., Nature Immunol. 12: 509-17, 2011). While TLRs present on the cell surface (e.g., TLR-4) and endosomes (e.g., TLR-9) sense extracellular and vacuolar pathogens, the productive growth cycle of multiple pathogens including viruses and intracellular bacteria occurs in the cytosol. The compartmentalization of extracellular, vacuolar, and cytosolic PRRs has led to the hypothesis that the innate immune system can sense productively replicating pathogenic microbes by monitoring the cytosol (Vance et al., Cell Host & Microbe 6: 10-21, 2009). This provides a rationale for the use of agonists that activate PRRs comprising the cytosolic surveillance pathway and may be an effective strategy for the design of effective vaccines for eliciting cellular immunity, an immune correlate of protection against intracellular pathogens and therapeutic benefit in cancer.

Type I interferons (IFN-α, IFN-β) are the signature cytokines induced by two distinct TLR-independent cytosolic signaling pathways. In the first pathway, various forms of single-stranded and double-stranded (ds) RNA are sensed by RNA helicases, including retinoic acid-inducible gene I (RIG-I) and melanoma differentiation-associated gene 5 (MDA-5), and through the IFN-β promoter stimulator 1 (IPS-1) adaptor protein mediate phosphorylation of the IRF-3 transcription factor, leading to induction of IFN-β (Ireton and Gale, Viruses 3: 906-19, 2011). IPS-1⁻/⁻ deficient mice have increased susceptibility to infection with RNA viruses. Sensors that signal through the IPS-1 pathway are directly targeted for inactivation by various viral proteins, demonstrating a requirement of this cytosolic host defense pathway to control productive virus infection. Synthetic dsRNA, such as polyinosinic:polycytidylic acid (poly (I:C) and poly ICLC, an analog that is formulated with poly L lysine to resist RNase digestion, is an agonist for both TLR3 and MDA5 pathways, is a powerful inducer of IFN-β, and is currently being evaluated in several diverse clinical settings (Caskey et al., J. Exp. Med. 208: 2357-77, 2011).

STING (Stimulator of Interferon Genes) is a central mediator for the second cytosolic pathway that triggers type 1 interferon, in response to sensing cytosolic double-stranded (ds) DNA from infectious pathogens or aberrant host cells (Danger Associated Molecular Patterns, DAMPS) (Barber, Immunol. Rev 243: 99-108, 2011). Alternatively known as TMEM173, MITA, ERIS, and MPYS, STING was discovered using cDNA expression cloning methods as a MyD88-independent host cell defense factor expressed in macrophages, dendritic cells (DCs) and fibroblasts was found to induce expression of IFN-β and NF-κB dependent pro-inflammatory cytokines in response to sensing cytoplasmic DNA, in response to infection with herpes simplex virus (Ishikawa and Barber, Nature 455: 674-79, 2008).

Cyclic dinucleotides (CDNs) have been studied as ubiquitous small molecule second messengers synthesized by bacteria which regulate diverse processes including motility and formation of biofilms (Romling et al., Micrb. Mol. Biol. Rev., 77: 1-52, 2013). CDNs are also a ligand for STING (Burdette et al., Nature 478: 515-18, 2011). In response to binding CDNs, STING activates signaling through the TBK-1/IRF-3 axis and NF-κB axis and induces the expression of IFN-β and other co-regulated genes (Burdette and Vance, Nat Immunol. 14: 19-26, 2013; McWhirter et al., J. Exp. Med. 206: 1899-1911, 2009). Cyclic (c)-di-AMP is secreted by multidrug resistance efflux pumps from the intracellular bacterium *Listeria monocytogenes* into the cytosol of infected host antigen presenting cells, and is correlated with CD4⁺ and CD8⁺ T cell-mediated protection in the mouse listeriosis model (Woodward et al., Science 328, 1703-05, 2010; Crimmins et al., Proc. Natl. Acad. Sci. USA 105: 10191-10196, 2008). Induction of IFN-3 in Lm-infected macrophages is dependent upon activation of the STING signaling pathway, and the level of type I IFN induced by c-di-AMP in macrophages from MyD88⁻/⁻ Trif⁻/⁻ or C57BL/6 parental mice is indistinguishable (Leber et al., PLoS Pathog 4(1): e6. doi:10.1371, 2008; Witte et al., mBio 4: e00282-13, 2012). In contrast, IFN-β is not induced by CDNs in macrophages derived from goldenticket (gt) mice encoding a nonfunctional mutant STING protein (Sauer et al., Infect. Immun. 79: 688-94, 2011). The extracellular bacterium, *Vibrio cholera*, produces a hybrid c-GMP-AMP (cGAMP) molecule, which also induces the STING pathway (Davies et al., Cell 149: 358-70, 2012). The activation of innate immunity with these ubiquitous second messengers suggests that sensing CDNs may be integral to host defense against bacterial infection.

While STING was discovered as being the critical sensor for inducing the production of IFN-β in response to infection with herpes simplex virus, how the DNA from this viral pathogen was detected in the cytoplasm initially remained elusive. This conundrum was solved with the discovery of cyclic GMP-AMP synthase (cGAS), a host cell nucleotidyl transferase that directly binds dsDNA, and in response synthesizes a second messenger, cyclic GMP-AMP (cGAMP), which activates the STING pathway and induces IFN-β expression (Sun et al., Science 339: 786-91, 2013; Wu et al., Science 339: 826-30, 2013). Cells without a functional cGAS are unable to express IFN-β in response to stimulation with cytosolic DNA. It was later shown that cells expressing a particular STING allele were non-responsive to stimulation by CDNs, but responsive to stimulation with dsDNA in a cGAS-dependent and TLR9 (MyD88)-independent manner (Diner et. al., 2013). This observation was incompatible with a mechanism defined by cGAS synthesizing STING-activating CDN ligands in response to sensing cytosolic dsDNA. This apparent paradox was resolved by several independent investigators, who demonstrated that cGAS produces a non-canonical CDN (c-GMP-AMP; cGAMP) that activates STING alleles that are non-responsive to canonical CDNs (Civril et al., Nature 498: 332-37, 2013, Diner et al., 2013, Gao et al., 2013, Ablasser et al., Nature 498: 380-84, 2013, Kranzusch et al., Cell Reports 3: 1362-68, 2013, Zhang et al., Mol. Cell. 51: 226-35, 2013). cGAMP thus functions as a second messenger that binds to and activates STING. Unlike the CDN second messengers produced by bacteria, in which the two purine nucleosides are joined by a phosphate bridge with bis-(3', 5') linkages, the internucleotide phosphate bridge in the cyclic-GMP-AMP synthesized by cGAS is joined by non-canonical 2',5' and 3',5' linkages (alternatively termed "mixed" linkages or ML), represented c[G(2',5')pA(3',5')p]. These 2',5'-3',5' molecules bind STING with nM affinity, some 300-fold better than bacterial c-di-GMP. Thus, it has been suggested that the 2',5'-3',5' molecules represent much more potent physiological ligands in terms of STING targeting. Zhang et al., 2013; see also, Xiao and Fitzgerald, Mol. Cell 51: 135-39, 2013. The differences in internucleotide phosphate bridge structures between CDNs produced by bacteria [canonical bis-(3', 5') linkages] and by host cell cGAS (non-canonical 2',5' and 3',5' linkages) indicates that the STING receptor evolved to distinguish between CDNs produced by bacteria or by host cell cGAS.

Human STING has known polymorphisms, including alleles encoding histidine at position 232, which are refractory to canonical CDNs, but not non-canonical CDNs (Diner et al., 2013, Jin et al., 2011). Single nucleotide polymorphisms in the hSTING gene have been shown to affect the responsiveness to bacterial-derived canonical CDNs (Diner et al., 2013; Gao et al., 2013; Conlon et. al., 2013). Five haplotypes of hSTING have been identified (WT, REF, HAQ, AQ and Q alleles), which vary at amino acid positions 71, 230, 232 and 293 (Jin et al., 2011; Yi et al., 2013). Cells expressing hSTING reportedly respond poorly to stimulation with bacterial CDNs cGAMP, c-di-AMP and c-di-GMP having bis-(3', 5') linkages, but are responsive to the endogenously produced cGAS product, ML cGAMP (Diner et al., 2013). Therefore, the published literature indicates that for broad activation of all human STING alleles it is desirable that the CDN internucleotide phosphate bridge have a non-canonical, mixed linkage c[G(2',5')pA(3',5')p] structure. Examples of cyclic purine dinucleotides are described in some detail in, e.g., U.S. Pat. Nos. 7,709,458 and 7,592,326; WO2007/054279, WO2014/093936, and WO2014/189805; and Yan et al., Bioorg. Med. Chem Lett. 18: 5631 (2008).

Native CDN molecules are sensitive to degradation by phosphodiesterases that are present in host cells, for example in antigen presenting cells, which take up vaccine formulations that contain said native CDN molecules. The potency of a defined adjuvant may be diminished by such degradation, as the adjuvant would be unable to bind and activate its defined PRR target. Lower adjuvant potency could be measured, for example by a lower amount of induced expression of a signature molecule of innate immunity (e.g., IFN-β), correlated with weaker vaccine potency, as defined by the magnitude of a measured antigen-specific immune response.

Definitions

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" or "co-administered" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration. By "administered simultaneously" it is meant to be implied that two or more agents be administered at essentially the same time, although not necessarily administered as a single composition or by the same route of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) receptor can encompass GM-CSF, a mutein or derivative of GM-CSF, a peptide mimetic of GM-CSF, a small molecule that mimics the biological function of GM-CSF, or an antibody that stimulates GM-CSF receptor.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms with from 1 to about 6 carbon atoms being more preferred. The term "lower alkyl" as used herein includes from 1 to about 6 carbon atoms. Alkyl groups as used herein may optionally include one or more further substituent groups.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHl domains; (ii) a F(ab')2 fragment, a bivalent fragment comprising two Fab fragments linked by a disulfide bridge at the hinge region; (iii) a Fd fragment consisting of the VH and CHl domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "di-OH reference compound" as used herein refers to a known ML-CDN compound lacking any 2' and/or 3' fluoro substituent of the mono- or di-F-ML-CDN compounds as described herein, instead having an —OH substituent at these positions. Preferably, the known di-OH reference compound for the mono- or di-F-ML-CDN compounds as described herein has the same bases as the mono- or di-F-ML-CDN compound, and has the same phosphodiester linkage (e.g. phosphodiester or the thiophosphate analog). For example, the di-OH reference compound for 2'3'-RR-(3'F-A)(2'F-A), 2'3'-RR-(3'F-A)(A), 2'3'-RR-(A)(2'F-A), and 2'3'-RR-(3'βF-A)(2'F-A) is 2'3'-RR-(A)(A); the di-OH reference compound for 2'3'-RR-(G)(2'F-A), 3'2'-RR-(2'F-G)(3'F-A), and 3'2'-RR-(2'F-G)(A) is 2'3'-RR-(G)(A); and the di-OH reference compound for 2'3'-(G)(2'F-A) and 2'3'-(3'F-G)(2'F-A) is 2'3'-(G)(A). The di-OH reference compounds 2'3'-RR-(A)(A) and 2'3'-RR-(G)(A) are described, for example, in PCT publication WO 2014/189805.

By "an agent that enhances permeability" or "an agent that enhances uptake" as used herein as it relates to cell permeability or uptake of compound by cells, is an agent that enhances the permeability of a cell to a compound or enhances the uptake of a compound by the cell, either in vitro, or in vivo. The mono- and di-F-ML-CDN compounds as described herein, or di-OH reference compound can be compared in an in vitro cell based assay, wherein the assay may be performed with or without an agent, such as digitonin, that allows for the compound to be taken up by the cell. The mono- and di-F-ML-CDN compounds as described herein are surprisingly active in such cell based assays without the need for such an agent that enhances permeability of the cell or enhances uptake of the compound by the cell, for example in the THP-1 cell assay as described herein. Compositions comprising the mono- and di-F-ML-CDN compounds as described herein can be formulated without an agent that enhances permeability of the cell or enhances uptake of the compound by the cell, for example without a delivery vehicle that enhances permeability of the cell or enhances cellular uptake. Such additives or delivery vehicles include, without limitation, lipid or lipid-like adjuvants, liposomes, interbilayer crosslinked multilamellar vesicles, nanocarriers, nanoparticles and the like, such as nanoparticles comprising Poly(lactic acid) (PLA), Poly(glycolic acid) (PGA), and/or their copolymers such as biodegradable poly(D,L-lactic-co-glycolic acid) [PLGA]-based or poly anhydride-based nanoparticles or microparticles.

By "substantially purified" with regard to CDNs of the invention is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the CDN activity present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8$ $M^{-1}$. Affinity is calculated as $K_d = k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "prodrug" as used herein refers to a modification of contemplated compounds, wherein the modified compound exhibits less pharmacological activity (as compared to the modified compound) and wherein the modified compound is converted within the body (e.g., in a target cell or target organ) back into the unmodified form through enzymatic or non-enzymatic reactions. In certain embodiments, the hydroxyl on one ribose comprises a prodrug leaving group. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011. Examples include, but are not limited to, leaving groups removed by cellular esterases, a C6 to C18 fatty acid ester, a myristoyl ester, a pentanoyl ester, a hexanoyl ester, and a heptanoyl ester. For example, the mono-2'F-ML-CDN or mono-3'F-ML-CDN compounds as described herein can include substitution at the 3' hydroxyl or 2' hydroxyl, respectively, to form such esters.

The term "subject" or "individual" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

"Vaccine" encompasses preventative vaccines. Vaccine also encompasses therapeutic vaccines, e.g., a vaccine administered to a mammal that comprises a condition or disorder associated with the antigen or epitope provided by the vaccine.

Cyclic Purine Dinucleotides

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyzed by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3

(IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

Cyclic purine dinucleotides for use as precursors to derive the CDNs of the present invention are described in some detail in, e.g., Gao et al., Cell (2013) 153: doi: 10.1016/j.cell.2013.04.046; U.S. Pat. Nos. 7,709,458 and 7,592,326; WO2007/054279, WO2014/093936, and WO2014/189805; and Yan et al., Bioorg. Med. Chem Lett. 18: 5631 (2008). These CDNs may be modified using standard organic chemistry techniques in order to produce the CDNs of the present invention.

The mono- or di-F-ML-CDN compounds of the present invention as described herein are potent STING agonists, and demonstrate unexpected improvement over known non-fluoro substituted ML-CDN compounds, such as 2'3'-RR-(A)(A), a STING agonist which has been shown to be efficacious in mouse tumor models (Corrales et al., Cell Reports 2015, 11:1018-1031). The mono- or di-F-ML-CDN compounds of the present invention are compared to known compounds that differ in the substitution of the 2' and 3' position, for example a di-OH reference compound such as 2'3'-(A)(A), 2'3'-(G)(A), 3'2'-(G)(A), 2'3'-RR-(A)(A) or 2'3'-RR-(G)(A). The properties of the mono- or di-F-ML-CDN compounds are demonstrated in Examples 14-16 below, where the compounds demonstrate an improvement over the di-OH reference compound as having one or more of i) a higher $T_m$ shift in a DSF assay as described in Example 14 for one or more of hSTING (WT), hSTING (HAQ) or hSTING (REF); ii) a higher relative expression of IFN-β transcript in an hPBMC assay as described in Example 15 for one or more of hSTING (WT), hSTING (HAQ) or hSTING (REF); or iii) a lower EC50 in a THP1 cellular assay as described in Example 16, where preferably the THP1 assay is performed in the absence of digitonin. In some embodiments, the mono- or di-F-ML-CDN demonstrates an improvement over the di-OH reference compound as having two or more of i) a higher $T_m$ shift in a DSF assay as described in Example 14 for one or more of hSTING (WT), hSTING (HAQ) or hSTING (REF); ii) a higher relative expression of IFN-β transcript in an hPBMC assay as described in Example 15 for one or more of hSTING (WT), hSTING (HAQ) or hSTING (REF); or iii) a lower EC50 in a THP1 cellular assay as described in Example 16, where preferably the THP1 assay is performed in the absence of digitonin. In some embodiments, the mono- or di-F-ML-CDN demonstrates an improvement over the di-OH reference compound as having each of i) a higher $T_m$ shift in a DSF assay as described in Example 14 for one or more of hSTING (WT), hSTING (HAQ) or hSTING (REF); ii) a higher relative expression of IFN-β transcript in an hPBMC assay as described in Example 15 for one or more of hSTING (WT), hSTING (HAQ) or hSTING (REF); or iii) a lower EC50 in a THP1 cellular assay as described in Example 16, where preferably the THP1 assay is performed in the absence of digitonin. In some embodiments of the mono- or di-F-ML-CDN compounds as described herein, the mono- or di-F-ML-CDN compound has at least a 2-fold, at least a 5-fold, at least a 10-fold, at least a 50-fold, at least a 100-fold, at least a 500-fold, or at least a 1000-fold higher relative expression of IFN-β transcript in an hPBMC assay as described in Example 15 for hSTING REF allele as compared to 2'3'-RR-(A)(A). In some embodiments, the mono- or di-F-ML-CDN compound has an EC50 in the THP1 assay described in Example 16 without addition of digitonin that is at least 2-fold, at least 3-fold, at least 4-fold, at least 5-fold, at least 6-fold, at least 7-fold, or at least 8-fold lower than the EC50 of a di-OH reference compound. In some embodiments, the mono- or di-F-ML-CDN compound has an EC50 in the THP1 cellular assay without addition of an agent that enhances the permeability of the compound to the cell or an agent that enhances the uptake of the compound by the cell that is less than 40 µM, less than 30 µM, less than 20 µM, less than 15 µM, or less than 10 µM. In some embodiments, the mono- or di-F-ML-CDN compound has an EC50 in the THP1 assay described in Example 16 without addition of digitonin that is less than 40 µM, less than 30 µM, less than 20 µM, less than 15 µM, or less than 10 µM.

The mono- or di-F-ML-CDN compounds of the present invention as described herein can be phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases S1 and P1, RNases, serum nucleases and snake venom phosphodiesterase. In addition, the potential for crossing the lipid bilayer increases.

A phosphorothioate linkage is inherently chiral. The skilled artisan will recognize that the phosphates in this structure may each exist in R or S forms. Thus, Rp,Rp, Sp,Sp, Sp,Rp, and Rp,Sp forms are possible. As noted above, the mono- or di-F-ML-RR-CDN compounds of the present invention are preferably of the Rp,Rp form, e.g. 2'F-ML-RR-CDN, 3'F-ML-RR-CDN or 2'3'F-ML-RR-CDN compounds as described herein.

As noted above, the mono- or di-F-ML-CDN compounds also include prodrug forms of the CDNs. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

The term "substantially pure" as used herein with regard to dithio-diphosphate ML cyclic purine dinucleotides refers to an Rp,Rp form which is at least 75% pure relative to other possible stereochemistries at the chiral phosphorus centers indicated in the mono- or di-F-ML-RR-CDN compounds as described herein. By way of example, a "substantially pure 2'3'-RR-(G)(2'F-A)" would be at least 75% pure with regard to the Rp,Sp, Sp,Rp and Sp,Sp, i.e. with respect to 2'3'-RS-(G)(2'F-A), 2'3'-SR-(G)(2'F-A), and 2'3'-SS-(G)(2'F-A). In preferred embodiments, a substantially pure cyclic purine dinucleotide is at least 85% pure, at least 90% pure, at least 95% pure, at least 97% pure, and at least 99% pure. While a substantially pure cyclic purine dinucleotide preparation of the invention is "stereochemically pure," this is not meant to indicate that all CDNs within the preparation having a particular stereochemistry at these chiral centers are otherwise identical. For example, a substantially pure cyclic purine dinucleotide preparation may contain a combination of 2'3'-RR-(G)(2'F-A)thiophosphate and 2'3'-RR-(A)(2'F-A) thiophosphate and still be a substantially pure cyclic purine dinucleotide preparation. Such a preparation may also include other components as described hereinafter that are advantageous for patient treatment, provided that all CDNs within the preparation having a particular stereochemistry at these chiral centers.

The mono- or di-F-ML-CDN compounds and compositions thereof described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the mono- or di-F-ML-CDN and compositions thereof described herein are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

The mono- or di-F-ML-CDN compounds and compositions thereof described herein may be administered before, after, and/or simultaneously with an additional therapeutic or prophylactic composition or modality. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

Because of the adjuvant properties of the compounds of the present invention, their use may also be combined with other therapeutic modalities including other vaccines, adjuvants, antigen, antibodies, and immune modulators. Examples are provided below.

Adjuvants

In addition to the mono- or di-F-ML-CDN compounds and compositions thereof described herein described above, the compositions or methods of the present invention may further comprise one or more additional substances which, because of their nature, can act to stimulate or otherwise utilize the immune system to respond to the cancer antigens present on the targeted tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), and/or pathogen-associated molecular patterns ("PAMPs"). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

Immune Checkpoint Inhibitors

The mono- and di-F-ML-CDN compounds as described herein can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, or a TIGIT pathway antagonist. In some embodiments, the immune checkpoint inhibitor is selected from the group consisting of an anti-CTLA-4 antibody, an anti-PD-1 antibody, an anti-Tim-3 antibody, an anti-Vista antibody, an anti-BTLA antibody, an anti-LAG-3 antibody, an anti-TIGIT antibody, an anti-CD47 antibody, or an anti-SIRPα antibody.

The mono- and di-F-ML-CDN compounds as described herein can be used in combination with CTLA-4 pathway antagonists. In some embodiments, the combination is used to treat a solid tumor or a hematologic malignancy. CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma. In some embodiments, the CTLA-4 pathway antogonist is an anti-CTLA-4 antibody molecule selected from the group consisting of tremelimumab and ipilimumab. In some embodiments, the anti-CTLA-4 antibody is an anti-CTLA-4 antibody as disclosed in e.g., U.S. Pat. No. 5,811,097.

Ipilimumab (Yervoy™, a CTLA-4 antibody, also known as MDX-010, CAS No. 477202-00-9) and tremelimumab (IgG2 monoclonal antibody available from Pfizer, formerly known as ticilimumab, CP-675,206) are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1 (PD-1), B and T lymphocyte attenuator, transforming growth factor beta β, interleukin-10, and vascular endothelial growth factor.

In some embodiments, the mono- and di-F-ML-CDN compounds as described herein can be used in combination with an anti-CTLA-4 antibody and an anti-PD-1 antibody. In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

The mono- and di-F-ML-CDN compounds as described herein can be used in combination with PD-1 pathway antagonists. In some embodiments, the combination is used to treat a solid tumor or a hematologic malignancy. PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. Anti-PD-1 antibody molecules (e.g. Nivolumab (Opdivo™), pembrolizumab (Keytruda™), and pidilizumab), and AMP-224 have been reported in the literature to be examples of PD-1 pathway blockers which may find use in the present invention. In some embodiments, the PD-1 pathway antagonist is an anti-PD-1 antibody molecule selected from the group consisting of nivolumab, pembrolizumab or pidilizumab.

In some embodiments, the anti-PD-1 antibody is nivolumab. Alternative names for nivolumab include MDX-1106, MDX-1106-04, ONO-4538, or BMS-936558. In some embodiments, the anti-PD-1 antibody is nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is nivolumab, and having a sequence disclosed herein (or a sequence substantially identical or similar thereto, e.g., a sequence at least 85%, 90%, 95% identical or higher to the sequence specified).

The heavy chain amino acid sequence of nivolumab is as follows:

(SEQ ID NO: 1)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

The light chain amino acid sequence of nivolumab is as follows:

(SEQ ID NO: 2)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some embodiments, the anti-PD-1 antibody is pembrolizumab. Pembrolizumab (also referred to as lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. In one embodiment, the inhibitor of PD-1 is pembrolizumab, and having a sequence disclosed herein (or a sequence substantially identical or similar thereto, e.g., a sequence at least 85%, 90%, 95% identical or higher to the sequence specified).

The heavy chain amino acid sequences of pembrolizumab is as follows:

(SEQ ID NO: 3)
QVQLVQSGVE VKKPGASVKV SCKASGYTFT NYYMYWVRQA PGQGLEWMGG    50

INPSNGGTNF NEKFKNRVTL TTDSSTTTAY MELKSLQFDD TAVYYCARRD   100

-continued

```
YRFDMGFDYW GQGTTVTVSS ASTKGPSVFP LAPCSRSTSE STAALGCLVK    150

DYFPEPVTVS WNSGALTSGV HTFPAVLQSS GLYSLSSVVT VPSSSLGTKT    200

YTCNVDHKPS NTKVDKRVES KYGPPCPPCP APEFLGGPSV FLFPPKPKDT    250

LMISRTPEVT CVVVDVSQED PEVQFNWYVD GVEVHNAKTK PREEQFNSTY    300

RVVSVLTVLH QDWLNGKEYK CKVSNKGLPS SIEKTISKAK GQPREPQVYT    350

LPPSQEEMTK NQVSLTCLVK GFYPSDIAVE WESNGQPENN YKTTPPVLDS    400

DGSFFLYSRL TVDKSRWQEG NVFSCSVMHE ALHNHYTQKS LSLSLGK       447
```

The light chain amino acid sequences of pembrolizumab is as follows:

```
                                                 (SEQ ID NO: 4)
EIVLTQSPAT LSLSPGERAT LSCRASKGVS TSGYSYLHWY QQKPGQAPRL     50

LIYLASYLES GVPARFSGSG SGTDFTLTIS SLEPEDFAVY YCQHSRDLPL    100

TFGGGTKVEI KRTVAAPSVF IFPPSDEQLK SGTASVVCLL NNFYPREAKV    150

QWKVDNALQS GNSQESVTEQ DSKDSTYSLS STLTLSKADY EKHKVYACEV    200

THQGLSSPVT KSFNRGEC                                      218
```

In some embodiments, the anti-PD-1 antibody is pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

In some embodiments, the anti-PD-1 antibody is AMP 514 (Amplimmune), or an anti-PD-1 antibody as disclosed in U.S. Pat. No. 8,609,089, US 2010028330, and/or US 20120114649.

In some embodiments the PD-1 pathway antagonist is an anti-PD-1 antibody molecule disclosed in US 2015/0210769, published on Jul. 30, 2015, entitled "Antibody Molecules to PD-1 and Uses Thereof".

In one embodiment, the anti-PD-1 antibody molecule includes at least one or two heavy chain variable domain (optionally including a constant region), at least one or two light chain variable domain (optionally including a constant region), or both, comprising the amino acid sequence of BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto.

In yet another embodiment, the anti-PD-1 antibody molecule includes at least one, two, or three complementarity determining regions (CDRs) from a heavy chain variable region and/or a light chain variable region of an antibody described in US 2015/0210769, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 therein, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1 therein.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-PD-1 antibody molecule includes: (a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; (b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769; (c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each as disclosed in Table 1 of US 2015/0210769; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each as disclosed in Table 1 of US 2015/0210769.

In another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each as disclosed in Table 1 of US 2015/0210769.

In some embodiments the PD-1 pathway antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342) is a PD-L2 Fc fusion soluble receptor that blocks the interaction between PD-1 and B7-H1.

In some embodiments the PD-1 pathway antagonist is a PD-L1 or PD-L2 inhibitor. In some embodiments the PD-L1 or PD-L2 inhibitor is an anti-PD-L1 antibody or an anti-PD-L2 antibody.

In some embodiments, the PD-L1 inhibitor is an anti-PD-L1 antibody. Exemplary non-limiting combinations and uses of the anti-PD-L1 antibody molecules are disclosed in US 2016/0108123, published Apr. 21, 2016, entitled "Antibody Molecules to PD-L1 and Uses Thereof".

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1 of US 2016/0108123, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes: (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11, each disclosed in Table 1 of US 2016/0108123.

In one embodiment, the anti-PD-L1 antibody molecule includes: (i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Table 1 of US 2016/0108123.

In one embodiment, the anti-PD-L1 antibody molecule comprises the VHCDR1 amino acid sequence of SEQ ID NO: 1. In another embodiment, the anti-PD-L1 antibody molecule comprises the VHCDR1 amino acid sequence of SEQ ID NO: 4. In yet another embodiment, the anti-PD-L1 antibody molecule comprises the VHCDR1 amino acid sequence of SEQ ID NO: 195, each disclosed in Table 1 of US 2016/0108123.

In some embodiments, the anti-PD-L1 inhibitor is chosen from YW243.55.570, MPDL3280A, MEDI-4736, MSB-0010718C, or MDX-1105. In some embodiments, the PD-L1 inhibitor is an anti-PD-L1 antibody MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed therein (or a sequence substantially identical or similar thereto, e.g., a sequence at least 85%, 90%, 95% identical or higher to the sequence specified).

The heavy chain amino acid sequence (SEQ ID NO: 24 as disclosed in WO2013/079174) of MSB0010718C includes at least the following:

(SEQ ID NO: 5)
EVQLLESGGGLVQPGGSLRLSCAASGFTFSSYIMMWVRQAPGKGLEWVSS

IYPSGGITFYADKGRFTISRDNSKNTLYLQMNSLRAEDTAVYYCARIKLG

TVTTVDYWGQGTLVTVSS

The light chain amino acid sequence (SEQ ID NO: 25 as disclosed in WO2013/079174) of MSB0010718C includes at least the following:

(SEQ ID NO: 6)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

EGTGTKVTVL

In one embodiment, the PD-L1 inhibitor is YW243.55.S70. The YW243.55.S70 antibody is an anti-PD-L1 antibody as described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342

The mono- and di-F-ML-CDN compounds as described herein can be used in combination with TIM-3 pathway antagonists. In some embodiments, the combination is used to treat a solid tumor or a hematologic malignancy. In some embodiments, the TIM-3 pathway antagonist is an anti-TIM-3 antibody. In some embodiments, anti-TIM-3 antibody molecules are disclosed in US 2015/0218274, published on Aug. 6, 2015, entitled "Antibody Molecules to TIM-3 and Uses Thereof".

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto.

In yet another embodiment, the anti-TIM-3 antibody molecule includes at least one, two, or three complementarity determining regions (CDRs) from a heavy chain variable region and/or a light chain variable region of an antibody described in US 2015/0218274, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3- hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 therein; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Table 1-4 therein.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4 therein. In one embodiment, one or more of the CDRs (or collectively all of the CDRs) have one, two, three, four, five, six or more changes, e.g., amino acid substitutions or deletions, relative to the amino acid sequence shown in Tables 1-4 therein, or encoded by a nucleotide sequence shown in Tables 1-4 therein.

In one embodiment, the anti-TIM-3 antibody molecule includes: (a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; (d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274; (e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each as disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each as disclosed in Tables 1-4 of US 2015/0218274.

In some embodiments, the TIM-3 pathway antagonist is an anti-TIM-3 antibody as disclosed in U.S. Pat. No. 8,552,156, WO 2011/155607, EP 2581113 or U.S. Publication No.: 2014/044728.

The mono- and di-F-ML-CDN compounds as described herein can be used in combination with LAG-3 pathway antagonists. In some embodiments, the combination is used to treat a solid tumor or a hematologic malignancy. In some embodiments, the LAG-3 pathway antagonist is an anti-LAG-3 antibody. In some embodiments the anti-LAG-3 antibody molecules are disclosed in US 2015/0259420, filed Mar. 13, 2015, entitled "Antibody Molecules to LAG-3 and Uses Thereof".

In one embodiment, the anti-LAG-3 antibody molecule includes at least one or two heavy chain variable domain (optionally including a constant region), at least one or two light chain variable domain (optionally including a constant region), or both, comprising the amino acid sequence of any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three complementarity determining regions (CDRs) from a heavy chain variable region and/or a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1 of US 2015/0259420, or encoded by the nucleotide sequence in Table 1 therein; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein. In certain embodiments, the anti-PD-L1 antibody molecule includes a substitution in a light chain CDR, e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1 of US 2015/0259420, or encoded by a nucleotide sequence shown in Table 1 therein. In one embodiment, one or more of the CDRs (or collectively all of the CDRs) have one, two, three, four, five, six or more changes, e.g., amino acid substitutions or deletions, relative to the amino acid sequence shown in Table 1 therein, or encoded by a nucleotide sequence shown in Table 1 therein.

In one embodiment, the anti-LAG-3 antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each as disclosed in Table 1 of US 2015/0259420.

In another embodiment, the anti-LAG-3 antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3, each as disclosed in Table 1 of US 2015/0259420; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each as disclosed in Table 1 of US 2015/0259420.

In one embodiment, the anti-LAG-3 antibody molecule comprises the VHCDR1 amino acid sequence of SEQ ID NO: 1 as disclosed in Table 1 of US 2015/0259420. In another embodiment, the anti-LAG-3 antibody molecule comprises the VHCDR1 amino acid sequence of SEQ ID NO: 4 as disclosed in Table 1 of US 2015/0259420. In yet another embodiment, the anti-LAG-3 antibody molecule comprises the VHCDR1 amino acid sequence of SEQ ID NO: 286, as disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

The mono- and di-F-ML-CDN compounds as described herein can be used in combination with APRIL antagonists. In some embodiments, the combination is used to treat a hematologic malignancy. In some embodiments, the APRIL antagonist is an anti-APRIL antibody. In some embodiments the anti-APRIL antibody molecule is hAPRIL.01A or hAPRIL.03A (Guadagnoli et al., Blood 2011 117:6856-6865; doi: 10.1182/blood-2011-01-330852.

T-Cell Receptor Agonists

The mono- and di-F-ML-CDN compounds as described herein can be used in combination with a T-cell receptor agonist, such as a CD28 agonist, an OX40 agonist, a GITR agonist, a CD137 agonist, a CD27 agonist or an HVEM agonist.

The mono- and di-F-ML-CDN compounds as described herein can be used in combination with a CD27 agonist. Exemplary CD27 agonists include an anti-CD27 agonistic antibody, e.g. as described in PCT Publication No. WO 2012/004367.

The mono- and di-F-ML-CDN compounds as described herein can be used in combination with CD47/SIRPα pathway antagonists. In some embodiments, the combination is used to treat a solid tumor or a hematologic malignancy. In some embodiments, the CD47/SIRPα pathway antagonist is an anti-CD47 antibody. In some embodiments the anti-CD47 antibody molecule is Hu5F9-G4 (Liu et al., PLoS One 10(9):e0137345. doi: 10.1371/journal.pone.0137345, 2015. In some embodiments, the CD47/SIRPα pathway antagonist is an anti-SIRPα antibody. In some embodiments the anti-SIRPα antibody molecule is disclosed in WO2015138600 or WO2013056352. In some embodiments, the CD47/SIRPα pathway antagonist is a SIRPα variant as described in Weiskopf et al., Science 2013; 341(6141):10.1126/science.1238856. doi: 10.1126/science. 1238856.

The mono- and di-F-ML-CDN compounds as described herein can be used in combination with a GITR agonist. In some embodiments, the combination is used to treat a solid tumor or a hematologic malignancy. Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, U.S. Pat. No. 8,709,424, PCT Publication No.: WO 2013/039954, International Publication No.: WO2013/039954, U.S. Publication No.: US2014/0072566, International Publication NO.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479.

In one embodiment, the mono- and di-F-ML-CDN compounds as described herein is used in combination with a GITR agonist used in combination with a PD-1 inhibitor, e.g., as described in WO2015/026684.

In another embodiment, the mono- and di-F-ML-CDN compounds as described herein is used in combination with a GITR agonist used in combination with a TLR agonist, e.g., as described in WO2004060319, and International Publication No.: WO2014012479.

TLR Agonists

The mono- and di-F-ML-CDN compounds as described herein can be used in combination with a Toll like receptor agonist. The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific $CD4^+$ and $CD8^+$ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
Glucopyranosyl lipid adjuvant (GLA), a TLR-4 agonist;
bacterial flagellin, a TLR-5 agonist;
sialyl-Tn (STn), a carbohydrate associated with the MUC1 mucin on a number of human cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the mono- or di-F-ML-CDN compounds that bind to STING and induce STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Antibody Therapeutics

The mono- and di-F-ML-CDN compounds as described herein can be used in combination with therapeutic antibodies. In some embodiments, the mechanism of action of the therapeutic antibody is Antibody-Dependent Cell-Mediated Cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC.

The following are an exemplary list of antibodies which may be used together with the mono- and di-F-ML-CDN compounds of the present invention.

Muromonab-CD3: Used to prevent acute rejection of organ, e.g., kidney, transplants. The humanized versions show promise in inhibiting the autoimmune destruction of beta cells in Type 1 diabetes mellitus.

Infliximab (Remicade®) and adalimumab (Humira®): Bind to tumor necrosis factor-alpha (TNF-α). Used in some inflammatory diseases such as rheumatoid arthritis, psoriasis, Crohn's disease.

Omalizumab (Xolair®). Binds to IgE thus preventing IgE from binding to mast cells. Used against allergic asthma.

Daclizumab (Zenapax®). Binds to part of the IL-2 receptor exposed at the surface of activated T cells. Used to prevent acute rejection of transplanted kidneys.

Rituximab (trade name=Rituxan®). Binds to the CD20 molecule found on most B-cells and is used to treat B-cell lymphomas.

Ibritumomab (trade name=Zevalin®). This is a monoclonal antibody against the CD20 molecule on B cells (and lymphomas) conjugated to isotopes. Given to the lymphoma patient supplemented with Rituxan.

Tositumomab (Bexxar®). This is a conjugate of a monoclonal antibody against CD20 and the radioactive isotope iodine-131 (131I).

Cetuximab (Erbitux®). Blocks HER1, a receptor for epidermal growth factor (EGF) that is found on some tumor cells (some breast cancers, lymphomas).

Trastuzumab (Herceptin®). Blocks HER2, a growth factor receptor over-expressed in some 20% of breast cancers.

Adcetris®. A conjugate of a monoclonal antibody that binds CD30, a cell-surface molecule expressed by the cells of some lymphomas but not found on the normal stem cells needed to repopulate the bone marrow.

Alemtuzumab (Campath-1H®). Binds to CD52, a molecule found on lymphocytes and depletes both T cells and B cells. Has produced complete remission of chronic lymphocytic leukemia and shows promise in preventing rejection of kidney transplants.

Lym-1 (Oncolym®). Binds to the HLA-DR-encoded histocompatibility antigen that can be expressed at high levels on lymphoma cells.

Ipilimumab (Yervoy®) that acts to enhance the body's own immune response to tumors.

Vitaxin. Binds to a vascular integrin (alpha-v/beta-3) found on the blood vessels of tumors but not on the blood vessels supplying normal tissues. In Phase II clinical trials, Vitaxin has shown some promise in shrinking solid tumors without harmful side effects.

Bevacizumab (Avastin®). Binds to vascular endothelial growth factor (VEGF) preventing it from binding to its receptor. Used for the treatment of colorectal cancers.

Abciximab (ReoPro®). Inhibits the clumping of platelets by binding the receptors on their surface that normally are linked by fibrinogen. Helpful in preventing reclogging of the coronary arteries in patients who have undergone angioplasty.

Additional therapeutic antibodies that may be used in combination with the mono- and di-F-ML-CDN compounds as described herein include a prolactin receptor (PRLR) inhibitor, e.g. as disclosed in U.S. Pat. No. 7,867,493, a HER3 inhibitor, e.g. as disclosed in PCT Publication No. WO 2012/022814, an EGFR2 and/or EGFR4 inhibitor, e.g. as disclosed in PCT Publication No. WO 2014/160160, an M-CSF inhibitor, e.g. as disclosed in PCT Publication No. WO 2004/045532, an anti-APRIL antibody, e.g. as disclosed in U.S. Pat. No. 8,895,705, or an anti-SIRPα or anti-CD47 antibody, e.g. as disclosed in U.S. Pat. Nos. 8,728,476 and 8,562,997.

In one embodiment, the combination, e.g., a combination comprising one or more mono- or di-F-ML-CDN compounds as described herein, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, the mono- or di-F-ML-CDN compound is used in combination with human monoclonal antibody molecule (Compound A26) described in U.S. Pat. No. 7,867,493 to treat a disorder such as, a cancer, a prostate cancer, or a breast cancer.

In another embodiment, the combination, e.g., a combination comprising one or more mono- or di-F-ML-CDN compounds as described herein, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, the mono- or di-F-ML-CDN compound is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer. In some embodiments, Compound A31 is a human monoclonal antibody molecule. In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the combination, e.g., a combination comprising one or more mono- or di-F-ML-CDN compounds as described herein, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425 as described therein), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, the mono- or di-F-ML-CDN compound is used in combination with Compound A32, or in further combination with a compound as described in Table 2, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer. In some embodiments, Compound A32 is an antibody molecule drug conjugate against an FGFR2 and/or FGFR4, e.g., mAb 12425.

In another embodiment, the combination, e.g., a combination comprising one or more mono- or di-F-ML-CDN compounds as described herein, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, the mono- or di-F-ML-CDN compound is used in combination with Compound A33, or a compound as described in PCT Publication No. WO 2004/045532, to treat a disorder such as a cancer, a prostate cancer, a breast cancer, or pigmented villonodular synovitis (PVNS). In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

Delivery Agents

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833 describes suitable liposomal preparations. Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammoniumpropane, and nod-like receptor agonists. Advantageously, these liposomal formulations can be used to deliver one or more mono- or di-F-ML-CDN compounds and compositions thereof described herein in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Technology*, 3$^{rd}$ *Edition*, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., U.S. Patent Application 20100310602).

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

Chemotherapeutic Agents

In additional embodiments the methods described herein, the mono- or di-F-ML-CDN compounds as described herein are used in combination with chemotherapeutic agents (e.g. small molecule pharmaceutical compounds). Thus the methods further involve administering to the subject an effective amount of one or more chemotherapeutic agents as an additional treatment or a combination treatment. In certain embodiments the one or more chemotherapeutic agents is selected from the group consisting of abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), enzalutamide, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In additional embodiments the methods described herein, the mono- or di-F-ML-CDN compounds as described herein are used in combination with chemotherapeutic agents and/or additional agents for treating the indications as described in the methods herein. In some embodiments, the mono- or di-F-ML-CDN compounds as described herein are used in combination with one or more agents selected from the group consisting of sotrastaurin, nilotinib, 5-(2,4-dihydroxy-5-isopropylphenyl)-N-ethyl-4-(4-(morpholinomethyl)phenyl)isoxazole-3-carboxamide, dactolisib, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one, 3-(2,6-dichloro-3,5-dimethoxyphenyl)-1-(6-((4-(4-ethylpiperazin-1-yl)phenyl)amino)pyrimidin-4-yl)-1-methylurea, buparlisib, 8-(2,6-difluoro-3,5-dimethoxyphenyl)-N-(4-((dimethylamino)methyl)-1H-imidazol-2-yl)quinoxaline-5-carboxamide, (S)—N1-(4-methyl-5-(2-(1,1,1-trifluoro-2-methylpropan-2-yl)pyridin-4-yl)thiazol-2-yl)pyrrolidine-1,2-dicarboxamide, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one, deferasirox, letrozole, (4S,5R)-3-(2'-amino-2-morpholino-4'-(trifluoromethyl)-[4,5'-bipyrimidin]-6-yl)-4-(hydroxymethyl)-5-methyloxazolidin-2-one, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one, 4-((2-(((1R,2R)-2-hydroxycyclohexyl)amino)benzo[d]thiazol-6-yl)oxy)-N-methylpicolinamide, imatinib mesylate, 2-fluoro-N-methyl-4-(7-(quinolin-6-ylmethyl)imidazo[1,2-b][1,2,4]triazin-2-yl)benzamide, ruxolitinib, panobinostat, osilodrostat, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, sonidegib phosphate, ceritinib. 7-cyclopentyl-N,N-dimethyl-2-((5-(piperazin-1-yl)pyridin-2-yl)amino)-7H-pyrrolo[2,3-d]pyrimidine-6-carboxamide, N-(4-((1R,3S,5S)-3-amino-5-methylcyclohexyl)pyridin-3-yl)-6-(2,6-difluorophenyl)-5-fluoropicolinamide, 2-(2',3-dimethyl-[2,4'-bipyridin]-5-yl)-N-(5-(pyrazin-2-yl)pyridin-2-yl)acetamide, encorafenib, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide, binimetinib, midostaurin, everolimus, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine, pasireotide diaspartate, dovitinib, (R,E)-N-(7-chloro-1-(1-(4-(dimethylamino)but-2-enoyl)azepan-3-yl)-1H-benzo[d]imidazol-2-yl)-2-methylisonicotinamide, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide, 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine, 5-chloro-N2-(4-(1-ethylpiperidin-4-yl)-2-fluoro-5-methylphenyl)-$N^4$-(5-methyl-1H-pyrazol-3-yl)pyrimidine-2,4-diamine, valspodar, and vatalanib succinate.

In one embodiment, the combination, e.g., a combination comprising one or more mono- or di-F-ML-CDN compounds as described herein, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, the mono- or di-F-ML-CDN compound is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis. In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the combination, e.g., a combination comprising one or more mono- or di-F-ML-CDN compounds as described herein, is used in combination with a BCR-ABL inhibitor, TASIGNA (Compound A2, nilotinib), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, the mono- or di-F-ML-CDN compound is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension. In one embodiment, the BCR-ABL inhibitor or TASIGNA is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the combination, e.g., a combination comprising one or more mono- or di-F-ML-CDN compounds as described herein, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051. In one embodiment, the mono- or di-F-ML-CDN compound is used in combination with 5-(2,4-dihydroxy-5-isopropylphenyl)-N-ethyl-4-(4-(morpholinomethyl)phenyl)isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination, e.g., a combination comprising one or more mono- or di-F-ML-CDN compounds as described herein, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, the mono- or di-F-ML-CDN compound is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination, e.g., a combination comprising one or more mono- or di-F-ML-CDN compounds as described herein, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, the mono- or di-F-ML-CDN compound is used in combination with Compound A5, or a compound as described in U.S. Pat. No. 8,552,002, to treat a disorder such as a digestive/gastrointestinal cancer, a hematological cancer, or a solid tumor. In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the combination, e.g., a combination comprising one or more mono- or di-F-ML-CDN compounds as described herein, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, the mono- or di-F-ML-CDN compound is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer. In one embodiment, the PI3K inhibitor or Buparlisib (Compound A6) is administered at a dose of about 100 mg (e.g., per day).

In another embodiment, the combination, e.g., a combination comprising one or more mono- or di-F-ML-CDN compounds as described herein, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386, to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, the mono- or di-F-ML-CDN compound is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis. In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment the combination, e.g., a combination comprising one or more mono- or di-F-ML-CDN compounds as described herein, is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082, to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl) pyrrolidine-1,2-dicarboxamide (Compound A8) or a compound disclosed PCT Publication No. WO 2010/029082. In one embodiment, the mono- or di-F-ML-CDN compound is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer. In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the combination, e.g., a combination comprising one or more mono- or di-F-ML-CDN compounds as described herein, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, the mono- or di-F-ML-CDN compound is used in combination with a compound disclosed in PCT Publication No. WO 2010/149755, to treat prostate cancer.

In another embodiment, the combination, e.g., a combination comprising one or more mono- or di-F-ML-CDN compounds as described herein, is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786, to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, the mono- or di-F-ML-CDN compound is used in combination with (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3 (4H)-one (Compound A10), or a compound disclosed in PCTPublication No. WO 2011/076786, to treat a disorder such as a solid tumor. In one embodiment, the HDM2 inhibitor or (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3 (4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the combination, e.g., a combination comprising one or more mono- or di-F-ML-CDN compounds as described herein, is used in combination with an iron chelating agent, Deferasirox (also known as EXJADE; Compound A111), or a compound disclosed in PCT Publication No. WO 1997/049395, to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, the mono- or di-F-ML-CDN compound is used in combination with Deferasirox (Compound A11), or a compound disclosed in PCT Publication No. WO 1997/049395, to treat iron overload, hemochromatosis, or myelodysplasia.

In another embodiment, the combination, e.g., a combination comprising one or more mono- or di-F-ML-CDN compounds as described herein, is used in combination with an aromatase inhibitor, Letrozole (also known as FEMARA; Compound A12), or a compound disclosed in U.S. Pat. No. 4,978,672, to treat a disorder, e.g., a disorder described herein. In one embodiment, the aromatase inhibitor is Letrozole (Compound A12) or a compound disclosed in U.S. Pat. No. 4,978,672. In one embodiment, the mono- or di-F-ML-CDN compound is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination, e.g., a combination comprising one or more mono- or di-F-ML-CDN compounds as described herein, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826, to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, the mono- or di-F-ML-CDN compound is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the combination, e.g., a combination comprising one or more mono- or di-F-ML-CDN compounds as described herein, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, the mono- or di-F-ML-CDN compound is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105, to treat a disorder such as a cancer or a soft tissue sarcoma.

In another embodiment, the combination, e.g., a combination comprising one or more mono- or di-F-ML-CDN compounds as described herein, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, the mono- or di-F-ML-CDN compound is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the combination, e.g., a combination comprising one or more mono- or di-F-ML-CDN compounds as described herein, is used in combination with an apoptosis inducer and/or an angiogenesis inhibitor, such as Imatinib mesylate (also known as GLEEVEC; Compound A16) or a compound disclosed in PCT Publication No. WO1999/003854, to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, the mono- or di-F-ML-CDN compound is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis. In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the combination, e.g., a combination comprising one or more mono- or di-F-ML-CDN compounds as described herein, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, the mono- or di-F-ML-CDN compound is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia. In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the combination, e.g., a combination comprising one or more mono- or di-F-ML-CDN compounds as described herein, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, the mono- or di-F-ML-CDN compound is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia. In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the combination, e.g., a combination comprising one or more mono- or di-F-ML-CDN compounds as described herein, is used in combination with a histone deacetylase (HDAC) inhibitor. In some embodiments, the HDAC inhibitor is selected from the group consisting of panobinostat, vorinostat, romidepsin, chidamide, valproic acid, belinostat, pyroxamide, mocetinostat, abexinostat, entinostat, pracinostat, resminostat, givinostat, quisinostat, ricolinostat, CUDC-101, AR-42, CHR-2845, CHR-3996, 4SC-202, and CG200745. In some embodiments, the combination comprising one or more mono- or di-F-ML-CDN compounds as described herein, is used in combination with a histone deacetylase (HDAC) inhibitor, Panobinostat (Compound A19), or a compound disclosed in PCT Publication No. WO 2014/072493, to treat a disorder, e.g., a disorder described herein. In one embodiment, the HDAC inhibitor is Panobinostat (Compound A19) or a compound disclosed in PCT Publication No. WO 2014/072493. In one embodiment, the mono- or di-F-ML-CDN compound is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer. In one embodiment, the HDAC inhibitor or Panobinostat (Compound A19) is administered at a dose of about 20 mg (e.g., per day).

In another embodiment, the combination, e.g., a combination comprising one or more mono- or di-F-ML-CDN compounds as described herein, is used in combination with an inhibitor of one or more of cytochrome P450 (e.g., 11B2), aldosterone or angiogenesis, Osilodrostat (Compound A20), or a compound disclosed in PCT Publication No. WO2007/024945, to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, the mono- or di-F-ML-CDN compound is used in combination with Osilodrostat (Compound A20), or a compound disclosed in PCT Publication No. WO2007/024945, to treat a disorder such as Cushing's syndrome, hypertension, or heart failure therapy.

In another embodiment, the combination, e.g., a combination comprising one or more mono- or di-F-ML-CDN compounds as described herein, is used in combination with a IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, the mono- or di-F-ML-CDN compound is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder. In one embodiment, the IAP inhibitor or (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the combination, e.g., a combination comprising one or more mono- or di-F-ML-CDN compounds as described herein, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120, to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, the mono- or di-F-ML-CDN compound is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation. In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the combination, e.g., a combination comprising one or more mono- or di-F-ML-CDN compounds as described herein, is used in combination with an Alk inhibitor, ceritinib (also known as ZYKADIA; Compound A23) or a compound disclosed in PCT Publication No. WO 2007/131201, to treat a disorder, e.g., a disorder described herein. In one embodiment, the Alk inhibitor is ceritinib (Compound A23) or a compound disclosed in PCT Publication No. WO 2007/131201. In one embodiment, the mono- or di-F-ML-CDN compound is used in combination with ceritinib (Compound A23), or a compound disclosed in PCT Publication No. WO 2007/131201, to treat a disorder such as non-small cell lung cancer or solid tumors. In one embodiment, the Alk inhibitor or ceritinib (Compound A23) is administered at a dose of approximately 750 mg, e.g., once daily.

In another embodiment, the combination, e.g., a combination comprising one or more mono- or di-F-ML-CDN compounds as described herein, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980, to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or 8,685,980. In one embodiment, the mono- or di-F-ML-CDN compound is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980, to treat a disorder such as a lymphoma, a neurologic cancer, a melanoma, a breast cancer, or a solid tumor. In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the combination, e.g., a combination comprising one or more mono- or di-F-ML-CDN compounds as described herein, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124, to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, the mono- or di-F-ML-CDN compound is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination, e.g., a combination comprising one or more mono- or di-F-ML-CDN compounds as described herein, is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849, to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, the mono- or di-F-ML-CDN compound is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer). In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the combination, e.g., a combination comprising one or more mono- or di-F-ML-CDN compounds as described herein, is used in combination with a BRAF inhibitor, Encorafenib (Compound A29), or a compound disclosed in PCT Publication No. WO 2011/025927, to treat a disorder, e.g., a disorder described herein. In one embodiment, the BRAF inhibitor is Encorafenib (Compound A29) or a compound disclosed in PCT Publication No. WO 2011/025927. In one embodiment, the mono- or di-F-ML-CDN compound is used in combination with Encorafenib (Compound A29), or a compound disclosed in PCT Publication No. WO 2011/025927, to treat a disorder such as a non-small cell lung cancer, a melanoma, or a colorectal cancer. In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the combination, e.g., a combination comprising one or more mono- or di-F-ML-CDN compounds as described herein, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, the mono- or di-F-ML-CDN compound is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination, e.g., a combination comprising one or more mono- or di-F-ML-CDN compounds as described herein, is used in combination with a MEK inhibitor, Binimetinib (Compound A34), or a compound disclosed in PCT Publication No. WO 2003/077914, to treat a disorder, e.g., a disorder described herein. In one embodiment, the MEK inhibitor is Binimetinib (Compound A34), or a compound disclosed in PCT Publication No. WO 2003/077914. In one embodiment, the mono- or di-F-ML-CDN compound is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer. In one embodiment, the MEK inhibitor or Binimetinib (Compound A34) is administered at a dose of about 45 mg, e.g., twice daily.

In another embodiment, the combination, e.g., a combination comprising one or more mono- or di-F-ML-CDN compounds as described herein, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347, to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, the mono- or di-F-ML-CDN compound is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeration, a diabetic complication, or a dermatologic disorder.

In another embodiment, the combination, e.g., a combination comprising one or more mono- or di-F-ML-CDN compounds as described herein, is used in combination with a TOR inhibitor (e.g., mTOR inhibitor), Everolimus (also known as AFINITOR; Compound A36) or a Compound disclosed in PCT Publication No. WO 2014/085318, to treat a disorder, e.g., a disorder described herein). In one embodiment, the TOR inhibitor is Everolimus (Compound A36) or a Compound disclosed in PCT Publication No. WO 2014/085318. In one embodiment, the mono- or di-F-ML-CDN compound is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer. In one embodiment, the TOR inhibitor or Everolimus is (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the combination, e.g., a combination comprising one or more mono- or di-F-ML-CDN compounds as described herein, is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377, to treat a disorder, e.g., a disorder described herein. In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, the mono- or di-F-ML-CDN compound is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the combination, e.g., a combination comprising one or more mono- or di-F-ML-CDN compounds as described herein, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761, to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, the mono- or di-F-ML-CDN compound is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a neurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the combination, e.g., a combination comprising one or more mono- or di-F-ML-CDN compounds as described herein, is used in combination a signal transduction modulator and/or angiogenesis inhibitor, Dovitinib (Compound A39) or a compound disclosed in PCT Publication No. WO 2009/115562, to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, the mono- or di-F-ML-CDN compound is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the combination, e.g., a combination comprising one or more mono- or di-F-ML-CDN compounds as described herein, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, to treat a disorder, e.g., a disorder described herein. In one embodiment, the EGFR inhibitor is (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, the mono- or di-F-ML-CDN compound is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor. In one embodiment, the EGFR inhibitor or (R,E)-N-(7-chloro-1-(1-(4-(dimethylamino)but-2-enoyl) azepan-3-yl)-H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the combination, e.g., a combination comprising one or more mono- or di-F-ML-CDN compounds as described herein, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687, to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, the mono- or di-F-ML-CDN compound is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination, e.g., a combination comprising one or more mono- or di-F-ML-CDN compounds as described herein, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655, to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, the mono- or di-F-ML-CDN compound is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the combination, e.g., a combination comprising one or more mono- or di-F-ML-CDN compounds as described herein, is used in combination a P-Glycoprotein 1 inhibitor, Valspodar (also known as AMDRAY; Compound A46) or a compound disclosed in EP 296122, to treat a disorder, e.g., a disorder described herein. In one embodiment, the P-Glycoprotein 1 inhibitor is Valspodar (Compound A46) or a compound disclosed in EP 296122. In one embodiment, the mono- or di-F-ML-CDN compound is used in combination with Valspodar (Compound A46), or a compound disclosed in EP 296122, to treat a disorder such as a cancer or a drug-resistant tumor.

In another embodiment, the combination, e.g., a combination comprising one or more mono- or di-F-ML-CDN compounds as described herein, is used in combination one or more of a VEGFR inhibitor, Vatalanib succinate (Compound A47) or a compound disclosed in WO 98/35958, to treat a disorder, e.g., a disorder described herein. In one embodiment, the VEGFR inhibitor is Vatalanib succinate (Compound A47) or a compound disclosed in WO 98/35958. In one embodiment, the mono- or di-F-ML-CDN compound is used in combination with Vatalanib succinate (Compound A47), or a compound disclosed in EP 296122, to treat cancer.

In another embodiment, the combination, e.g., a combination comprising one or more mono- or di-F-ML-CDN compounds as described herein, is used in combination with an IDH inhibitor or a compound disclosed in WO2014/141104, to treat a disorder, e.g., a disorder described herein. In one embodiment, the IDH inhibitor is a compound disclosed in PCT Publication No. WO2014/141104. In one embodiment, the mono- or di-F-ML-CDN compound is used in combination with a compound disclosed in WO2014/141104 to treat a disorder such as a cancer.

In another embodiment, the combination, e.g., a combination comprising one or more mono- or di-F-ML-CDN compounds as described herein, is used in combination with a BCL-ABL inhibitor or a compound disclosed in PCT Publication No. WO2013/171639, WO2013/171640, WO2013/171641, or WO2013/171642, to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, the mono- or di-F-ML-CDN compound is used in combination with a compound disclosed in PCT Publication No. WO2013/171639, WO2013/171640, WO2013/171641, or WO2013/171642 to treat a disorder such as a cancer.

In another embodiment, the combination, e.g., a combination comprising one or more mono- or di-F-ML-CDN compounds as described herein, is used in combination with a c-RAF inhibitor or a compound disclosed in PCT Publication No. WO2014/151616, to treat a disorder, e.g., a disorder described herein. In one embodiment, the c-RAF inhibitor is Compound A50 or a compound disclosed in PCT Publication No. WO2014/151616. In one embodiment, the mono- or di-F-ML-CDN compound is used in combination with a compound disclosed in PCT Publication No. WO2014/151616 to treat a disorder such as a cancer.

In another embodiment, the combination, e.g., a combination comprising one or more mono- or di-F-ML-CDN compounds as described herein, is used in combination with an ERK1/2 ATP competitive inhibitor or a compound disclosed in PCT Publication No. WO2015/066188, to treat a disorder, e.g., a disorder described herein. In one embodiment, the ERK1/2 ATP competitive inhibitor is a compound disclosed in PCT Publication No. WO2015/066188. In one embodiment, the mono- or di-F-ML-CDN compound is used in combination with Compound A51 or a compound disclosed in PCT Publication No. WO2015/066188 to treat a disorder such as a cancer. In some embodiments, the combination, e.g., a combination comprising a mono- or di-F-ML-CDN compound described herein, and Compound A51 or a compound disclosed in PCT Publication No. WO2015/066188, is administered in combination with one or more agents selected from, Compound A8, Compound A17, Compound A23, Compound A24, Compound A27, Compound A29, and Compound A33.

In some embodiments, the combination, e.g., a combination comprising one or more mono- or di-F-ML-CDN compounds as described herein, is administered in combination with an anti-cancer agent having a known activity in an immune cell assay, e.g., in one or more of a huMLR assay, a T cell proliferation assay, and a B-cell proliferation assay, where such assays are known in the art, and can be used to demonstrate the compounds will not inhibit an immune response (i.e. demonstrate little or no inhibition in such assays). An IC50 in such assays can be determined for the compounds to be used in combination with the mono- or di-F-ML-CDN compound. In embodiments, the anti-cancer agent has an IC50 of, e.g., >1 µM, 1-4 µM, or greater than 4 µM, e.g., 4-10 µM or 4-20 µM, or greater than 20 µM. In embodiments, the second therapeutic agent is chosen from one or more of: Compound A9, Compound A16, Compound A17, Compound A21, Compound A22, Compound A25, Compound A28, Compound A48, and Compound A49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

TABLE 2

Therapeutic agents that can be administered in combination with the mono- or di-F-ML-CDN compounds as described herein.

| Compound designation/ generic name | Patent/Reference | Compound Structure |
|---|---|---|
| A1 Sotrastaurin | EP 1682103 U.S. Pat. No. 2007/142401 WO 2005/039549 | 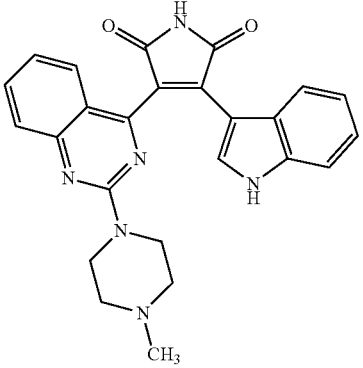 [SMILES: CN1CCN(c2nc(C3=C(c4c[nH]c5ccccc45)C(=O)NC3=O)c3ccccc3n2)CC1] |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A2<br>Nilotinib HCl monohydrate TASIGNA ® | WO 2004/005281<br>U.S. Pat. No. 7,169,791 | 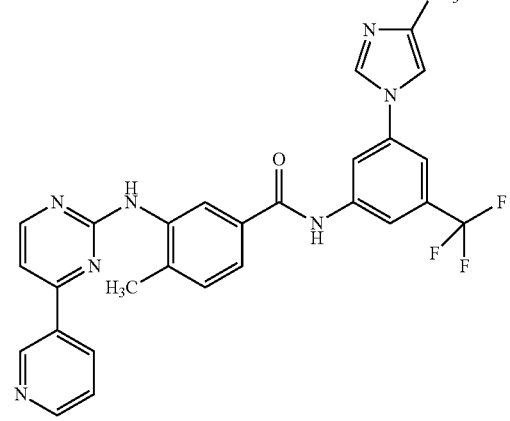<br>HCl•H$_2$O |
| A3 | WO 2010/060937<br>WO 2004/072051<br>EP 1611112<br>U.S. Pat. No. 8,450,310 | 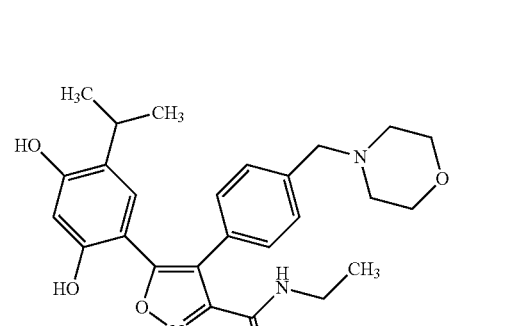 |
| A4<br>Dactolisib | WO 2006/122806 | 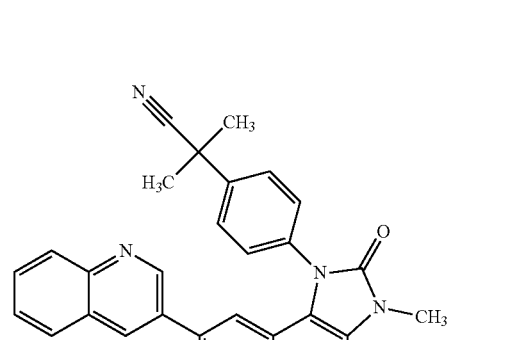 |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A5 | U.S. Pat. No. 8,552,002 | 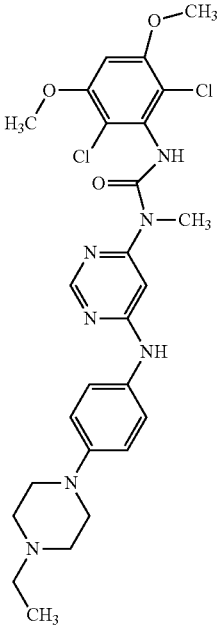 [SMILES: CCN1CCN(c2ccc(Nc3cc(N(C)C(=O)Nc4c(Cl)c(OC)cc(OC)c4Cl)ncn3)cc2)CC1] |
| A6 Buparlisib | WO 2007/084786 | 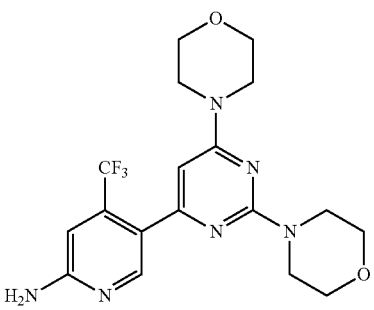 [SMILES: Nc1cc(C(F)(F)F)c(-c2cc(N3CCOCC3)nc(N3CCOCC3)n2)cn1] |
| A7 | WO 2009/141386 US 2010/0105667 | 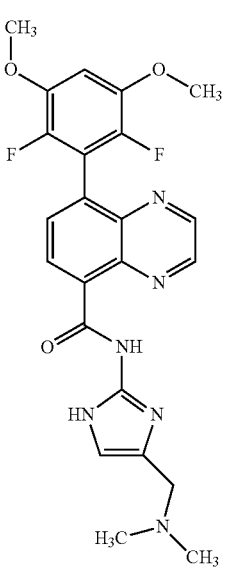 [SMILES: COc1cc(OC)c(F)c(-c2ccc(C(=O)Nc3nc(CN(C)C)c[nH]3)c3nccnc23)c1F] |

TABLE 2-continued

Therapeutic agents that can be administered in combination with the mono- or di-F-ML-CDN compounds as described herein.

| Compound designation/ generic name | Patent/Reference | Compound Structure |
|---|---|---|
| A8 | WO 2010/029082 | 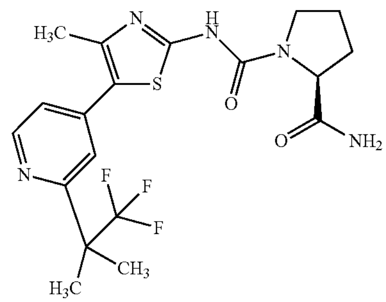 [SMILES: Cc1nc(NC(=O)N2CCC[C@H]2C(N)=O)sc1-c1ccnc(C(C)(C)C(F)(F)F)c1] |
| A9 CYP17 inhibitor | WO 2010/149755 U.S. Pat. No. 8,263,635 B2 EP 2445903 B1 | |
| A10 | WO 2011/076786 | 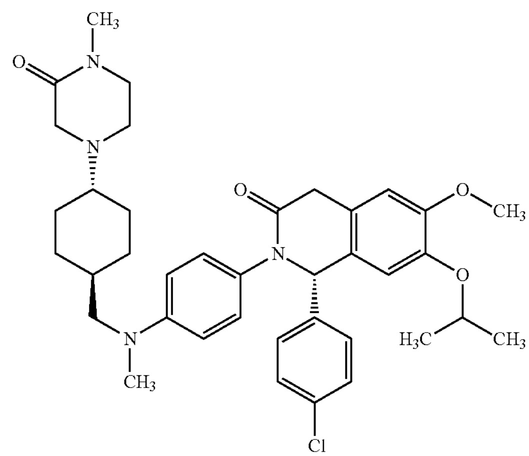 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] |
| A11 Deferasirox EXJADE ® | WO 1997/049395 | 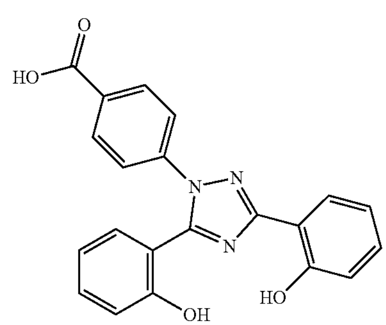 [SMILES: O=C(O)c1ccc(-n2nc(-c3ccccc3O)nc2-c2ccccc2O)cc1] |
| A12 Letrozole FEMARA ® | U.S. Pat. No. 4,978,672 | 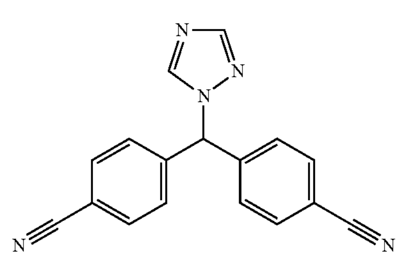 [SMILES: N#Cc1ccc(C(c2ccc(C#N)cc2)n2cncn2)cc1] |

TABLE 2-continued

Therapeutic agents that can be administered in combination with the mono- or di-F-ML-CDN compounds as described herein.

| Compound designation/ generic name | Patent/Reference | Compound Structure |
|---|---|---|
| A13 | WO 2013/124826<br>US 2013/0225574 | 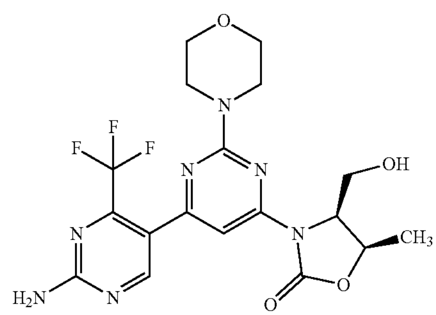 [SMILES: C[C@H]1OC(=O)N(c2cc(-c3cnc(N)nc3C(F)(F)F)nc(N3CCOCC3)n2)[C@H]1CO] |
| A14 | WO 2013/111105 | 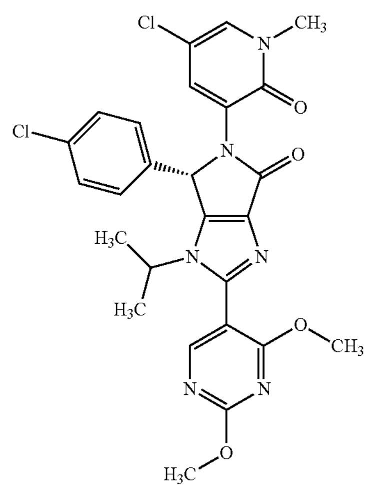 [SMILES: COc1ncc(-c2nc3c(n2C(C)C)[C@H](c2ccc(Cl)cc2)N(c2cc(Cl)cn(C)c2=O)C3=O)c(OC)n1] |
| A15 | WO 2005/073224 | 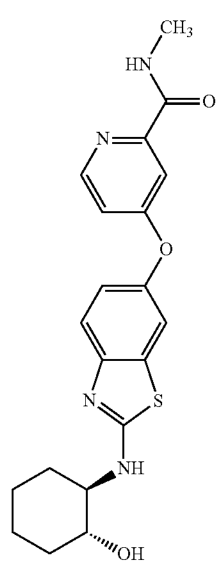 [SMILES: CNC(=O)c1cc(Oc2ccc3nc(N[C@@H]4CCCC[C@H]4O)sc3c2)ccn1] |

TABLE 2-continued

Therapeutic agents that can be administered in combination with the mono- or di-F-ML-CDN compounds as described herein.

| Compound designation/ generic name | Patent/Reference | Compound Structure |
|---|---|---|
| A16 Imatinib mesylate GLEEVEC ® | WO 1999/003854 | mesylate |
| A17 | EP 2099447 U.S. Pat. No. 7,767,675 U.S. Pat. No. 8,420,645 | dihydrochloric salt |

TABLE 2-continued
Therapeutic agents that can be administered in combination with the mono- or di-F-ML-CDN compounds as described herein.
| Compound designation/ generic name | Patent/Reference | Compound Structure |
| --- | --- | --- |
| A18 Ruxolitinib phosphate JAKAFI ® | WO 2007/070514 EP 2474545 U.S. Pat. No. 7,598,257 WO 2014/018632 | 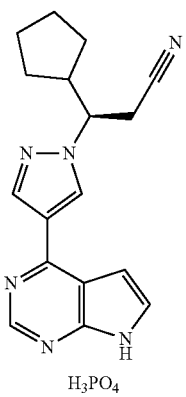 |
| A19 Panobinostat | WO 2014/072493 WO 2002/022577 EP 1870399 | 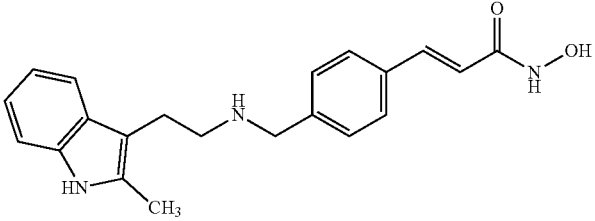 [SMILES: Cc1[nH]c2ccccc2c1CCNCc1ccc(/C=C/C(=O)NO)cc1] |
| A20 Osilodrostat | WO 2007/024945 | 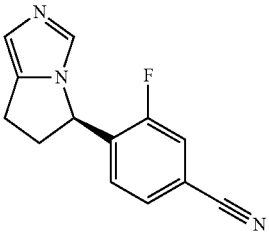 [SMILES: N#Cc1ccc([C@H]2CCc3cncn32)c(F)c1] |
| A21 | WO 2008/016893 EP 2051990 U.S. Pat. No. 8,546,336 | 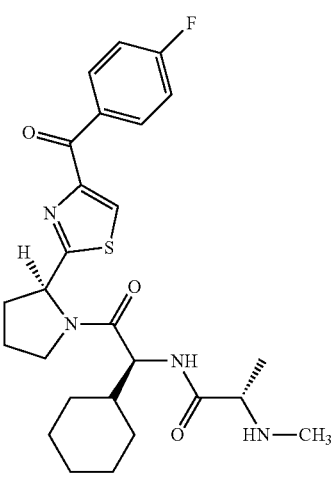 [SMILES: CN[C@@H](C)C(=O)N[C@H](C(=O)N1CCC[C@H]1c1nc(C(=O)c2ccc(F)cc2)cs1)C1CCCCC1] |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A22 Sonidegib phosphate | WO 2007/131201 EP 2021328 U.S. Pat. No. 8,178,563 | 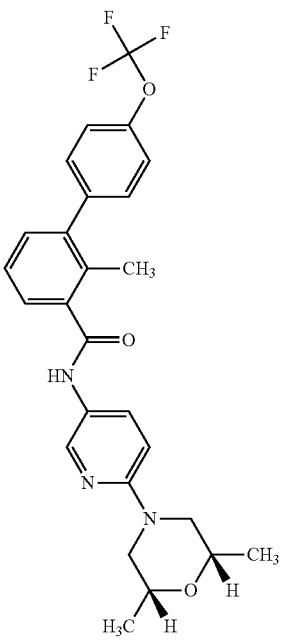 [SMILES: Cc1c(C(=O)Nc2ccc(N3C[C@@H](C)O[C@@H](C)C3)nc2)cccc1-c1ccc(OC(F)(F)F)cc1] |
| A23 Ceritinib ZYKADIA ™ | WO 2008/073687 U.S. Pat. No. 8,039,479 | 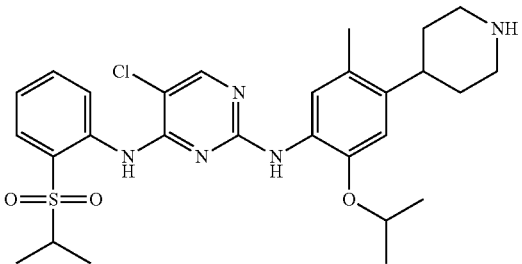 [SMILES: Cc1cc(Nc2ncc(Cl)c(Nc3ccccc3S(=O)(=O)C(C)C)n2)c(OC(C)C)cc1C1CCNCC1] |
| A24 | U.S. Pat. No. 8,415,355 U.S. Pat. No. 8,685,980 | 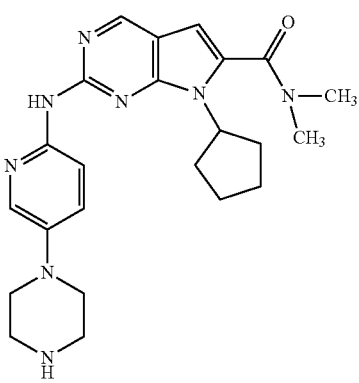 [SMILES: CN(C)C(=O)c1cc2cnc(Nc3ccc(N4CCNCC4)cn3)nc2n1C1CCCC1] |

TABLE 2-continued

Therapeutic agents that can be administered in combination with the mono- or di-F-ML-CDN compounds as described herein.

| Compound designation/ generic name | Patent/Reference | Compound Structure |
|---|---|---|
| A25 | WO 2010/007120 | 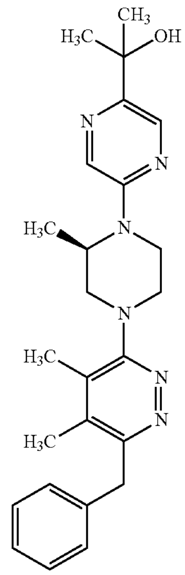 [SMILES: Cc1c(Cc2ccccc2)nnc(N2CCN(c3cnc(C(C)(C)O)cn3)[C@H](C)C2)c1C] |
| A26 | U.S. Pat. No. 7,867,493 | Human monoclonal antibody to PRLR |
| A27 | WO 2010/026124<br>EP 2344474<br>US 2010/0056576<br>WO 2008/106692 | 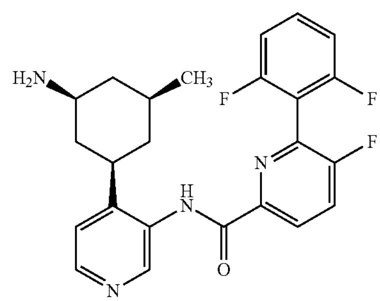 [SMILES: C[C@@H]1C[C@H](N)C[C@H](c2ccncc2NC(=O)c2ccc(F)c(-c3c(F)cccc3F)n2)C1] |
| A28 | WO 2010/101849 | 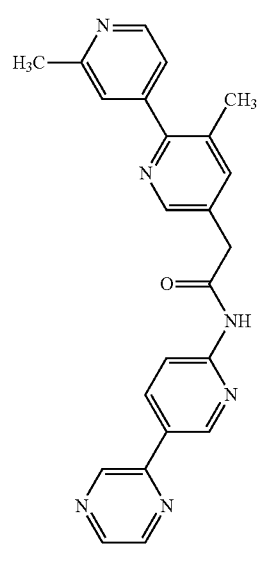 [SMILES: Cc1cc(-c2ncc(CC(=O)Nc3ccc(-c4cnccn4)cn3)cc2C)ccn1] |

TABLE 2-continued

Therapeutic agents that can be administered in combination with the mono- or di-F-ML-CDN compounds as described herein.

| Compound designation/ generic name | Patent/Reference | Compound Structure |
|---|---|---|
| A29 Encorafenib | WO 2011/025927 | 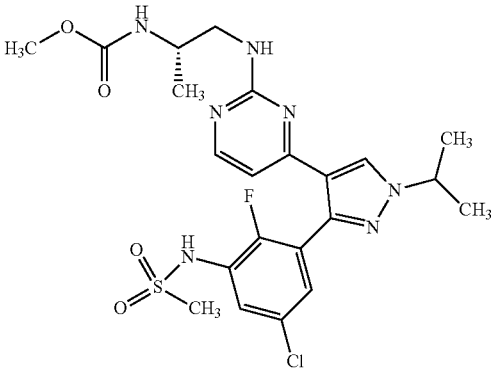 [SMILES: COC(=O)N[C@@H](C)CNc1nccc(-c2cn(C(C)C)nc2-c2cc(Cl)cc(NS(C)(=O)=O)c2F)n1] |
| A30 | WO 2011/101409 | 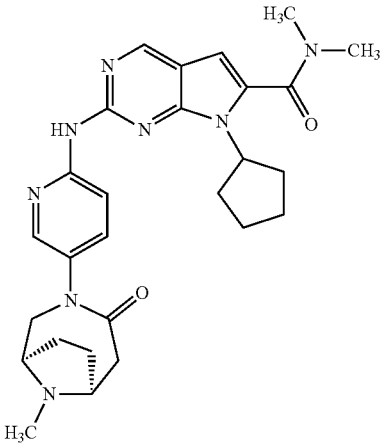 [SMILES: CN(C)C(=O)c1cc2cnc(Nc3ccc(N4C[C@H]5CC[C@@H](CC4=O)N5C)cn3)nc2n1C1CCCC1] |
| A31 | WO 2012/022814<br>EP 2606070<br>U.S. Pat. No. 8,735,551 | Human monoclonal antibody to HER3 |
| A32 | WO 2014/160160<br>Ab: 12425 (see Table 1, paragraph [00191])<br>Linker: SMCC (see paragraph [00117]<br>Payload: DM1 (see paragraph [00111]<br>See also Claim 29 | Antibody Drug Conjugate (ADC) |
| A33 | WO 2004/045532 | Monoclonal antibody or Fab to M-CSF |
| A34 Binimetinib | WO 2003/077914 | 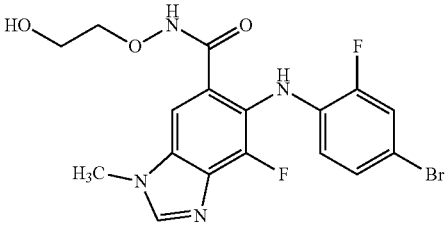 [SMILES: Cn1cnc2c(F)c(Nc3ccc(Br)cc3F)c(C(=O)NOCCO)cc21] |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A35 Midostaurin | WO 2003/037347<br>EP 1441737<br>US 2012/252785 | 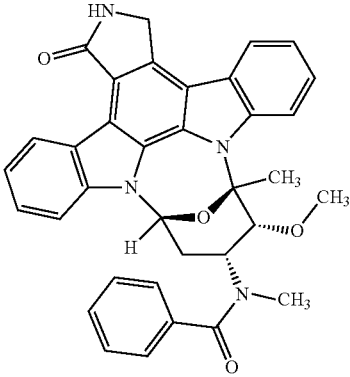 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] |
| A36 Everolimus AFINITOR ® | WO 2014/085318 | 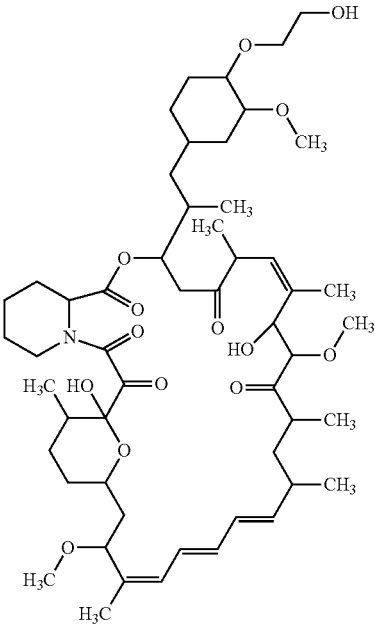 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A37 | WO 2007/030377<br>U.S. Pat. No. 7,482,367 | 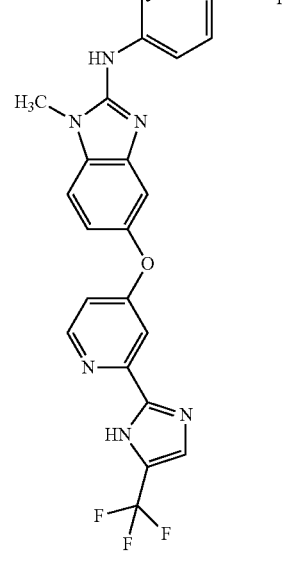 |
| A38<br>Pasireotide diaspartate<br>SIGNIFOR ® | WO 2002/010192<br>U.S. Pat. No. 7,473,761 | 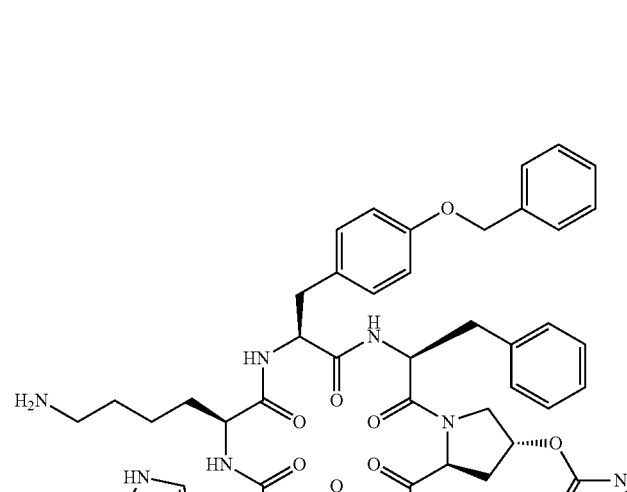 |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A39 Dovitinib | WO 2009/115562 U.S. Pat. No. 8,563,556 | 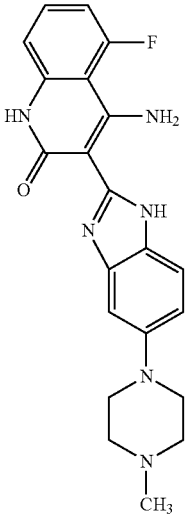 [SMILES: CN1CCN(c2ccc3[nH]c(-c4c(N)c5c(F)cccc5[nH]c4=O)nc3c2)CC1] |
| A40 | WO 2013/184757 | 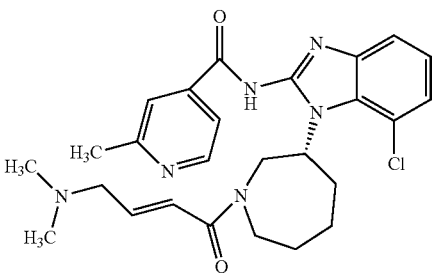 [SMILES: Cc1cc(C(=O)Nc2nc3cccc(Cl)c3n2[C@@H]2CCCCN(C(=O)/C=C/CN(C)C)C2)ccn1] |
| A41 | WO 2006/122806 | 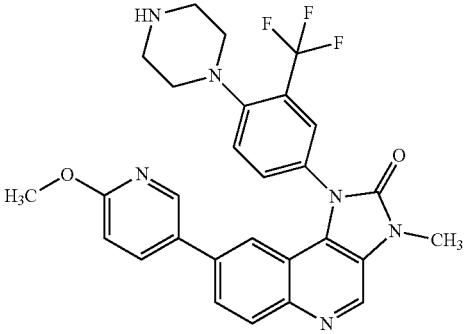 |

TABLE 2-continued
Therapeutic agents that can be administered in combination with the mono- or di-F-ML-CDN compounds as described herein.
| Compound designation/ generic name | Patent/Reference | Compound Structure |
| --- | --- | --- |
| A42 | WO 2008/073687<br>U.S. Pat. No. 8,372,858 | 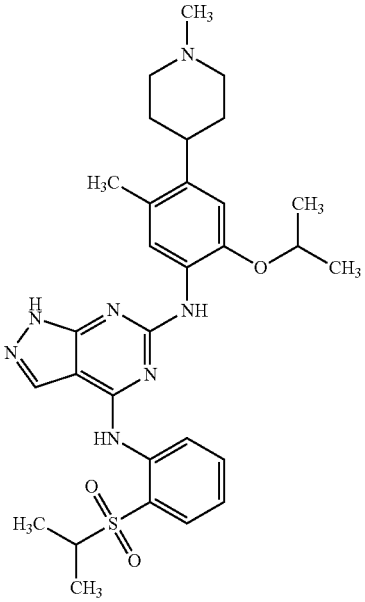 [SMILES: Cc1cc(Nc2nc(Nc3ccccc3S(=O)(=O)C(C)C)c3cn[nH]c3n2)c(OC(C)C)cc1C1CCN(C)CC1] |
| A43 | WO 2010/002655<br>U.S. Pat. No. 8,519,129 | 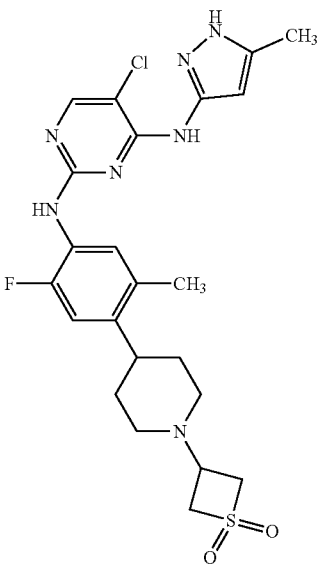 [SMILES: Cc1cc(Nc2nc(Nc3cc(C)c(C4CCN(C5CS(=O)(=O)C5)CC4)cc3F)ncc2Cl)n[nH]1] |

TABLE 2-continued
Therapeutic agents that can be administered in combination with the mono- or di-F-ML-CDN compounds as described herein.
| Compound designation/ generic name | Patent/Reference | Compound Structure |
|---|---|---|
| A44 | WO 2010/002655<br>U.S. Pat. No. 8,519,129 | 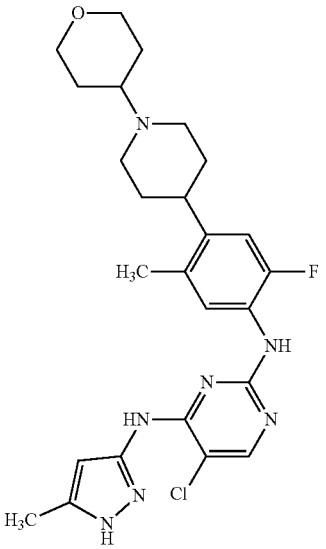 [SMILES: Cc1cc(Nc2nc(Nc3cc(C)c(C4CCN(C5CCOCC5)CC4)cc3F)ncc2Cl)n[nH]1] |
| A45 | WO 2010/002655 | 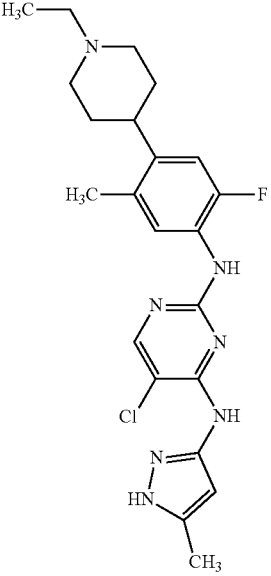 [SMILES: CCN1CCC(c2cc(F)c(Nc3ncc(Cl)c(Nc4cc(C)[nH]n4)n3)cc2C)CC1] |

TABLE 2-continued

Therapeutic agents that can be administered in combination with the mono- or di-F-ML-CDN compounds as described herein.

| Compound designation/ generic name | Patent/Reference | Compound Structure |
|---|---|---|
| A46 Valspodar AMDRAY ™ | EP 296122 | [structure] |
| A47 Vatalanib succinate | WO 98/35958 | [structure] succinate |
| A48 | WO 2014/141104 | IDH inhibitor |
| A49 | WO 2013/171639 WO 2013/171640 WO 2013/171641 WO 2013/171642 | BCR-ABL inhibitor |
| A50 | WO 2014/151616 | cRAF inhibitor |
| A51 | WO 2015/066188 | ERK1/2 ATP competitive inhibitor |

Immunomodulatory Cell Lines

By "inactivated tumor cell" is meant a tumor cell (either "autologous" or "allogeneic" to the patient) which has been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

In some embodiments, the inactivated tumor cells of the present invention are modified to express and secrete one or more heat shock proteins. For example, gp96-Ig fusion proteins can be expressed and secreted to stimulate an immune response (Yamazaki et al., The Journal of Immunology, 1999, 163:5178-5182; Strbo et al., Immunol Res. 2013 December; 57(1-3):311-25). In some embodiments the inactivated tumor cells are modified to express and secrete a gp96-Ig fusion protein.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946. A form of GM-CSF-expressing genetically modified cancer cells or a "cytokine-expressing cellular vaccine" for the treatment of pancreatic cancer is described in U.S. Pat. Nos. 6,033,674 and 5,985,290.

Other suitable cytokines which may be expressed by such inactivated tumor cells and/or bystander cells instead of, or together with, GM-CSF include, but are not limited to, one or more of CD40 ligand, FLT-3 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Vaccines

In certain embodiments, the CDN compositions are administered in conjunction with one or more vaccines intended to stimulate an immune response to one or more predetermined antigens. Examples of target antigens that may find use in the invention are listed in the following table. The target antigen may also be a fragment or fusion polypeptide comprising an immunologically active portion of the antigens listed in the table. This list is not meant to be limiting.

Vaccine compositions can comprise a bacterial cell that is transformed to express the polypeptide antigen or to deliver a polynucleotide which is subsequently expressed in cells of the vaccinated individual as an antigen of interest. A number of bacterial species have been developed for use as vaccines and can be used as a vaccine platform in present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. The present invention contemplates the use of attenuated, commensal, and/or killed but metabolically active bacterial strains as vaccine platforms. In preferred embodiments the bacterium is *Listeria monocytogenes*.

TABLE 1

List of antigens for use in combination with the mono- or di-F-ML-CDN compounds as described herein.

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein B (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular | GenBank Acc. No. NM_004484. Nakatsura, et al. (2003) Biochem. Biophys. Res. Commun. 306: 16-25; Capurro, et al. (2003) |

TABLE 1-continued

List of antigens for use in combination with the mono- or di-F-ML-CDN compounds as described herein.

| Antigen | Reference |
|---|---|
| carcinoma and melanoma). | Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |

TABLE 1-continued

List of antigens for use in combination with the mono-
or di-F-ML-CDN compounds as described herein.

| Antigen | Reference |
| --- | --- |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, eg., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastroenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |

TABLE 1-continued

List of antigens for use in combination with the mono- or di-F-ML-CDN compounds as described herein.

| Antigen | Reference |
|---|---|
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See. e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |
| | *Francisella tularensis* antigens |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. |

TABLE 1-continued

List of antigens for use in combination with the mono-
or di-F-ML-CDN compounds as described herein.

| Antigen | Reference |
|---|---|
| | (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |

Malarial antigens

| Antigen | Reference |
|---|---|
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A`13; AJ494905; AJ490565). |

Viruses and viral antigens

| Antigen | Reference |
|---|---|
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |

TABLE 1-continued

List of antigens for use in combination with the mono- or di-F-ML-CDN compounds as described herein.

| Antigen | Reference |
| --- | --- |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; |

TABLE 1-continued

List of antigens for use in combination with the mono- or di-F-ML-CDN compounds as described herein.

| Antigen | Reference |
|---|---|
| | AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |

TABLE 1-continued

List of antigens for use in combination with the mono-
or di-F-ML-CDN compounds as described herein.

| Antigen | Reference |
| --- | --- |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis, Streptococcus pyogenes* (Group A Strep), *Streptococcus agalactia* (Group B Strep), *Streptococcus pneumonia, Staphylococcus aureus, Escherichia coli, Haemophilus influenzae, Neisseria meningitidis, Neisseria gonorrheae, Vibrio cholerae, Salmonella* species (including *typhi, typhimurium*), *enterica* (including *Helicobactor pylori Shigella flexneri* and other Group D *shigella* species), *Burkholderia mallei, Burkholderia pseudomallei, Klebsiella pneumonia, Clostridium* species (including *C. difficile*), *Vibrio parahaemolyticus* and *V. vulnificus*. This list is not meant to be limiting.

Tumor Neoantigens

As discussed above, tumor-associated antigens, which are expressed (or overexpressed) by tumor cells but also by some normal tissues, may find use in combination with the mono- or di-F-ML-CDN compounds as described herein. However, attempts to target tumor-associated antigens can lead to severe toxicities due to normal tissue destruction. "Neoantigens" are tumor-specific antigens that arise via mutations that alter amino acid coding sequences. Because some neoantigens may be expressed, processed and presented on the cell surface, they may provide a target that is recognized by T cells that does not exhibit central and peripheral tolerance and that lack the ability to induce normal tissue destruction. Thus, the mono- or di-F-ML-CDN compounds as described herein may be administered in conjunction with one or more vaccines intended to stimulate an immune response to one or more neoantigens.

The neoantigens finding use in the present invention may be mutations that are shared generally by certain classes of tumors, such as EGFRvIII in malignant gliomas, KIAA1440 in renal cancer, NF-YC in lung cancer, etc. In certain applications, referred to under the umbrella of "personalized medicine," neoantigens finding use in the present invention may be mutations that are not shared between patients at meaningful frequencies and may therefore be considered patient-specific. In these applications, cancer exome-based sequencing analysis may be used to collect a set of mutations which are filtered through predictive algorithms that identify which of the identified mutations may be processed and presented as a peptide-MHC complex, a process referred to as "epitope prediction." Such methods are described, for example, in Schumacher and Schreiber, Science 348: 69-74, 2015.

In certain embodiments, the administration of neoantigens may be effected using one or more of the following strategies (this list is not meant to be limiting):

inactivated or attenuated bacteria or viruses comprising the antigen of interest;
purified antigens;
live viral or bacterial delivery vectors recombinantly engineered to express and/or secrete antigens;
antigen presenting cell (APC) vectors, such as a dendritic cell (DC) vector, which comprise cells that are loaded with an antigen, or transfected with a composition comprising a nucleic acid encoding the antigen;
liposomal antigen delivery vehicles; and
naked DNA vectors and naked RNA vectors.

In addition to the use of neoantigens in combination with the mono- or di-F-ML-CDN compounds as described herein, such combinations may further comprise the administration of one or more one or more additional pharmaceutically active components, for example those selected from the group consisting of an immune checkpoint inhibitor (e.g. CTLA-4, PD-1, Tim-3, Vista, BTLA, LAG-3 and TIGIT pathway antagonists; PD-1 antagonists agents; PD-L1 antagonists; a CD47/SIRPα pathway antagonist such as antibodies targeting CD47 or SIRPα; an APRIL antagonist; a TLR agonist; an inactivated or attenuated bacteria which induce innate immunity; a composition that mediates innate immune activation via Toll-like Receptors (TLRs), via (NOD)-like receptors (NLRs), via Retinoic acid inducible gene-based (RIG)-I-like receptors (RLRs), via C-type lectin receptors (CLRs), or via pathogen-associated molecular patterns (PAMPs); and a chemotherapeutic agent.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. "Non-parenteral administration" encompasses oral, buccal, sublingual, topical, transdermal, ophthalmic, otic, nasal, rectal, cervical, pulmonary, mucosal, and vaginal routes. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. Intra-tumoral (directly into the tumor mass) or peri-tumoral (around the tumor mass) administration of the compounds of the present invention may directly activate locally infiltrating DC, directly promote tumor cell apoptosis or sensitize tumor cells to cytotoxic agents. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the mono- or di-F-ML-CDN compounds as described herein when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs may have different physical properties such as density, shape, hardness, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjust the conditions used during the crystallization or recrystallization of the compound.

For solvates of compounds of this invention, or salts thereof, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethyl sulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

Because of their potential use in medicine, the salts of the compounds of this invention are preferably pharmaceutically acceptable. Suitable pharmaceutically acceptable salts include those described by P. Heinrich Stahl and Camille G. Wermuth in Handbook of Pharmaceutical Salts: Properties, Selection, and Use, $2^{nd}$ ed. (Wiley-VCH: 2011) and also Remington's Pharmaceutical Sciences, $18^{th}$ ed. (Mack Publishing, Easton Pa.: 1990) and also Remington: The Science and Practice of Pharmacy, $19^{th}$ ed. (Mack Publishing, Easton Pa.: 1995). Salt encompassed within the term "pharmaceutically acceptable salts" refer to non-toxic salts of the compounds in this invention.

Salts of the compounds of this invention containing a basic amine or other basic functional group may be prepared by any suitable method known in the art, including treatment of the free bases with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, formic acid, alginic acid, pyruvic acid, oxalic acid, glycolic acid, salicylic acid, pyranosildyl acid, such as glucuronic acid or galacturonic acid, alphahydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, glycolate, resinate, lactates, camsylates, tartrates, mandelates, and sulfonates, such as xylenesulfonates, methanesulfonates, propanesulfonates, naphthalene-1-sulfonates and naphthalene-2-sulfonates.

Salts of the compounds of this invention containing a phosphate diester, phosphorothioate diester or other acidic functional group can be prepared by reacting with a suitable base. Pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, zinc, as well as salts made from physiologically acceptable organic bases such as diethylamine, isopropylamine, olamine, benzathine, benethamine, tromethamine (2-amino-2-(hydroxymethyl)propane-1,3-diol), morpholine, epolamine, piperidine, piperazine, picoline, dicyclohexylamine, N,N'-dibenzylethylenediamine, 2-hydroxyethylamine, tri-(2-hydroxyethyl)amine, chloroprocaine, choline, deanol, imidazole, diethanolamine, ethylenediamine, meglumine (N-methylglucamine), procaine, dibenzylpiperidine, dehydroabietylamine, glucamine, collidine, quinine, quinolone, erbumine and basic amino acids such as lysine and arginine.

The mono- or di-F-ML-CDN compounds as described herein that include salts thereof can be described by structures wherein the —SH or —OH in the phosphate or thiophosphate bond (i.e. X1 or X2 of the compounds as described herein) are represented as —S— or —O— with a corresponding cation to form salts of the compounds as described herein. For example, salts of compounds of the first aspect as described herein can be represented by the following structures:

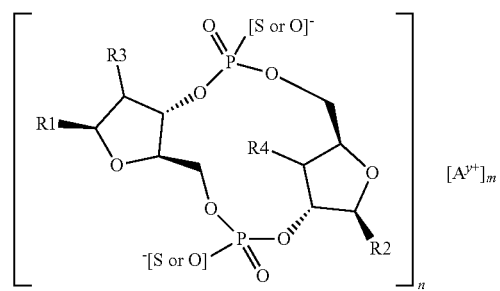

wherein $A^{y+}$ represents a mono or polyvalent salt cation, and n and m are the lowest possible whole number for a given y. For example when $A^{y+}$ is monovalent, i.e. when y is 1, such as $Na^+$, $K^+$, $NH_4^+$, $TEAH^+$ or the like, n is 1 and m is 2; when y is 2, such as $Ca^{2+}$, $Mg^{2+}$ and the like, n is 1 and m is 1; when y is 3, e.g. $Al^{3+}$ or the like, n is 3 and m is 2. For example, salts of a monovalent or divalent salt cation can be represented as

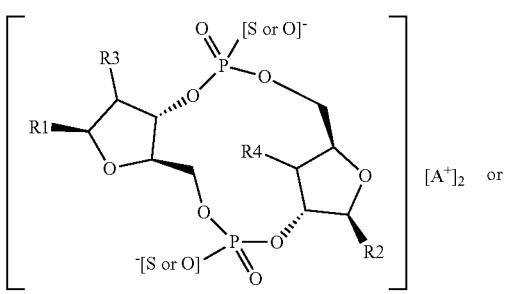

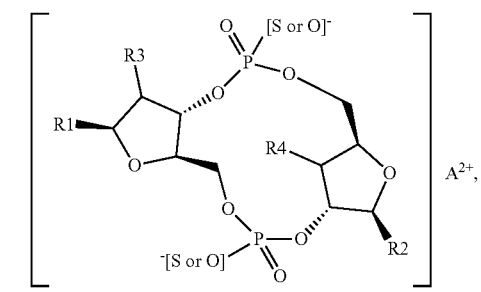

respectively, or in cases where n=1, these can be represented without brackets, e.g. as

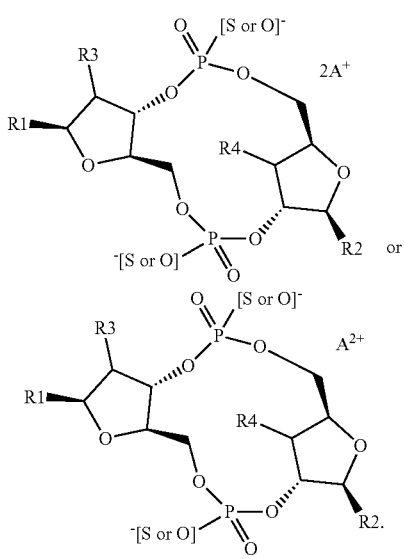

Alternatively, monovalent salts can be depicted with A+ adjacent each of the —S— or —O—. For example, the sodium salt of a mono- or di-F-ML-RR-CDN compounds as described herein can be depicted as

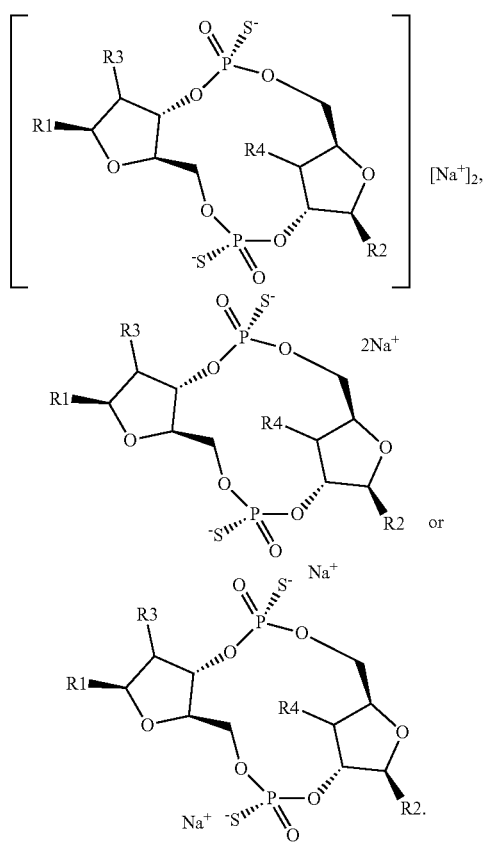

Other non-pharmaceutically acceptable salts, e.g. trifluoroacetate or triethylammonium may be used, for example in the isolation of compounds of the invention, and are included within the scope of this invention.

The invention includes within its scope all possible stoichiometric and non-stoichiometric forms of the salts of the compounds of this invention.

If a compound of this invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of this invention containing a phosphate diester, phosphorothioate diester or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

An effective amount of a mono- or di-F-ML-CDN compound, or a pharmaceutically acceptable salt, pharmaceutically acceptable solvate or pharmaceutically acceptable hydrate thereof as described herein, for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of a pharmaceutical composition comprising the mono- or di-F-ML-CDN compound, or a pharmaceutically acceptable salt, pharmaceutically acceptable solvate or pharmaceutically acceptable hydrate thereof as described herein. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days;

every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

As noted, the compositions of the present invention are preferably formulated as pharmaceutical compositions for parenteral or enteral delivery. A typical pharmaceutical composition for administration to an animal subject comprises a pharmaceutically acceptable vehicle such as aqueous solutions, non-toxic excipients, including salts, preservatives, buffers and the like. See, e.g., *Remington's Pharmaceutical Sciences*, 15th Ed., Easton ed., Mack Publishing Co., pp 1405-1412 and 1461-1487 (1975); *The National Formulary XIV,* 14th Ed., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/mono- or di-F-ML-CDN compound or compositions thereof described herein.

The heterologous arm of the regimen may comprise delivery of one or more antigens (e.g., one or more neoantigens) using one or more of the following strategies:

inactivated or attenuated bacteria or viruses comprising the antigen of interest, which are particles that have been treated with some denaturing condition to render them ineffective or inefficient in mounting a pathogenic invasion;

purified antigens, which are typically naturally-produced antigens purified from a cell culture of the pathogen or a tissue sample containing the pathogen, or a recombinant version thereof;

live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;

antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer); liposomal antigen delivery vehicles; and naked DNA vectors and naked RNA vectors which may be administered by a gene gun, electroporation, bacterial ghosts, microspheres, microparticles, liposomes, polycationic nanoparticles, and the like.

By way of example, a prime/boost regimen may comprise the administration of one or more mono- or di-F-ML-CDN compounds as described herein by a parenteral route (e.g., intra- or peri-tumoral injection), and this may be followed by "boost" administration of one or more antigens (e.g., neoantigens) using one or more of the strategies described above. As described above, the antigen administration may be combined with a second administration of one or more mono- or di-F-ML-CDN compounds as described herein, with administration of one or more immune checkpoint inhibitors, with administration of CD47/SIRPα pathway antagonists, with administration of TLR agonists, with administration of APRIL antagonists, etc., or combinations thereof.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

EXAMPLES

The following examples serve to illustrate the present invention. These examples are in no way intended to limit the scope of the invention.

General Methods

Anhydrous solvents and reagents suitable for solution phase oligonucleotide synthesis were purchased from commercial suppliers (Aldrich, ChemGenes Corporation, Wilmington, Mass., USA) and handled under dry argon or nitrogen using anhydrous technique. Phosphoramidite coupling reactions and H-phosphonate cyclizations were carried out in anhydrous acetonitrile or pyridine under dry argon or nitrogen. The starting materials for all reactions in dry pyridine were dried by concentration (three times) from pyridine, unless indicated otherwise. Chromatography conditions were as follows unless indicated otherwise in the examples below. Preparative silica gel flash chromatography was carried out under medium pressure chromatography (MPLC) using RediSep Rf silica columns (Teledyne Isco, Lincoln, Nebr.) on a Combiflash Rf+ UV-Vis (Teledyne Isco) using gradients of methanol in dichloromethane. Reverse phase preparative chromatography was executed under MPLC conditions using RediSep Rf C18 Aq columns (Teledyne Isco) on a Combiflash Rf+ UV-Vis using gradients of acetonitrile in aqueous 10 mM TEAA solution. Analytical high pressure liquid chromatography (HPLC) was performed on a Shimadzu Prominence HPLC with a photodiode array detector monitoring at 254 nm using a either a Microsorb 10 micron C18 250×4.6 mm or a Thermo Scientific Acclaim™ 120 5 μm C18 100×4.6 mm column and gradients of 10 mM TEAA and acetonitrile. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate of 50 mL/min. Solid phase extractions using C-18 Sep-Pak (Waters) were carried out at loadings of 3% (wt/wt). For the compounds of Examples 2-12, Analytical LCMS were recorded using a Shimadzu LCMS system featuring a Prominence HPLC coupled to a Shimadzu LCMS-2020 single quadrupole mass spectrometer, using an electrospray ionization source (ESI). For the synthesis of intermediate compounds, LCMS data were recorded as described in Example 1.

The final compounds may exist as the TEAH salt, with conversion to other salt forms (including but not limited to Na and $NH_4$) using standard ion exchange techniques or other well known methods is possible.

Assignments of Stereochemistry at the phosphorus were made in analogy to literature methods (Zhao et al. Nucleosides, Nucleotides, and Nucleic Acid 289:352-378, 2009) or as discussed in the examples below.

Compound names were generated using the software program ChemBioDraw Ultra V 14.0 available from CambridgeSoft Corporation, 100 CambridgePark Drive, Cambridge, Mass. 02140 USA. Abridged names of compounds for which a name could not be generated by ChemBioDraw, or reference compounds used in the examples, are provided in the following Table 3. Reference compounds 2'3'-RR-(G)(A) and 2'3'-RR-(A)(A) were prepared as described in PCT Publication No. WO2014/189805, incorporated by reference with respect to such syntheses. Structures in the examples may also be represented as salts, e.g. —$O^-$ $A^+$ or —$S^-$ $A^+$, where $A^+$ is the salt cation.

TABLE 3

Abridged compound names and structures.

| Example number and abridged Compound names | Structure |
|---|---|
| Example 2 Compound 5 2'3'-RR-(3'F-A)(2'F-A); dithio-[$R_P$, $R_P$]-cyclic-[3'F-A(2',5')p-2'F-A(3',5')p] | 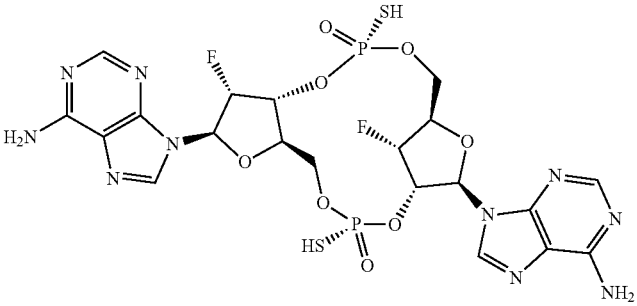 [SMILES: Nc1ncnc2c1ncn2[C@@H]1O[C@@H]2CO[P@@](=O)(S)O[C@@H]3[C@H](F)[C@@H](CO[P@@](=O)(S)O[C@H]2[C@H]1F)O[C@H]3n1cnc2c(N)ncnc21] |

TABLE 3-continued

Abridged compound names and structures.

| Example number and abridged Compound names | Structure |
|---|---|
| Example 2 Compound 5a<br>2'3'-RS-(3'F-A)(2'F-A);<br>dithio-[$R_P$, $S_P$]-cyclic-<br>[3'F-A(2',5')p-2'F-A(3',5')p] | 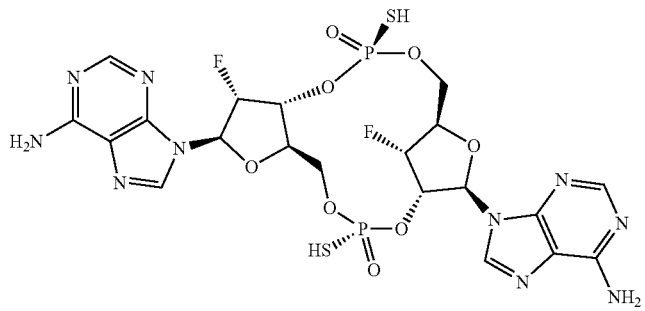 |
| Example 2 Compound 5b<br>2'3'-SR-(3'F-A)(2'F-A);<br>dithio-[$S_P$, $R_P$]-cyclic-<br>[3'F-A(2',5')p-2'F-A(3',5')p] | 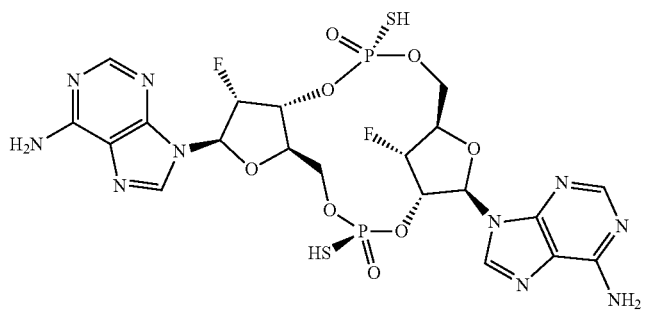 [SMILES: Nc1ncnc2c1ncn2[C@@H]1O[C@@H]2CO[P@](=O)(S)O[C@@H]3[C@H](F)[C@@H](CO[P@@](=O)(S)O[C@H]2[C@H]1F)O[C@H]3n1cnc2c(N)ncnc21] |
| Example 2 Compound 5c<br>2'3'-SS-(3'F-A)(2'F-A);<br>dithio-[$S_P$, $S_P$]-cyclic-<br>[3'F-A(2',5')p-2'F-A(3',5')p] | 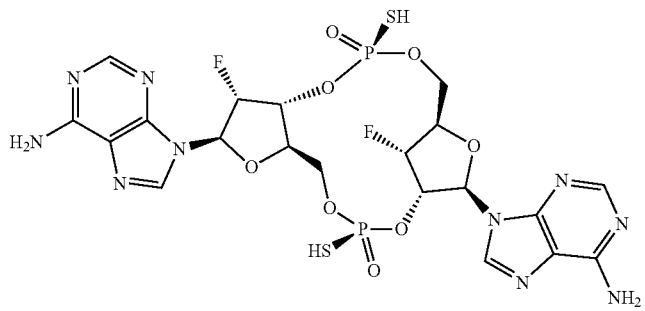 [SMILES: Nc1ncnc2c1ncn2[C@@H]1O[C@@H]2CO[P@](=O)(S)O[C@@H]3[C@H](F)[C@@H](CO[P@](=O)(S)O[C@H]2[C@H]1F)O[C@H]3n1cnc2c(N)ncnc21] |
| Example 3 Compound 10<br>2'3'-RR-(3'βF-A)(2'F-A);<br>dithio-[$R_P$, $R_P$]-cyclic-<br>[3'βF-A(2',5')p-2'F-A(3',5')p] | 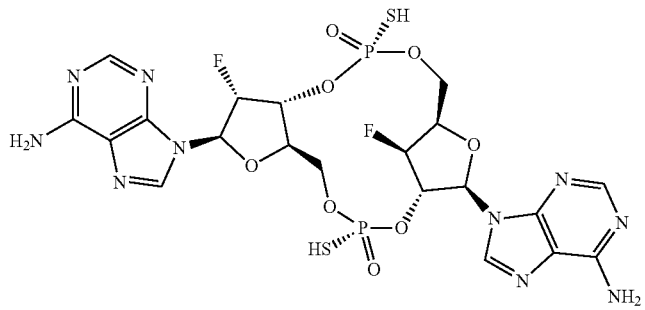 [SMILES: Nc1ncnc2c1ncn2[C@@H]1O[C@@H]2CO[P@@](=O)(S)O[C@@H]3[C@@H](F)[C@@H](CO[P@@](=O)(S)O[C@H]2[C@H]1F)O[C@H]3n1cnc2c(N)ncnc21] |

TABLE 3-continued

Abridged compound names and structures.

| Example number and abridged Compound names | Structure |
|---|---|
| Example 3 Compound 10a<br>2'3'-RS-(3'βF-A)(2'F-A);<br>dithio-[$R_P$, $S_p$]-cyclic-<br>[3'βF-A(2',5')p-2'F-A(3',5')p] | 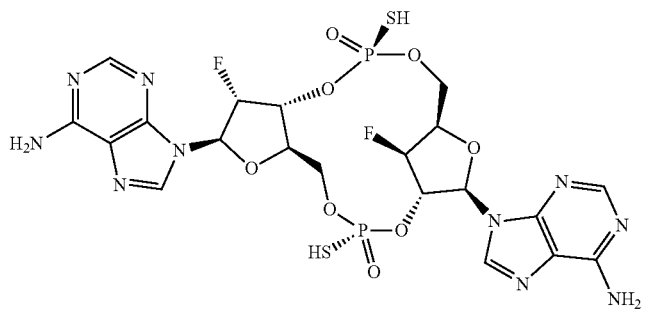 [SMILES: Nc1ncnc2c1ncn2[C@@H]1O[C@@H]2CO[P@@](=O)(S)O[C@@H]3[C@@H](F)[C@@H](CO[P@](=O)(S)O[C@H]2[C@H]1F)O[C@H]3n1cnc2c(N)ncnc21] |
| Example 4 Compound 16<br>2'3'-RR-(A)(2'F-A);<br>dithio-[$R_P$, $R_P$]-cyclic-<br>[A(2',5')p-2'F-A(3',5')p] | 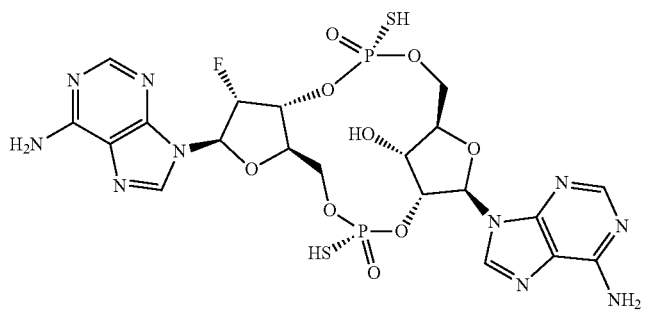 [SMILES: Nc1ncnc2c1ncn2[C@@H]1O[C@@H]2CO[P@@](=O)(S)O[C@@H]3[C@H](O)[C@@H](CO[P@@](=O)(S)O[C@H]2[C@H]1F)O[C@H]3n1cnc2c(N)ncnc21] |
| Example 4 Compound 16a<br>2'3'-SR-(A)(2'F-A);<br>dithio-[$S_P$, $R_P$]-cyclic-<br>[A(2',5')p-2'F-A(3',5')p] | 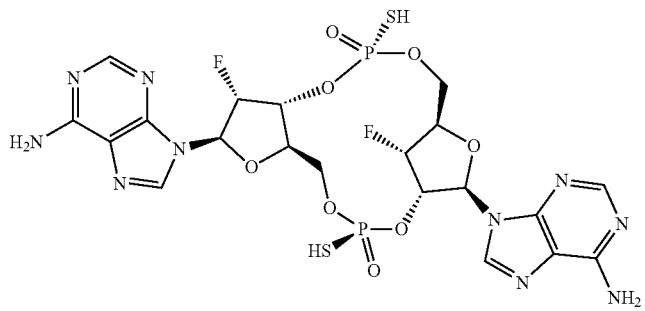 [SMILES: Nc1ncnc2c1ncn2[C@@H]1O[C@@H]2CO[P@](=O)(S)O[C@@H]3[C@H](F)[C@@H](CO[P@@](=O)(S)O[C@H]2[C@H]1F)O[C@H]3n1cnc2c(N)ncnc21] |
| Example 5 Compound 20<br>2'3'-RR-(3'F-A)(A);<br>dithio-[$R_P$, $R_P$]-cyclic-<br>[3'F-A(2',5')p-A(3',5')p] | 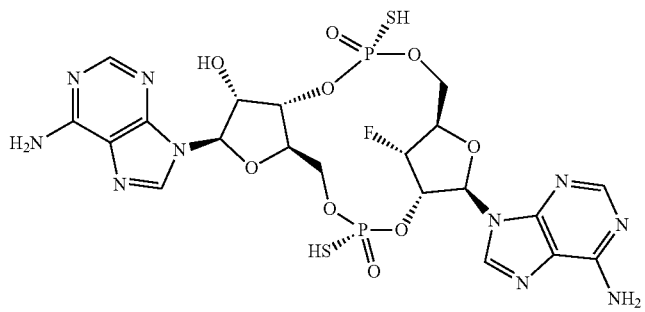 [SMILES: Nc1ncnc2c1ncn2[C@@H]1O[C@@H]2CO[P@@](=O)(S)O[C@@H]3[C@H](F)[C@@H](CO[P@@](=O)(S)O[C@H]2[C@H]1O)O[C@H]3n1cnc2c(N)ncnc21] |

TABLE 3-continued

Abridged compound names and structures.

| Example number and abridged Compound names | Structure |
|---|---|
| Example 5 Compound 20a<br>2'3'-RS-(3'F-A)(A);<br>dithio-[R$_P$, S$_P$]-cyclic-<br>[3'F-A(2',5')p-A(3',5')p] | 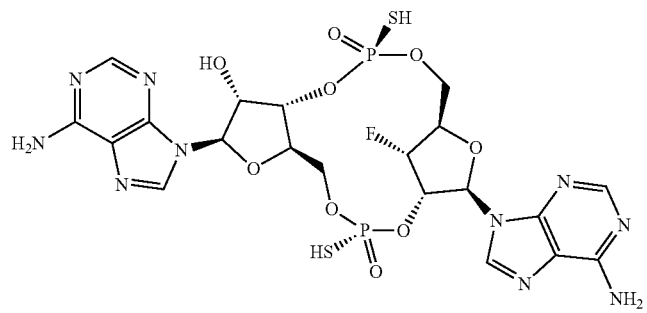 [SMILES: Nc1ncnc2c1ncn2[C@@H]1O[C@@H]2CO[P@@](=O)(S)O[C@@H]3[C@H](F)[C@@H](CO[P@](=O)(S)O[C@H]2[C@H]1O)O[C@H]3n1cnc2c(N)ncnc21] |
| Example 6 Compound 26<br>2'3'-RR-(G)(2'F-A);<br>dithio-[R$_P$, R$_P$]-cyclic-<br>[G(2',5')p-2'F-A(3',5')p] | 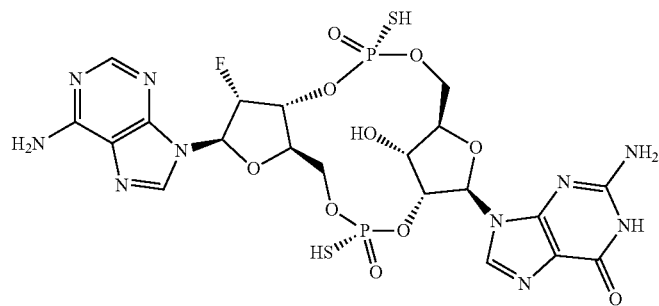 |
| Example 6 Compound 26a<br>2'3'-SR-(G)(2'F-A);<br>dithio-[S$_P$, R$_P$]-cyclic-<br>[G(2',5')p-2'F-A(3',5')p] | 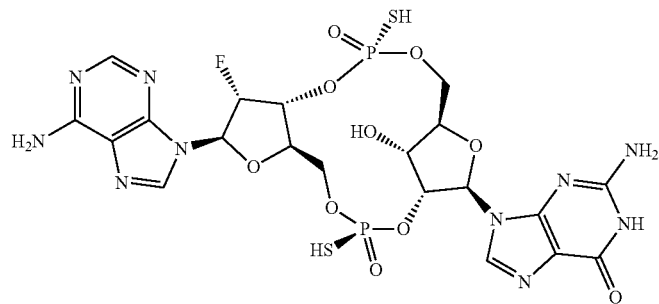 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@](=O)(S)O[C@@H]2[C@@H]3O)c(=O)[nH]1] |
| Example 6, Compound 50<br>2'3'-RR-(3'decanoyl-O-G) (2'F-A)<br>dithio-[R$_P$, R$_P$]-cyclic-<br>[3'decanoyl-O-G(2',5')p-2'F-A(3',5')p] | 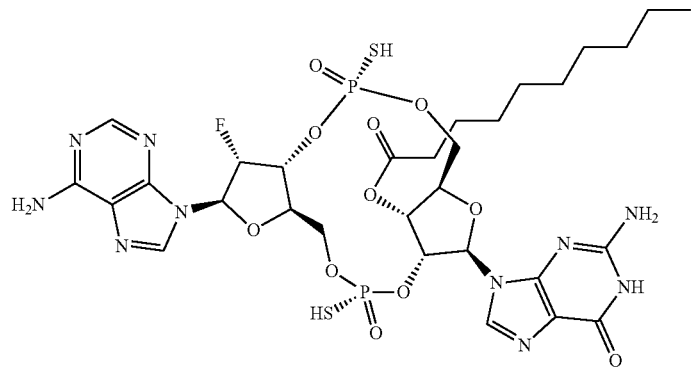 [SMILES: CCCCCCCCCC(=O)O[C@H]1[C@H]2O[P@](=O)(S)OC[C@H]3O[C@@H](n4cnc5c(N)ncnc54)[C@H](F)[C@@H]3O[P@](=O)(S)OC[C@H]1O[C@H]2n1cnc2c(=O)[nH]c(N)nc21] |

TABLE 3-continued

Abridged compound names and structures.

| Example number and abridged Compound names | Structure |
|---|---|
| Example 7 Compound 32<br>3'2'-RR-(2'F-G)(3'F-A);<br>dithio-[$R_P$, $R_P$]-cyclic-<br>[2'F-G(3',5')p-3'F-A(2',5')p] | 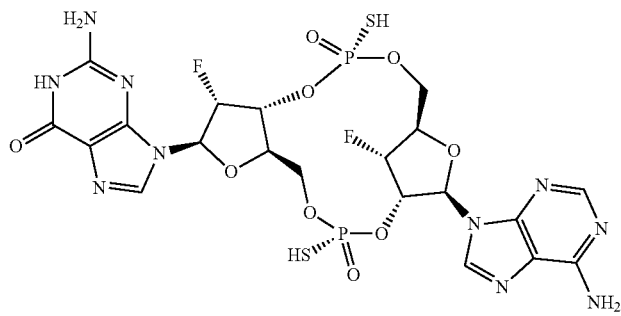 [SMILES: Nc1nc2c(ncn2[C@@H]2O[C@@H]3CO[P@@](=O)(S)O[C@@H]4[C@H](F)[C@@H](CO[P@@](=O)(S)O[C@H]3[C@H]2F)O[C@H]4n2cnc3c(N)ncnc32)c(=O)[nH]1] |
| Example 7 Compound 32a<br>3'2'-RS-(2'F-G)(3'F-A);<br>dithio-[$R_P$, $S_P$]-cyclic-<br>[2'F-G(3',5')p-3'F-A(2',5')p] | 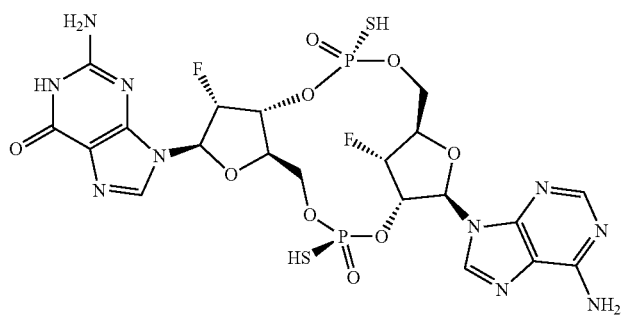 [SMILES: Nc1nc2c(ncn2[C@@H]2O[C@@H]3CO[P@](=O)(S)O[C@@H]4[C@H](F)[C@@H](CO[P@@](=O)(S)O[C@H]3[C@H]2F)O[C@H]4n2cnc3c(N)ncnc32)c(=O)[nH]1] |
| Example 7 Compound 32b<br>3'2'-SS-(2'F-G)(3'F-A);<br>dithio-[$S_P$, $S_P$]-cyclic-<br>[2'F-G(3',5')p-3'F-A(2',5')p] | 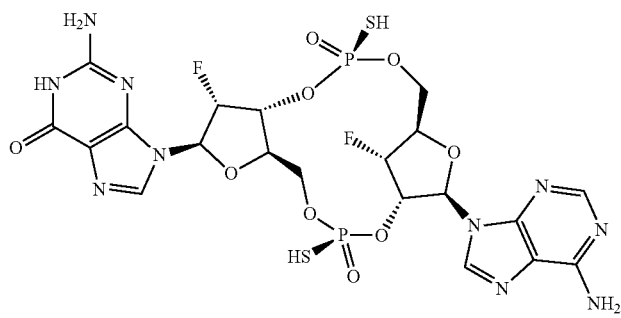 [SMILES: Nc1nc2c(ncn2[C@@H]2O[C@@H]3CO[P@](=O)(S)O[C@@H]4[C@H](F)[C@@H](CO[P@](=O)(S)O[C@H]3[C@H]2F)O[C@H]4n2cnc3c(N)ncnc32)c(=O)[nH]1] |
| Example 8 Compound 35<br>3'2'-RR-(2'F-G)(A);<br>dithio-[$R_P$, $R_P$]-cyclic-<br>[2'F-G(3',5')p-A(2',5')p] | 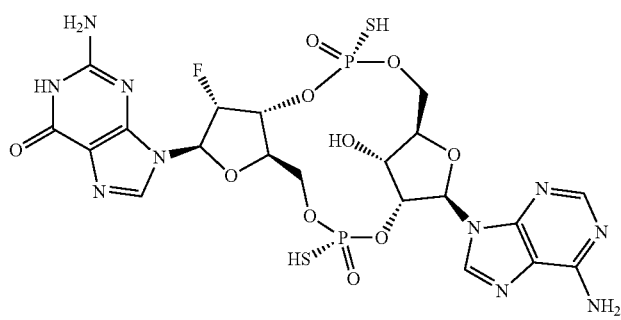 [SMILES: Nc1nc2c(ncn2[C@@H]2O[C@@H]3CO[P@@](=O)(S)O[C@@H]4[C@H](O)[C@@H](CO[P@@](=O)(S)O[C@H]3[C@H]2F)O[C@H]4n2cnc3c(N)ncnc32)c(=O)[nH]1] |

TABLE 3-continued

Abridged compound names and structures.

| Example number and abridged Compound names | Structure |
|---|---|
| Example 8 Compound 35a<br>3'2'-RS-(2'F-G)(A);<br>dithio-[R$_P$, S$_P$]-cyclic-<br>[2'F-G(3',5')p-A(2',5')p] | 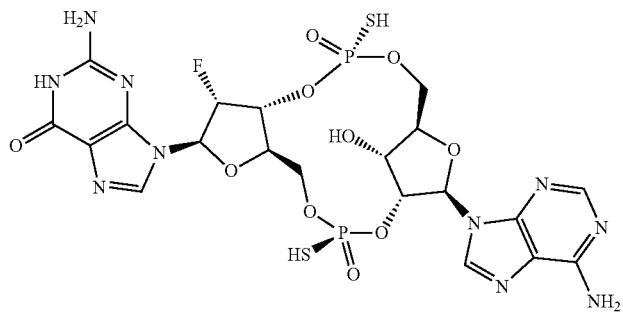 [SMILES: Nc1nc2c(ncn2[C@@H]2O[C@@H]3CO[P@](=O)(S)O[C@@H]4[C@H](O)[C@@H](CO[P@@](=O)(S)O[C@H]3[C@H]2F)O[C@H]4n2cnc3c(N)ncnc32)c(=O)[nH]1] |
| Example 8 Compound 35b<br>3'2'-SR-(2'F-G)(A);<br>dithio-[S$_P$, R$_P$]-cyclic-<br>[2'F-G(3',5')p-A(2',5')p] | 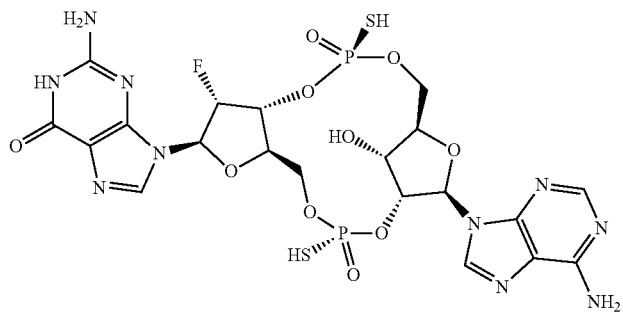 [SMILES: Nc1nc2c(ncn2[C@@H]2O[C@@H]3CO[P@@](=O)(S)O[C@@H]4[C@H](O)[C@@H](CO[P@](=O)(S)O[C@H]3[C@H]2F)O[C@H]4n2cnc3c(N)ncnc32)c(=O)[nH]1] |
| Example 9 Compound 38<br>2'3'-(G)(2'F-A);<br>cyclic-[G(2',5')p-2'F-A(3',5')p] | 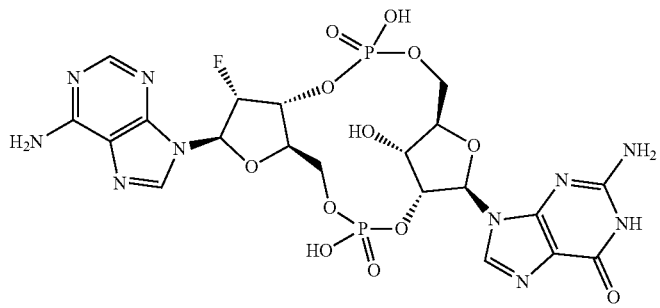 |
| Example 10 Compound 40<br>2'3'-(3'F-G)(2'F-A);<br>cyclic-[3'F-G(2',5')p-2'F-A(3',5')p] | 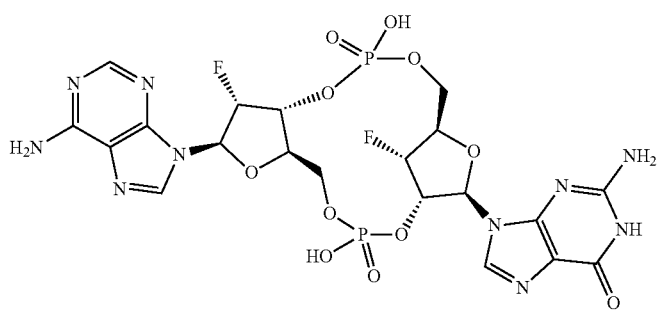 [SMILES: Nc1nc2c(ncn2[C@@H]2O[C@@H]3COP(=O)(O)O[C@H]4[C@@H](F)[C@H](n5cnc6c(N)ncnc65)O[C@@H]4COP(=O)(O)O[C@@H]2[C@@H]3F)c(=O)[nH]1] |

US 10,906,930 B2

TABLE 3-continued

Abridged compound names and structures.

| Example number and abridged Compound names | Structure |
|---|---|
| Example 11 Compound 45<br>2'3'-RR-(3'H-A)(2'F-A);<br>dithio-[$R_P$, $R_P$]-cyclic-<br>[3'H-A(2',5')p-2'F-A(3',5')p] | 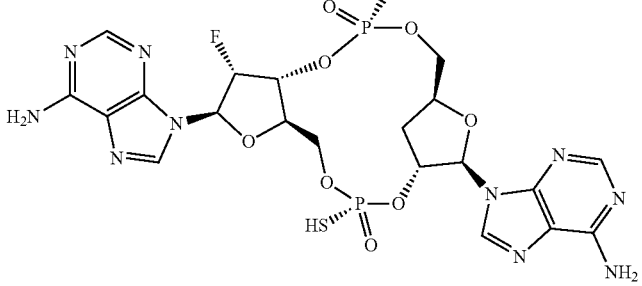 |
| Example 11 Compound 45a<br>2'3'-RS-(3'H-A)(2'F-A);<br>dithio-[$R_P$, $S_P$]-cyclic-<br>[3'H-A(2',5')p-2'F-A(3',5')p] | 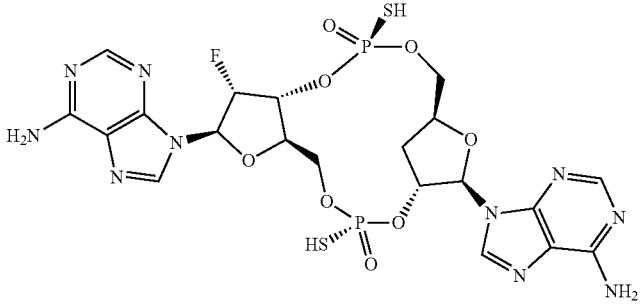 [SMILES: Nc1ncnc2c1ncn2[C@@H]1O[C@@H]2CO[P@@](=O)(S)O[C@@H]3C[C@@H](CO[P@](=O)(S)O[C@H]2[C@H]1F)O[C@H]3n1cnc2c(N)ncnc21] |
| Example 12 Compound 49<br>2'3'-RR-(3'F-G)(2'F-A);<br>dithio-[$R_P$, $R_P$]-cyclic-<br>[3'F-G(2',5')p-2'F-A(3',5')p] | 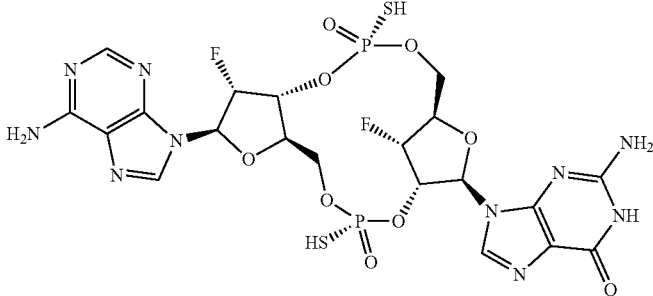 |
| Example 12 Compound 49a<br>2'3'-RS-(3'F-G)(2'F-A);<br>dithio-[$R_P$, $R_P$]-cyclic-<br>[3'F-G(2',5')p-2'F-A(3',5')p] | 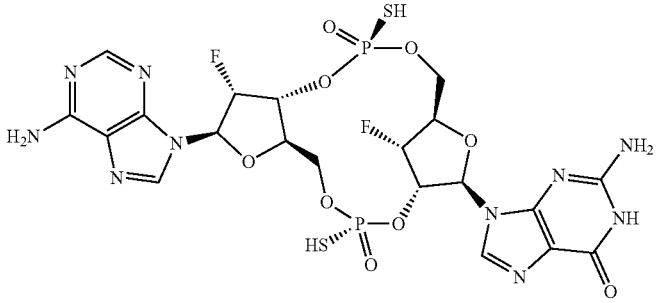 [SMILES: Nc1nc2c(ncn2[C@@H]2O[C@@H]3CO[P@](=O)(S)O[C@H]4[C@@H](F)[C@H](n5cnc6c(N)ncnc65)O[C@@H]4CO[P@@](=O)(S)O[C@@H]2[C@@H]3F)c(=O)[nH]1] |
| Example 13 Compound 53<br>dithio 2'3'-(3'βF-A)(A);<br>dithio-cyclic-<br>[3'βF-A(2',5')p-A(3',5')p] | 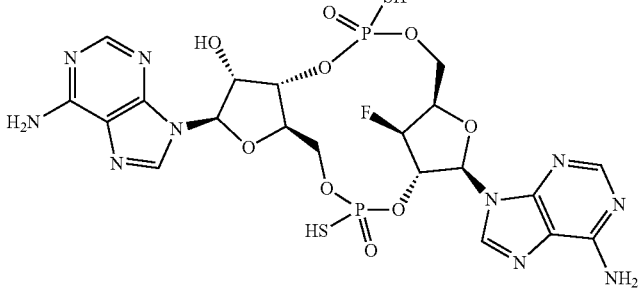 |

TABLE 3-continued

Abridged compound names and structures.

Example number and abridged Compound names | Structure

2'3'-RR-(A)(A);
dithio-[R_P, R_P]-cyclic-[A(2',5')pA(3',5')p]

2'3'-SR-(A)(A);
dithio-[S_P, R_P]-cyclic-[A(2',5')pA(3',5')p]

2'3'-RR-(G)(A);
dithio-[R_P, R_P]-cyclic-[G(2',5')pA(3',5')p]

2'3'-(G)(A);
cyclic-[G(2',5')pA(3',5')p]

Abbreviations and Acronyms. SalPCl=Salicyl chlorophosphite. DCA=dichloroacetic acid. DDTT=3-((N,N-dimethyl-aminomethylidene)amino)-3H-1,2,4-dithiazole-5-thione. DAST=diethylaminosulfur trifluoride. NaHCO_3=sodium bicarbonate. DCM=CH_2Cl_2=dichloromethane. EtOH=ethanol. EtOAc=ethyl acetate. KOAc=potassium acetate. MeCN=acetonitrile. MeOH=methanol. DMAP=N,N-dimethylpyridin-4-amine. DMOCP=2-chloro-5,5-dimethyl-1,3,2-dioxaphosphorinane-2-oxide. DMTCl=4,4'-dimethoxytrityl chloride. DMT=4,4-dimethoxytrityl. N-phenyltriflamide=1,1,1-trifluoro-N-phenyl-N-((trifluoromethyl)sulfonyl)methanesulfonamide. TBAF=tetrabutylammonium fluoride. TBS=tert-butyldimethylsilyl. TEAA=Triethylammonium acetate. TEA=trimethylamine. TEAH=triethylammonium. TEAB=treithylammonium bicarbonate. TFA=trifluoroacetic acid. TMSCl=trimethylsilyl chloride. HF=hydrofluoric acid. THF=tetrahydrofuran. G=Guanine. $G^{ib}$=isobutyryl guanine. A=adenine. A^Bz=benzoyl adenine. AMA=ammonium hydroxide/40% methylamine solution in water.

Example 1: Synthesis of Intermediate Compounds

For the intermediate compounds of Scheme 1A, LCMS were recorded using a Waters System (Micromass ZQ mass spectrometer; Column: Sunfire C18 3.5 micron, 3.0×30 mm; gradient: 40-98% acetonitrile in water with 0.05% TFA over a 2.0 min period; flow rate 2 mL/min; column temperature 40° C.), referred to as Method A. For the intermediate compounds of Scheme 1B, Methods B-D, LCMS were recorded using a Waters System (Micromass SQ mass spectrometer; Column: Acquity UPLC BEH C18 1.7 micron, 2.1×50 mm). Method B: gradient: 2-98% acetonitrile in water+5 mM ammonium hydroxide over a 1.76 min period isocratic for 0.3 min before returning to 2% acetonitrile at 2.5 min-total run time 5.2 min; flow rate 1 mL/min; column temperature 50° C. Method C: gradient: 2-98% acetonitrile in water+5 mM ammonium hydroxide over a 4.40 min period isocratic for 0.65 min before returning to 2% acetonitrile at 5.19 min-total run time 5.2 min; flow rate 1 mL/min; column temperature 50° C. Method D: gradient 1% to 30% acetonitrile to 3.20 min then gradient: 30-98% acetonitrile in water with 0.1% Formic acid over a 5.2 min period; flow rate 1 mL/min; column temperature 50° C. For Scheme 1B, Method E, HRMS data were recorded using a Waters System (Acquity G2 Xevo QTof mass spectrometer; Column: Acquity BEH 1.7 micron, 2.1×50 mm; gradient: 40-98% acetonitrile in water with 0.1% Formic acid over a 3.4 min period, isocratic 98% acetonitrile for 1.75 min returning to 40% at 5.2 min; flow rate 1 mL/min; column temperature 50° C.). All masses reported are those of the protonated parent ions unless indicated otherwise.

Intermediates i6 (used in Examples 2 and 5) and i7 (used in Example 7) were prepared according to the following Scheme 1A:

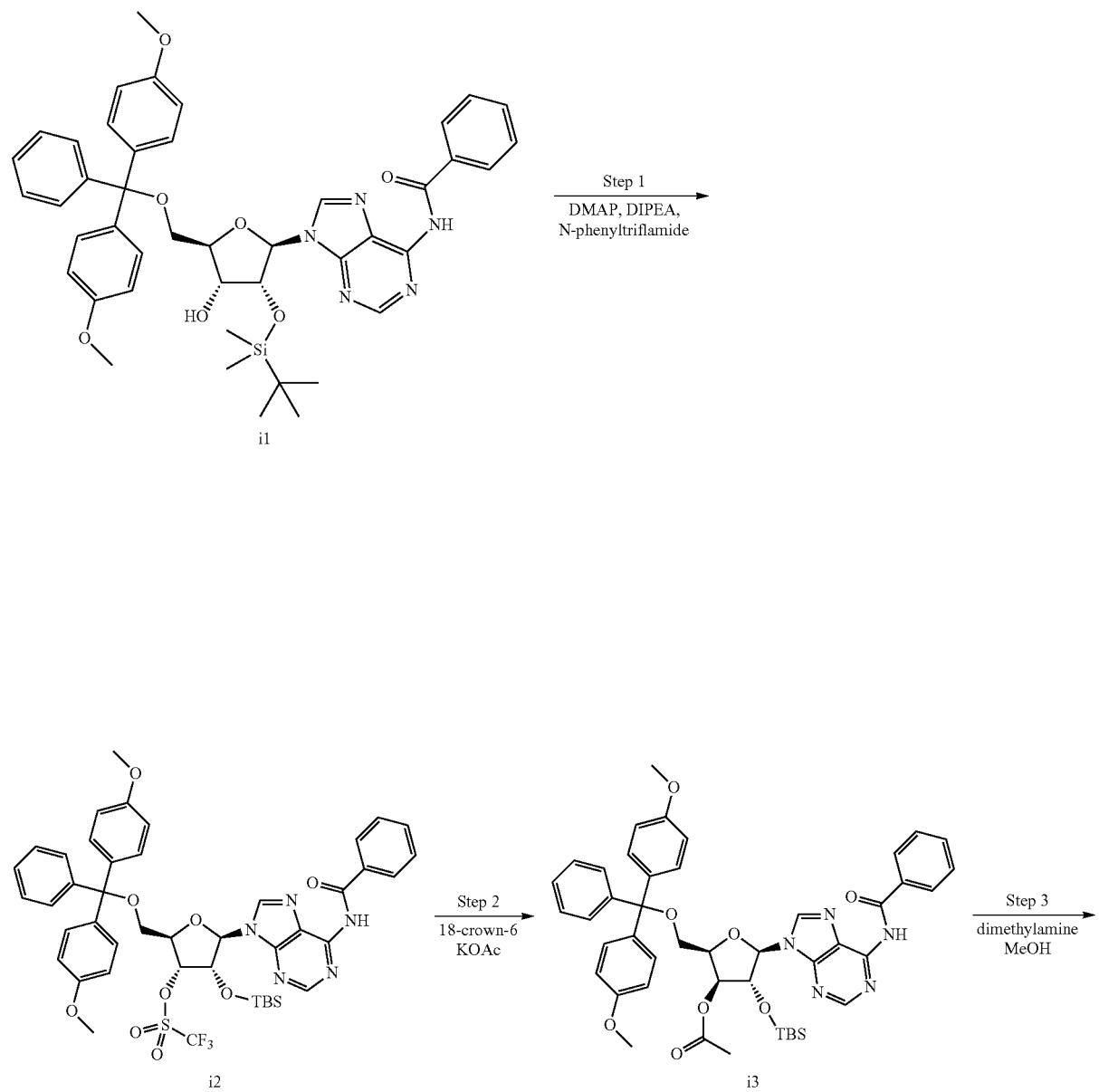

201

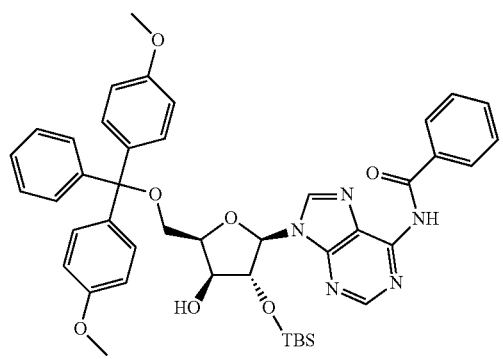

i4

Step 4
DAST →

202

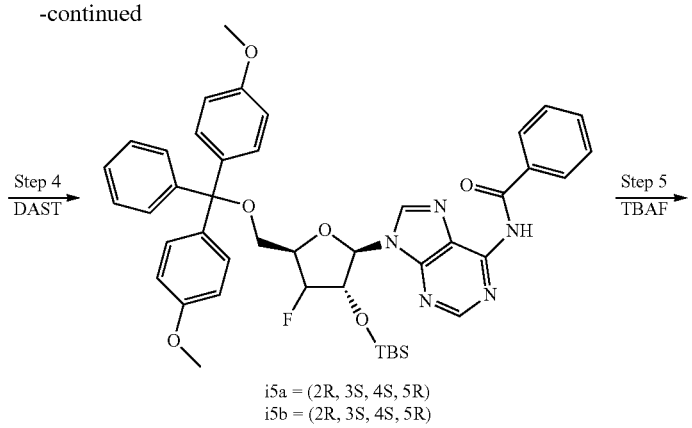

i5a = (2R, 3S, 4S, 5R)
i5b = (2R, 3S, 4S, 5R)

Step 5
TBAF →

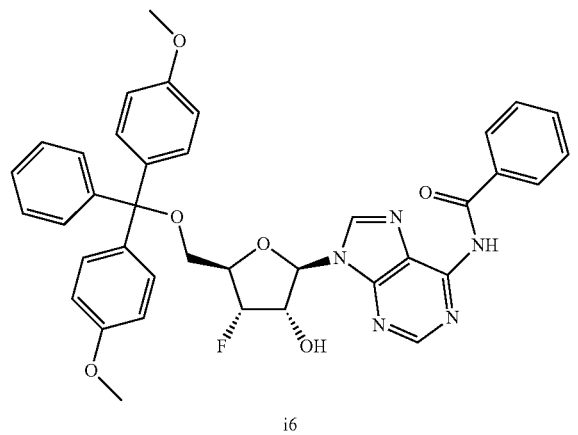

i6

Step 6
2-Cyanoethyl
N,N-diisopropylchloro-
phosphoramidite,
DIPEA, DMAP, THF
→

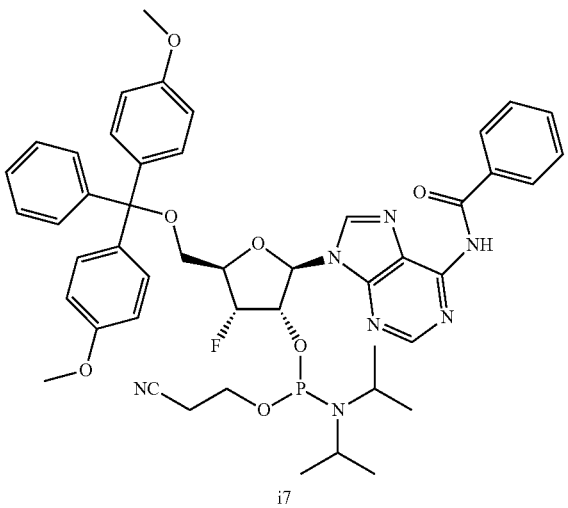 [SMILES: COc1ccc(C(OC[C@H]2O[C@@H](n3cnc4c(NC(=O)c5ccccc5)ncnc43)[C@H](OP(OCCC#N)N(C(C)C)C(C)C)[C@@H]2F)(c2ccccc2)c2ccc(OC)cc2)cc1]

i7

Step 1: Preparation of (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl Trifluoromethane-Sulfonate (i2)

A mixture of N-(9-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-9H-purin-6-yl)benzamide (i1, 5.6 g, 7.11 mmol, ChemGenes) and DMAP (0.174 g, 1.42 mmol) was suspended in anhydrous THF (35 mL), addition of DIPEA (6.21 mL, 35.5 mmol) created a solution to which N-phenyltriflamide (5.08 g, 14.21 mmol), was added. The mixture was stirred for 3.5 h at room temperature at which point it was poured into 5% brine (100 mL) and extracted with EtOAc (2×100 mL). The combined organic phases were dried (Na$_2$SO$_4$) the drying agent filtered-off and concentrated on silica gel (10 g) in vacuo. The crude material was purified by chromatography on silica gel (gradient elution 25-100% EtOAc/heptane) to give the desired compound i2 as a tan solid; 5.53 g; $^1$H NMR (400 MHz, CDCl$_3$) δ 9.05 (s, 1H), 8.68 (s, 1H), 8.18 (s, 1H), 8.06 (d, J=7.5 Hz, 2H), 7.66 (t, J=7.4 Hz, 1H), 7.61-7.48 (m, 4H), 7.48-7.25 (m, 7H), 6.88 (d, J=8.8 Hz, 4H), 6.04 (d, J=7.6 Hz, 1H), 5.50 (dd, J=7.5, 4.7 Hz, 1H), 5.32 (d, J=4.5 Hz, 1H), 4.50 (t, J=4.1 Hz, 1H), 3.82 (s, 6H), 3.77 (dt, J=10.8, 5.2 Hz, 1H), 3.41 (dd, J=10.8, 3.7 Hz, 1H), 0.77 (s, 9H), −0.01 (s, 3H), −0.46 (s, 3H); LCMS (Method A) $R_t$=1.65 min; m/z 920.5 [M+H]$^+$.

Step 2: Preparation of (2R,3S,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl Acetate (i3)

A mixture of compound i2 (5.5 g, 5.98 mmol), KOAc (2.93 g, 29.9 mmol), and 18-crown-6 (1,4,7,10,13,16-hexaoxacyclooctadecane, 0.79 g, 2.99 mmol) in toluene (40 mL) was heated at 110° C. for 4 h. The reaction mixture was then cooled to room temperature and silica gel (10 g) added and the solvent was removed in vacuo. The crude material was purified by chromatography on silica gel (gradient elution 25-100% EtOAc/heptane) to give the desired compound i3 as a tan solid: 3.3 g; $^1$H NMR (400 MHz, CDCl$_3$) δ 8.70 (s, 1H), 8.58 (s, 1H), 7.93 (s, 1H), 7.84 (d, J=7.5 Hz, 2H), 7.44 (t, J=7.4 Hz, 1H), 7.35 (t, J=7.6 Hz, 2H), 7.28 (d, J=7.2 Hz, 2H), 7.21-7.02 (m, 7H), 6.67 (dd, J=8.9, 2.1 Hz, 4H), 5.98 (s, 1H), 4.97 (dd, J=3.6, 1.4 Hz, 1H), 4.61-4.52 (m, 1H), 4.35 (s, 1H), 3.62 (s, 6H), 3.41 (dd, J=9.8, 6.2 Hz, 1H), 3.18 (dd, J=9.8, 5.6 Hz, 1H), 1.53 (s, 3H), 0.77 (s, 9H), 0.03 (s, 3H), 0.0 (s, 3H). LCMS (Method A) $R_t$ 1.68 min; m/z 830.2 [M+H]$^+$.

Step 3: Preparation of N-(9-((2R,3R,4S,5R)-5-((bis(4-methoxyphenyl)(phenyl)methoxy)methyl)-3-((tert-butyldimethylsilyl)oxy)-4-hydroxytetrahydrofuran-2-yl)-9H-purin-6-yl)benzamide (i4)

Compound i3 (6.78 g, 8.17 mmol) was dissolved in MeOH (120 mL) and a 2.0 M dimethylamine solution in MeOH (20.4 mL, 40.8 mmol) was added. The reaction mixture was stirred for 17 h at room temperature. Silica gel (12 g) was added and the solvent was removed in vacuo. The crude material was purified by chromatography on silica gel (gradient elution 25-75% EtOAc/heptane) to give the desired compound i4 as a tan solid: 3.9 g; $^1$H NMR (400 MHz, CDCl$_3$) δ 8.94 (s, 1H), 8.65 (s, 1H), 8.16 (s, 1H), 7.97-7.90 (m, 2H), 7.58-7.38 (m, 3H), 7.38-7.32 (m, 2H), 7.32-7.00 (m, 7H), 6.80-6.65 (m, 4H), 5.83 (d, J=1.2 Hz, 1H), 5.38 (d, J=8.0 Hz, 1H), 4.42 (s, 1H), 4.29 (t, J=4.6 Hz, 1H), 4.02-3.95 (m, 1H), 3.75-3.61 (m, 6H), 3.53 (d, J=5.0 Hz, 2H), 0.81 (s, 9H), 0.0 (s, 6H). LCMS (Method A) $R_t$ 1.57 min; m/z 788.2 [M+H]$^+$.

Step 4: Preparation of N-(9-((2R,3S,4S,5R)-5-((bis(4-methoxyphenyl)(phenyl)methoxy)methyl)-3-((tert-butyldimethylsilyl)oxy)-4-fluorotetrahydrofuran-2-yl)-9H-purin-6-yl)benzamide (i5a) and N-(9-((2R,3S,4R,5R)-5-((bis(4-methoxyphenyl)(phenyl)methoxy)methyl)-3-((tert-butyldimethylsilyl)oxy)-4-fluorotetrahydrofuran-2-yl)-9H-purin-6-yl)benzamide (i5b)

Compound i4 (750 mg, 0.952 mmol) was dissolved in anhydrous DCM (7 mL) under an inert nitrogen atmosphere and the solution was cooled to 0° C. A 1.0 M solution of DAST (1.90 mL, 1.90 mmol) was added and the reaction subsequently stirred at −5° C. for 17 h using a cryo-cool to control the reaction temperature. The vessel was warmed to 0° C. and saturated NaHCO$_3$ (2 mL) was added. After 30 minutes of stirring the mixture was diluted with 5% brine (20 mL) and extracted with EtOAc (2×20 mL). The combined organics were dried (Na$_2$SO$_4$) with the drying agent filtered off, silica gel (2 g) added to the filtrate and the solvent removed in vacuo. The crude material was purified by chromatography on silica gel (gradient elution 10-75% EtOAc/heptane) to give a mixture of diastereoisomers i5a and i5b as a tan solid: 193 mg; Major (2R,3S,4S,5R) diastereoisomer LCMS (Method A) $R_t$ 1.53 min; m/z 790.4 (M+H)$^+$; Minor (2R,3S,4R,5R) diastereoisomer $R_t$ 1.58 min; m/z 790.4 [M+H]$^+$.

Step 5: Preparation of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (i6)

The diastereomeric mixture of i5a and i5b (2.0 g, 2.53 mmol) was dissolved in anhydrous THF (100 mL) and cooled to −42° C. under an inert nitrogen atmosphere before 1.0 M TBAF (3.80 mL, 3.80 mmol) was added. The reaction was stirred for 2.5 h, then quenched with saturated NaHCO$_3$ (20 mL). The cold bath was removed, and the slurry was stirred for 10 minutes before the mixture was diluted with 5% brine (150 mL) and extracted with DCM (2×100 mL). The combined organic phases were dried (Na$_2$SO$_4$), with the drying agent filtered off, silica gel (4 g) added to the filtrate and the solvent removed in vacuo. The crude material was purified by chromatography on silica gel (gradient elution 25-100% EtOAc/heptane) to give the desired compound i6 as a white solid: 355 mg; $^1$H NMR (400 MHz, CDCl$_3$) δ 9.16 (s, 1H), 8.64 (s, 1H), 8.23 (s, 1H), 7.99 (d, J=7.5 Hz, 2H), 7.59 (t, J=7.4 Hz, 1H), 7.48 (t, J=7.6 Hz, 2H), 7.41-7.31 (m, 3H), 7.31-7.11 (m, 7H), 6.79 (d, J=8.9 Hz, 4H), 6.16 (d, J=7.3 Hz, 1H), 5.77 (br s, 1H), 5.27-5.10 (m, 2H), 4.53 (dt, J=28.0 Hz, 3.4 Hz, 1H), 3.77 (s, 6H), 3.51 (dd, J=10.7, 3.7 Hz, 1H), 3.34 (dd, J=10.7, 3.3 Hz, 1H); $^{19}$F NMR (376.4 MHz, CDCl$_3$) δ−197.5; $^{13}$C NMR (101 MHz, CDCl$_3$) δ 164.66, 158.64, 158.62, 152.60, 151.43, 149.34, 144.22, 141.66, 135.29, 135.13, 133.40, 132.93, 129.96, 128.87, 127.99, 127.93, 127.86, 127.07, 122.65, 113.26, 93.85, 92.02, 87.56 (d, J=144 Hz), 83.56 (d, J=23 Hz), 77.30, 74.63 (d, J=16 Hz), 62.82 (d, J=11 Hz), 55.26; LCMS (Method A) $R_t$ 0.89 min; m/z 676.3 [M+H]$^+$.

Step 6: Preparation of (2R,3S,4R,5R)-2-(6-benzamido-9H-purin-9-yl)-5-((bis(4-methoxyphenyl)(phenyl)methoxy)methyl)-4-fluorotetrahydrofuran-3-yl (2-cyanoethyl) Diisopropylphosphoramidite (i7)

To a dried solution of i6 (830 mg, 1.4 mmole, 1 eq) in THF (5.0 mL) was added DMAP (18 mg, 0.15 mmole, 0.1 eq) and DIPEA (0.9 mL, 5.5 mmole, 4 eq). 2-Cyanoethyl N,N-diisopropylchlorophosphoramidite (340 µL, 1.5 mmole, 1.1 eq) was slowly added and the reaction proceeded for 16 h. The reaction mixture was diluted with EtOAc (that was prewashed with a 5% NaHCO$_3$ aq solution) and washed with a brine solution (5×100 mL). The combined aqueous layers were extracted with EtOAc and all the organic layers were combined, dried over Na$_2$SO$_4$, filter, and concentrated. MPLC-SiO$_2$ (DCM:Hex:TEA 50:44:6) gave 810 mg of i7 as a mixture of diastereomers at the phosphorus stereocenter. LCMS (50-100% MeCN/10 mm TEAA for 10 mins then 100% MeCN for 14 mins at 1 mL/min) $R_t$ 12.3 and 13.0 min; m/z 877.15 [M+H]$^+$.

Intermediate i13 (used in Example 3) was prepared according to the following Scheme 1B:

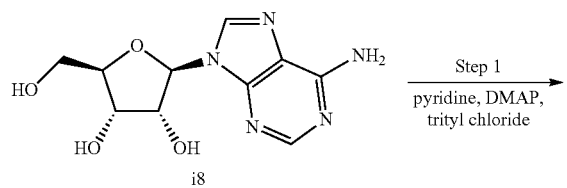
Step 1
pyridine, DMAP,
trityl chloride
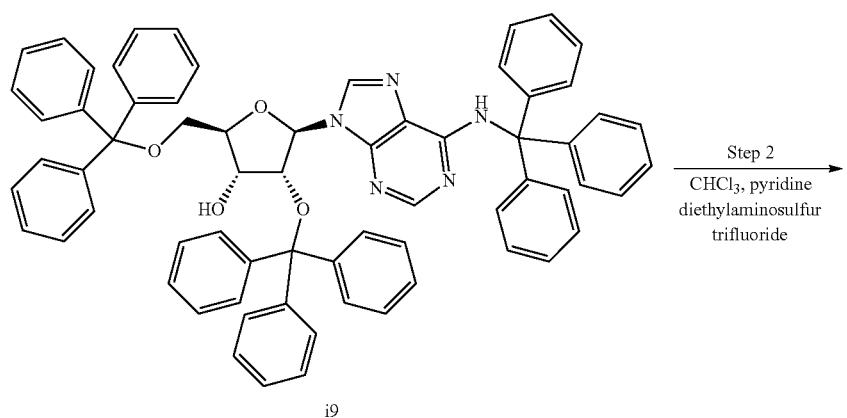
i9
Step 2
CHCl₃, pyridine
diethylaminosulfur
trifluoride
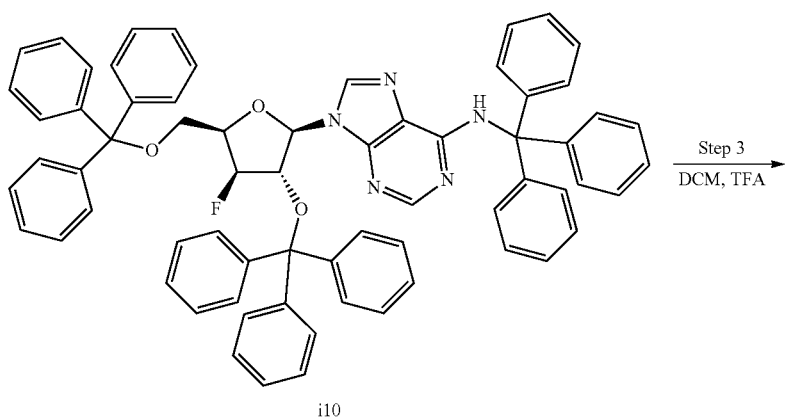
i10
Step 3
DCM, TFA
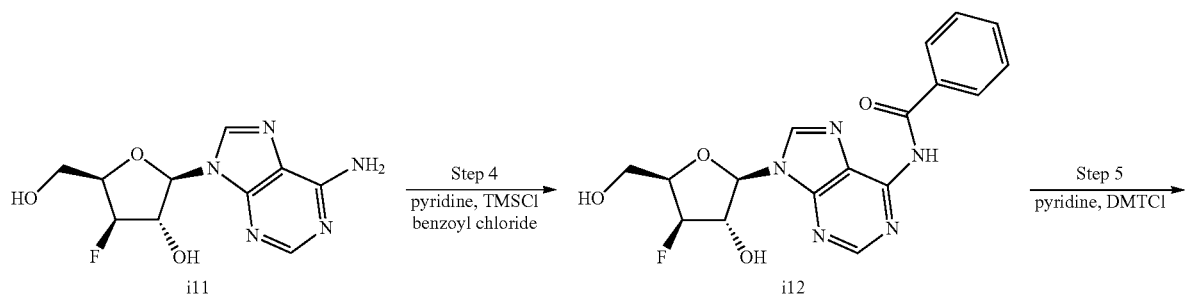
i11 → Step 4 pyridine, TMSCl benzoyl chloride → i12 → Step 5 pyridine, DMTCl

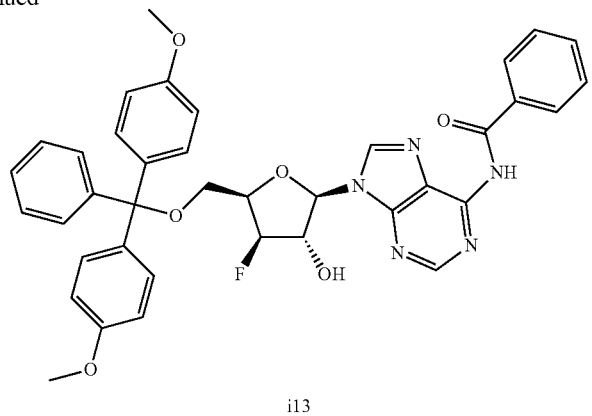

i13

Step 1: Preparation of (2R,3R,4R,5R)-5-(6-(tritylamino)-9H-purin-9-yl)-4-(trityloxy)-2-((trityloxy)methyl) Tetrahydrofuran-3-ol (i9)

To a solution of adenosine (i8, 5.0 g, 18.7 mmol) in pyridine (250 mL, 3.09 mol) at room temperature was added DMAP (1.943 g, 15.9 mmol) followed by trityl chloride (17.47 g, 62.7 mmol). The resulting mixture was stirred at 80° C., after 24 h additional trityl chloride (6.2 g, 22.3 mmol) was added and continued stirring at 80° C. After 48 h, additional trityl chloride (5.2 g, 18.7 mmol) was added and stirring continued for a further 48 h at which point the reaction was cooled to room temperature and quenched by addition of EtOH (50 mL). The reaction mixture was concentrated in vacuo and the resulting residue was then suspended in toluene (35 mL), filtered to remove solid, and concentrated in vacuo. The resulting crude material was purified by chromatography on silica gel (gradient elution 0-10% B/A where A=8:1 $CH_2Cl_2$:Heptane, B=EtOAc) to afford the desired compound i9: 3.27 g; $^1$H NMR (400 MHz, $CDCl_3$) δ 7.94 (s, 1H), 7.90 (s, 1H), 7.39-7.45 (m, 6H), 7.14-7.35 (m, 36H), 7.06-7.12 (m, 6H), 7.02 (br s, 1H), 6.35 (d, J=7.5 Hz, 1H), 5.15 (dd, J=7.4, 4.6 Hz, 1H), 4.07 (t, J=3.0 Hz, 1H), 3.28 (dd, J=10.5, 3.5 Hz, 1H), 3.01 (dd, J=10.4, 3.3 Hz, 1H), 2.85 (d, J=4.5 Hz, 1H), 2.26 (s, 1H); LCMS (Method B) $R_t$ 4.22 min; m/z 995.5 [M+H]$^+$.

Step 2: Preparation of 9-((2R,3S,4S,5R)-4-fluoro-3-(trityloxy)-5-((trityloxy)methyl)tetrahydrofuran-2-yl)-N-trityl-9H-purin-6-amine (i10)

To a solution of compound i9 (5.72 g, 5.75 mmol) in $CHCl_3$ (145 mL) at room temperature was added pyridine (11.6 mL, 144 mmol) followed by diethylaminosulfur trifluoride (3.80 mL, 28.8 mmol). The resulting mixture was stirred at room temperature for 24 h after which time the reaction was quenched by addition of a solution of sat. aq. $NaHCO_3$ (150 mL). The mixture was diluted further with $CH_2Cl_2$ (150 mL), the layers were separated and the organic layer was further washed with water (2×150 mL) and dried ($Na_2SO_4$). After filtering off the drying agent, the filtrate was concentrated in vacuo. The resulting crude material was purified by chromatography on silica gel (gradient elution 0-45% EtOAc/Heptane) to afford the desired compound i10: 2.91 g; $^1$H NMR (400 MHz, $CDCl_3$) δ 8.05 (s, 1H), 7.57 (s, 1H), 7.27-7.36 (m, 18H), 7.07-7.25 (m, 28H), 6.81 (br s, 1H), 6.40 (d, J=1.3 Hz, 1H), 4.31 (dd, J=14.0, 1.3 Hz, 1H), 4.02-4.23 (m, 1H), 3.63, (dd, J=50.2, 1.8 Hz, 1H), 3.40 (dd, J=8.9, 7.2 Hz, 1H), 3.20 (dd, J=9.7, 6.4 Hz, 1H); $^{19}$F NMR (376.4 MHz, $CDCl_3$) δ−199.59; HRMS (Method E) $R_t$ 3.28 min; m/z 996.4261 [M+H]$^+$.

Step 3: Preparation of (2R,3S,4R,5R)-2-(6-amino-9H-purin-9-yl)-4-fluoro-5-(hydroxymethyl)tetra-hydro-furan-3-ol (i11)

A solution of compound i10 (3.92 g, 3.94 mmol) in $CH_2Cl_2$ (40 mL) was cooled to 0° C. after which time trifluoroacetic acid (3.94 mL, 51.2 mmol) was added dropwise. The resulting dark yellow mixture was allowed to stir at 0° C. for 10 min and then warmed to room temperature and stirred for 16 h. Upon completion the reaction was quenched by the addition of water (20 mL) and diluted with $CH_2Cl_2$ (50 mL). The combined layers were lyophilized overnight. The resulting crude material from lyophilization was purified by chromatography on silica gel (isocratic elution 10% MeOH/$CH_2Cl_2$) to afford the desired compound i11: 858 mg; $^1$H NMR (400 MHz, DMSO-$d_6$) δ 8.17 (s, 1H), 8.10 (s, 1H), 7.35 (br s, 2H), 6.29 (d, J=4.6 Hz, 1H), 5.94 (d, J=2.5 Hz, 1H), 4.97-5.24 (m, 2H), 4.71-4.80 (m, 1H), 4.20-4.43 (m, 1H), 3.64-3.84 (m, 2H); $^{19}$F NMR (376.4 MHz, DMSO-$d_6$) δ−200.84; LCMS (Method C) $R_t$ 0.44 min; m/z 270.0 [M+H]$^+$.

Step 4: Preparation of N-(9-((2R,3S,4R,5R)-4-fluoro-3-hydroxy-5-(hydroxymethyl)tetrahydro-furan-2-yl)-9H-purin-6-yl)benzamide (i12)

To a solution of compound i11 (488 mg, 1.27 mmol) in pyridine (6.0 mL) at room temperature was added TMSCl (0.81 mL, 6.37 mmol). The resulting mixture was stirred at room temperature for 15 min after which time benzoyl chloride (0.74 mL, 6.37 mmol) was added and stirring was continued at room temperature. After 3 h the reaction was cooled to 0° C. and quenched by addition of water (1.5 mL). The mixture was allowed to stir for 10 min after which time concentrated ammonia (3.0 mL) was added and the reaction was warmed to room temperature. After an additional 30 min the reaction was diluted with water (10 mL) and extracted with EtOAc (3×50 mL). The combined organic layers were dried ($Na_2SO_4$), the drying agent filtered off and the filtrate concentrated in vacuo. The resulting crude material was triturated from diethyl ether to afford the desired compound i12: 240 mg; $^1$H NMR (400 MHz, DMSO-$d_6$) δ 11.22 (br s, 1H), 8.78 (s, 1H), 8.43 (s, 1H), 8.02-8.08 (m, 2H), 7.62-7.68 (m, 1H), 7.52-7.59 (m, 2H), 6.38 (d, J=4.8

Hz, 1H), 6.1 (d, J=2.3 Hz, 1H), 5.04-5.22 (m, 2H), 4.80-4.88 (m, 1H), 4.31-4.44 (m, 1H), 3.70-3.84 (m, 2H); $^{19}$F NMR (376.4 MHz, DMSO-$d_6$) δ−200.61; LCMS (Method D) $R_t$ 1.47 min; m/z 374.3 [M+H]$^+$.

Step 5: Preparation of N-(9-((2R,3S,4R,5R)-5-((bis(4-methoxyphenyl)(phenyl)methoxy)methyl)-4-fluoro-3-hydroxytetrahydrofuran-2-yl)-9H-purin-6-yl)benzamide (i13)

To a solution compound i12 (720 mg, 1.93 mmol) in pyridine (3.5 mL) at room temperature was added 4,4'-dimethoxytriphenylmethyl chloride (686 mg, 2.03 mmol). The resulting mixture was stirred at room temperature for 16 h after which time MeOH (5 mL) was added and the mixture was concentrated in vacuo. The resulting crude material was purified by chromatography on silica gel (gradient elution 0-10% MeOH/CH$_2$Cl$_2$) to afford the desired compound i13: 885 mg; $^1$H NMR (600 MHz, DMSO-$d_6$) δ 11.24 (s, 1H), 8.78 (s, 1H), 8.24 (s, 1H), 8.04 (d, J=7.6 Hz, 2H), 7.63-7.67 (m, 1H), 7.53-7.58 (m, 2H), 7.38-7.46 (m, 4H), 7.25-7.31 (m, 6H), 7.20-7.24 (m, 1H), 6.86 (dd, J=12.1, 8.7 Hz, 4H), 6.44 (d, J=4.5 Hz, 1H), 6.14 (d, J=1.9 Hz, 1H), 5.20 (dd, J=51.4, 2.3 Hz, 1H), 4.88 (br d, J=15.5 Hz, 1H), 4.54-4.63 (m, 1H), 3.72 (d, J=3.8 Hz, 6H), 3.38-3.43 (m, 2H); $^{19}$F NMR (376.4 MHz, DMSO-$d_6$) δ−199.41; HRMS (Method E) $R_t$ 1.23 mins; m/z 676.2561 [M+H]$^+$.

Intermediates i16 N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (used in Example 12) was prepared according to the following Scheme 1C:

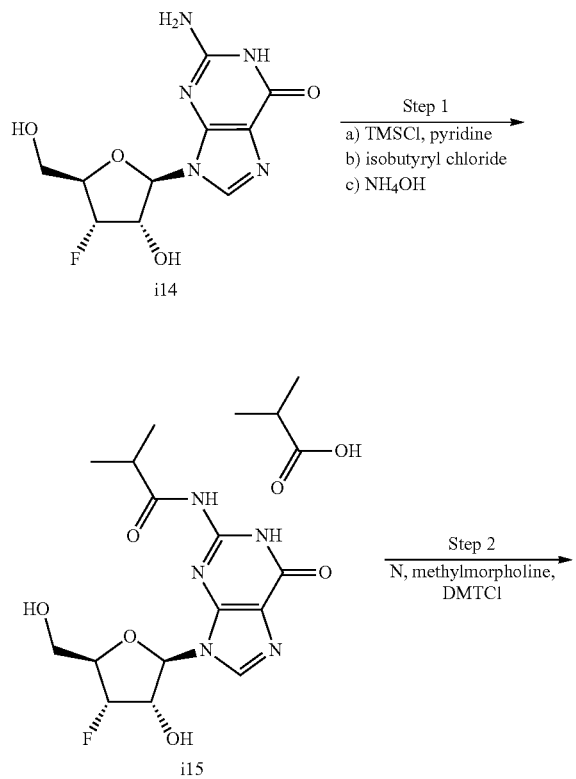

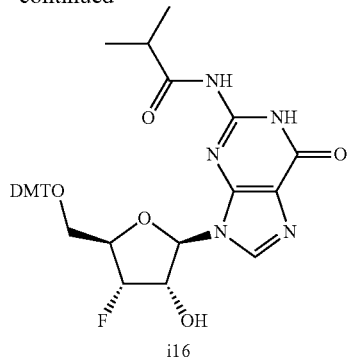

Step 1: Preparation of N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide Isobutyric Acid Salt (i15)

To a solution of 2-amino-9-((2R,3S,4S,5R)-4-fluoro-3-hydroxy-5-(hydroxymethyl)tetrahydrofuran-2-yl)-1,9-dihydro-6H-purin-6-one (i14, 1.69 g, 5.91 mmol, Carbosynth, San Diego, Calif.) in pyridine (27.0, 334 mmol) at room temperature was added chlorotrimethylsilane (5.67 mL, 44.4 mmol) dropwise over 5 min. The reaction was stirred at room temperature for 2 h after which time the solution was cooled to 0° C. and isobutyryl chloride (1.86 mL, 17.74 mmol) was added dropwise over 10 min. The mixture was allowed to stir at 0° C. for 5 min and then warmed to room temperature for 3.5 h. The reaction was then cooled to 0° C. and quenched by addition of water (9.0 mL), stirred for 10 min at 0° C. and then warmed to room temperature. After stirring for 5 min, concentrated ammonia (28% aq. NH$_4$OH solution, 18 mL) was added and the mixture was stirred for 35 min, the mixture was then diluted with water (80 mL) and washed with DCM (40 mL). The aqueous layer was separated and concentrated in vacuo with the resulting crude material then purified by chromatography on silica gel (gradient elution 0-50% MeOH/CH$_2$Cl$_2$) to afford the compound i15 (1.32 g): $^1$H NMR (400 MHz, CD$_3$OD) δ 8.27 (s, 1H), 6.01 (d, J 7.6 Hz, 1H), 5.02-5.20 (m, 1H), 4.76-4.84 (m, 1H), 4.29-4.41 (m, 1H), 3.79 (d, J=3.3 Hz, 2H), 2.72 (hept, J 6.8 Hz, 1H), 2.47 (hept, J 6.8 Hz, 1H), 1.23 (d, J 6.8 Hz, 6H), 1.12 (d, J 6.8 Hz, 6H); $^{19}$F NMR (376 MHz, CD$_3$OD) δ−200.84; LCMS (method F) Rt 0.66 min; m/z 356.2 (M+H+).

Step 2: Preparation of N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (i16)

To a suspension of compound i15 (2.18 g, 6.14 mmol) in 1:1 THF:CHCl$_3$ (400 mL) at room temperature was added N-methylmorpholine (2.70 mL, 24.54 mmol) followed by 4,4'-dimethoxytrityl chloride (8.32 g, 24.54 mmol) in a single portion. The mixture was stirred at room temperature for 35 min after which time the reaction was quenched by addition of sat. aq. NaHCO$_3$ solution (250 mL). The organic layer was separated layers and the aqueous layer further extracted with DCM (2×150 mL). The combined organic layers were dried (MgSO$_4$) the drying agent then filtered off and the filtrate concentrated in vacuo to give an oil. The resulting crude material was purified by chromatography on silica gel (gradient 0-60% EtOAc/heptane to remove N-methylmorpholine, followed by 0-60% MeOH/DCM) to afford to the compound i16 (3.57 g): $^1$H NMR (400 MHz, CD$_3$OD) δ 8.04 (s, 1H), 7.36-7.42 (m, 2H), 7.17-7.31 (m, 7H), 6.78-6.85 (m, 4H), 6.00 (d, J 7.1 Hz, 1H), 5.00-5.25 (m, 2H), 4.41 (m, 1H), 3.76 (s, 6H), 3.46 (dd, J 10.6, 4.3 Hz, 1H), 3.37 (dd, J 10.6, 3.0 Hz, 1H), 2.57 (hept, J 6.8 Hz, 1H), 1.19 (d, J 6.8 Hz, 3H), 1.16 (d, J 6.8 Hz, 3H); $^{19}$F NMR (376 MHz, CD$_3$OD) δ −200.35; LCMS (method C) Rt 2.16 min; m/z 658.3 (M+H+).

Example 2: Synthesis of 2'3'-RR-(3'F-A)(2'F-A) (5) and 2'3'-RS-(3'F-A)(2'F-A) (5a)

2'3'-RR-(3'F-A)(2'F-A) (5), also referred to as dithio-[R$_P$, R$_P$]-cyclic-[3'F-A(2',5')p-2'F-A(3',5')p], was prepared according to the following Scheme 2:

Step 1: Preparation of (2R,3S,4R,5R)-2-(6-benzamido-9H-purin-9-yl)-4-fluoro-5-(hydroxymethyl)tetrahydrofuran-3-yl Hydrogen Phosphonate (1)

To a solution of N-(9-((2R,3S,4S,5R)-5-((bis(4-methoxyphenyl)(phenyl)methoxy)methyl)-4-fluoro-3-hydroxytetrahydrofuran-2-yl)-9H-purin-6-yl)benzamide (i6, Example 1 Scheme 1A, 0.75 g, 1.1 mmol) in 1,4-dioxane (8 mL) and pyridine (2.5 mL) was added a solution of SalPCl (0.27 g, 1.3 mmol) in 1,4-dioxane (4 mL). After 45 minutes, to the stirring reaction mixture at room temperature was introduced water (1 mL), and the mixture was poured into a 1N aqueous NaHCO$_3$ solution (40 mL). This aqueous mixture was extracted with EtOAc (3×40 mL) and the layers were partitioned. The EtOAc extracts were combined and concentrated to dryness as a colorless foam. The resulting foam was purified by silica gel chromatography (0% to 50% MeOH with 0.5% pyridine in CH$_2$Cl$_2$) to obtain the inter-

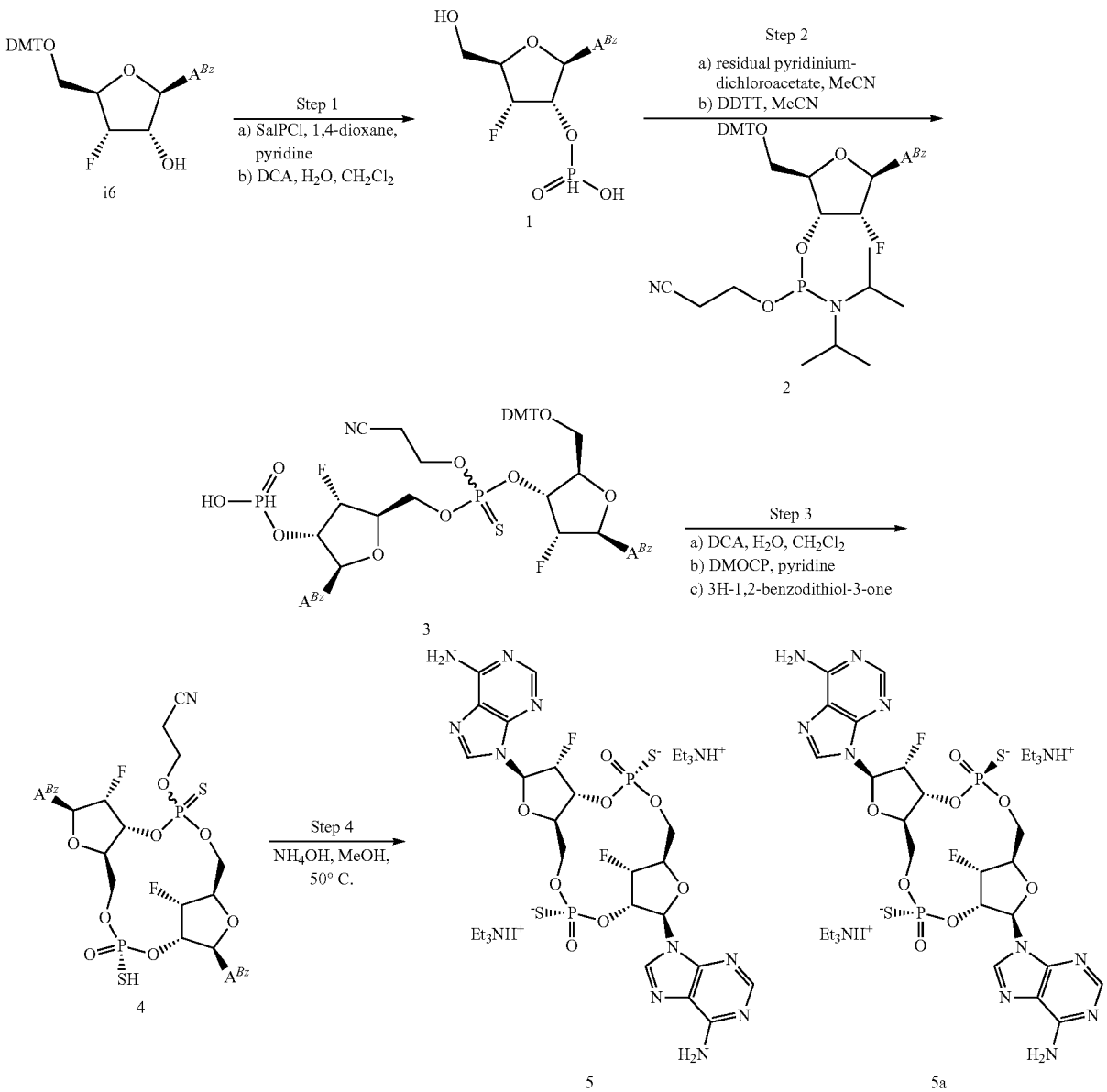

mediate (2R,3S,4R,5R)-2-(6-benzamido-9H-purin-9-yl)-5-((bis(4-methoxyphenyl)(phenyl)methoxy)methyl)-4-fluorotetrahydrofuran-3-yl hydrogen phosphonate (220 mg, 27%) as a colorless foam. To a solution of this intermediate (220 mg, 0.3 mmol) in $CH_2Cl_2$ (4 mL) was added water (0.05 mL) and a 6% (v/v) solution of DCA in $CH_2Cl_2$ (3.8 mL). After ten minutes, to the red solution was charged pyridine (0.4 mL), which resulted in a white mixture. The white mixture was concentrated in vacuo and water was removed as an azeotrope after concentration with MeCN (20 mL). This azeotrope process was repeated two more times with MeCN (20 mL). On the last evaporation, the white slurry of compound 1 was left in MeCN (5 mL).

Step 2: Preparation of (2R,3S,4R,5R)-2-(6-benzamido-9H-purin-9-yl)-5-(((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphorothioyl)oxy)methyl)-4-fluorotetrahydrofuran-3-yl Hydrogen Phosphonate (3)

A solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (2, 0.31 g, 0.36 mmol, ChemGenes) in MeCN (20 mL) was dried through concentration in vacuo. This process was repeated two more times to remove water as an azeotrope. On the last azeotrope, to a solution of compound 2 in MeCN (1.5 mL) was introduced ten 3 Å molecular sieves and the solution was stored under an atmosphere of nitrogen. To a stirring mixture of compound 1 with residual pyridinium dichloroacetate in MeCN (5 mL) was added the solution of compound 2 in MeCN (1.5 mL). After five minutes, to the stirring mixture was added DDTT (68 mg, 0.33 mmol), which resulted in a yellow mixture. After 30 minutes, the yellow mixture was concentrated in vacuo to give the desired compound 3 as a yellow oil.

Step 3: Preparation of Protected 2'3'-dithio-(3'F-A)(2'F-A) (4)

To a solution of compound 3 (~371 mg, 0.3 mmol) in $CH_2Cl_2$ (4 mL) was added water (0.04 mL) and a 6% (v/v) solution of DCA in $CH_2Cl_2$ (4 mL). After ten minutes, to the red solution was introduced pyridine (5 mL), which turned the red solution into a yellow mixture. The yellow mixture was concentrated in vacuo until approximately 3 mL of the yellow mixture remained. To the yellow mixture was introduced pyridine (5 mL) and the mixture was evaporated until approximately 3 mL of the yellow mixture remained, and addition of pyridine and evaporation to 3 mL was repeated. To the stirring yellow mixture in pyridine (3 mL) was added DMOCP (0.165 g, 0.9 mmol). After seven minutes, to the dark orange solution was added water (0.15 mL), followed immediately by the introduction of 3H-1,2-benzodithiol-3-one (75 mg, 0.45 mmol). After five minutes, the dark orange solution was poured into a 1N aqueous $NaHCO_3$ solution (40 mL). After fifteen minutes, the biphasic mixture was extracted with EtOAc (50 mL). After separating the layers, the aqueous layer was back extracted twice with EtOAc (50 mL). The organic extracts were combined and concentrated. To the concentrated yellow oil was added toluene (20 mL) and the mixture was evaporated to remove residual pyridine. This procedure was repeated twice with toluene (20 mL). The resulting oil was purified by silica gel chromatography (0% to 10% MeOH in $CH_2Cl_2$) to obtain compound 4 (20 mg, 7%) as a white solid.

Step 4: Preparation of 2'3'-RR-(3'F-A)(2'F-A) (5)

To a stirring solution of compound 4 (20 mg, 0.02 mmol) in MeOH (1.0 mL) was added aqueous ammonium hydroxide (0.5 mL) and the orange slurry was heated to 50° C. After ninety minutes, the yellow solution was allowed to cool and later concentrated in vacuo. The yellow residue was purified by reverse phase silica gel chromatography (0% to 20% MeCN in 10 mM aqueous TEAA) to obtain compound 5 (5.3 mg, 76%, purity 99%) as a white bis-triethylammonium salt after lyophilization. LCMS-ESI: 694 [M−H]$^-$ (calculated for $C_{20}H_{22}F_2N_{10}O_8P_2S_2$: 693.30); $R_t$: 8.372 min. $^1$H NMR (400 MHz, 45° C., $D_2O$) δ 8.61 (s, 1H), 8.43 (s, 1H), 8.23 (s, 1H), 8.14 (s, 1H), 6.57 (d, J=16.4 Hz, 1H), 6.44 (d, J=8.8 Hz, 1H), 5.90 (dd, J=30.0, 3.5 Hz, 1H), 5.75 (dd, J=28.0, 3.5 Hz, 1H), 5.67 (td, J=8.0, 3.5 Hz, 1H), 5.47-5.38 (m, 1H), 4.93 (d, J=25.0 Hz, 1H), 4.74-4.59 (m, 3H), 4.46 (dd, J=12.0, 3.5 Hz, 1H), 4.28 (d, J=12.0 Hz, 1H), 3.34 (q, J=7.0 Hz, 12H), 1.43 (t, J=7.0 Hz, 18H). $^{19}$F NMR (400 MHz, 45° C., $D_2O$) δ −197.95 to −198.23 (m), −200.24 to −200.35 (m). $^{31}$P NMR (45° C., $D_2O$) δ 54.98, 52.70.

The 2'3'-RS-(3'F-A)(2'F-A) (5a) was isolated in the final purification step as the bis-triethylammonium salt. LCMS-ESI: 694 [M−H]$^-$ (calculated for $C_{20}H_{22}F_2N_{10}O_8P_2S_2$: 693.30); $R_t$: 7.973 min. In a scale-up of this reaction, the SR and SS isomers were also isolated: 2'3'-SR-(3'F-A)(2'F-A) (5b); LCMS-ESI: 693.65 [M−H]$^-$ (calculated for $C_{20}H_{22}F_2N_{10}O_8P_2S_2$: 694.05); $R_t$: 7.057' min, and 2'3'-SS-(3'F-A)(2'F-A) (5c); LCMS-ESI: 695.65 [M+H]; 693.65 [M−H]$^-$ (calculated for $C_{20}H_{22}F_2N_{10}O_8P_2S_2$: 694.05); $R_t$: 6.327' min. LCMS for all four isomers used a 10 min gradient of 2% to 50% MeCN in 20 mM aqueous $NH_4OAc$.

The substantially pure compound 5 (2'3'-RR-(3'F-A)(2'F-A)) was co-crystallized with wild type STING protein, and the x-ray structure of this compound bound to STING confirmed the stereochemistry as depicted in Scheme 2, compound 5. The corresponding stereoisomer having S configuration on the A-3'-5'-A phosphorus was separated from compound 5, where the retention time of the S isomer was 8.128 min. While additional compounds below have not yet been co-crystallized, experience with these compounds indicates that the Rp, Rp isomer consistently has a longer retention time than the corresponding Rp, Sp isomer or Sp, Rp isomer. While the Rp, Rp and Rp, Sp or Sp, Rp isomers typically demonstrate improvements in STING binding relative to the di-OH analogues, the identity of the Rp, Rp isomers in the following examples is further verified as having improved biological activity (e.g. binding to STING, induction of IFNβ) than the Rp, Sp or Sp, Rp isomer.

Example 3: Synthesis of 2'3'-RR-(3'βF-A)(2'F-A) (10) and 2'3'-RS-(3'βF-A)(2'F-A) (10a)

2'3'-RR-(3'βF-A)(2'F-A) (10), also referred to as dithio-[R$_P$, R$_P$]-cyclic-[3'βF-A(2',5')p-2'F-A(3',5')p], was prepared according to the following Scheme 3:

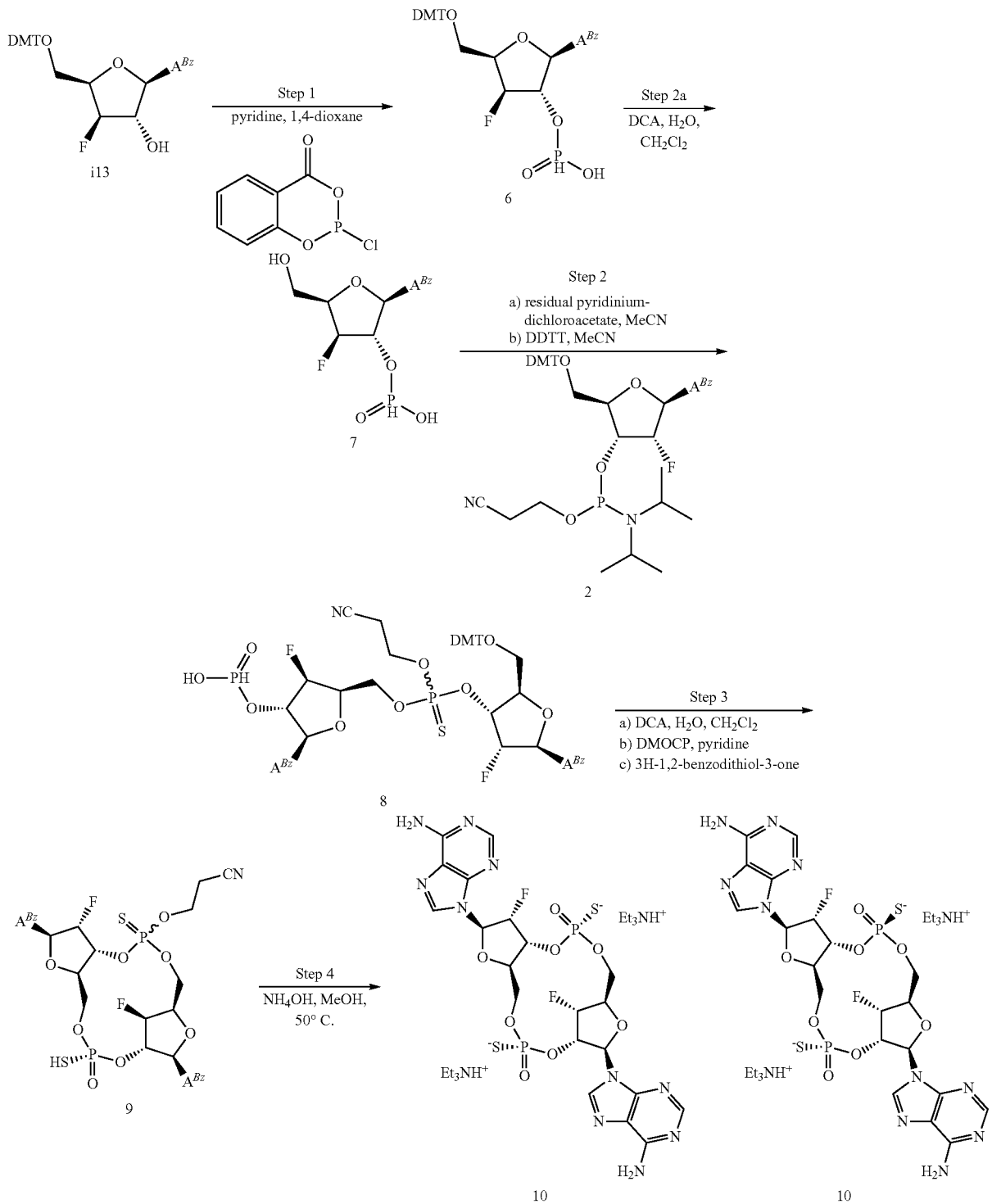

Step 1: Preparation of (2R,3S,4S,5R)-2-(6-benzamido-9H-purin-9-yl)-5-((bis(4-methoxyphenyl)(phenyl)methoxy)methyl)-4-fluorotetrahydrofuran-3-yl Hydrogen Phosphonate (6)

To a solution of N-(9-((2R,3S,4R,5R)-5-((bis(4-methoxyphenyl)(phenyl)methoxy)methyl)-4-fluoro-3-hydroxytetrahydrofuran-2-yl)-9H-purin-6-yl)benzamide (i13, Example 1, Scheme 1B; 630 mg, 0.92 mmole, 1 eq) in dioxane (7.1 mL) was added pyridine (1.9 mL, 24 mmole, 26 eq) followed by 2-chloro-4H-1,3,2-Benzodioxaphoshorin-4-one (225 g, 1.10 mmole, 1.2 eq). The reaction mixture was stirred for 30 min. The mixture was quenched with 5 mL of water followed by 1.9 g NaHCO$_3$ in 52 mL of water. After extraction with EtOAc (3×62 mL) and DCM (1×50 mL), the combined organic layers were dried with Na$_2$SO$_4$, filtered and concentrated to give 0.92 g crude compound 6. Prep MPLC-SiO$_2$ (99% DCM:1% (99.5% MeOH, 0.5% pyridine) to 50:50) gave 460 mg of compound 6.

Step 2: Preparation of (2R,3S,4S,5R)-2-(6-benzamido-9H-purin-9-yl)-5-(((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy) phosphorothioyl)oxy)methyl)-4-fluorotetrahydrofuran-3-yl Hydrogen Phosphonate (8)

Compound 2 (see Example 2, Scheme 2, Step 2, 750 mg, 0.86 mmole, 1.3 eq) was coevaporated with anhydrous acetonitrile (3×10 mL) leaving 4 mL of acetonitrile. (Step 2a) To a solution of compound 6 (490 mg, 0.67 mmole, 1 eq) in DCM (8.0 mL) was added water (0.12 mL) followed by 8.0 mL of a 6% DCA in DCM solution. The reaction mixture was stirred for 10 minutes then quenched with pyridine (93 µL) and concentrated in vacuo. The mixture was coevaporated with anhydrous acetonitrile (3×5 mL) leaving 1.8 mL of compound 7 in acetonitrile. The solution of compound 2 (750 mg) in anhydrous acetonitrile (4 mL) was added and stirred for 3 minutes. After the addition of DDTT (150 mg), the reaction mixture was stirred for 30 min then concentrated in vacuo to give 2.1 g of crude compound 8.

Step 3: Preparation of Protected 2'3'-dithio-(3'βF-A)(2'F-A) (9)

To a solution of crude compound 8 (2.1 g) in DCM (16 mL) was added water (120 µL) followed by 16 mL of a 6% DCA in DCM solution. The reaction mixture was stirred for 10 minutes then quenched with pyridine (6.6 mL). The mixture was concentrated to remove the DCM, then coevaporated with anhydrous pyridine (1×20 mL) leaving 13 mL. DMOCP (370 mg, 2.0 mmole, 3 eq) was added and stirred for 3 min followed by water (0.37 mL, 20 mmole, 30 eq) and immediately after with 3H-1,2-benzodithiol-3-one (170 mg, 1.0 mmole, 1.5 eq). The reaction was allowed to proceed for 5 min and was diluted with a 3% solution of NaHCO$_3$ (100 mL) and extracted with 100 mL of a 1:1 solution of diethyl ether and EtOAc, then 100 mL DCM. The combined organic layers were concentrated to give 1 g of crude compound 9. Prep MPLC-SiO$_2$ (100% DCM to 15% DCM/MeOH) gave 170 mg of 9 as a mixture of diastereomers.

Step 4: Preparation of 2'3'-RR-(3'βF-A)(2'F-A) (10)

To a solution of 9 (170 mg, 0.17 mmole, 1 eq) in EtOH (3 mL) was added conc NH$_4$OH (3 mL). The mixture was sealed with a cap and parafilm, and heated to 50° C. for 3 h. The mixture was then cooled to rt, sparged with Ar gas for 10 minutes and concentrated in vacuo. Prep MPLC-C18 (100% 10 mM TEAA to 20% acetonitrile/10 mM TEAA) gave 7.0 mg of compound 10 (R$_t$: 7.94 min, 94% purity) and 4.1 mg of the R,S diastereomer (R$_t$: 7.00 min). LCMS-ESI: 693.7 [M−H]$^-$ (calculated for C$_{20}$H$_{22}$F$_2$N$_{10}$O$_8$P$_2$S$_2$: 694.05); $^1$H NMR (400 MHz, 45° C., D$_2$O) δ 8.49 (s, 1H), 8.44 (s, 2H), 8.36 (s, 1H), 6.62 (d, J=18.4 Hz, 1H), 6.54 (s, 1H), 5.99-5.94 (m, 1H), 5.87-5.81 (m, 1H), 5.36 (m. 1H), 5.25-5.10 (m, 1H), 5.07-4.95 (m, 1H), 4.85-4.60 (m, 3H), 4.32 (d, J=14.4 Hz, 1H), 3.34 (q, J=6.8 Hz, 12H), 2.11 (s, 0.73H), 1.43 (t, J=7.2 Hz, 18H), 5.25-5.10. $^{19}$F NMR (376 MHz, 45° C., D$_2$O) δ−199.1; −203.1 (td, J=56.0, 24.0 Hz), 200.1 (td, J=56.0, 24.0, 20.0 Hz), $^{31}$P NMR (162 MHz, 45° C., D$_2$O) δ 57.2; 54.6.

The 2'3'-RS-(3'βF-A)(2'F-A) (10a) was isolated in the final purification step as the bis-triethylammonium salt.

Example 4: Synthesis of 2'3'-RR-(A)(2'F-A) (16) and 2'3'-SR-(A)(2'F-A) (16a)

2'3'-RR-(A)(2'F-A) (16), also referred to as dithio-[R$_P$, R$_P$]-cyclic-[A(2',5')p-2'F-A(3',5')p], was prepared according to the following Scheme 4:

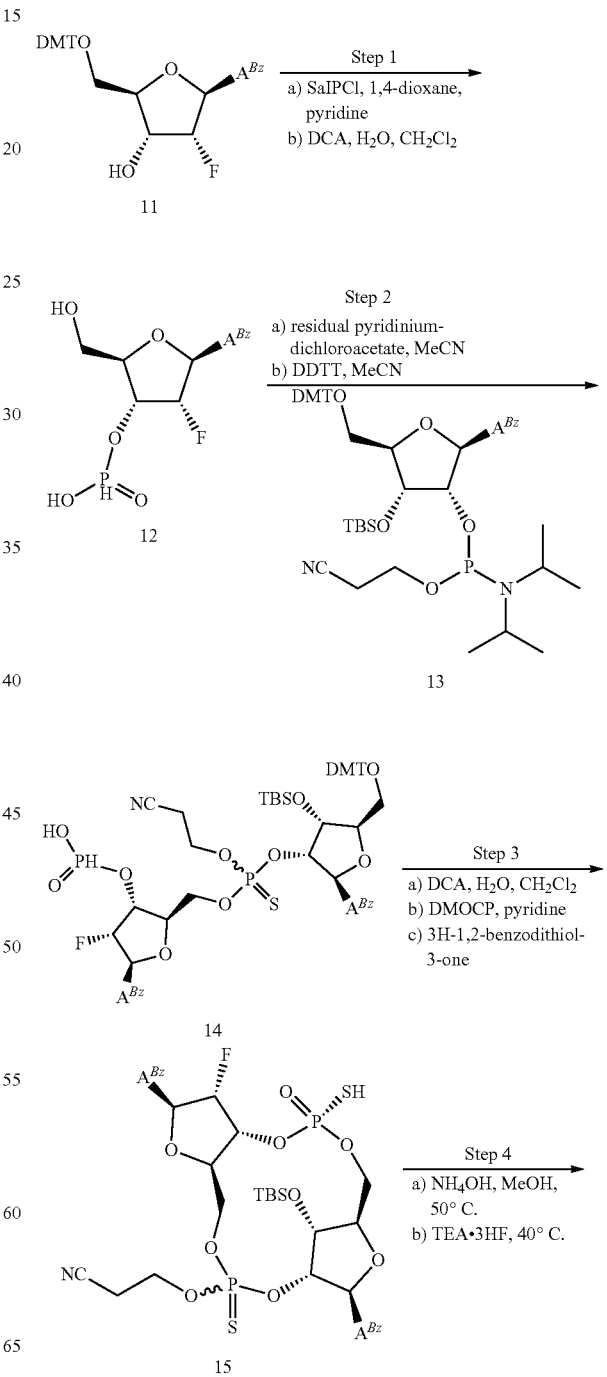

-continued

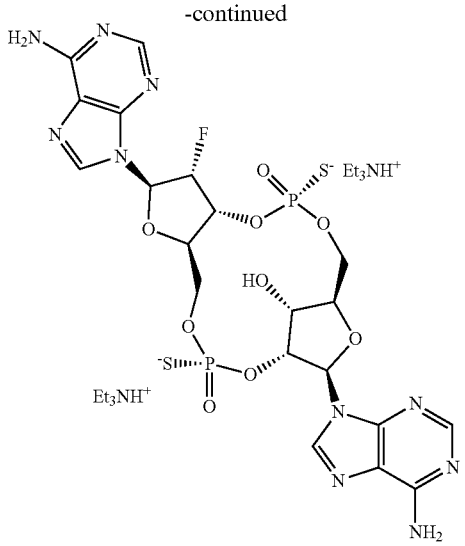

16

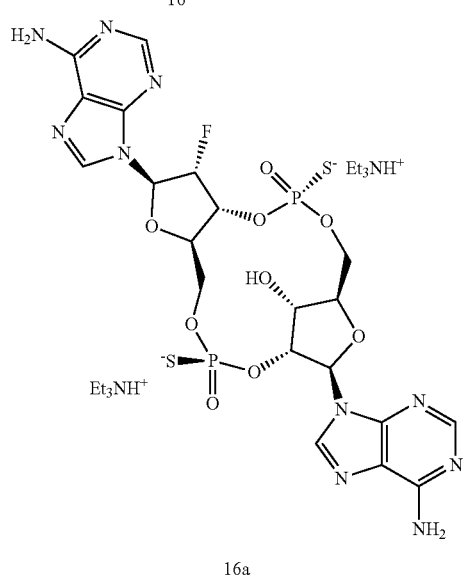

16a

Step 1: Preparation of (2R,3R,4R,5R)-5-(6-benzamido-9H-purin-9-yl)-4-fluoro-2-(hydroxymethyl)tetrahydrofuran-3-yl Hydrogen Phosphonate (12)

To a stirring solution of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (11, 1.5 g, 2.3 mmol, ChemGenes) in 1,4-dioxane (20 mL) and pyridine (6.7 mL) was added a solution of SalPC1 (0.45 g, 2.3 mmol) in 1,4-dioxane (10 mL). After 30 minutes, to the stirring reaction mixture at room temperature was introduced water (3 mL), and the mixture was poured into a 1N aqueous NaHCO$_3$ solution (60 mL). This aqueous mixture was extracted with EtOAc (2×120 mL) and the layers were separated. The EtOAc extracts were combined and concentrated to dryness as a colorless foam. The colorless foam was dissolved in CH$_2$Cl$_2$ (25 mL) to give a colorless solution. To this solution was added water (0.4 mL) and a 6% (v/v) solution of DCA in CH$_2$Cl$_2$ (23 mL). After ten minutes, to the red solution was charged pyridine (3.0 mL), which turned the red solution into a white mixture. This white mixture was concentrated in vacuo and water was removed as an azeotrope after concentration with MeCN (33 mL). This azeotrope process was repeated two more times with MeCN (33 mL). On the last evaporation, the white slurry of compound 12 was left in MeCN (10 mL).

Step 2: Preparation of (2R,3R,4R,5R)-5-(6-benzamido-9H-purin-9-yl)-2-((((((2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl)oxy)(2-cyanoethoxy)phosphorothioyl)oxy)methyl)-4-fluorotetrahydrofuran-3-yl Hydrogen Phosphonate (14)

A solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (13, 1.0 g, 2.3 mmol, ChemGenes) in MeCN (15 mL) was dried through concentration in vacuo. This process was repeated three more times to remove water as an azeotrope. On the last azeotrope, to the solution of compound 13 in MeCN (8 mL) was introduced ten 3 Å molecular sieves and this solution was stored under an atmosphere of nitrogen. To a stirring mixture of compound 12 with residual pyridinium dichloroacetate in MeCN (10 mL) was added the solution of compound 13 in MeCN (8 mL). After five minutes, to the stirring mixture was added DDTT (520 mg, 2.6 mmol), which resulted in a yellow mixture. After 30 minutes, the yellow mixture was concentrated in vacuo to give compound 14 as a yellow oil.

Step 3: Preparation of Protected 2'3'-dithio-(A)(2'F-A) (15)

To a solution of compound 14 in CH$_2$Cl$_2$ (30 mL) was added water (0.2 mL) and a 6% (v/v) solution of DCA in CH$_2$Cl$_2$ (30 mL). After ten minutes, to the red solution was introduced pyridine (10 mL), which turned the solution into a yellow mixture. The yellow mixture was concentrated in vacuo until approximately 10 mL of the yellow mixture remained. To the yellow mixture was introduced pyridine (40 mL) and the mixture was evaporated until approximately 20 mL of the yellow mixture remained, and addition of pyridine and evaporation to 20 mL was repeated. To the stirring yellow mixture in pyridine (20 mL) was added DMOCP (0.9 g, 4.8 mmol). After seven minutes, to the dark orange solution was added water (0.8 mL), followed immediately by the introduction of 3H-1,2-benzodithiol-3-one (0.4 g, 2.4 mmol). After five minutes, the dark orange solution was poured into a 1N aqueous NaHCO$_3$ solution (200 mL), which resulted in a biphasic mixture. After stirring for ten minutes, the biphasic mixture was extracted with EtOAc (100 mL) and diethyl ether (100 mL). After separating the layers, the aqueous layer was back extracted twice with 200 mL of EtOAc/diethyl ether (1:1). The organic extracts were combined and concentrated. To the concentrated yellow oil was added toluene (75 mL) and the mixture was evaporated to remove residual pyridine. This procedure was repeated twice with toluene (75 mL). The resulting oil was purified by silica gel chromatography (0% to 10% MeOH in CH$_2$Cl$_2$) to obtain compound 15 (90 mg, 10%) as an orange oil.

Step 4: Preparation of 2'3'-RR-(A)(2'F-A) (16)

To a stirring solution of compound 15 (90 mg, 0.08 mmol) in methanol (1.0 mL) was added aqueous ammonium hydroxide (1.0 mL) and the orange slurry was heated to 50° C. After two hours, the orange solution was allowed to cool and concentrated in vacuo. To the residual solid was introduced triethylamine trihydrofluoride (0.6 mL) and the yellow solution was heated to 40° C. After two hours, the yellow solution was allowed to cool to room temperature. This yellow solution was slowly added to a cooled solution of IM TEAB (3 mL) and TEA (0.5 mL). The yellow mixture was allowed to stir for 30 min. The yellow mixture was purified by reverse phase silica gel chromatography (0% to 20% MeCN in 10 mM aqueous TEAA) to obtain compound 16 (14 mg, 27%, purity 89%) separated from the R,S diastereomer ($R_t$: 11.927 min) as a white bis-triethylammonium salt after lyophilization. LCMS-ESI: 692 [M−H]− (calculated for $C_{20}H_{23}FN_{10}O_9P_2S_2$: 691.25); $R_t$: 14.712 min. $^1$H NMR (400 MHz, 45° C., D$_2$O) δ 8.62 (s, 1H), 8.42 (s, 1H), 8.26 (s, 1H), 8.17 (s, 1H), 6.57 (d, J=16.4 Hz, 1H), 6.40 (d, J=8.0 Hz, 1H), 5.81 (dd, J=50.0, 4.0 Hz, 1H), 5.58 (td, J=8.8, 4.0 Hz, 1H), 5.42-5.35 (m, 1H), 5.05 (d, J=4.4 Hz, 1H), 4.77-4.59 (m, 4H), 4.43 (dd, J=12, 4.0 Hz, 1H), 4.28 (dd, J=12.0, 4.0 Hz, 1H), 3.34 (q, J=7.0 Hz, 12H), 1.43 (t, J=7.0 Hz, 18H). $^{19}$F NMR (400 MHz, 45° C., D$_2$O) δ−200.17 to −200.41 (m). $^{31}$P NMR (45° C., D$_2$O) δ 55.16, 52.19.

The 2'3'-SR-(A)(2'F-A) (16a) was isolated in the final purification step as the bis-triethylammonium salt. LCMS-ESI: 692 [M−H]− (calculated for $C_{20}H_{23}FN_{10}O_9P_2S_2$: 691.25); $R_t$: 11.977 min.

Example 5: Synthesis of 2'3'-RR-(3'F-A)(A) (20) and 2'3'-RS-(3'F-A)(A) (20a)

2'3'-RR-(3'F-A)(A) (20), also referred to as dithio-[R$_P$, R$_P$]-cyclic-[3'F-A(2',5')p-A(3',5')p], was prepared according to the following Scheme 5:

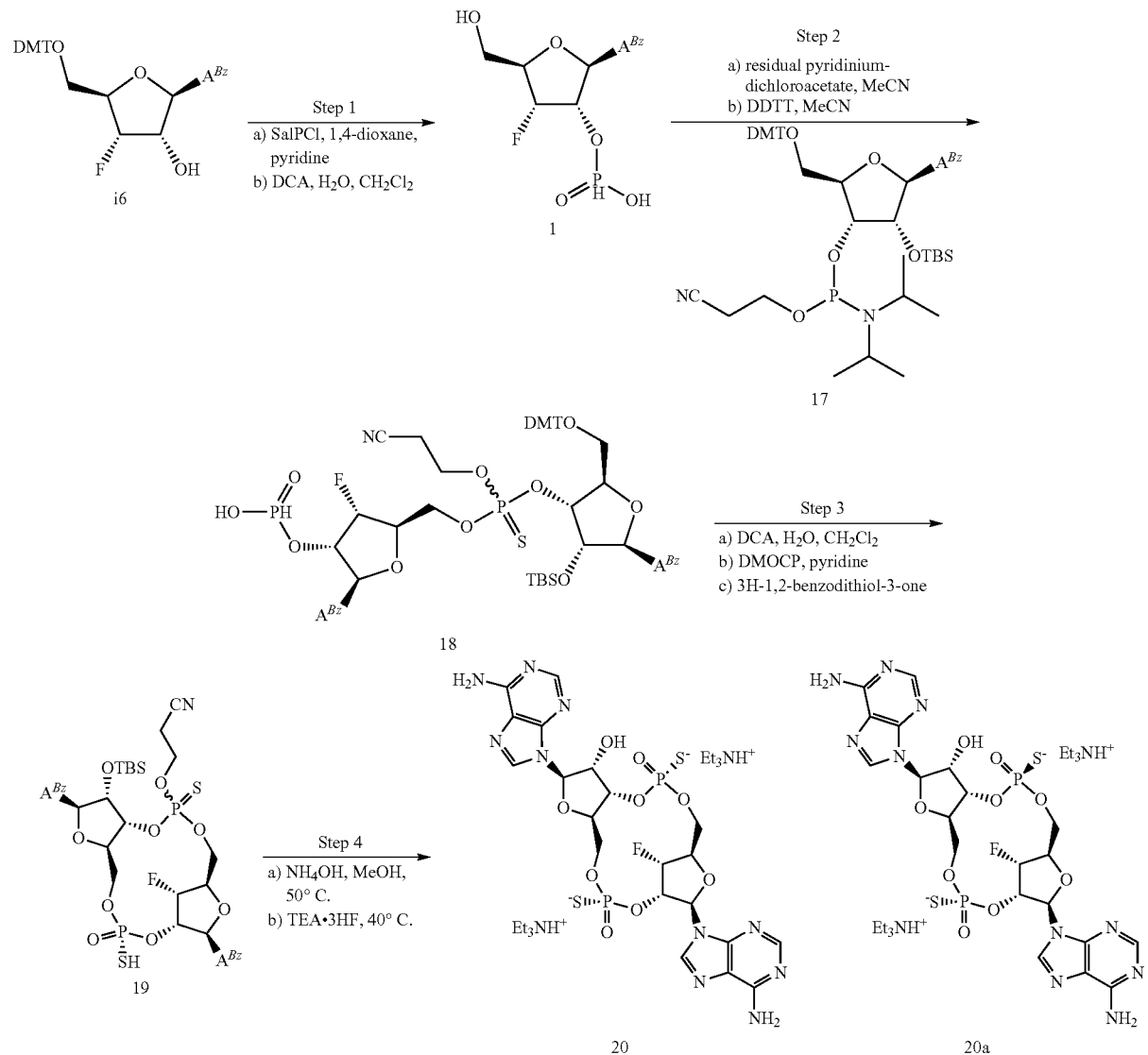

Step 1: Preparation of (2R,3S,4R,5R)-2-(6-benzamido-9H-purin-9-yl)-4-fluoro-5-(hydroxymethyl) tetrahydrofuran-3-yl Hydrogen Phosphonate (1)

N-(9-((2R,3S,4S,5R)-5-((bis(4-methoxyphenyl)(phenyl) methoxy)methyl)-4-fluoro-3-hydroxytetrahydrofuran-2-yl)-9H-purin-6-yl)benzamide i6 (Example 1 Scheme 1A) was reacted according to the methods of Scheme 2 Step 1 (Example 2) to provide compound 1.

Step 2: Preparation of (2R,3S,4R,5R)-2-(6-benzamido-9H-purin-9-yl)-5-(((((2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl)oxy)(2-cyanoethoxy)phosphorothioyl)oxy)methyl)-4-fluorotetrahydrofuran-3-yl Hydrogen Phosphonate (18)

A solution of (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (17, 0.811 g, 0.82 mmol, ChemGenes) in MeCN (20 mL) was dried through concentration in vacuo. This process was repeated two more times to remove water as an azeotrope. On the last azeotrope, to the solution of compound 17 in MeCN (2.5 mL) was introduced ten 3 Å molecular sieves and the solution was stored under an atmosphere of nitrogen. To a stirring mixture of compound 1 with residual pyridinium dichloroacetate in MeCN (10 mL) was added the solution of compound 17 in MeCN (2.5 mL). After five minutes, to the stirring mixture was added DDTT (145 mg, 0.71 mmol). After 30 minutes, the yellow mixture was concentrated in vacuo to give compound 18 as a yellow oil.

Step 3: Preparation of Protected 2'3'-dithio-(3'F-A)(A) (19)

To a solution of compound 18 (~855 mg, 0.6 mmol) in CH$_2$Cl$_2$ (10 mL) was added water (0.08 mL) and a 6% (v/v) solution of DCA in CH$_2$Cl$_2$ (10 mL). After ten minutes, to the red solution was introduced pyridine (3 mL), which turned the red solution into a yellow mixture. The yellow mixture was concentrated in vacuo until approximately 10 mL of the yellow mixture remained. To the yellow mixture was introduced pyridine (15 mL) and the mixture was evaporated until approximately 10 mL of the yellow mixture remained, and addition of pyridine and evaporation to 10 mL was repeated. To the stirring yellow mixture in pyridine (10 mL) was added DMOCP (0.350 g, 1.9 mmol). After seven minutes, to the dark orange solution was added water (0.3 mL), followed immediately by the introduction of 3H-1,2-benzodithiol-3-one (160 mg, 0.95 mmol). After five minutes, the dark orange solution was poured into a 1N aqueous NaHCO$_3$ solution (100 mL). After stirring for fifteen minutes, the biphasic mixture was extracted with EtOAc (50 mL). After separating the layers, the aqueous layer was back extracted three times with EtOAc (50 mL). The organic extracts were combined and concentrated. To the concentrated yellow oil was added toluene (50 mL) and the mixture was evaporated to remove residual pyridine. This procedure was repeated twice with toluene (50 mL). The resulting oil was purified by silica gel chromatography (0% to 10% MeOH in CH$_2$Cl$_2$) to obtain compound 19 (37 mg, 11%) as a white solid.

Step 4: Preparation of 2'3'-RR-(3'F-A)(A) (20)

To a stirring solution of compound 19 (37 mg, 0.03 mmol) in methanol (1.0 mL) was added aqueous ammonium hydroxide (0.5 mL) and the orange slurry was heated to 50° C. After three hours, the orange solution was allowed to cool and concentrated in vacuo. To the residual solid was introduced triethylamine trihydrofluoride (0.5 mL) and the yellow solution was heated to 40° C. After four hours, the yellow solution was allowed to cool to room temperature. The yellow solution was slowly added to a cooled solution of IM TEAB (3 mL) and TEA (0.5 mL). The yellow mixture was allowed to stir for 30 min. The yellow mixture was purified by reverse phase silica gel chromatography (0% to 20% MeCN in 10 mM aqueous TEAA) to obtain compound 20 (9.4 mg, 39%, purity 99%) separated from the R,S diastereomer (R$_t$: 6.546 min) as a white bis-triethylammonium salt after lyophilization. LCMS-ESI: 693 [M–H]$^-$ (calculated for C$_{20}$H$_{23}$FN$_{10}$O$_9$P$_2$S$_2$: 692.00); R$_t$: 8.397 min. $^1$H NMR (400 MHz, 45° C., D$_2$O) δ 8.65 (s, 1H), 8.44 (s, 1H), 8.28 (s, 1H), 8.21 (s, 1H), 6.45 (d, J=8.4 Hz, 1H), 6.29 (d, J=3.0 Hz, 1H), 5.90 (dd, J=52.0, 4.0 Hz, 1H), 5.69 (td, J=8.0, 4.0 Hz, 1H), 5.39-5.29 (m, 1H), 5.04 (m, 1H), 4.95 (d, J=25.0 Hz, 1H), 4.77-4.50 (m, 3H), 4.49 (m, 1H), 4.30 (m, 1H), 3.29 (q, J=7.0 Hz, 12H), 1.41 (t, J=7.0 Hz, 18H). $^{19}$F NMR (400 MHz, 45° C., D$_2$O) δ–198.10 to –198.38 (m). $^{31}$P NMR (45° C., D$_2$O) δ 54.7, 52.9.

The 2'3'-RS-(3'F-A)(A) (20a) was isolated in the final purification step as the bis-triethylammonium salt. LCMS-ESI: 693 [M–H]$^-$ (calculated for C$_{20}$H$_{23}$FN$_{10}$O$_9$P$_2$S$_2$: 692.00); R$_t$: 6.546 min.

Example 6: Synthesis of 2'3'-RR-(G)(2'F-A) (26) and 2'3'-SR-(G)(2'F-A) (26a)

2'3'-RR-(G)(2'F-A) (26), also referred to as dithio-[R$_P$, R$_P$]-cyclic-[G(2',5')p-2'F-A(3',5')p], was prepared according to the following Scheme 6:

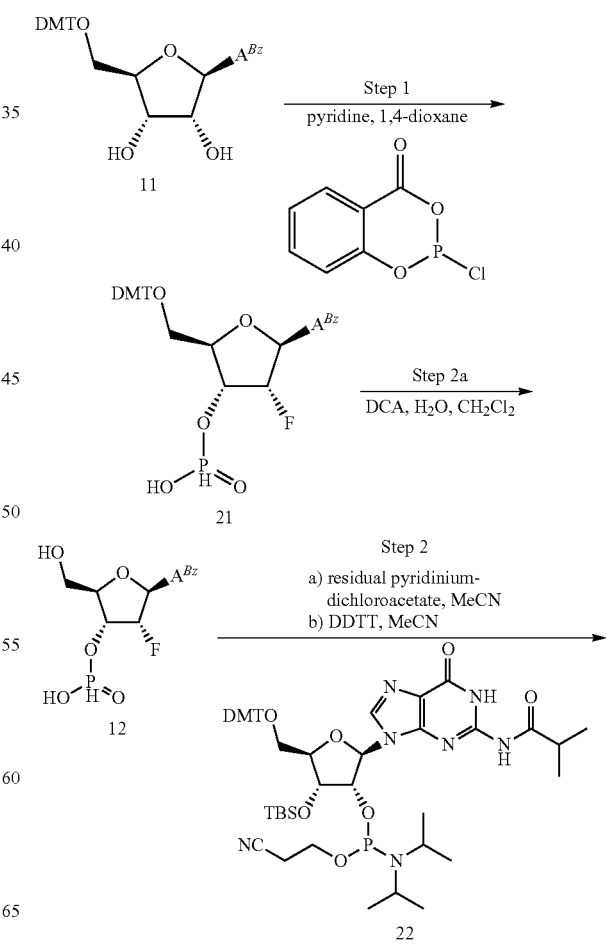

-continued

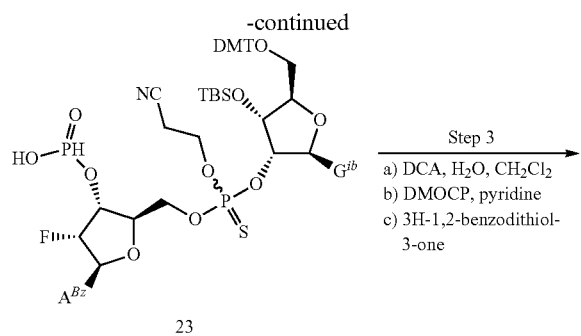

23

Step 3
a) DCA, H₂O, CH₂Cl₂
b) DMOCP, pyridine
c) 3H-1,2-benzodithiol-3-one

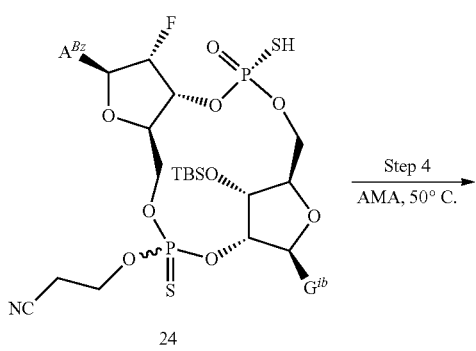

24

Step 4
AMA, 50° C.

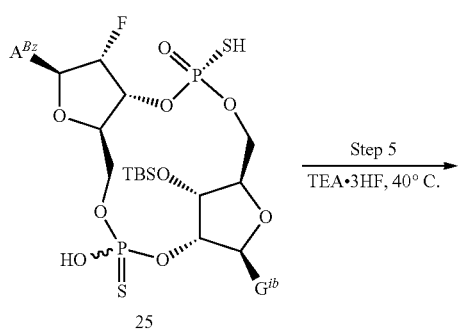

25

Step 5
TEA·3HF, 40° C.

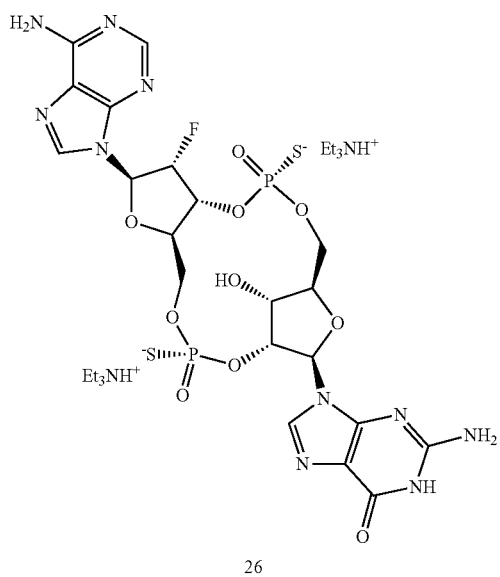

26

-continued

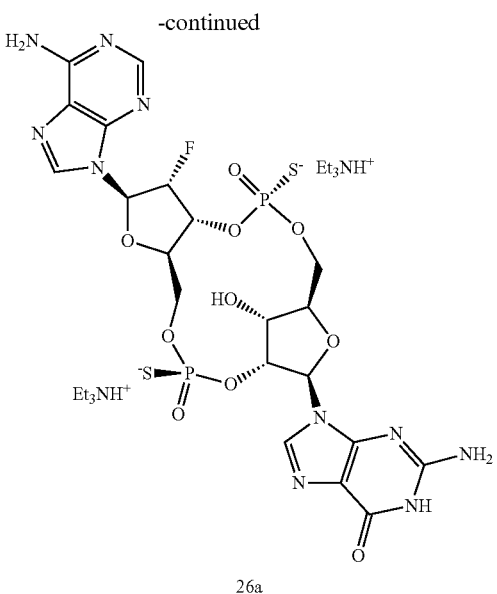

26a

Step 1: Preparation of (2R,3S,4R,5R)-2-(6-benzamido-9H-purin-9-yl)-5-((bis(4-methoxyphenyl)(phenyl)methoxy)methyl)-4-fluorotetrahydrofuran-3-yl Hydrogen Phosphonate (21)

To a solution of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide 11 (5.0 g, 7.4 mmole, 1 eq, ChemGenes) in dioxane (45 mL) was added pyridine (13 mL) followed by 2-chloro-4H-1,3,2-benzodioxaphoshorin-4-one (1.05 g, 5.18 mmole, 0.7 eq). The reaction mixture was stirred for 1 h and additional 2-chloro-4H-1,3,2-benzodioxaphoshorin-4-one (2.0 g, 9.8 mmole, 1.3 eq) was added. The mixture was quenched with 7.5 mL of water followed by 300 mL of a sat. NaHCO₃ solution. After extraction with EtOAc, the combined organic layers were dried with Na₂SO₄, filtered and concentrated to give 5.8 g crude compound 21. Prep MPLC-C18 (100% 10 mM TEAA to 60% acetonitrile in 10 mM TEAA) of 3.2 g of the crude material gave 1.3 g of compound 21.

Step 2: Preparation of (2R,3R,4R,5R)-5-(6-benzamido-9H-purin-9-yl)-2-(((((2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl)oxy)(2-cyanoethoxy)phosphorothioyl)oxy)methyl)-4-fluorotetrahydrofuran-3-yl Hydrogen Phosphonate (23)

(2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl (2-cyanoethyl) diisopropylphosphoramidite (22, 2.2 g, 2.3 mmole, 1.3 eq, ChemGenes) was coevaporated with anhydrous acetonitrile (3×10 mL) leaving 7 mL of acetonitrile. (Step 2a) To a solution of compound 21 (1.3 g, 1.75 mmole, 1 eq) in DCM (21 mL) was added water (0.32 mL) followed by 22.3 mL of a 6% DCA in DCM solution. The reaction mixture was stirred for 10 minutes then quenched with pyridine (2.4 mL) and concentrated in vacuo to give compound 12 with residual pyridinium dichloroacetate. The crude mixture of compound 12 was coevaporated with anhydrous acetonitrile (3×10 mL) leaving 2.4 mL of acetonitrile. The solution of compound 22 (2.2 g) in anhydrous acetonitrile (7 mL) was added and stirred for 3 minutes. After the addition of DDTT (0.4 g), the reaction mixture was stirred for 30 min then concentrated in vacuo to give compound 23.

Step 3: Preparation of Protected 2'3'-dithio-(G)(2'F-A) (24)

To a solution of compound 23 in DCM (42 mL) was added water (1.7 mL) followed by 42 mL of a 6% DCA in DCM solution. The reaction mixture was stirred for 10 minutes then quenched with pyridine (17.6 mL). The mixture was concentrated to remove the DCM, then coevaporated with anhydrous pyridine (1×50 mL) leaving 35 mL. DMOCP (1 g, 2.6 mmole, 1.5 eq) was added and stirred for 3 min followed by water (0.92 mL, 51 mmole, 29 eq) and immediately after with 3H-1,2-benzodithiol-3-one (0.45 g, 2.7 mmole, 1.5 eq). The reaction was allowed to proceed for 5 minutes and was diluted with a 3% solution of $NaHCO_3$ (250 mL) and extracted with 250 mL of a 1:1 solution of ether and EtOAc then 250 mL DCM. The combined organic layers were concentrated to give 3 g of crude compound 24. Prep MPLC-$SiO_2$ (100% DCM to 15% DCM/MeOH) gave 70 mg of compound 24 as a mixture of diastereomers.

Step 4: Preparation of Protected 2'3'-dithio-(G)(2'F-A) (25)

To a solution of compound 24 (70 mg, 0.067 mmole, 1 eq) in EtOH (0.2 mL) was added AMA (0.5 mL). The mixture was sealed with a cap and parafilm and heated to 50° C. for 90 min. The mixture was then cooled to rt, sparged with Ar gas for 10 minutes and concentrated in vacuo to give 37 mg of crude compound 25 as a mixture of diastereomers.

Step 5: Preparation of 2'3'-RR-(G)(2'F-A) (26)

To the crude mixture of compound 25 (37 mg, 0.045 mmole, 1 eq) was added TEA 3HF (0.4 mL). The reaction was heated to 50° C. for 2.5 h. The mixture was poured into a 0° C. solution of TEA (0.8 mL) and TEAB (2.1 mL) and allowed to warm to rt while stirring. Half of the solution was desalted and purified (col.1) using a prep-MPLC-C18 (100% 20 mM $NH_4OAc$ to 20% acetonitrile/20 mM $NH_4OAc$) to give 1 mg of compound 26 (80% pure by HPLC). The other half of the solution was purified (col.2) with an extended gradient resulting in minimal separation. Fractions from col. 1 that contained the R,S isomer were combined with fractions from col.2 and lyophilized over 2 nights. The combined mass of the fractions were purified via prep HPLC (6-18% acetonitrile/10 mM TEAA) to give 1 mg of compound 26 (>95% pure, $R_t$: 9.84 min) and 2 mg of the R,S isomer (85% pure, $R_t$: 8.8 min) as the TEAH salt. LCMS-ESI: 708.8. [M−H]− (Calculated for $C_{20}H_{23}FN_{10}O_{10}P_2S_2$: 708.53); $^1$H NMR (400 MHz, 45° C., $D_2O$) δ 8.46 (s, 1H), 8.43 (s, 1H), 8.03 (s, 1H), 6.63 (d, J=13.2 Hz, 1H), 6.09 (d, J=7.2 Hz, 1H), 5.93 (m, 1H), 5.83-5.67 (m, 2H), 5.46-5.39 (m, 1H), 4.85 (s, 1H), 4.61 (s, 2H), 4.33 (d, J=11.2 Hz, 1H), 4.26 (d, J=12.4 Hz, 1H), 3.37-3.34 (m, 12H), 1.45-1.42 (t, J=6.0 Hz, 18H). $^{19}$F NMR (376 MHz, 45° C., $D_2O$) δ−201.3−−201.7, $^{31}$P NMR (162 MHz, 45° C., $D_2O$) δ 55.7; 51.4.

The 2'3'-SR-(G)(2'F-A) (26a) was isolated in the final purification step as the bis-triethylammonium salt. $^1$H NMR (400 MHz, 45° C., $D_2O$) δ 8.68 (s, 1H), 8.45 (s, 1H), 8.03 (s, 1H), 6.64 (d, J=14, 1H), 6.14-6.11 (m, 1H), 6.00-5.90 (m, 1H), 5.70 (d, J=52, 1H), 5.55-5.40 (m, 1H), 4.60 (d, J=18.8, 4H), 4.32-4.25 (m, 3H), 3.35-3.34 (m, 12H), 1.43 (t, J=6.8, 18H); $^{13}$P NMR (162 MHz, 45° C., ($D_2O$) δ 55.9, 54.2; HRMS (FT-ICR) m/z calcd for $C_{20}H_{23}FN_{10}O_{10}P_2S_2$: (M+H)+ 709.05, found 709.75; HPLC (2-50% Acetonitrile in 20 mM $NH_4OAC$ buffer—20 min) 8.79 min.

The compound 2'3'-RR-(G)(2'F-A) 26 was further reacted according to the following Scheme 6a:

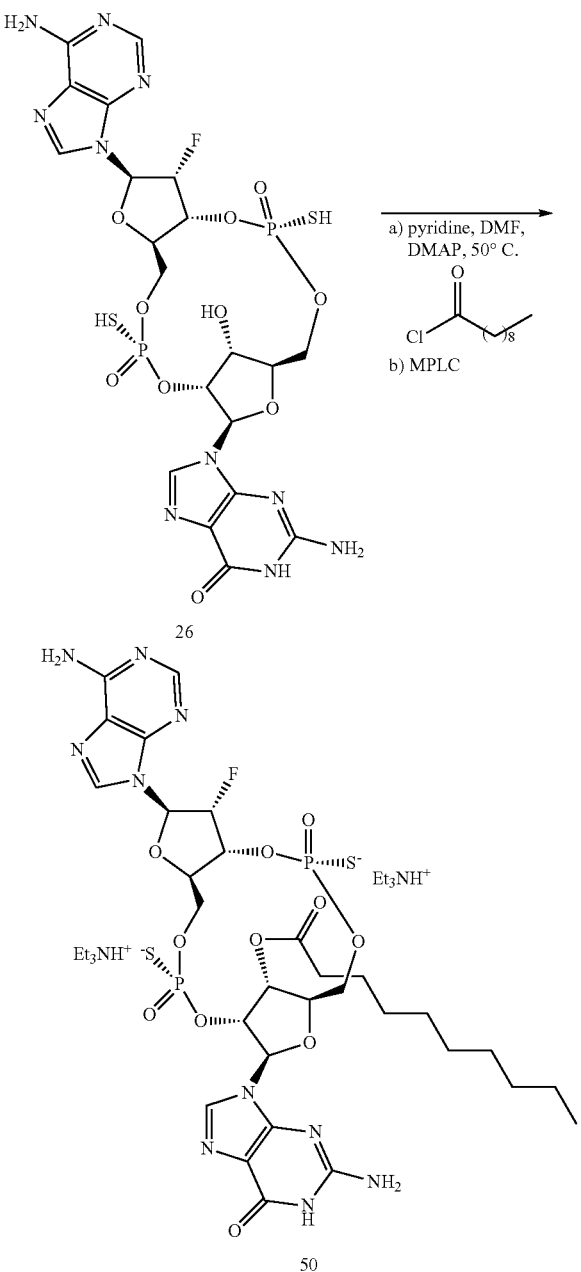

where 1.1 mL of anhydrous pyridine was added to a solution of compound 26 (50 mg, 0.071 mmol, 1 eq) in anhydrous DMF (2.2 mL), followed by decanoyl chloride (36 μL, 0.176 mmol, 2.5 eq) and DMAP (20 mg). The reaction mixture was stirred at 50° C. for 11 days, then quenched with MeOH (10 mL) and concentrated in vacuo. The resulting material was purified by preparative MPLC (15.5 g-C18 column, gradient of 0-100% acetonitrile in TEAA (10 mM): 0% for 2.25 min, 0-20% over 4.5 min, 20% for 2.25 min, 20-60% over 27 min, 60% for 2.25 min, 60-100% over 2.25 min, 100% for 4.5 min) to provide 5.2 mg of 2'3'-RR-(3'decanoyl-O-G)(2'F-A) compound 50 as the triethylammonium salt. LCMS 2-80% MeCN in aqueous 10 mM TEAA over 10 min, $R_t$ 9.57 min, >95% purity. LCMS-ESI: 863.9 [M+H]$^+$ (Calculated for $C_{30}H_{41}FN_{10}O_{11}P_2S_2$: 862.19).

Example 7: Synthesis of 3'2'-RR-(2'F-G)(3'F-A) (32), 3'2'-RS-(2'F-G)(3'F-A) (32a) and 3'2'-SS-(2'F-G)(3'F-A) (32b)

3'2'-RR-(2'F-G)(3'F-A) (32), also referred to as dithio-[$R_P$, $R_P$]-cyclic-[2'F-G(3',5')p-3'F-A(2',5')p], was prepared according to the following Scheme 7:

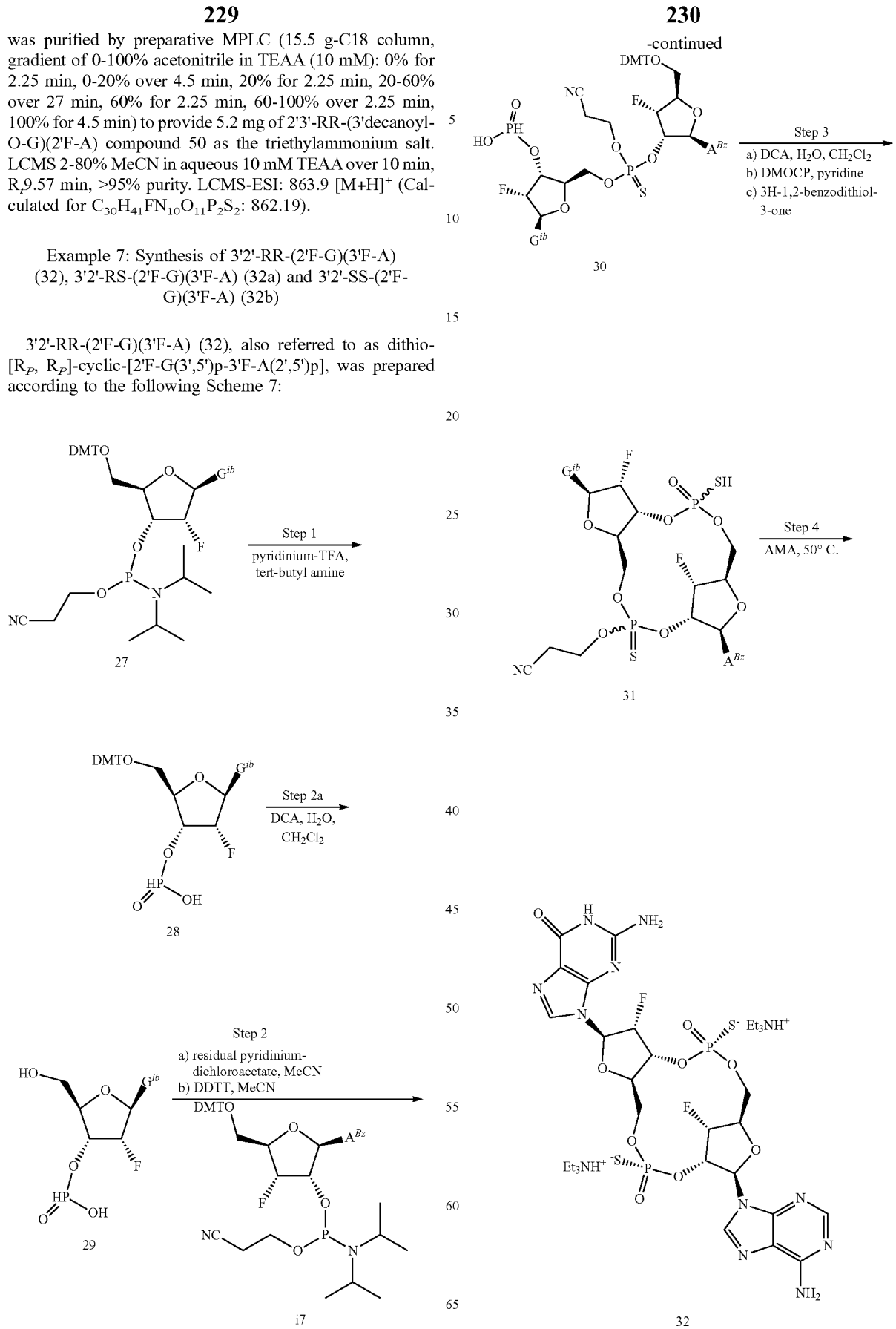

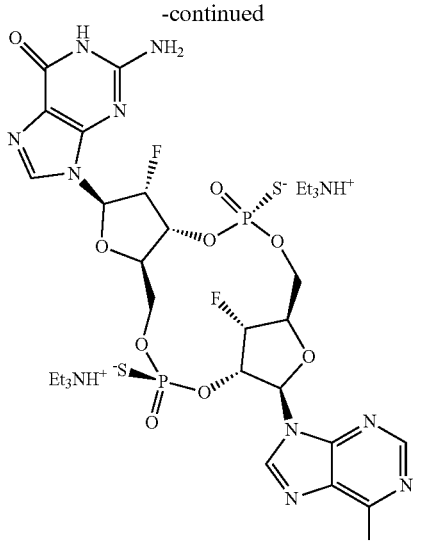

32a

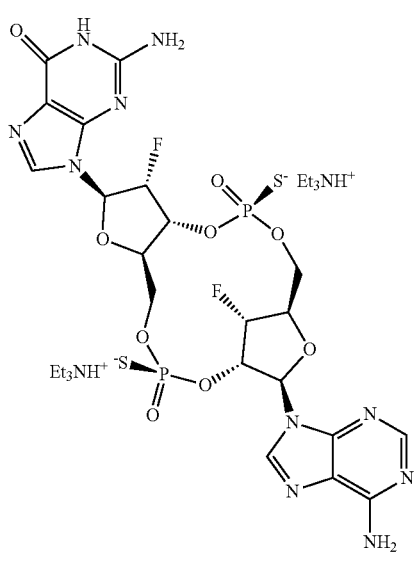

32b

Step 1: Preparation of (2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl Hydrogen Phosphonate (28)

To a solution of (2R,3R,4R,5R)-2-((bis(4-methoxyphenyl)(phenyl)methoxy)methyl)-4-fluoro-5-(2-isobutyramido-6-oxo-1,6-dihydro-9H-purin-9-yl)tetrahydrofuran-3-yl (2-cyanoethyl) diisopropylphosphoramidite (27, 2.1 g, 2.5 mmole, 1 eq, ChemGenes) in acetonitrile (12 mL) was added water (0.087 mL) followed by pyridinium trifluoroacetate (0.57 g, 3.0 mmole, 1.2 eq). The reaction was stirred for 7 min and tert-butyl amine (12.1 mL, 0.12 mole, 47 eq) was added. After 10 min of stirring the reaction was concentrated to give 2.95 g of crude compound 28. Prep MPLC-SiO$_2$ (99% DCM:1% (MeOH, 0.5% pyridine) to 60:40) gave 1.84 g of compound 28.

Step 2: Preparation of (2R,3R,4R,5R)-2-((((((2R,3S,4R,5R)-2-(6-benzamido-9H-purin-9-yl)-5-((bis(4-methoxyphenyl)(phenyl)methoxy)methyl)-4-fluoro-tetrahydrofuran-3-yl)oxy)(2-cyanoethoxy)phosphorothioyl)oxy)methyl)-4-fluoro-5-(2-isobutyramido-6-oxo-1,6-dihydro-9H-purin-9-yl)tetrahydrofuran-3-yl Hydrogen Phosphonate (30)

Compound i7 (Example 1, Scheme 1A, 810 mg, 0.93 mmole, 1 eq) was coevaporated with anhydrous acetonitrile (3×10 mL) leaving 3 mL of acetonitrile. (Step 2a) To a solution of compound 28 (670 mg, 0.93 mmole, 1 eq) in DCM (9.4 mL) was added water (0.16 mL) followed by 9.5 mL of 6% DCA in DCM solution. The reaction mixture was stirred for 10 minutes then quenched with pyridine (1.4 mL) and concentrated in vacuo to give (2R,3R,4R,5R)-4-fluoro-2-(hydroxymethyl)-5-(2-isobutyramido-6-oxo-1,6-dihydro-9H-purin-9-yl)tetrahydrofuran-3-yl hydrogen phosphonate compound 29. The crude mixture of 29 was coevaporated with anhydrous acetonitrile (3×10 mL) leaving 5.0 mL of acetonitrile. The solution of compound i7 (810 mg) in anhydrous acetonitrile (3 mL) was added to the solution of compound 29 in acetonitrile and stirred for 5 minutes. After the addition of DDTT (0.22 g), the reaction mixture was stirred for 30 minutes then concentrated in vacuo to give 2.8 g of crude compound 30.

Step 3: Preparation of Protected 3'2'-dithio-(2'F-G)(3'F-A) (31)

To a solution of crude compound 30 (2.8 g) in DCM (19 mL) was added water (0.11 mL) followed by 19 mL of a 6% DCA in DCM solution. The reaction mixture was stirred for 10 minutes then quenched with pyridine (8 mL). The mixture was condensed in vacuo to remove the DCM, then coevaporated twice with anhydrous pyridine (1×3 mL and 1×5 mL) leaving 5 mL. DMOCP (0.5 g, 2.7 mmole) was added and stirred for 7 minutes followed by water (0.44 mL, 24 mmole) and immediately after with 3H-1,2-benzodithiol-3-one (0.20 g, 1.2 mmole). The reaction was allowed to proceed for 5 minutes and was diluted with a 1M solution of NaHCO$_3$ (44 mL) and extracted with EtOAc (3×33 mL). The combined organic layers were concentrated in vacuo then coevaporated with toluene (3×10 mL) to give 2.1 g of crude compound 31. Prep MPLC-SiO$_2$ (100% DCM to 50% DCM/MeOH) gave 30 mg of compound 31 as a mixture of stereoisomers.

Step 4: Preparation of 3'2'-RR-(2'F-G)(3'F-A) (32)

To a solution of compound 31 (30 mg, 0.032 mmole, 1 eq) in EtOH (0.3 mL) was added AMA (0.5 mL). The mixture was sealed with a cap and parafilm, stirred, and heated to 50° C. for 90 minutes. The mixture was then cooled to room temperature and concentrated in vacuo to give 27 mg of crude compound 32 in a mixture of stereoisomers. The reaction was purified using a prep-MPLC-C18 (100% 10 mM TEAA to 25% acetonitrile/10 mM TEAA) to give 2 mg of compound 32 (>95% pure, $R_t$: 7.78 min) and 0.2 mg of the R,S isomer ($R_t$: 7.10 min) as the TEAH salt. LCMS-ESI: 710.7 [M−H]$^-$ (Calculated for $C_{20}H_{22}F_2N_{10}O_9P_2S_2$: 710.05); $^1$H NMR (400 MHz, 45° C., D$_2$O) δ 8.62 (s, 1H), 8.29 (s, 1H), 7.94 (s, 1H), 6.47 (d, J=8.8 Hz, 1H), 6.40 (d, J=18.0 Hz, 1H), 5.93 (m, 1H), 5.82 (d, J=12.0 Hz, 1H), 5.70-5.59 (m, 2H), 4.97 (s, 1H), 4.91 (s, 1H), 4.51 (d, J=9.6 Hz, 1H), 4.40 (d, J=10.4 Hz, 1H), 4.31-4.27 (m, 1H), 3.37-3.32 (q, J=5.6 Hz, 10H), 1.43 (t, J=6.0 Hz, 15H). $^{19}$F NMR (376 MHz, 45° C., D₂O) δ –197.6--197.9; –198.6--198.8, ³¹P NMR (162 MHz, 45° C., D₂O) δ 55.1; 53.7.

The compound 3'2'-RS-(2'F-G)(3'F-A) (32a) was also isolated in the final purification step as the bis-triethylammonium salt. ¹H NMR (400 MHz, 45° C., D₂O) δ 8.62 (s, 1H), 8.29 (s, 1H), 6.47 (d, J=8.8 Hz, 1H), 6.12 (d, J=18 Hz, 1H), 5.93-5.59 (m, 4H), 4.98 (d, J=25.6 Hz, 1H), 4.52-4.27 (m, 3H), 3.34 (q, J=5.6 Hz, 10H), 1.43 (t, J=6 Hz, 15H).

The compound 3'2'-SS-(2'F-G)(3'F-A) (32b) was also isolated in the final purification step as the bis-triethylammonium salt. ¹H NMR (400 MHz, 45° C., D₂O) δ 9.02 (s, 1H), 8.38 (s, 1H), 8.04 (s, 1H), 6.48 (d, J=8.0 Hz, 1H), 6.40 (d, J=18.8 Hz, 1H), 6.08-5.55 (m, 4H), 4.90 (d, J=25.2 Hz, 1H), 4.67-4.25 (m, 3H), 3.33 (q, J=5.6 Hz, 14H), 1.42 (t, J=6.0 Hz, 22H).

Example 8: Synthesis of 3'2'-RR-(2'F-G)(A) (35) and 3'2'-RS-(2'F-G)(A) (35a)

3'2'-RR-(2'F-G)(A) (35), also referred to as dithio-[R$_P$, R$_P$]-cyclic-[2'F-G(3',5')p-A(2',5')p], was prepared according to the following Scheme 8:

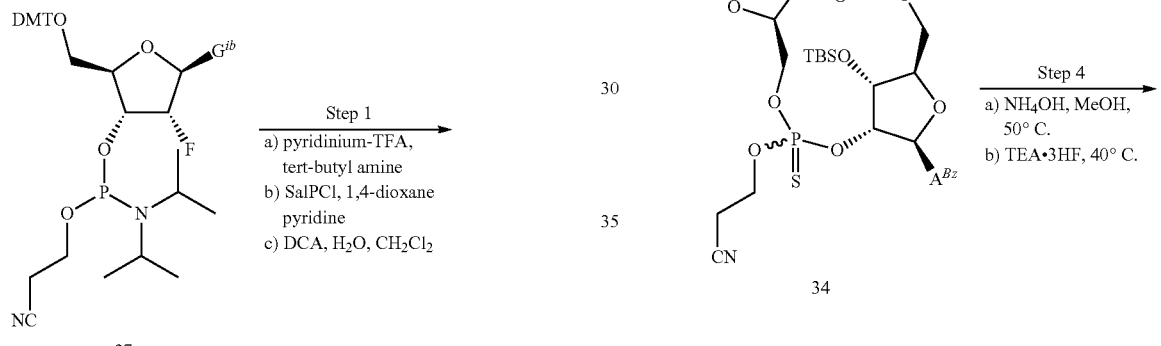

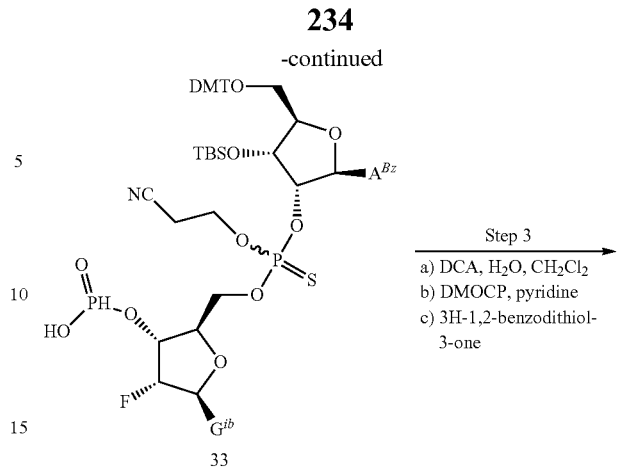

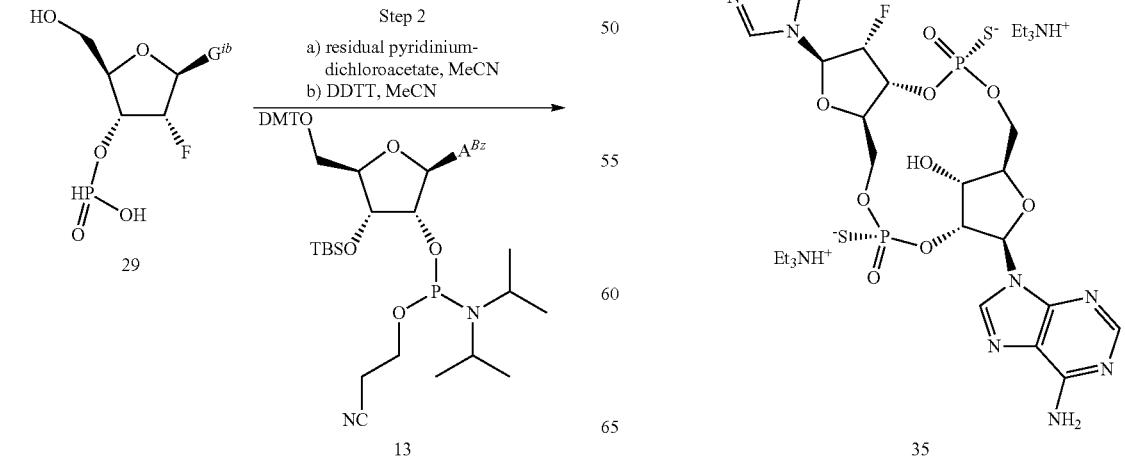

-continued

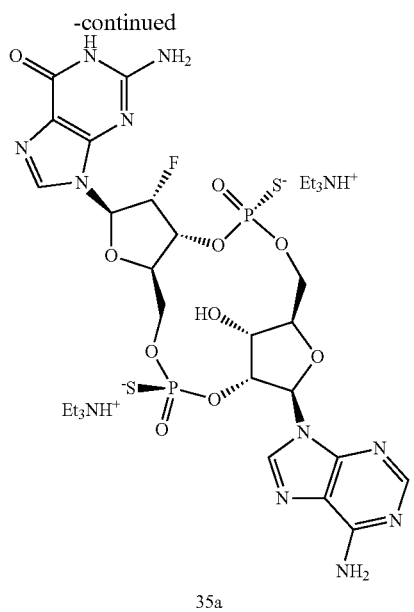

35a

Step 1: Preparation of (2R,3R,4R,5R)-4-fluoro-2-(hydroxymethyl)-5-(2-isobutyramido-6-oxo-1,6-dihydro-9H-purin-9-yl)tetrahydrofuran-3-yl Hydrogen Phosphonate (29)

To a solution of compound 27 (2.0 g, 2.3 mmol) in MeCN (14 mL) and H$_2$O (0.09 mL) was added pyridinium trifluoroacetate (587 mg, 3.03 mmol). After ten minutes, to the colorless reaction solution was introduced tert-butylamine (11.5 mL). After five minutes, the colorless solution was concentrated under reduced pressure and water was removed as an azeotrope after concentration with MeCN (20 mL). This azeotrope process was repeated two more times with MeCN (15 mL) to give a colorless foam, which contained a mixture of N-(9-((2R,3R,4R,5R)-5-((bis(4-methoxyphenyl)(phenyl)methoxy)methyl)-3-fluoro-4-hydroxytetrahydrofuran-2-yl)-6-oxo-6,9-dihydro-1H-purin-2-yl)isobutyramide and compound 28 (see Example 7). To this mixture in 1,4-dioxane (20 mL) was added a solution of SalPC1 (0.197 g, 1.0 mmol) in 1,4-dioxane (10 mL). After five minutes, to the peach colored reaction mixture was added pyridine (6.5 mL). After 35 minutes, to the reaction mixture at room temperature was introduced water (4 mL), and after ten minutes, the reaction mixture was poured into a 1N aqueous NaHCO$_3$ solution (100 mL). This aqueous mixture was extracted with EtOAc (3×100 mL). The EtOAc extracts were combined and concentrated to dryness as a colorless foam. The colorless foam was dissolved in CH$_2$Cl$_2$ (25 mL) to give a colorless solution. To this colorless solution was added water (0.3 mL) and a 6% (v/v) solution of DCA in CH$_2$Cl$_2$ (25 mL). After ten minutes of stirring at room temperature, to the orange solution was charged pyridine (3.0 mL), which turned the orange solution into a white mixture. This white mixture was concentrated in vacuo and water was removed as an azeotrope after concentration with MeCN (30 mL). This azeotrope process was repeated one more time with MeCN (30 mL). On the last evaporation, the resulting peach solution of compound 29 was left in MeCN (6 mL).

Step 2: Preparation of (2R,3R,4R,5R)-2-((((((2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl)oxy)(2-cyanoethoxy)phosphorothioyl)oxy)methyl)-4-fluoro-5-(2-isobutyramido-6-oxo-1,6-dihydro-9H-purin-9-yl)tetrahydrofuran-3-yl Hydrogen Phosphonate (33)

A solution of compound 13 (see Example 4, 3.3 g, 3.4 mmol) in MeCN (15 mL) was dried through concentration in vacuo until 5 mL of the solution remained. To this 5 mL solution was added MeCN (10 mL) and the solution was concentrated in vacuo until 5 mL of the solution remained. This process was repeated two more times to remove water as an azeotrope. On the last azeotrope, to the solution of compound 13 in MeCN (5 mL) was introduced 3 Å molecular sieves and this solution was stored under an atmosphere of nitrogen. To a stirring mixture of compound 29 with residual pyridin-1-ium dichloroacetate in MeCN (6 mL) was added the solution of compound 13 in MeCN (5 mL). After five minutes, to the stirred mixture was added DDTT (530 mg, 2.6 mmol), which resulted in a yellow solution. After 1 hour, the yellow mixture was concentrated under reduced pressure to give compound 33 as a yellow oil.

Step 3: Preparation of Protected 3'2'-dithio-(2'F-G)(A) (34)

To a solution of compound 33 in CH$_2$Cl$_2$ (55 mL) was added water (0.4 mL) and a 6% (v/v) solution of DCA in CH$_2$Cl$_2$ (50 mL). After ten minutes of stirring at room temperature, to the orange solution was introduced pyridine (20 mL), which turned the solution into a yellow mixture. The yellow mixture was concentrated in vacuo until approximately 15 mL of the yellow mixture remained. To the yellow mixture was introduced pyridine (33 mL) and the mixture was evaporated until approximately 15 mL of the yellow mixture remained. To the yellow mixture was added pyridine (50 mL) and the mixture was concentrated until approximately 15 mL of the yellow mixture remained, and addition of pyridine was repeated with evaporation to 20 mL. An additional amount of pyridine (50 mL) was added to the mixture. To the stirring yellow mixture in pyridine (70 mL) was added DMOCP (1.4 g, 7.5 mmol). After five minutes, to the dark orange solution was added water (1.4 mL), followed immediately by the introduction of 3H-1,2-benzodithiol-3-one (0.6 g, 3.5 mmol). After eight minutes, the dark orange solution was poured into a 1N aqueous NaHCO$_3$ solution (400 mL). After fifteen minutes, the biphasic mixture was extracted with EtOAc (250 mL). After the layers were separated, the aqueous layer was back extracted twice with EtOAc (250 mL and then 150 mL). The organic extracts were combined and concentrated. To the concentrated yellow oil was added toluene (75 mL) and the mixture was evaporated to remove residual pyridine. This procedure was repeated once more with toluene (75 mL). The resulting oil was purified by silica gel chromatography (0% to 10% MeOH in CH$_2$Cl$_2$) to obtain compound 34 (1.0 g, 43%) as a yellow oil.

Step 4: Preparation of 3'2'-RR-(2'F-G)(A) (35)

To a stirred solution of compound 34 (816 mg, 0.08 mmol) in EtOH (4.0 mL) was added AMA (12.0 mL) and the yellow slurry was heated to 50° C. After three hours, the yellow solution was allowed to cool and concentrated in vacuo. To the residual beige solid was introduced triethylamine trihydrofluoride (5.1 mL) and the yellow solution was heated to 40° C. After two hours, the yellow solution was allowed to cool to room temperature. This yellow solution was slowly added to a cooled solution of 1M TEAB (31 mL) and TEA (5 mL). The yellow mixture was allowed to stir for 30 min, then purified by reverse phase silica gel chromatography (0% to 20% MeCN in 10 mM aqueous TEAA) to obtain compound 35 (104 mg, 38%, purity 95%) separated from the R,S diastereomer ($R_t$: 6.11 min) as a white bis-triethylammonium salt after lyophilization. LCMS-ESI: 707.80 [M–H]⁻ (calculated for $C_{20}H_{23}FN_{10}O_{10}P_2S_2$: 708.53); $R_t$: 6.67 min by LCMS conditions (2% to 50% MeCN in 20 mM aqueous NH₄OAc over 10 min). ¹H NMR (400 MHz, 45° C., D₂O) β 8.64 (s, 1H), 8.30 (s, 1H), 7.94 (s, 1H), 7.90 (d, J=6.8 Hz, 1H), 7.68 (t, J=6.8 Hz, 1H), 6.41 (s, 1H), 6.40 (d, J=24.8 Hz, 1H), 5.85 (d, J=51.0 Hz, 1H), 5.52 (m, 2H), 4.92 (br s, 1H), 4.77-4.62 (m, 4H), 4.50 (m, 1H), 4.36 (m, 1H), 4.27 (m, 1H), 3.34 (q, J=7.0 Hz, 12H), 1.42 (t, J=7.0 Hz, 18H). ¹⁹F NMR (400 MHz, 45° C., D₂O) δ 198.71, 198.82. ³¹P NMR (45° C., D₂O) δ 55.19, 53.07.

The 3'2'-RS-(2'F-G)(A) (35a) was isolated in the final purification step as the bis-triethylammonium salt. LCMS-ESI: 707.80 [M–H]⁻ (calculated for $C_{20}H_{23}FN_{10}O_{10}P_2S_2$: 708.53); $R_t$: 6.15 min by LCMS conditions (2% to 50% MeCN in 20 mM aqueous NH₄OAc over 10 min). ¹H NMR. (400 MHz, 45° C., D₂O) δ 8.76 (s, 1H), 8.35 (s, 1H), 8.05 (s, 1H), 6.45-6.37 (m, 2H), 6.05 (s, 1H), 65.91 (s, 1H), 5.7-5.6 (m, 1H), 5.51-5.48 (m, 1H), 4.75-4.54 (m, 4H), 4.31-4.20 (m, 2H), 3.33 (q, J=6.8 Hz, 6H), 2.05 (s, 8H), 1.41 (t, J=6.8 Hz, 6H). ¹⁹P NMR (400 MHz, 45° C., D₂O) δ 58.10.

In a scale-up of this reaction, starting with compound 27 (5.0 g, 5.9 mmol) to compound 29 with compound 13 (7.5 g, 7.7 mmol) and carried through per above to the purification step, 3'2'-SR-(2'F-G)(A) (35b, 90.3 mg, 2%) was isolated as a white triethylammonium salt after lyophilization: LCMS-ESI: 709.70 [M+H]⁻ (calculated for $C_{20}H_{23}FN_{10}O_{10}P_2S_2$: 708.53); $R_t$: 5.13 min by LCMS conditions (2% to 80% MeCN in 20 mM aqueous NH₄OAc over 10 min). ¹H NMR. (400 MHz, D₂O) δ 8.79 (s, 1H), 8.08 (s, 1H), 7.76 (s, 1H), 6.16-6.09 (m, 2H), 5.77-5.65 (d, J=40 Hz, 1H), 5.45-5.56 (m, 1H), 5.58-5.45 (m, 2H), 5.31-5.23 (m, 1H), 4.51 (s, 1H), 4.39-4.30 (m, 3H), 4.25-4.20 (m, 1H), 4.03-4.00 (m, 1H), 3.96-3.93 (m, 1H), 3.05 (q, J=8.8 Hz, 18H), 1.81 (s, 4H), 1.12 (t, J=8.8 Hz, 27H). ¹⁹F NMR (400 MHz, D₂O) δ–200.98 to –201.21. ³¹P NMR (400 MHz, D₂O) δ 58.06, 53.35.

Example 9: Enzymatic Synthesis of 2'3'-(G)(2'F-A) (38)

2'3'-(G)(2'F-A) (38), also referred to as cyclic-[G(2',5')p-2'F-A(3',5')p], was prepared enzymatically according to the following Scheme 9:

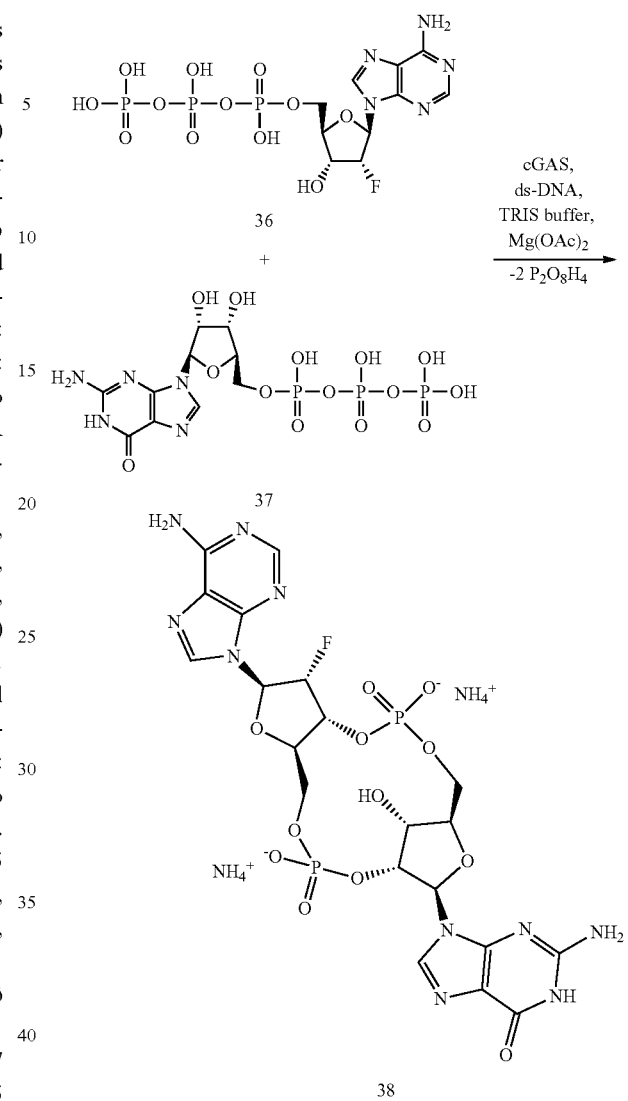

The reaction was carried out in duplicate in parallel: to 100 mM aqueous 2'F-dATP (36, 250 μL, 0.025 mmol; N-1007, TriLink Biotechnologies, San Diego, Calif., USA), 100 mM aqueous GTP (37, 250 μL, 0.025 mmol, Sigma Cat. No 51120), Herring Sperm DNA solution (250 μL, 10 mg/mL aq.; #9605-5-D, Trevigen Inc., Gaithersburg, Md., USA) and human cGAS (1500 μL, 2.1 mg/mL, prepared as described in next paragraph) was added reaction buffer (50 mM TRIS, 2.5 mM magnesium acetate, 10 mM KCl, pH adjusted to 8.2 with aq. NaOH 5 M; 25 mL). The reaction was incubated for 16 hours at 37° C. and 150 rpm on an orbital shaker. Completion of the reaction was confirmed through analysis of an aliquot (100 μL) of the reaction mixture, diluted with acetonitrile (100 μL), centrifuged and the desired compound formation determined by UV analysis. The reactions were mixed with acetonitrile (20 mL), incubated at room temperature on an orbital shaker for 10 minutes and after subsequent centrifugation (7000 g for 5 min) the supernatant was filtrated through a paper filter. The filtrate was mixed with acetic acid (100 μL) and directly loaded onto a 20×250 mm Inertsil Amide 5 m column (flow rate 30 mL/min; solvent A: aqueous 10 mM ammonium acetate, 2 mM acetic acid, solvent B: acetonitrile; using an isocratic elution using 26% phase A/74% phase B, fraction size 50 mL). The fractions containing the desired compound 38 were combined and the solvents were evaporated in vacuo to a final volume of about 10 mL. The concentrated compound 38 solution from the first chromatography was re-purified by direct injection onto 1×50 cm Sephadex G10 HPLC column (flow rate 1.0 mL/min; mobile phase containing 0.25 mM ammonium hydroxide and 25% acetonitrile) with UV detection at 250 nm. All fractions containing the desired compound 38 were combined and dried by lyophilisation to give 4.5 mg of compound 38 as the bis-ammonium salt; $^1$H NMR (600.1 MHz, D$_2$O) δ 8.35 (br s, 1H), 8.06 (br s, 1H), 7.77 (s, 1H), 6.31 (d, J=12.8 Hz, 1H), 5.86 (s, 1H), 5.62 (s, 1H), 5.35 (d, J=50.8 Hz, 1H), 4.97 (d, J=19.0 Hz, 1H), 4.46 (s, 1H), 4.42 (s, 1H), 4.33 (s, 1H), 4.24 (s, 1H), 4.21 (s, 2H), 3.97 (s, 1H); MS m/z 677.2 [M+H]$^+$.

The cGAS used in this example and Example 10 were prepared by cloning and expression of human and mouse cGAS. The coding region of human or mouse cGAS comprising amino acid 155-522 (human) and amino acid 147-507 (mouse) was cloned into a pET based expression vector. The resulting expression construct contained an N-terminal 6×-His-tag followed by a ZZ-tag and an engineered HRV3C protease cleavage side allowing generation of human cGAS 155-522 and mouse cGas 147-507 with an N-terminal extension of a Gly-Pro. Both plasmids were transformed in the *E. coli* strain • BL21 (DE3) phage resistant cells (C2527H, New England BioLabs, Ipswich, Mass.) for bacterial expression. The phage resistant *E. coli* cells BL21 (DE3) harboring the cGas expression plasmids were expressed at a 1.5 L scale in Infors bioreactors. Precultures were grown in LB medium.

1.5 L auto-induction media (Studier, Protein Expr Purif. 2005 May; 41(1):207-34) containing Kanamycin (50 µg/mL) were inoculated with 100 mL preculture and cultivated to an OD of approximately 10 under the following conditions: temperature 37° C.; stirrer (cascade regulation via pO$_2$) 500; pH 7.0; pO$_2$ (cascade regulation on) 5%; flow 2.5 L/min; and gas mix (cascade regulation via pO$_2$) 0. The temperature was then reduced to 18° C. and expression was run over night. Cells were harvested by centrifugation and lysed by using an Avestin EmulsiFlex French press. Purification was done according the published protocol by Kato et al. (PLoS One, 2013, 8(10) e76983) using Ni-affinity chromatography, a heparin purification step to remove DNA and a final size exclusion chromatography. cGAS eluted as a homogenous fraction and was concentrated to at least 5 mg/mL.

```
Human cGAS:
                                             (SEQ ID NO: 7)
GPDAAPGASK LRAVLEKLKL SRDDISTAAG MVKGVVDHLL

LRLKCDSAFR GVGLLNTGSY YEHVKISAPN EFDVMFKLEV

PRIQLEEYSN TRAYYFVKFK RNPKENPLSQ FLEGEILSAS

KMLSKFRKII KEEINDIKDT DVIMKRKRGG SPAVTLLISE

KISVDITLAL ESKSSWPAST QEGLRIQNWL SAKVRKQLRL

KPFYLVPKHA KEGNGFQEET WRLSF-SHIEK EILNNHGKSK

TCCENKEEKC CRKDCLKLMK YLLEQLKERF KDKKHLDKFS

SYHVKTAFFH VCTQNPQDSQ WDRKDLGLCF DNCVTYFLQC

LRTEKLENYF IPEFNLFSSN LIDKRSKEFL TKQIEYERNN

EFPVFDEF
```

Example 10: Enzymatic Synthesis of 2'3'-(3'F-G)(2'F-A) (40)

2'3'-(3'F-G)(2'F-A) (41), also referred to as cyclic-[3'F-G(2',5')p-2'F-A(3',5')p], was prepared enzymatically according to the following Scheme 10:

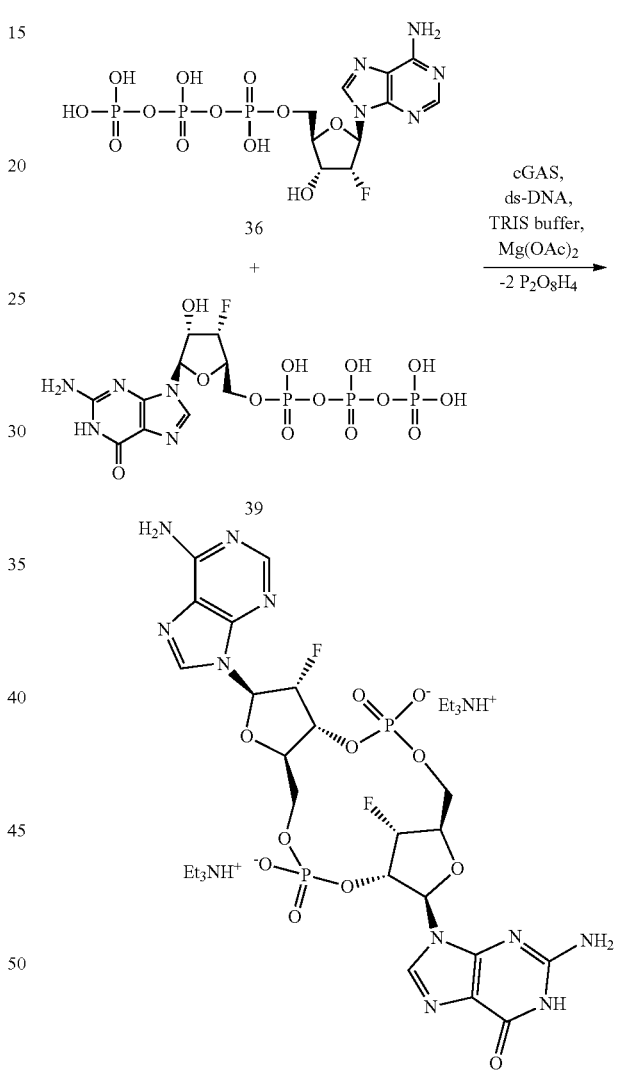

The reaction was performed four times in parallel, each on a 26 mL scale: to 100 mM aqueous 2'F-dATP (36, 250 µL, 0.025 mmol), 100 mM aqueous 3'F-d GTP (39, 250 µL, 0.025 mmol; N-3002, TriLink Biotechnologies), Herring Sperm DNA solution (800 µL, 10 mg/mL aq.; #9605-5-D, Trevigen Inc.) and mouse cGAS preparation (250 µL, 6.5 mg/mL, prepared as described for human cGAS above) was added reaction buffer (50 mM TRIS, 2.5 mM magnesium acetate, pH adjusted to 8.2 with aq. NaOH 5 M; 25 mL). The reaction was incubated for 16 hours at 37° C. and 150 rpm on an orbital shaker. The reactions were mixed with acetonitrile (20 mL) and incubated at room temperature on an orbital shaker for 10 min. After subsequent centrifugation (7000 g for 5 min) the supernatant of all four reactions was combined and filtrated through a paper filter. The filtrate was evaporated in vacuo to a residual volume of approximately 20 mL and mixed with 0.5 mL acetic acid (0.5 mL) and 1.0M aqueous triethylammonium acetate (5 mL). The crude material was directly injected onto the Chromolith RP18e 2.1×10 cm column. Chromatography (flowrate 80 mL/min; isocratic mobile 10 mM triethylammonium acetate and 1 vol % acetonitrile) yielded the desired compound 40 fractions which were combined, mixed with aqueous 25% ammonia solution (20 μL) and dried by lyophilisation. The compound 40 was obtained as bis-triethylammonium salt; 39.8 mg; $^1$H NMR (600.1 MHz, D$_2$O) δ 8.16 (s, 1H), 8.13 (s, 1H), 7.73 (s, 1H), 6.33 (d, J=13.9 Hz, 1H), 5.91 (d, J=8.6 Hz, 1H), 5.61 (m, 1H), 5.40 (dd, J=51.5, 2.6 Hz, 1H), 5.30 (dd, J=53.3, 3.2 Hz, 1H), 4.98 (m, 1H), 4.56 (d, J=25.8 Hz, 1H), 4.44 (d, J=9.0 Hz, 1H), 4.39 (d, J=11.8 Hz, 1H), 4.20 (m, 1H), 4.08 (d, J=12.4 Hz, 1H), 4.04 (d, J=11.8 Hz, 1H), 3.06 (q, J=7.3 Hz, 12H), 1.13 (t, J=7.3 Hz, 18H); $^{31}$P NMR (376.4 MHz, D$_2$O) δ −1.68, −2.77; $^{19}$F NMR (376.4 MHz, D$_2$O) δ −199.72, −203.23; MS 677.2 [M−H]$^-$.

```
Mouse cGAS:
                                      (SEQ ID NO: 8)
GPDKLKKVLD KLRLKRKDIS EAAETVNKVV ERLLRRMQKR

ESEFKGVEQL NTGSYYEHVK ISAPNEFDVM FKLEVPRIEL

QEYYETGAFY LVKFKRIPRG NPL-SHFLEGE VLSATKMLSK

FRKIIKEEVK EIKDIDVSVE KEKPGSPAVT LLIRNPEEIS

VDIILALESK GSWPISTKEG LPIQGWLGTK VRTNLRREPF

YLVPKNAKDG NSFQGETWRL SF-SHTEKYIL NNHGIEKTCC

ESSGAKCCRK ECLKLMKYLL EQLKKEFQEL DAFCSYHVKT

AIFHMWTQDP QDSQWDPRNL SSCFDKLLAF FLECLRTEKL

DHYFIPKFNL FSQELIDRKS KEFLSKKIEY ERNNGFPIFD KL
```

Example 11: Synthesis of 2'3'-RR-(3'H-A)(2'F-A) (45) and 2'3'-RS-(3'H-A)(2'F-A) (45a)

2'3'-RR-(3'H-A)(2'F-A) (45), also referred to as dithio-[R$_P$, R$_P$]-cyclic-[3'H-A(2',5')p-2'F-A(3',5')p], and 2'3'-RS-(3'H-A)(2'F-A) (45a), also referred to as dithio-[Rp, Sp]-cyclic-[3'H-A(2',5')p-2'F-A(3',5')p], were prepared according to the following Scheme 11:

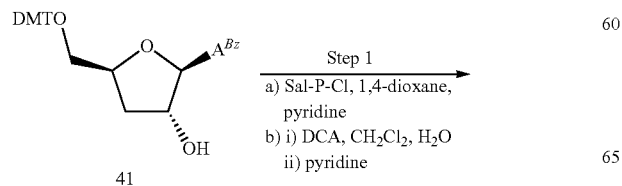

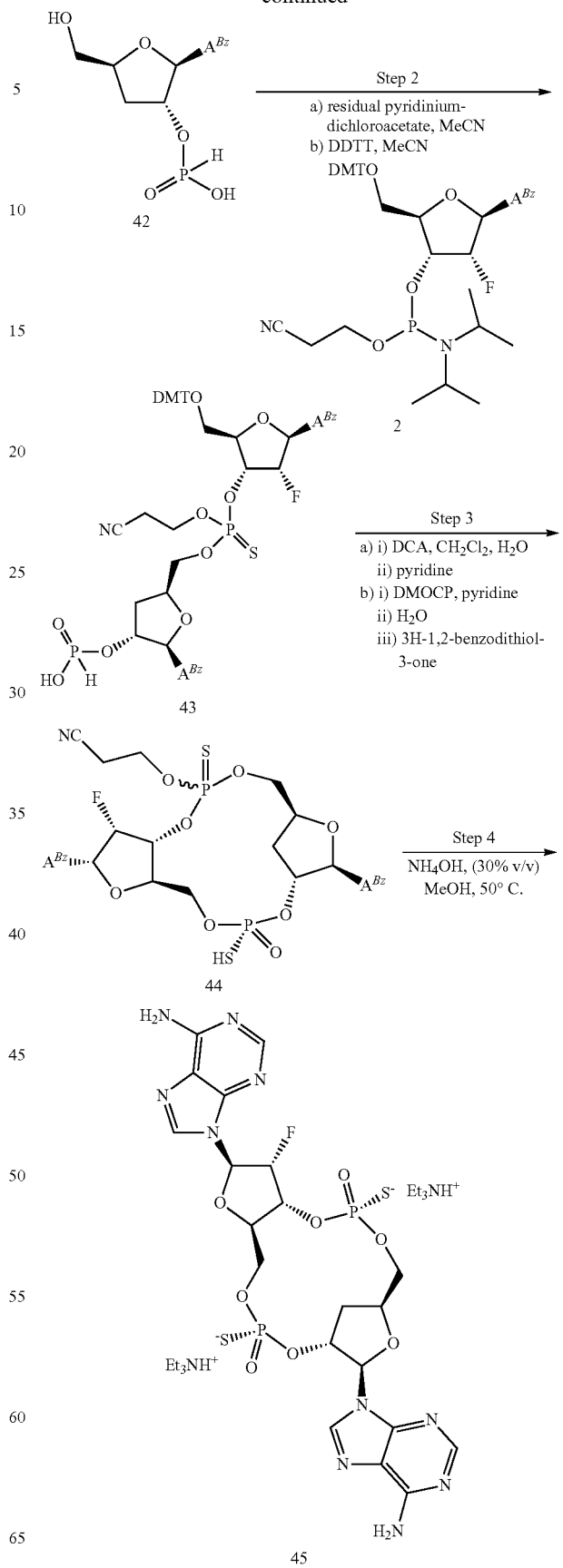

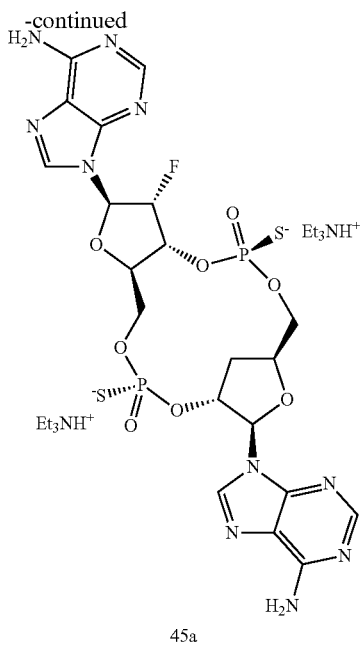

45a

Step 1: Preparation of (2R,3R,5S)-2-(6-benzamido-9H-purin-9-yl)-5-(hydroxymethyl)tetrahydrofuran-3-yl Hydrogen Phosphonate (42)

To a solution of N-(9-((2R,3R,5S)-5-((bis(4-methoxyphenyl)(phenyl)methoxy)methyl)-3-hydroxytetrahydrofuran-2-yl)-9H-purin-6-yl)benzamide (41, 1.0 g, 1.5 mmol, Berry & Associates, Dexter, Mich.) in 1,4-dioxane (16 mL) and pyridine (6 mL) was added a solution of SalPCl (462 mg, 2.3 mmol) in 1,4-dioxane (8 mL). After 30 min at room temperature, the reaction mixture was poured into a 1N aqueous NaHCO₃ solution (100 mL). This aqueous mixture was extracted with EtOAc (3×100 mL), and the layers were partitioned. The EtOAc extracts were combined and concentrated to dryness in vacuo to obtain intermediate as a colorless solid. The colorless solid was dissolved in CH₂Cl₂ (15 mL) to give a colorless solution. To this solution was added water (270 µL) and a 6% (v/v) solution of DCA in CH₂Cl₂ (15 mL). After 10 min of stirring at room temperature, to the red solution was charged pyridine (2 mL). The resulting white mixture was concentrated in vacuo and water was removed as an azeotrope after concentration with MeCN (50 mL). This azeotrope process was repeated two more times with MeCN (50 mL). On the last evaporation, the resulting light peach oil of compound 42 was left in MeCN (20 mL).

Step 2: Preparation of (2R,3R,5S)-5-2-(6-benzamido-9H-purin-9-yl)-5-(((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphorothioyl)oxy)methyl)tetrahydrofuran-3-yl Hydrogen Phosphonate (43)

A solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (2, 1.7 g, 2.0 mmol, ChemGenes) in MeCN (20 mL) was dried in vacuo. This process was repeated two more times to remove water as an azeotrope, leaving a solution of compound 2 in MeCN (10 mL) after the last azeotrope. Ten 3 Å molecular sieves were introduced and the solution was stored under an atmosphere of nitrogen. To a stirred mixture of compound 42 with residual pyridin-1-ium dichloroacetate in MeCN (20 mL) was added the solution of compound 2 in MeCN (10 mL). After 8 min, to the stirred mixture was added DDTT (350 mg, 1.7 mmol). After 1 h, the yellow mixture was concentrated in vacuo to give compound 43 as a yellow oil.

Step 3: Preparation of Protected 2'3'-dithio-(3'H-A)(2'F-A) (44)

To a yellow solution of compound 43 in CH₂Cl₂ (28 mL) was added water (190 µL) and a 6% (v/v) solution of DCA in CH₂Cl₂ (26 mL). After 10 min at room temperature, to the red solution was introduced pyridine (6 mL). The resulting yellow solution was concentrated in vacuo until approximately 8 mL of the yellow mixture remained. To the yellow mixture was introduced pyridine (30 mL) and the mixture was concentrated in vacuo until approximately 15 mL of the yellow mixture remained. To the yellow mixture was added pyridine (20 mL) and the mixture was concentrated in vacuo until approximately 15 mL of the yellow mixture remained. To the remaining solution (15 mL) was added pyridine (25 mL) and the mixture was concentrated in vacuo until approximately 24 mL of the yellow mixture remained. To the stirred yellow mixture in pyridine (24 mL) was added DMOCP (845 mg, 4.6 mmol). After 5 min, to the brownish yellow solution was added water (0.8 mL), followed immediately by the introduction of 3H-1,2-benzodithiol-3-one (385 mg, 2.3 mmol). After 20 min, the brownish yellow solution was poured into a 1N aqueous NaHCO₃ solution (100 mL). After 20 min, the biphasic mixture was extracted with EtOAc (400 mL). After separation, the aqueous layer was back extracted with EtOAc (400 mL). The organic extracts were combined and concentrated in vacuo. To the concentrated yellow oil was added toluene (30 mL) and the mixture was evaporated in vacuo to remove residual pyridine. This procedure was repeated two more times with toluene (30 mL). The resulting oil was purified by silica gel chromatography (0% to 10% MeOH in CH₂Cl₂) to provide compound 44 (323 mg) as an orange foam.

Step 4: Preparation of 2'3'-RR-(3'H-A)(2'F-A) (45) and 2'3'-RS-(3'H-A)(2'F-A) (45a)

To a stirred solution of a mixture of compound 44 (323 mg, 0.36 mmol) in MeOH (3.5 mL) was added aqueous 30% NH₄OH (2 mL) and the milky slurry was heated at 50° C. After 2 h, the orange solution was allowed to cool to room temperature. After 1 h, the orange solution was concentrated in vacuo. The orange residue was purified by reverse phase silica gel chromatography (0% to 20% MeCN in 10 mM aqueous TEAA) to obtain compound 45 (68.0 mg, 57% yield) as a white tris-triethylammonium salt after lyophilization. LCMS-ESI: 677.05 [M+H]⁺ (calculated for $C_{20}H_{23}FN_{10}O_8P_2S_2$: 676.06) $R_t$: 2.111 min by UPLC conditions (2% to 20% MeCN in 20 mM aqueous NH₄OAc over 10 min). ¹H NMR (400 MHz, 45° C., D₂O) δ 8.49 (s, 1H), 8.43 (s, 1H), 8.41 (s, 1H), 8.32 (s, 1H), 6.60 (d, J=17 Hz, 1H), 6.33 (s, 1H), 5.84 (dd, J=51, 1 Hz, 1H), 5.49 (t, J=3.6 Hz, 1H), 5.40-5.22 (m, 1H), 4.85-4.65 (m, 4H), 4.45-4.37 (m, 1H), 4.31-4.18 (m, 1H), 3.33 (q, J=7.2 Hz, 18H), 3.05-2.95 (m, 1H), 2.75-2.65 (m, 1H), 1.42 (t, J=7.2 Hz, 27H). ³¹P NMR (45° C., D₂O) δ 56.19, 53.18.

The compound 2'3'-RS-(3'H-A)(2'F-A) (45a) was also isolated after purification in the reverse phase chromatography step (22 mg, 18%) as a white bis-triethylamonium salt after lyophilization. LCMS-ESI: 677.05 [M+H]$^+$ (calculated for $C_{20}H_{23}FN_{10}O_8P_2S_2$: 670.06); $R_t$: 1.880 min by the same UPLC conditions. $^1$H NMR. (400 MHz, 45° C., D$_2$O) δ 8.77 (s, 1H), 8.38 (s, 1H), 8.35 (s, 1H), 8.27 (s, 1H), 6.59 (d, J=16 Hz, 1H), 6.23 (br s, 1H), 6.11 (d, J=49 Hz, 1H), 5.51 (br s, 1H), 5.41-5.24 (m, 1H), 4.78-4.63 (m, 3H), 4.35-4.29 (m, 3H), 3.33 (q, J=7.2 Hz, 12H), 2.84 (br s, 2H), 1.42 (t, J=7.2 Hz, 18H). $^{31}$P NMR (45° C., D$_2$O) δ 54.10, 52.27.

Example 12: Synthesis of 2'3'-RR-(3'F-G)(2'F-A) (49) and 2'3'-RS-(3'F-G)(2'F-A) (49a)

2'3'-RR-(3'F-G)(2'F-A) (49), also referred to as dithio-[R$_P$, R$_P$]-cyclic-[3'F-G(2',5')p-2'F-A(3',5')p], and 2'3'-RS-(3'F-G)(2'F-A) (49a), also referred to as dithio-[Rp, Sp]-cyclic-[3'F-G(2',5')p-2'F-A(3',5')p], were prepared according to the following Scheme 12:

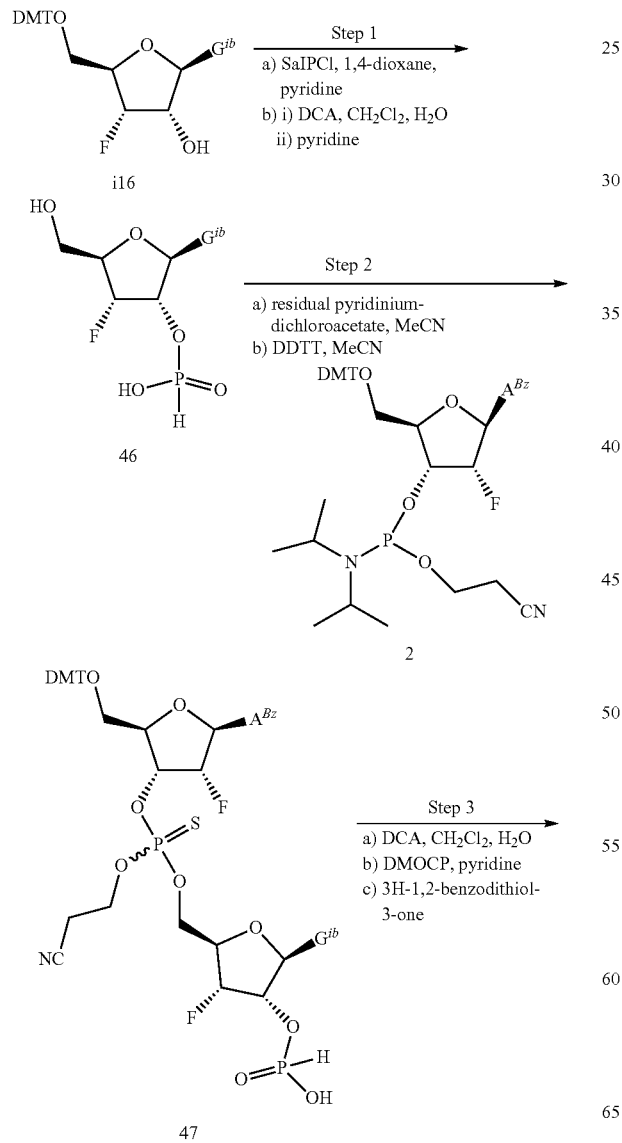

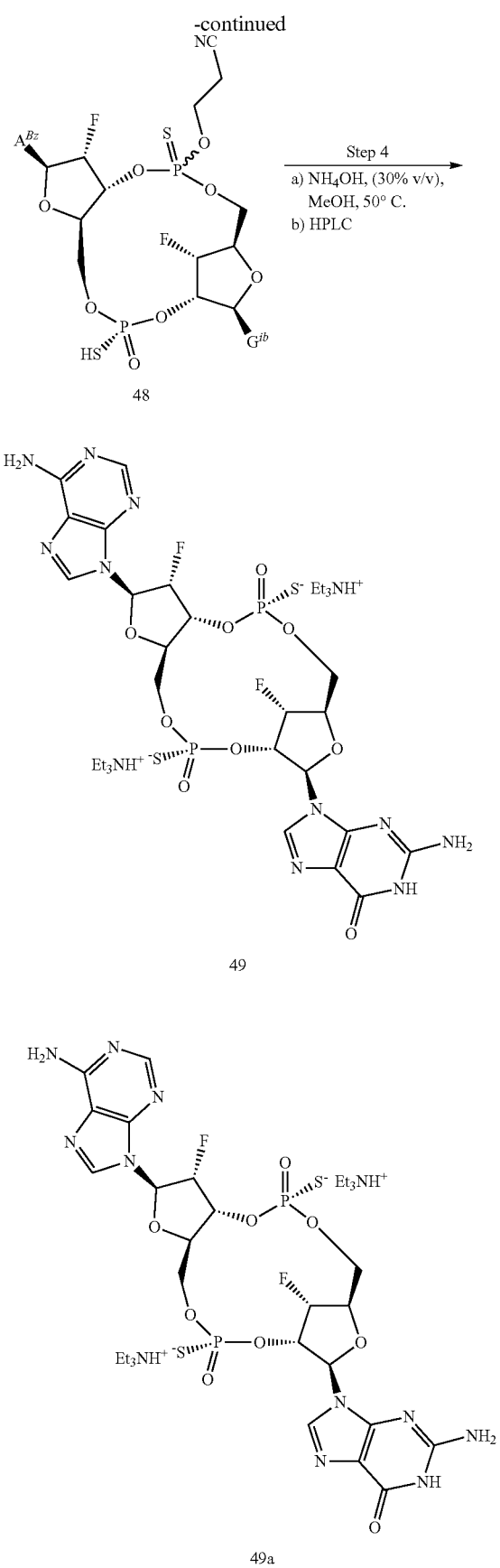

Step 1: Preparation of (2R,3S,4R,5R)-4-fluoro-5-(hydroxymethyl)-2-(2-isobutyramido-6-oxo-1,6-dihydro-9H-purin-9-yl)tetrahydrofuran-3-yl Hydrogen Phosphonate (46)

To a solution of N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide (i16, 501 mg, 1.2 mmol) in 1,4-dioxane (7 mL) and pyridine (2.3 mL) was added a solution of SalPC1 (207 mg, 1.0 mmol) in 1,4-dioxane (5 mL). After 1 h, to the stirred reaction mixture at room temperature was introduced water (1.2 mL), and after 30 min, the resulting mixture was poured into a 1N aqueous NaHCO$_3$ solution (50 mL). This aqueous mixture was extracted with EtOAc (3×40 mL), and the layers were partitioned. The EtOAc extracts were combined and concentrated to dryness in vacuo. The residue was purified by normal phase silica gel chromatography (1% to 50% MeOH with 0.5% pyridine in DCM) to obtain intermediate as a colorless oil. The colorless oil was dissolved in CH$_2$Cl$_2$ (15 mL) to give a colorless solution. To this solution was added water (150 µL) and a 7% (v/v) solution of DCA in CH$_2$Cl$_2$ (10 mL). After 10 min of stirring at room temperature, to the red solution was charged pyridine (1.2 mL). The resulting white mixture was concentrated in vacuo and water was removed as an azeotrope after concentration with MeCN (30 mL). This azeotrope process was repeated two more times with MeCN (20 mL). On the last evaporation, the resulting light peach oil of compound 46 was left in MeCN (15 mL).

Step 2: Preparation of (2R,3S,4R,5R)-5-(((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl Hydrogen Phosphonate (47)

To a solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (2, 629 mg, 0.7 mmol, ChemGenes) in MeCN (20 mL) was dried through concentration in vacuo. This process was repeated two more times to remove water as an azeotrope. On the last azeotrope, to the solution of compound 2 in MeCN (15 mL) was introduced ten 3 Å molecular sieves and the solution was stored under an atmosphere of nitrogen. To a stirred mixture of compound 46 with residual pyridin-1-ium dichloroacetate in MeCN (15 mL) was added the solution of compound 2 in MeCN (15 mL). After 20 min, to the stirred mixture was added DDTT (138 mg, 0.67 mmol). After 1 h, the yellow mixture was concentrated in vacuo to give compound 47 as a yellow paste.

Step 3: Preparation of Protected 2'3'-dithio-(3'F-G)(2'F-A) (48)

To a solution of compound 47 in CH$_2$Cl$_2$ (20 mL) was added water (100 µL) and a 6% (v/v) solution of DCA in CH$_2$Cl$_2$ (20 mL). After 15 min at room temperature, pyridine (10 mL) was added to the red solution, resulting in a yellow solution that was concentrated in vacuo to approximately 10 mL. To the yellow mixture, pyridine (25 mL) was added and the mixture was concentrated in vacuo to approximately 5 mL. To the yellow mixture, pyridine (20 mL) was added and the mixture was concentrated in vacuo to approximately 5 mL, then pyridine (45 mL) was added. To the stirred yellow mixture in pyridine (50 mL) was added DMOCP (361 mg, 2.0 mmol). After 10 min, to the brownish yellow solution was added water (0.7 mL), followed immediately by the introduction of 3H-1,2-benzodithiol-3-one (158 mg, 0.9 mmol). After 30 min, the brownish yellow solution was poured into a 1N aqueous NaHCO$_3$ solution (100 mL). After twenty minutes, the biphasic mixture was extracted with EtOAc (250 mL). After separation, the aqueous layer was back extracted with EtOAc (2×100 mL). The organic extracts were combined and concentrated in vacuo. To the concentrated yellow oil was added toluene (30 mL) and the mixture was evaporated in vacuo to remove residual pyridine. This procedure was repeated again with toluene (30 mL). The resulting oil was purified by silica gel chromatography (0% to 40% MeOH in CH$_2$Cl$_2$) to provide compound 48 (259 mg, 56% yield) with impurities as a yellow paste.

Step 4: Preparation of 2'3'-RR-(3'F-G)(2'F-A) (49) and 2'3'-RS-(3'F-G)(2'F-A) (49a)

To a stirred solution of a mixture of compound 48 (259 mg, 0.27 mmol) in EtOH (2.5 mL) was added aqueous AMA (4.8 mL) and the yellow solution was heated at 50° C. After 2 h, the colorless solution was allowed to cool and concentrated in vacuo. The colorless paste residue was purified by reverse phase silica gel chromatography (0% to 20% MeCN in 10 mM aqueous TEAA) to obtain compound 49 (32.0 mg, 17% yield) as a white bis-triethylammonium salt after lyophilization. LCMS-ESI: 708.85 [M−H]$^-$ (calculated for C$_{20}$H$_{22}$F$_2$N$_{10}$O$_9$P$_2$S$_2$: 710.05) R$_t$: 1.531 min by UPLC conditions (2% to 20% MeCN in 20 mM aqueous NH$_4$OAc over 10 min). $^1$H NMR (400 MHz, 45° C., D$_2$O) δ 8.44 (dd, J=16, 1.6 Hz, 2H), 8.03 (s, 1H), 6.60 (dd, J=14, 1.2 Hz, 1H), 6.17 (d, J=9.6 Hz, 1H), 6.09-5.85 (m, 1H), 5.73 (d, J=13 Hz, 1H), 5.60 (d, J=16 Hz, 1H), 5.49-5.35 (m, 1H), 4.87 (d, J=24.8 Hz, 1H), 4.80-4.65 (m, 2H), 4.32-4.30 (m, 3H), 3.33 (q, J=7.2 Hz, 12H), 1.42 (t, J=7.2 Hz, 18H). $^{19}$F NMR (400 MHz, 45° C., D$_2$O) δ−198.34 to −198.55. $^{31}$P NMR (45° C., D$_2$O) δ 55.69, 52.08.

The compound 2'3'-RS-(3'F-G)(2'F-A) (49a) was also isolated after purification in the reverse phase chromatography step (7.35 mg, 4%) as a white half-triethylamonium salt after lyophilization. LCMS-ESI: 708.95 [M−H]$^-$ (calculated for C$_{20}$H$_{22}$F$_2$N$_{10}$O$_9$P2S$_2$: 710.5); R$_t$: 1.298 min by the same UPLC conditions. $^1$H NMR. (400 MHz, 45° C., D$_2$O) δ 8.45 (s, 1H), 8.37 (s, 1H), 8.16 (s, 1H), 6.62 (d, J=15 Hz, 1H), 6.19 (s, 1H), 6.03 (d, J=49 Hz, 1H), 5.79-5.65 (m, 2H), 5.40-5.28 (m, 1H), 4.94 (d, J=24 Hz, 1H), 4.75-4.67 (m, 2H), 4.46 (s, 1H), 4.35 (s, 2H), 3.33 (s, 3H), 1.41 (s, 5H). $^{19}$F NMR (400 MHz, 45° C., D$_2$O) δ−198.63 to −198.70, −201.57.

Example 13: Synthesis of dithio-2'3'-(3'βF-A)(A) (53)

Dithio-2'3'-(3'3F-A)(A) (53), also referred to as dithio-cyclic-[3'βF-A(2',5')p-A(3',5')p], was prepared according to the following Scheme 13:

249 250

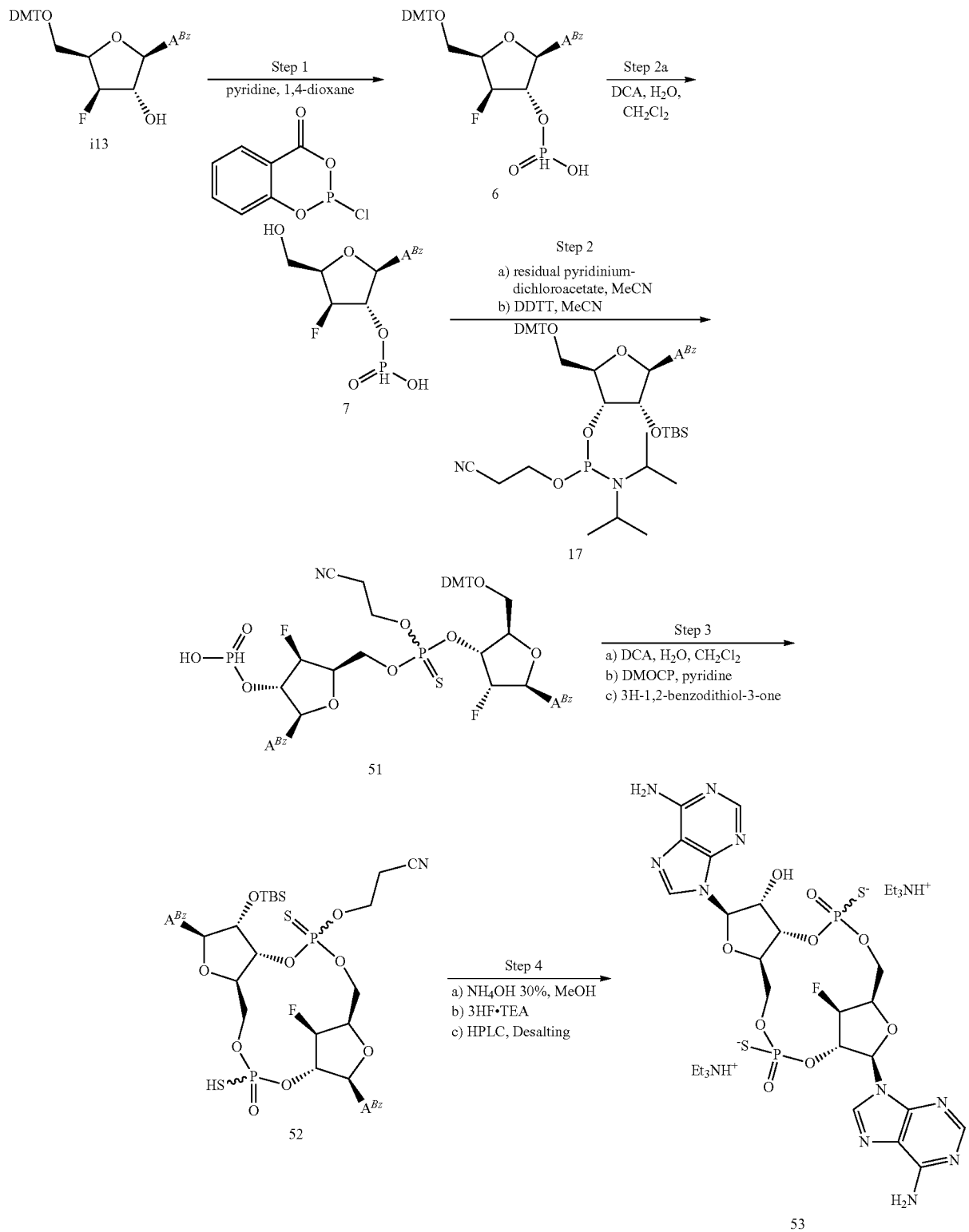

Step 1

Compound 6 was prepared similarly as described in Example 3 with compound i13 (1.0 g, 1.5 mmol) in 11 mL anhydrous dioxane, pyridine (6 mL) was added followed by 2-chloro-4H-1,3,2-Benzodioxaphoshorin-4-one (390 mg, 1.92 mmol, Sigma Aldrich) in 1.5 mL dioxane, stirred for 16 h. Water (3.0 mL) was added and the reaction mixture was partitioned between 1N aqueous NaHCO$_3$/EtOAc, and extracted with EtOAc (×3). The organic layers were combined and dried (Na$_2$SO$_4$), the solvent removed in vacuo and the resulting oil purified by chromatography on silica gel (gradient elution 0% to 30% MeOH/CH$_2$Cl$_2$) to provide compound 6 (418 mg, 38% yield) as a white solid. Unreacted starting material was recovered starting and re-subjected to the reaction conditions to give an additional 50 mg (27%) of compound 6: $^1$H NMR (400 MHz, DMSO-d$_6$) δ 11.25 (s, 1H), 8.77 (s, 1H), 8.25 (s, 1H), 8.05 (d, J=7.1 Hz, 2H), 7.65 (t, J=7.4 Hz, 1H), 7.55 (t, J=7.6 Hz, 2H), 7.46-7.37 (m, 2H), 7.33-7.15 (m, 7H), 6.86 (t, J=9.3 Hz, 4H), 6.24 (s, 1H), 5.98 (s, 1H), 5.39 (d, J=54.2 Hz, 1H), 5.26-5.11 (m, 1H), 4.72-4.40 (m, 1H), 3.72 (s, 6H), 3.30 (s, 2H); $^{19}$F NMR (376 MHz, DMSO-d6) δ−199.22; $^{31}$P NMR (162 MHz, DMSO-d$_6$) δ 0.08; LCMS (method F) R$_t$: 1.72 min; m/z 740.1 [M+H]$^+$.

Step 2: Preparation of (2R,3S,4S,5R)-2-(6-benzamido-9H-purin-9-yl)-5-(((((2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl)oxy)(2-cyanoethoxy)phosphorothioyl)oxy)methyl)-4-fluorotetrahydrofuran-3-yl Phosphonate (51)

(Step 2a) To a solution of compound 6 (468 mg, 0.63 mmol) in DCM (5 mL) was added water (0.100 mL) followed by 6 mL of a 6% DCA in DCM solution. The reaction mixture was stirred for 10 minutes then quenched with pyridine (0.700 mL) and concentrated in vacuo. The resulting oil was azeotroped using anhydrous MeCN (3×10 mL) to provide crude compound 7 as a clear yellow oil (277 mg, 0.63 mmol, crude): LCMS (method G) R$_t$: 0.38 min; m/z 438.1 [M+H]$^+$. Phosphoramidite 17 (613 mg, 0.62 mmol, 0.9 eq, Chemgenes) was dried by azeotroping in vacuo with MeCN (3×10 mL) before it was dissolved in anhydrous MeCN (3 mL) with 3A oven-dried molecular sieves. This solution was added via pipette into a stirred solution of the crude compound 7 in MeCN (5 mL). The reaction mixture was stirred at room temperature for an hour, then DDTT (169 mg, 0.82 mmol, 1.3 eq) was added; after a further 45 min the reaction mixture was concentrated in vacuo to give compound 51 (859 mg, 0.63 mmol) as a crude mixture of diastereoisomers: LCMS (method F) R$_t$ 2.31 and 2.34 min; m/z 1357.3 [M+H]$^+$.

Step 3: Protected dithio-2'3'-(3'βF-A)(A) (52)

To a solution of compound 51 (859 mg, 0.63 mmol) in DCM (10 mL) was added water (80 µL) followed by 6% v/v DCA in DCM (6 mL). The reaction mixture was stirred for 10 min and quenched with pyridine (2 mL). The mixture was concentrated in vacuo to remove the DCM, then azeotroped in vacuo with MeCN (2×10 mL) then anhydrous pyridine (2×30 mL). The latter solution was reduced to 20 mL before pyridine (20 mL) was added followed by DMOCP (351 mg, 1.9 mmol, 3.0 eq). The reaction mixture was then stirred for an hour before water (80 µL) was added, which was immediately followed by addition of 3H-1,2-benzodithiol-3-one (160 mg, 0.95 mmol, 1.5 eq). The reaction was stirred for 2 h then partitioned between 1 N NaHCO$_3$ (100 mL)/EtOAc and extracted with EtOAc (3×20 mL). The combined organic layers were concentrated in vacuo to give a viscous amber oil. This was azeotroped in vacuo with MeCN (4×100 mL) and the resulting semi-solid compound 52 was purified by chromatography on silica gel (gradient elution 0% to 20% MeOH/CH$_2$Cl$_2$) followed by HPLC purification (X-bridge 30×50 mm 5 µm column; MeCN/H$_2$O w/5 mM NH$_4$OH) to give two diastereomers: 52a (10 mg, 1.5%) LCMS (method F) R$_t$: 1.70 min; m/z 1068.3 [M+H]+; and 52b (35 mg, 5%)$^1$H NMR (400 MHz, DMSO-d$_6$) δ 11.20 (d, J=17.7 Hz, 2H), 8.87-8.65 (m, 3H), 8.36 (s, 1H), 8.05 (d, J=7.6 Hz, 7H), 7.70-7.41 (m, 8H), 6.35 (s, 1H), 6.14 (s, 2H), 5.97 (d, J=51.4 Hz, 1H), 5.17-4.98 (m, 3H), 4.58 (t, J=5.6 Hz, 1H), 4.36-4.06 (m, 1H), 3.88 (d, J=13.2 Hz, 1H), 2.89 (d, J=12.9 Hz, 2H), 0.88 (s, 9H), 0.13 (s, 3H), 0.11 (s, 3H); $^{19}$F NMR (376 MHz, DMSO-d$_6$) δ−203.48; $^{31}$P NMR (162 MHz, DMSO-d$_6$) δ 65.09, 53.10; LCMS (method F) R$_t$: 1.82 min; m/z 1068.3 [M+H]$^+$.

Step 4: Preparation of dithio-2'3'-(3'βF-A)(A) (53)

To a solution of the major diastereomer compound 52b (35 mg, 0.03 mmole, 1 eq) in MeOH (600 µL) was added concentrated NH$_4$OH (255 µL) and the solution was heated to 50° C. for 5 h. The mixture was then cooled to room temperature, concentrated in vacuo to remove MeOH, and purified using HPLC-C18 (X-bridge 30×50 mm 5 µm column MeCN/H$_2$O w/5 mM NH$_4$OH) to give the 2'-OTBS intermediate after lyophilization (13 mg, 0.01 mmol, 49%): $^1$H NMR (600 MHz, DMSO-d$_6$) δ 8.65 (s, 1H), 8.36 (d, J=15.1 Hz, 2H), 8.21 (s, 2H), 6.19 (s, 1H), 5.97 (d, J=6.0 Hz, 1H), 5.72 (d, J=50.5 Hz, 1H), 5.06 (dd, J=9.2, 3.9 Hz, 1H), 4.97-4.88 (m, 1H), 4.83 (d, J=11.4 Hz, 1H), 4.74 (s, 1H), 4.53-4.40 (m, 1H), 4.28-4.02 (m, 4H), 0.88 (s, 9H), 0.00 (s, 6H); $^{19}$F NMR (376 MHz, DMSO-d$_6$) δ−202.66; $^{31}$P NMR (162 MHz, DMSO-d$_6$) δ 59.85, 53.98; LCMS (method F) R$_t$: 1.53 min; m/z 807.1 [M+H]$^+$. This material (13 mg, 0.016 mmol) was dissolved in triethylamine trihydrofluoride (200 µL) and heated at 40° C. for 3 h. The reaction was cooled to room temperature and this solution was slowly added to a cooled solution of IM TEAB (3 mL) and triethylamine (0.5 mL). The mixture was allowed to stir for 1 h before MeCN was added and the solvent evaporated to dryness in vacuo. The compound was dissolved in deionized water (1 mL) and MeCN (1 mL) and the solution added onto a pre-conditioned GE-MiniTrap G-10 gravity column. The crude compound 53 was isolated as a white solid (9.2 mg, 6 µmol, 37%) with excess triethylammonium salt after lyophilization. Purification by chromatography on C18 silica gel (gradient eluent 0 to 80% MeCN/water) gave 53 (stereochemically pure diastereomer of unassigned stereochemistry) as its bis-triethylammonium salt containing ~0.5 eq of a triethylammonium salt: $^1$H NMR (400 MHz, DMSO-d$_6$) δ 8.44 (s, 1H), 8.17 (d, J=9.4 Hz, 2H), 8.00 (s, 1H), 7.34 (d, J=14.0 Hz, 4H), 7.13 (s, 1H), 6.94 (s, 1H), 6.10 (s, 1H), 5.88 (d, J=6.5 Hz, 1H), 5.66 (d, J=51.3 Hz, 1H), 5.00 (s, 1H), 4.93 (s, 1H), 4.77 (s, 1H), 4.69 (s, 1H), 4.44 (s, 1H), 4.19 (s, 1H), 4.13-3.95 (m, 3H), 3.06 (s, 15H), 1.16 (t, J=7.2 Hz, 23H); $^{19}$F NMR (376 MHz, DMSO) δ−202.86; $^{31}$P NMR (162 MHz, DMSO) δ 60.06, 54.06; HRMS for C$_{20}$H23FN$_{10}$O$_9$P$_2$S$_2$ calculated 693.0627 found 693.0629 [M+H]$^+$.

The HPLC methods used in this example are indicated with each sample. Method F: LCMS data were recorded using a Waters System (Micromass SQ mass spectrometer; Column: Acquity UPLC BEH C18 1.7 micron, 2.1×30 mm; gradient 1% to 30% acetonitrile to 3.20 mins then gradient: 30-98% acetonitrile in water with 5 mM ammonium hydroxide over a 1.55 min period before returning to 1% acetonitrile at 5.19 mins-total run time 5.2 mins; flow rate 1 mL/min; column temperature 50° C.). Method G: LCMS data were recorded using a Waters System (Micromass SQ mass spectrometer; Column: Acquity UPLC BEH C18 1.7 micron, 2.1×30 mm; gradient 1% to 30% acetonitrile to 1.20 mins then gradient: 30-98% acetonitrile in water with 5 mM ammonium hydroxide over a 0.55 min period before returning to 1% acetonitrile at 2.19 mins-total run time 2.2 mins; flow rate 1 mL/min; column temperature 50° C.).

Example 14: In Vitro Binding Analysis of Mono- and Di-F-ML-CDN Compounds with Purified STING Protein DNA encoding amino acids 140-379 (amino acid numbering corresponding to Swiss Prot Q86WV6) was amplified from plasmids containing the full length sequence of human STING alleles via polymerase chain reaction with the following primers: forward TACTTCCAATCCAATGCAGCCCCAGCTGAGATCTCTG (SEQ ID NO: 9) and reverse TTATCCACTTCCAATGTTATTATTATCAAGAGAAATCCGTGCGGAG (SEQ ID NO: 10). STING variant alleles were assigned according to Yi, et al, (2013), PLoS One, 8(10), e77846 (DOI: 10.1371/journal.pone.0077846. PCR products were cloned into bacterial expression vector encoding a N-terminal hexa-histidine affinity tag (6×HIS) followed by a small ubiquitin-like modifier (SUMO) solubility sequence (Butt, et al, (2005) Protein expression and purification 43.1, 1-9) and tobacco etch virus protease cleavage site (TEV) using ligation independent cloning (Aslanidis, et al, (1990) Nucleic acids research, 18.20, 6069-6074).

Plasmids encoding 6×HIS-SUMO-TEV-STING amino acids 140-379 were transformed into Rosetta2 (DE3) *E. coli* cells (EMD Millipore) for protein expression. Cells were grown in lysogeny broth at 37° C. until a 600 nM absorbance of 0.6 was reached. Cells were then transferred to 18° C. and protein expression was induced overnight by the addition of isopropyl β-D-1-thiogalactopyranoside to the media at a concentration of 0.25 mM. Cells were harvested by centrifugation at 6,000 times gravity for 10 minutes. Cell pellets were re-suspended on ice in a buffer containing 50 mM Tris hydrochloride (Tris-HCl) pH 7.5, 500 mM sodium chloride (NaCl), 20 mM imidazole, 10% glycerol, 1 mM tris(2-carboxyethyl)phosphine hydrochloride (TCEP) and protease inhibitor tablet (Pierce) (Buffer A). Cells were lysed using an S-450D sonifier (Emmerson industrial) on ice. Cell lysate was centrifuged at 15,000 times gravity for 30 minutes at 4° C. Soluble material was applied to nickel-nitrilotriacetic acid (Ni-NTA) coupled Sepharose CL-6B (Qiagen) for 1 hour with gentle rocking at 4° C. After transfer to a gravity flow poly-prep column (Bio-Rad), resin was washed extensively in buffer A. Protein was eluted from the column in a buffer containing 20 mM Tris-HCl pH 7.5, 150 mM NaCl, 300 mM imidazole, 10% glycerol and 0.5 mM TCEP. To remove the 6×HIS-SUMO tag eluted protein was mixed with TEV protease (Sigma) at a ratio of 1:250 (w:w) and dialyzed overnight against a buffer containing 20 mM Tris-HCl pH 7.5, 150 mM NaCl, 5 mM imidazole, 10% glycerol and 0.5 mM TCEP. TEV protease and 6×HIS-SUMO tags were depleted by the addition of Ni-NTA resin (Qiagen) to the sample, purified STING amino acids 140-379 was collected by removal of the resin using a poly-prep column. STING AA140-379 was concentrated with a 10,000 Dalton molecular weight cutoff centrifuge concentrator (EMD Millipore) to a final concentration of approximately 10 mg/mL. Protein was aliquoted, flash frozen in liquid nitrogen and stored at −80° C. until use.

Differential scanning fluorometry (DSF) is a technique that measures the ability of ligands to bind to and stabilize purified proteins (Niesen, et al, (2007) Nature protocols 2.9, 2212-2221). The protein is heated in the presence of a dye that binds to and fluoresces in hydrophobic environments. The protein is thermally denatured by heating resulting in increased dye binding to the unfolded protein and fluorescence. The temperature midpoint ($T_m$) of a proteins denaturation is established by calculating the half maximal value of the denaturation curve. The temperature midpoint of the protein in the presence of a ligand is directly related to the affinity of the ligand for the protein and therefore its ability to stabilize the protein at higher temperatures.

DSF was performed in a 20 μL reaction comprising 20 mM Tris-HCl pH 7.5, 150 mM NaCl, 1:500 dilution of SYPRO Orange (Life Technologies), 1 mg/mL purified STING AA140-379 protein and ligand at a concentration of 1 mM. Each of wild type hSTING, HAQ allele hSTING and REF allele hSTING were used with each of the reference compounds and compounds of the invention as listed in Table 4. The results for the phosphodiester compounds, and the dithiophosphate compounds with RR configuration, are also compared in FIGS. 1-3. Samples were placed in hard shell PCR plate (Bio-Rad). The fluorescence as a function of temperature was recorded in a CFX 96 real time PCR machine (Bio-Rad) reading on the HEX channel, excitation 450-490, emission 560-580 nm. The temperature gradient was from 15-80° C. ramping 0.5° C. per 15 seconds and recording every 0.5° C. After subtraction of the background signal from a sample lacking protein and ligand. The midpoint temperature ($T_m$) was calculated by fitting the curves of the fluorescence as a function of temperature to a Boltzmann sigmoidal function (Graph Pad Prism). The change in thermal stability of STING AA140-379 in the presence of ligand ($T_m$ Shift) was calculated by subtracting the $T_m$ (Protein and Ligand) from $T_m$ (Protein alone).

TABLE 4

$T_m$ shifts in hSTING WT, HAQ allele and REF allele

| Example/Compound | Compound name | hSTING $T_m$ Shift (° C.) | | |
|---|---|---|---|---|
| | | WT | HAQ | REF |
| Reference | 2'3'-RR-(A)(A) | 11.2 | 18.5 | 7.3 |
| Reference | 2'3'-SR-(A)(A) | 8.2 | 13.8 | 4.8 |
| Example 2 Compound 5 | 2'3'-RR-(3'F-A)(2'F-A) | 14.5 | 26.0 | 10.5 |
| Example 2 Compound 5a | 2'3'-RS-(3'F-A)(2'F-A) | 11.5 | 19.9 | 7.9 |
| Example 3 Compound 10 | 2'3'-RR-(3'βF-A)(2'F-A) | 11.8 | 20.6 | 6.4 |
| Example 3 Compound 10a | 2'3'-RS-(3'βF-A)(2'F-A) | 7.0 | 12.7 | 3.4 |
| Example 13 Compound 53 | Ditho-2'3'-(3'βF-A)(A) | 1.1 | 5.5 | −3.4 |
| Example 4 Compound 16 | 2'3'-RR-(A)(2'F-A) | 14.0 | 26.6 | 9.8 |
| Example 4 Compound 16a | 2'3'-SR-(A)(2'F-A) | 11.7 | 19.4 | 8.1 |
| Example 5 Compound 20 | 2'3'-RR-(3'F-A)(A) | 11.4 | 19.3 | 7.8 |
| Example 5 Compound 20a | 2'3'-RS-(3'F-A)(A) | 6.6 | 11.8 | 4.0 |
| Example 11 Compound 45 | 2'3'-RR-(3'H-A)(2'F-A) | 12.1 | 20.1 | 7.8 |
| Example 11 Compound 45a | 2'3'-RS-(3'H-A)(2'F-A) | 7.5 | 13.1 | 4.3 |
| Reference | 2'3'-RR-(G)(A) | 20.5 | 34.1 | 12.6 |
| Example 6 Compound 26 | 2'3'-RR-(G)(2'F-A) | 27.3 | 42.4 | 17.3 |
| Example 6 Compound 26a | 2'3'-SR-(G)(2'F-A) | 18.1 | 29.5 | 11.0 |
| Example 12 Compound 49 | 2'3'-RR-(3'F-G)(2'F-A) | 25.9 | 39.4 | 17.5 |

TABLE 4-continued

T_m shifts in hSTING WT, HAQ allele and REF allele

| Example/Compound | Compound name | hSTING $T_m$ Shift (° C.) | | |
|---|---|---|---|---|
| | | WT | HAQ | REF |
| Example 7 Compound 32 | 3'2'-RR-(2'F-G)(3'F-A) | 13.4 | 22.6 | 10.3 |
| Example 7 Compound 32a | 3'2'-RS-(2'F-G)(3'F-A) | 10.6 | 14.3 | 9.3 |
| Example 7 Compound 32b | 3'2'-SS-(2'F-G)(3'F-A) | 6.2 | 9.3 | 5.5 |
| Example 8 Compound 35 | 3'2'-RR-(2'F-G)(A) | 16.1 | 28.3 | 14.1 |
| Example 8 Compound 35a | 3'2'-RS-(2'F-G)(A) | 10.8 | 14.2 | 9.9 |
| Reference | 2'3'-(G)(A) | 16.1 | 26.8 | 7.0 |
| Example 9 Compound 38 | 2'3'-(G)(2'F-A) | 25.2 | 33.3 | 10.9 |
| Example 10 Compound 40 | 2'3'-(3'F-G)(2'F-A) | 24.0 | 36.7 | 11.9 |

Figure 1B:
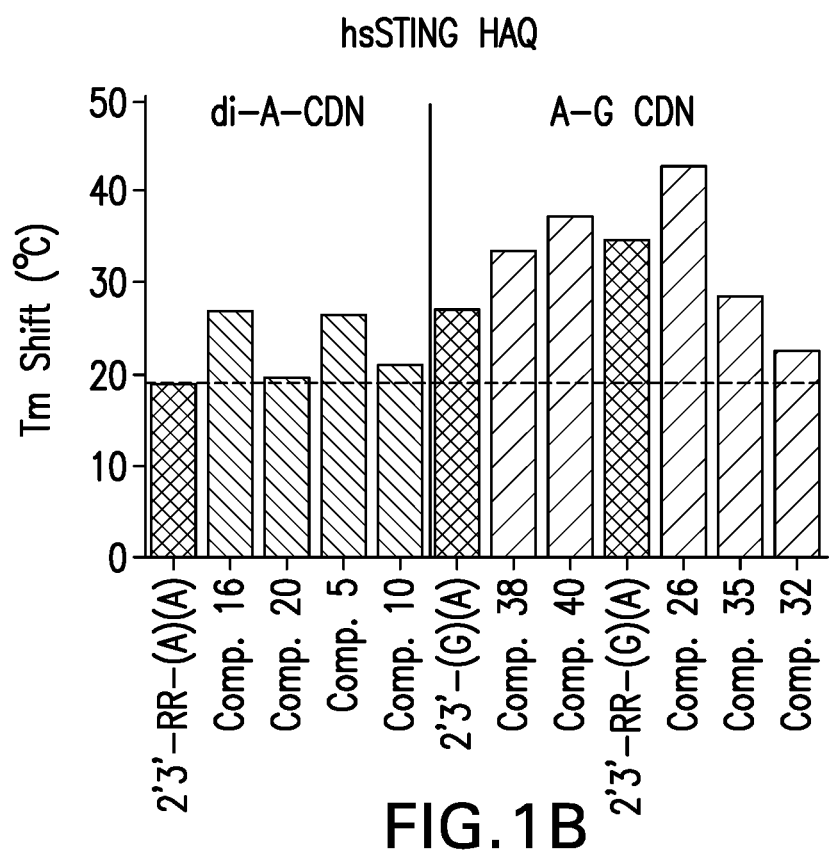
Figure 1C:
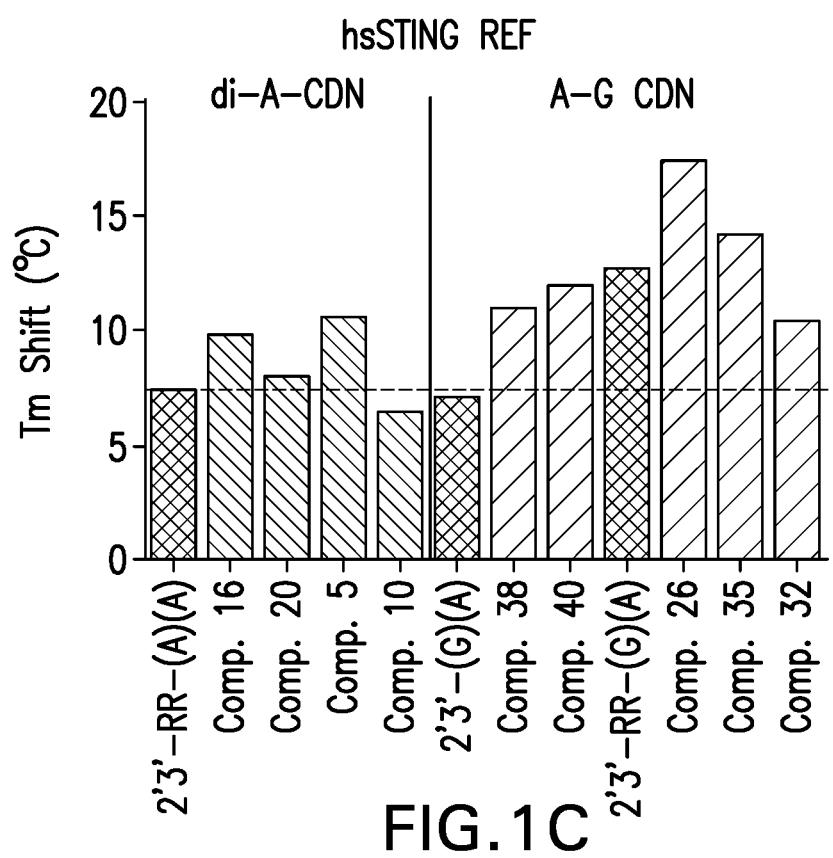

FIG. 1A (hSTING (WT)), 1B (hSTING (HAQ)) and IC (hSTING (REF)) show the $T_m$ shift for many of the dithiophosphate linked RR isomer compounds tested, as well as the two phosphodiester linked compounds. These figures show that for wild type and HAQ allele, the fluoro substituted compounds all had a $T_m$ shift greater than or equal to the 2'3'-RR-(A)(A) reference compound, which has been shown to be efficacious in mouse tumor models (Corrales et al., Cell Reports 2015, 11:1018-1031). Looking at the results of all compounds tested as shown in Table 4, of the di-adenine RR isomers, only the 2'3'-RR-(3'βF-A)(2'F-A) compound showed a $T_m$ shift less than the 2'3'-RR-(A)(A) for binding to the REF allele. The mono- or di-F substituted di-adenine RR isomer compounds had a $T_m$ shift greater than or approximately equal to the 2'3'-RR-(A)(A) di-OH reference compound for each of WT, HAQ allele and REF allele with the exception of 2'3'-RR-(3'βF-A)(2'F-A) as noted above. For the RS or SR isomers, while these all have a lower $T_m$ shift than the corresponding RR isomers, the compounds 2'3'-RS-(3'F-A)(2'F-A) and 2'3'-SR-(A)(2'F-A) show a higher $T_m$ shift than the di-OH reference 2'3'-SR-(A)(A) for each of WT, HAQ allele and REF allele. For the adenine-guanine compounds, both of the phosphodiester linked 2'3'-(G)(2'F-A) and 2'3'-(3'F-G)(2'F-A) compounds had a higher $T_m$ shift than the di-OH reference compound 2'3'-(G)(A). For the dithiophosphate linked RR isomer compounds, 2'3'-RR-(G)(2'F-A) and 2'3'-RR-(3'F-G)(2'F-A) had a higher $T_m$ shift than the di-OH reference 2'3'-RR-(G)(A) for each of WT, HAQ allele and REF allele. The 3'2'-RR-(2'F-G)(3'F-A) and 3'2'-RR-(2'F-G)(A) compounds showed good binding to all alleles. Reference compounds were not available for the RS or SR isomers of the guanine-adenine compounds. The mono- and di-F-ML-CDN compounds as described herein show good binding to STING based on the $T_m$ shift, with many of the compounds tested showing a higher $T_m$ shift than the di-OH reference compound for each of WT, HAQ allele and REF allele.

Example 15: Induction of Type I Interferon by Mono- and Di-F-ML-CDN Compounds in hPBMCs The induction of type I interferon was measured in human primary blood mononuclear cells (hPBMCs) to evaluate the potency of the mono- or di-F-ML-CDN compounds as described herein. hPBMCs from three unique donors were used: one donor was homozygous for the wild type (WT) STING allele (STING$^{WT/WT}$), one donor was homozygous for the so-called reference (REF) (R232H) STING allele (STING$^{REF/REF}$), and the third donor was homozygous for the HAQ (R71H, G230A, R293Q) STING allele (STING$^{HAQ/HAQ}$). The STING genotype of these donors was determined by PCR amplification and sequencing: genomic DNA was isolated from hPBMCs using Quick Extract DNA Extraction Solution (Epicentre) and was used to amplify regions of exon 3, 6, and 7 of the human STING gene. Primers for amplification and sequencing were: hSTING exon3F GCTGAGACAGGAGCTTTGG (SEQ ID NO: 11), hSTING exon3R AGCCAGAGAGGTTCAAGGA (SEQ ID NO: 12), hSTING exon6F GGCCAATGACCTGGGTCTCA (SEQ ID NO: 13), hSTING exon6R CACCCAGAATAGCATCCAGC (SEQ ID NO: 14), hSTING exon7F TCAGAGTTGGGTATCAGAGGC (SEQ ID NO: 15), hSTING exon7R ATCTGGTGTGCTGGGAAGAGG (SEQ ID NO: 16). STING variant alleles were assigned according to Yi, et al., 2013, PLoS One, 8(10), e77846 (DOI: 10.1371/journal.pone.0077846).

Cryopreserved hPBMCs were thawed and $10^6$ cells were either left untreated or treated with 10 μM of di-adenine compounds 2'3'-RR-(A)(A) (di-OH reference), 2'3'-RR-(A)(2'F-A) (Example 4, Compound 16), 2'3'-RR-(3'F-A)(A) (Example 5, Compound 20), 2'3'-RR-(3'F-A)(2'F-A) (Example 2, Compound 5), and 2'3'-RR-(3'βF-A)(2'F-A) (Example 3, Compound 10) or adenine-guanine compounds 2'3'-(G)(A) (di-OH reference), 2'3'-(G)(2'F-A) (Example 9, Compound 38), 2'3'-RR-(G)(A) (di-OH reference), 2'3'-RR-(G)(2'F-A) (Example 6, Compound 26), 3'2'-RR-(2'F-G)(A) (Example 8, Compound 35), and 3'2'-RR-(2'F-G)(3'F-A) (Example 7, Compound 32) in RMPI media supplemented with 10% fetal bovine serum and 1% Penicillin/Streptomycin. After 2 hours stimulation, cells were harvested by centrifugation and washed once in phosphate-buffered saline. Cellular RNA was isolated using the Aurum Total RNA 96 Kit and cDNA was synthesized using the iScript cDNA Synthesis Kit. Target (IFN-β) and reference (HSP90AB1 and GUSB) gene expression was assessed by real-time qRT-PCR using PrimePCR probe assays and the CFX96 gene cycler (all reagents and equipment from Bio-Rad). Relative IFN-β expression was compared to untreated cells and normalized to reference genes ($2^{-\Delta\Delta Ct}$ method).

Figure 2:
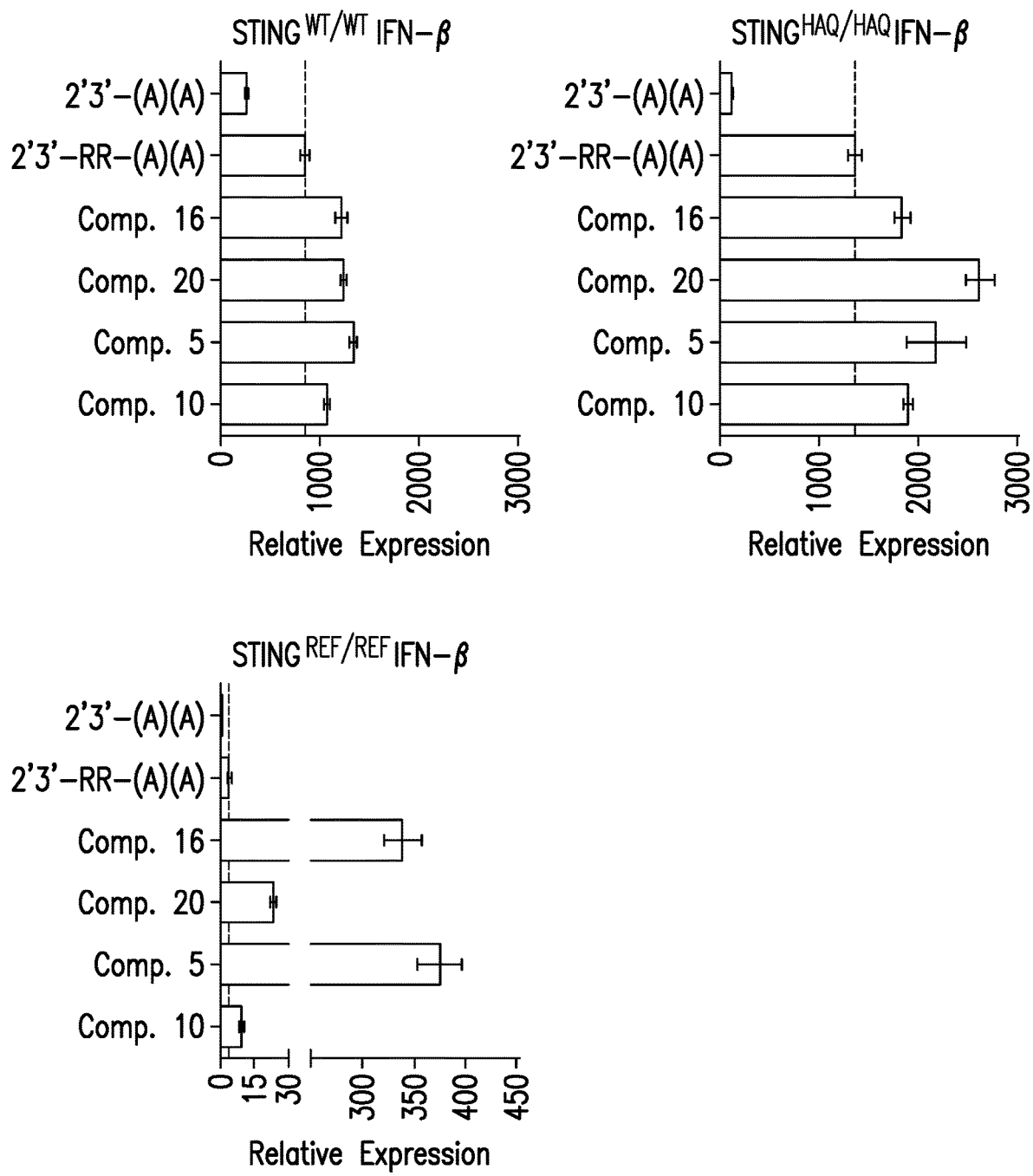
FIG. 2 depicts relative IFNβ expression by $STING^{WT/WT}$, $STING^{HAQ/HAQ}$ and $STING^{REF/REF}$ in human PBMCs at 2 hours following stimulation with 10 μM for di-adenine mono- or di-F-ML-CDN compounds.
Figure 3:
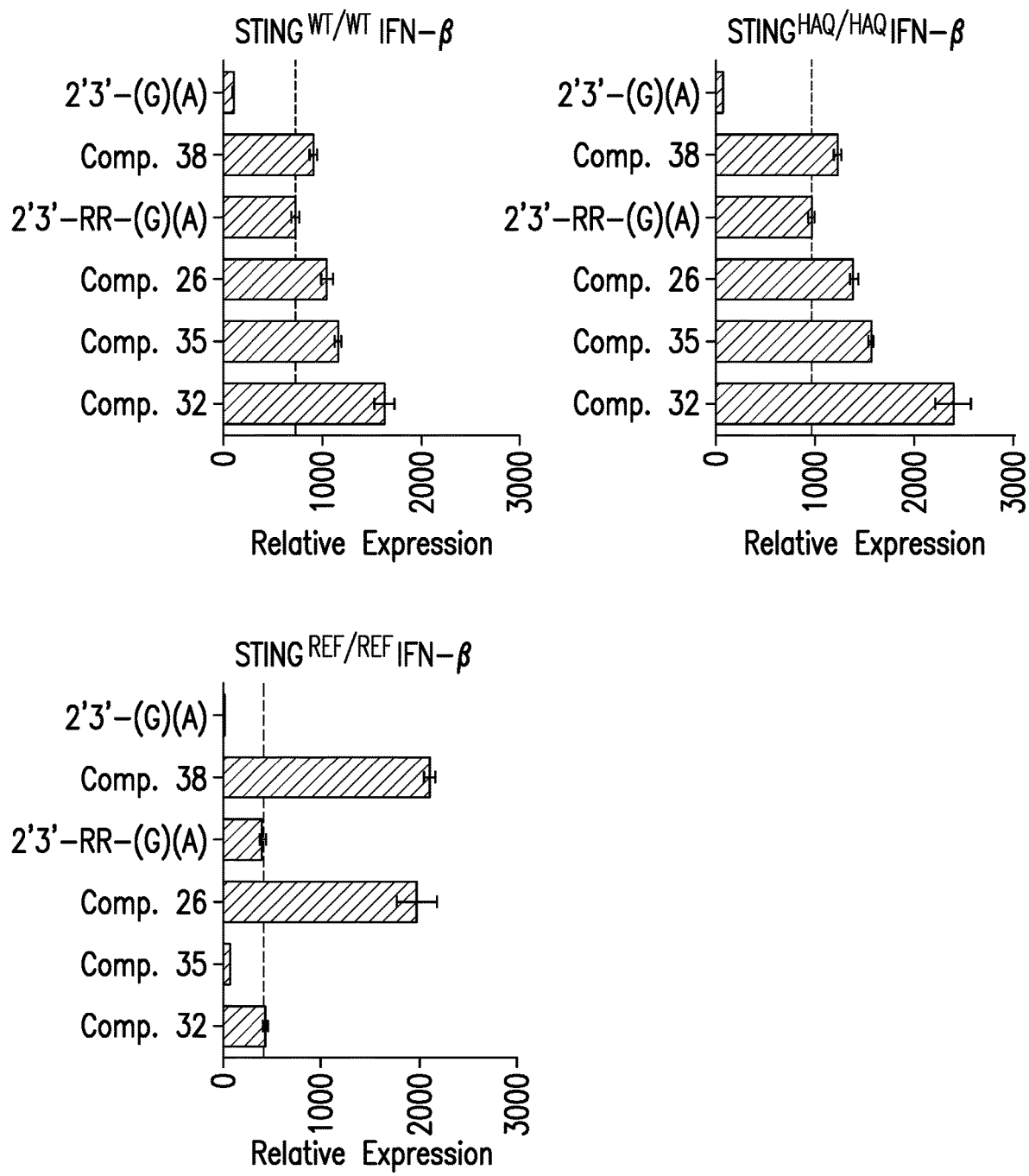
FIG. 3 depicts relative IFNβ expression by $STING^{WT/WT}$, $STING^{HAQ/HAQ}$ and $STING^{REF/REF}$ in human PBMCs at 2 hours following stimulation with 10 μM for guanine-adenine mono- or di-F-ML-CDN compounds.

FIG. 2 (di-adenine compounds) and FIG. 3 (guanine-adenine compounds) show the Relative Expression of IFN-β transcript by hPBMC homozygous for WT STING, the HAQ STING allele and the REF STING allele. Dotted lines in the graphs indicate the Relative Expression value for 2'3'-RR-(A)(A) or 2'3'-RR-(G)(A).

The di-adenine compounds 2'3'-RR-(A)(2'F-A) (Comp. 16), 2'3'-RR-(3'F-A)(A) (Comp. 20), 2'3'-RR-(3'F-A)(2'F-A) (Comp. 5) and 2'3'-RR-(3'(3F-A)(2'F-A) (Comp. 10) all stimulated higher levels of IFN-β transcripts than the di-OH reference compound 2'3'-RR-(A)(A) for each of WT, HAQ allele and REF allele of hSTING. The 2'3'-RR-(A)(2'F-A) and 2'3'-RR-(3'F-A)(2'F-A) show substantially higher levels (>80-fold higher) than 2'3'-RR-(A)(A) for the hSTING REF allele.

For the guanine-adenine compounds, the compound 2'3'-(G)(2'F-A) (Comp. 38) showed substantially higher levels (>100-fold higher) than the 2'3'-(G)(A) di-OH reference compound for each of WT, HAQ allele and REF allele of hSTING, even showing higher levels than the 2'3'-RR-(G)(A) compound. The compound 2'3'-RR-(G)(2'F-A) (Comp. 26) showed higher levels than the 2'3'-RR-(G)(A) di-OH reference compound for each of WT, HAQ allele and REF allele of hSTING, with >4-fold higher levels than the 2'3'-RR-(G)(A) di-OH reference compound for the hSTING REF allele. The compounds 3'2'-RR-(2'F-G)(A) (Comp. 35), and 3'2'-RR-(2'F-G)(3'F-A) (Comp. 32) were also very active, and stimulated higher levels of IFN-β transcripts than the di-OH compound 2'3'-RR-(G)(A) for the hSTING WT and the hSTING HAQ allele, while 3'2'-RR-(2'F-G)(3'F-A) stimulated approximately equal levels compared to the di-OH compound 2'3'-RR-(G)(A) for the hSTING REF allele.

Figure 4A:
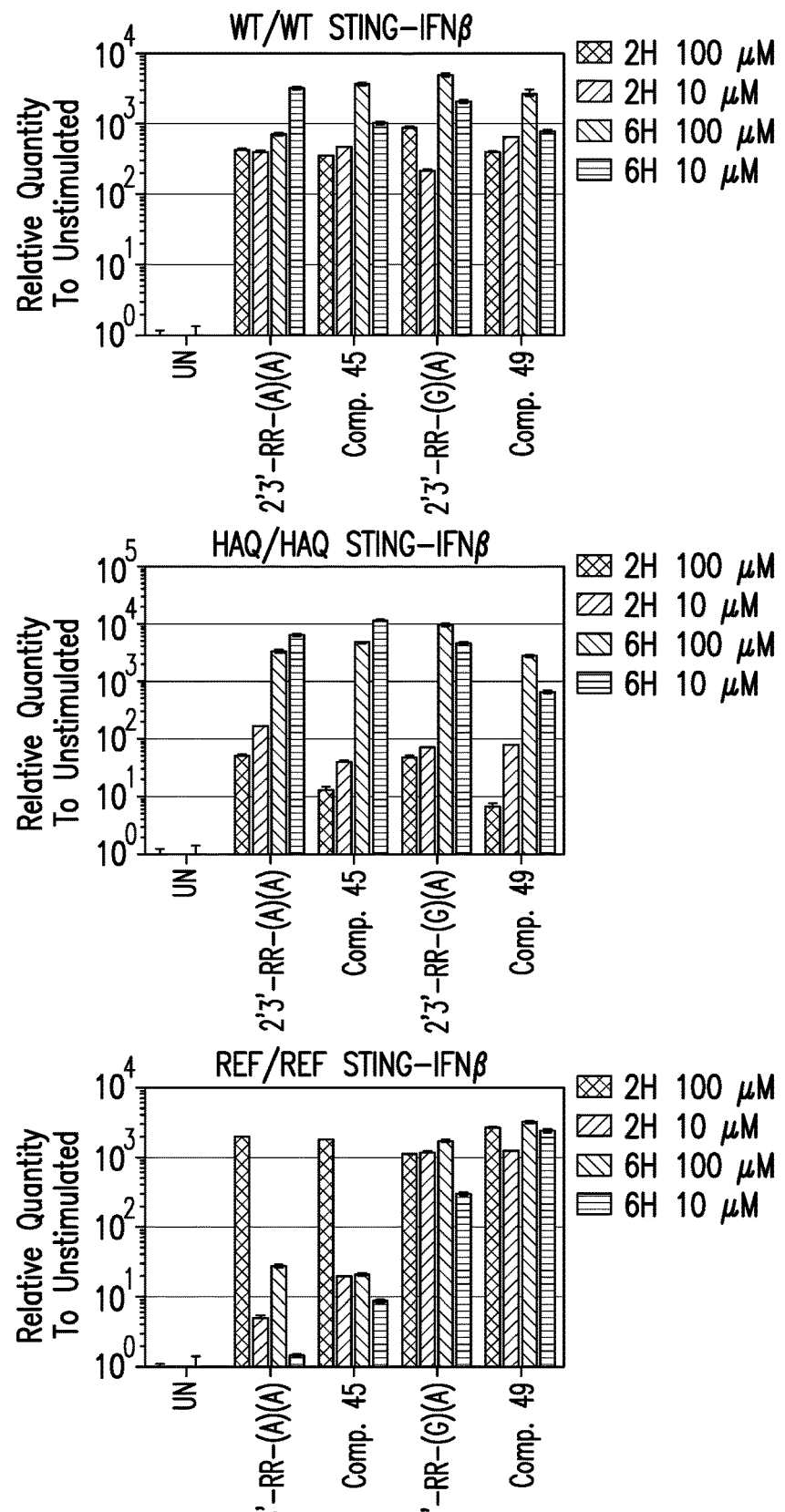
FIG. 4A-E depicts relative expression of IFNβ (4A), TNFα (4B), IFNγ (4C), IL-6 (4D) and IL-12p35 (4E) by $STING^{WT/WT}$, $STING^{HAQ/HAQ}$ and $STING^{REF/REF}$ in human PBMCs at 2 and 6 hours following stimulation with 10 μM or 100 μM of Compounds 45 and 49.
Figure 4B:
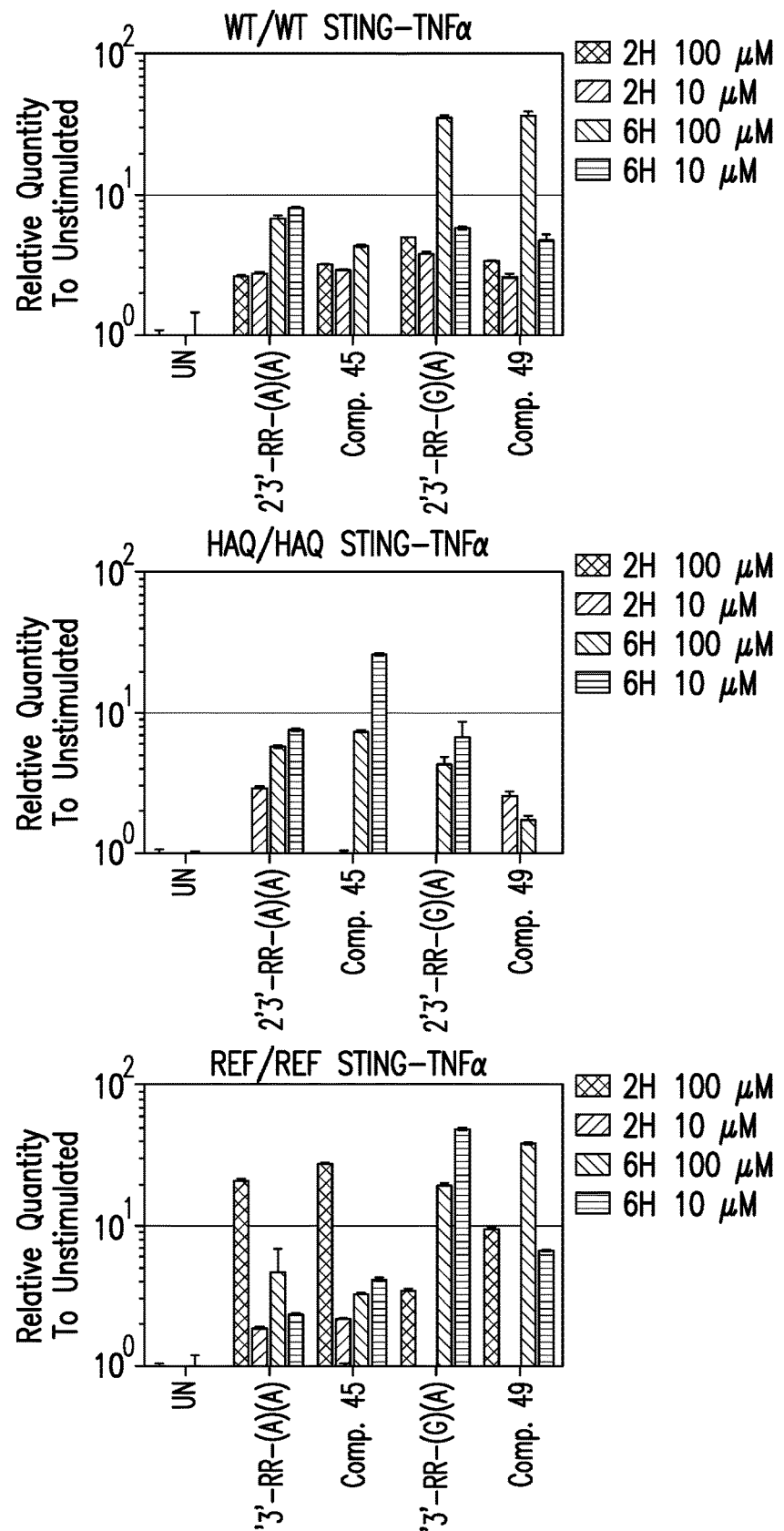
Figure 4C:
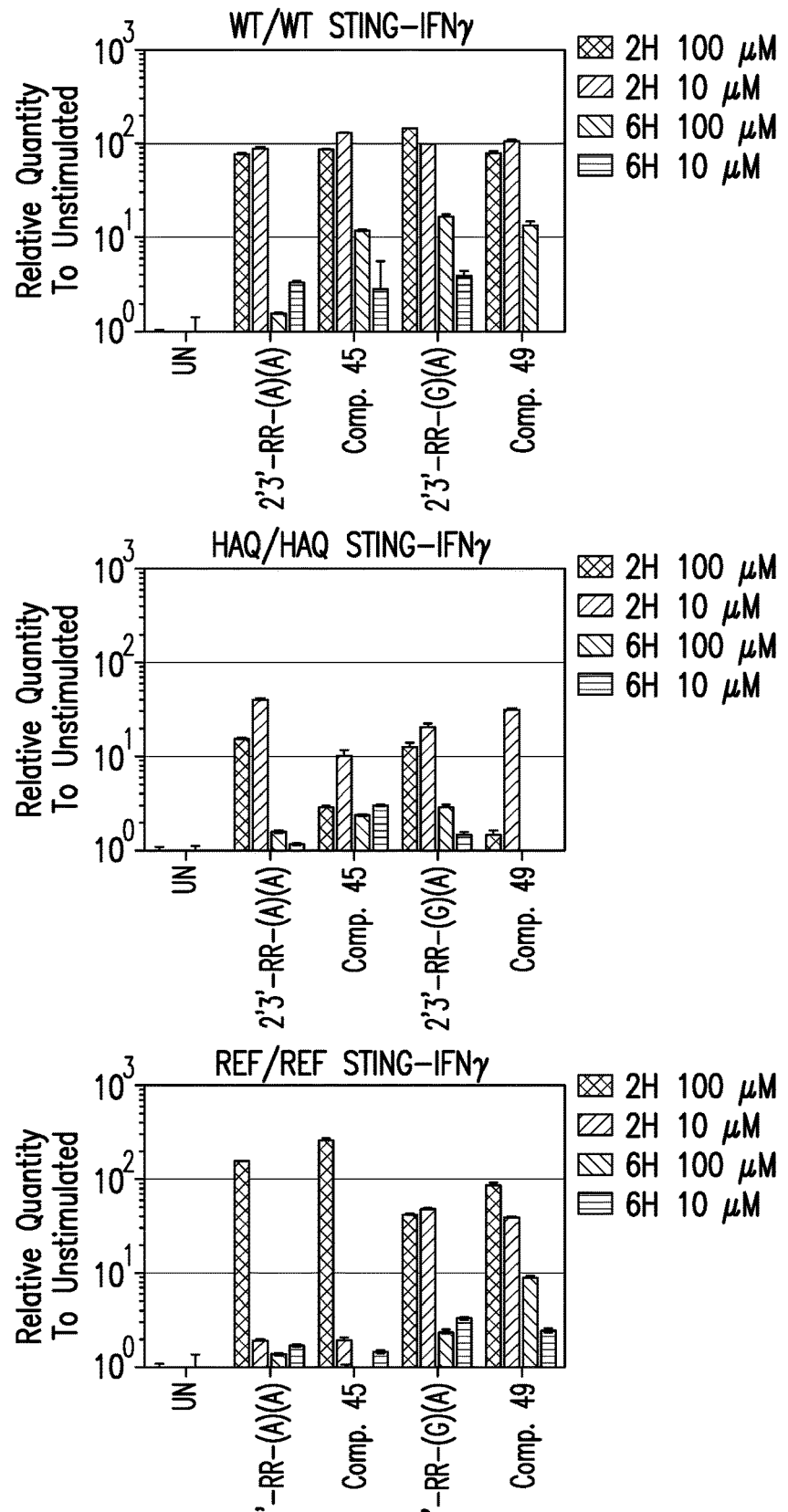
Figure 4D:
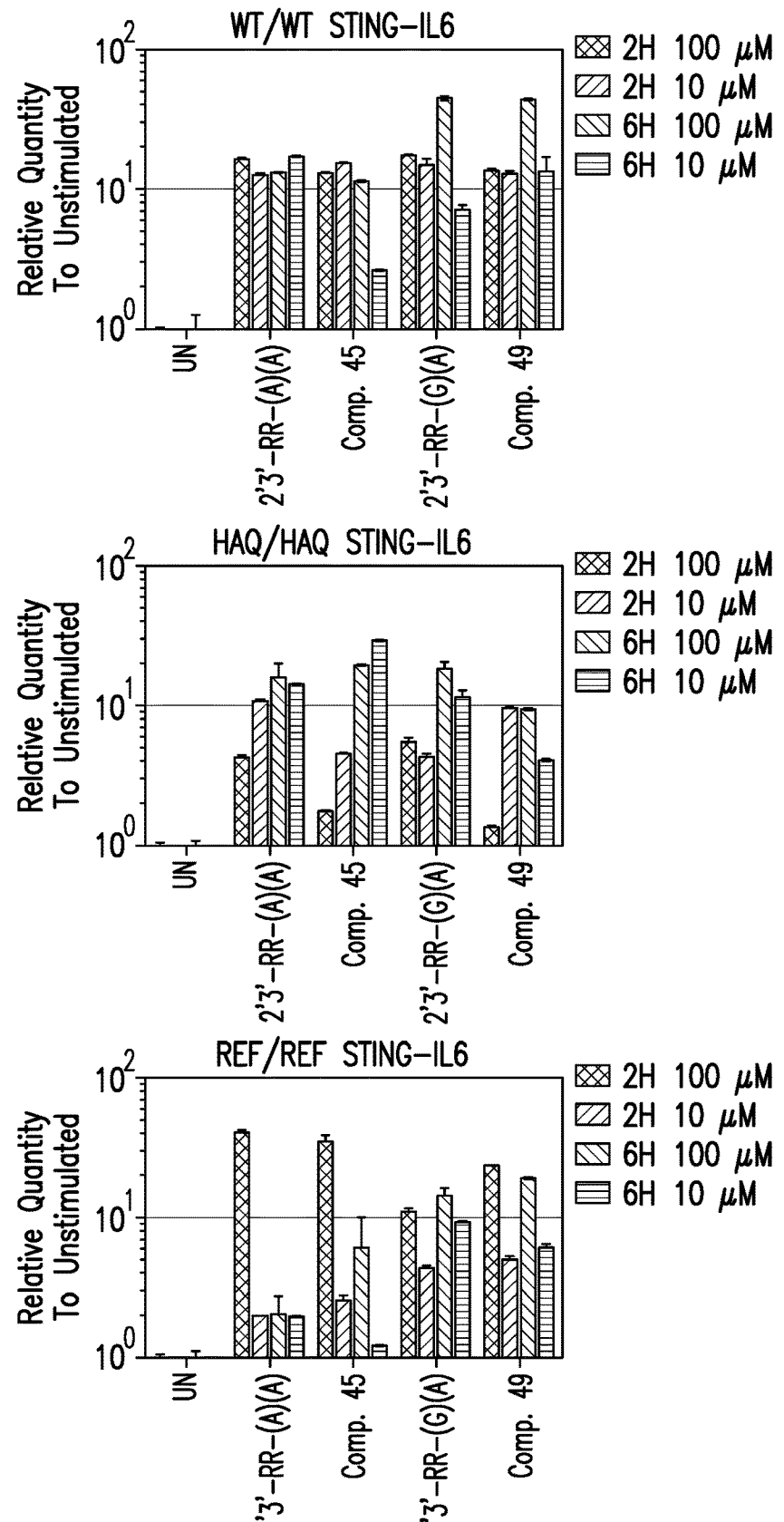
Figure 4E:
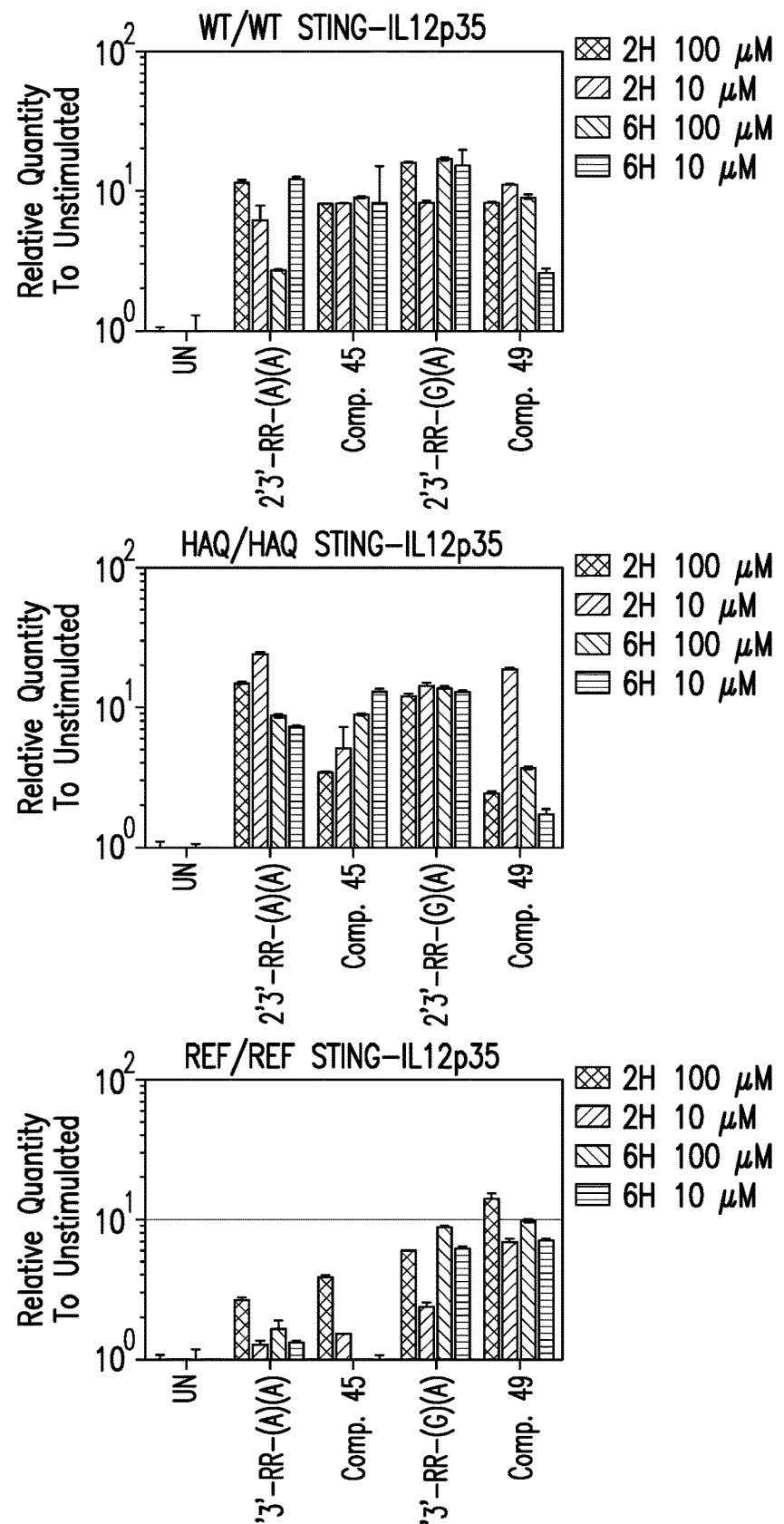

2'3'-RR-(3'H-A)(2'F-A) (Example 11, Compound 45) and (2'3'-RR-(3'F-G)(2'F-A) (Example 12, Compound 49) were similarly assayed in comparison to 2'3'-RR-(A)(A) and 2'3'-RR-(G)(A), where compounds were tested at 10 µM and 100 µM, and cells harvested at either 2 hours or 6 hours post stimulation. IFNβ expression was expressed relative to untreated cells. In addition to IFNβ, target genes included Th1-associated cytokines (IFNγ, IL-12p35) and NF-kB dependent inflammatory cytokines (TNFα, IL-6). Results are shown in FIG. 4A for IFNβ, 4B for TNFα, 4C for IFNγ, 4D for IL-6 and 4E for IL-12p35, for WT, HAQ allele and REF allele of hSTING. These results demonstrate both compound 45 and 49 are potent STING activators.

Example 16: Mono- and Di-F-ML-CDN Compounds Potently Activate Human STING Signaling in THP1 Cells To determine the relative level of type I interferon induced in human cells by each of the mono- or di-F-ML-CDN as a signature of adjuvant potency, 100,000 THP1-Dual cells (a human monocyte cell line containing the hSTING HAQ allele transfected with an IRF-3 inducible secreted luciferase reporter gene (Invivogen) which express secreted luciferase under the control of a promoter comprised of five IFN-stimulated response elements) were activated with 30 ng/mL phorbol 12-myristate 13-acetate overnight in a 96-well dish. Cells were washed with fresh media and incubated for 30 min at 37° C. with 5% $CO_2$ with compounds in 3 fold titration steps from 2,000 to 0.0338 µM in PB buffer (50 mM 4-(2-hydroxyethyl)-1-piperazineethanesulfonic acid, 100 mM KCl, 3 mM $MgCl_2$, 0.1 mM dithiothreitol, 85 mM sucrose, 1 mM ATP, 0.1 mM GTP and 0.2% bovine serum albumin). To measure type I interferon activation with uniform compound cell penetration, cells were stimulated with compounds in 4 fold titration steps from 12 to 0.00001 µM in PB buffer containing 10 µg/mL digitonin. After 30 minutes, cells were washed and fresh RPMI media containing 10% FBS was added, and cells were incubated at 37° C. with 5% $CO_2$. Cell culture supernatants from each sample were collected after overnight incubation, and 10 µL of the cell culture supernatants was added to 50 µL QUANTI-Luc reagent (Invivogen). Type I interferon activation was determined by measuring secreted luciferase levels on a SpectraMax M3 spectrophotometer (Molecular Devices). The EC50 value was determined from the dose-response curve for the 10 concentrations from the serial dilution of the reference compounds and compounds of the invention tested in this assay as listed in Table 5, showing the results without digitonin and, where available, with digitonin ("-" indicates compounds that were not tested with digitonin).

TABLE 5

EC50 with and without digitonin in THP1 cells (HAQ allele).

| Example/Compound | Compound name | EC50 (µM) No digitonin | EC50 (µM) +digitonin |
|---|---|---|---|
| Reference | 2'3'-RR-(A)(A) | 41.5 | 0.385 |
| Reference | 2'3'-SR-(A)(A) | 34.4 | — |
| Example 2 Compound 5 | 2'3'-RR-(3'F-A)(2'F-A) | 4.5 | 0.190 |
| Example 2 Compound 5a | 2'3'-RS-(3'F-A)(2'F-A) | 34.8 | — |
| Example 3 Compound 10 | 2'3'-RR-(3'βF-A)(2'F-A) | 4.6 | 0.271 |
| Example 3 Compound 10a | 2'3'-RS-(3'βF-A)(2'F-A) | 28.5 | — |
| Example 4 Compound 16 | 2'3'-RR-(A)(2'F-A) | 17.9 | 0.141 |
| Example 5 Compound 20 | 2'3'-RR-(3'F-A)(A) | 11.2 | 0.399 |
| Example 5 Compound 20a | 2'3'-RS-(3'F-A)(A) | >150 | — |
| Example 11 Compound 45 | 2'3'-RR-(3'H-A)(2'F-A) | 10.2 | — |
| Example 11 Compound 45a | 2'3'-RS-(3'H-A)(2'F-A) | 112.6 | — |
| Reference | 2'3'-RR-(G)(A) | 28.6 | 0.056 |
| Example 6 Compound 26 | 2'3'-RR-(G)(2'F-A) | 32.4 | 0.035 |
| Example 6 Compound 26a | 2'3'-SR-(G)(2'F-A) | 30.5 | — |
| Example 12 Compound 49 | 2'3'-RR-(3'F-G)(2'F-A) | 14.0 | — |
| Example 7 Compound 32 | 3'2'-RR-(2'F-G)(3'F-A) | 4.3 | — |
| Example 7 Compound 32a | 3'2'-RS-(2'F-G)(3'F-A) | 24.9 | — |
| Example 7 Compound 32b | 3'2'-SS-(2'F-G)(3'F-A) | >150 | — |
| Example 8 Compound 35 | 3'2'-RR-(2'F-G)(A) | 10.2 | 0.285 |
| Example 8 Compound 35a | 3'2'-RS-(2'F-G)(A) | 54.9 | — |
| Reference | 2'3'-(G)(A) | 252.5 | 0.029 |
| Example 9 Compound 38 | 2'3'-(G)(2'F-A) | 175.8 | 0.157 |
| Example 10 Compound 40 | 2'3'-(3'F-G)(2'F-A) | 56.6 | 0.019 |

The mono- and di-F di-adenine compounds 2'3'-RR-(A) (2'F-A), 2'3'-RR-(3'F-A)(A), 2'3'-RR-(3'F-A)(2'F-A), 2'3'-RR-(3'βF-A)(2'F-A) and 2'3'-RR-(3'H-A)(2'F-A) in the THP1 assay without digitonin permeabilization all show improved activity relative to the di-OH reference compound 2'3'-RR-(A)(A), with all having an EC50 of less than 20 µM. This demonstrates an enhanced cell permeability of the mono- or di-F adenine compounds in comparison to the reference compound. The di-F compounds 2'3'-RR-(3'F-A) (2'F-A) and 2'3'-RR-(3'βF-A)(2'F-A) having EC50 of approximately 5 µM are an 8-fold improvement over the 2'3'-RR-(A)(A) reference compound, though the results of the assay with digitonin for these compounds are at best improved by only 2-fold.

For the guanine-adenine compounds, the phosphodiester linked compounds 2'3'-(G)(2'F-A) and 2'3'-(3'F-G)(2'F-A) demonstrate improvement in the EC50 assay without digitonin, while the 2'3'-(G)(2'F-A) shows approximately 5-fold less activity in the assay with digitonin. For the dithiophosphate linked analogues, 2'3'-RR-(G)(2'F-A) shows an approximately 1.5-fold improvement in the activity in the assay with digitonin, while the activities are about the same without digitonin, as compared to the di-OH reference compound 2'3'-RR-(G)(A). The mono-F compound 3'2'-RR-(2'F-G)(A) shows approximately 3-fold improvement in the activity relative to 2'3'-RR-(G)(A) compound in the assay without digitonin, while being approximately 5-fold less active in the assay with digitonin. The di-F compounds 2'3'-RR-(3'F-G)(2'F-A) and 3'2'-RR-(2'F-G)(3'F-A) were approximately 2-fold and 7-fold more active, respectively, in the assay without digitonin relative to the reference compound 2'3'-RR-(G)(A). The mono- and di-F-ML-CDN compounds, in particular the RR isomer for dithiophosphate linked compounds, tended to have improved activity in the THP1 assay in the absence of digitonin, thus demonstrating superior cellular uptake properties in comparison to di-OH reference compounds.

Example 17: In Vivo Efficacy of Mono-F-ML-CDN Compounds 26 and 35

To assess the ability of the mono- and di-F-ML-CDN compounds to inhibit tumor growth and induce anti-tumor immune responses in an aggressive murine tumor model, 6-8 week old female C57BL/6 mice (8 mice per group) were implanted in the flank with B16.SIY melanoma cells ($1\times10^6$ cells in 100 µL PBS). Studies were performed in comparison to the reference compound 2'3'-RR-(A)(A), where mice were treated with 2'3'-RR-(G)(2'F-A) (Example 6, Compound 26), or 3'2'-RR-(2'F-G)(A) (Example 8, Compound 35). Each compound was dosed at 1, 10 and 100 µg in a total volume of 40 µL HBSS, and compared to 10 µg and 100 µg of 2'3'-RR-(A)(A) in a total volume of 40 µL HBSS, or HBSS vehicle control. Treatments began when tumors reached a volume of approximately 100 mm³, on approximately day 9 post tumor implantation. The compounds were administered by subcutaneous injection into the center of the tumor (IT) using a 27-gauge needle, for a total of three injections over one week. Tumors were measured twice weekly. Surviving mice were re-challenged after day 45 post-tumor implantation and monitored for ability to reject tumor outgrowth, as compared to tumor growth in naïve (unchallenged) mice.

Figure 5A:
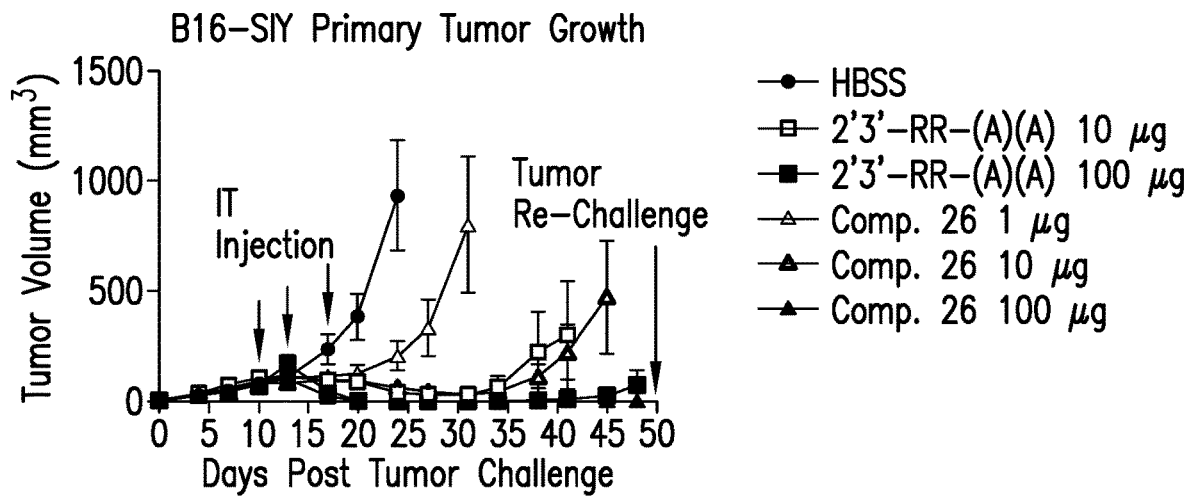
Figure 5B:
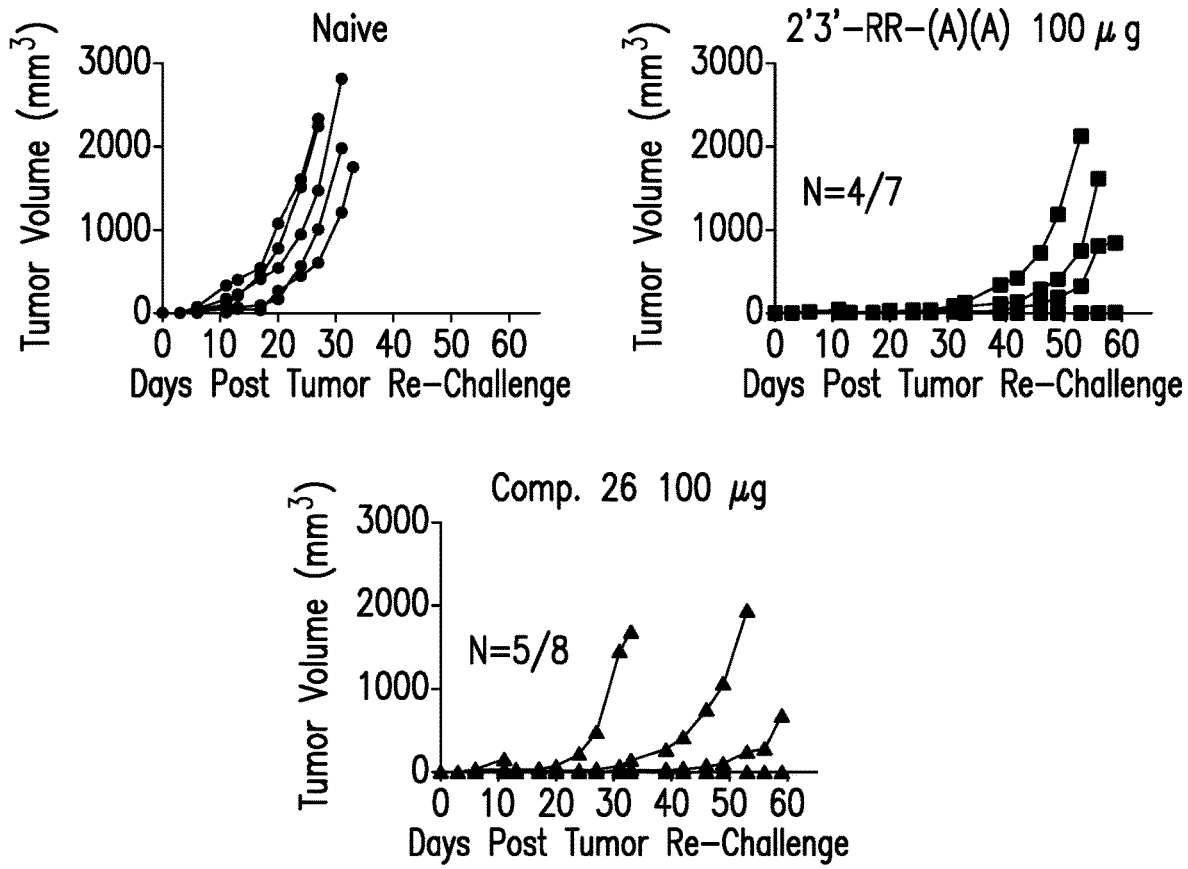

As shown in FIG. 5A, Compound 26 demonstrates potent tumor inhibition at all doses tested, comparable to the reference compound 2'3'-RR-(A)(A), with complete tumor rejection demonstrated at the 100 µg dose. Surviving mice in the 100 µg dose groups for the reference compound and Compound 26 were re-challenged with B16-SIY ($1\times10^6$ cells in 100 µL PBS) on day 45, and found to reject tumor implantation in the majority of mice, similar to the reference compound (FIG. 5B). Similarly, Compound 35 demonstrated potent tumor inhibition at all doses tested, with complete tumor rejection demonstrated at the 100 µg dose (FIG. 5C). Surviving mice in the 100 µg dose groups were re-challenged on day 56, and the majority of mice also rejected tumor challenge, similar to the reference compound 2'3'-RR-(A)(A) (FIG. 5D). These data demonstrate the potent and durable anti-tumor effects of the guanine-adenine mono-F-ML-CDN compounds in an aggressive murine tumor model.

To demonstrate that the anti-tumor effects are mediated by adaptive T cell immune responses, mice treated as above were bled on day 7 post 3rd IT injection and assessed for immune responses against the SIY tumor antigen by SIY-specific pentamer flow cytometry (FACS). PBMCs ($2\times10^5$) were prepared by Ficoll gradient and pre-incubated with anti-CD16/32 monoclonal antibody to block potential non-specific binding, then labeled with a PE-MHC class I pentamer (Proimmune, Sarasota, Fla.) consisting of murine H-2Kb complexed to SIYRYYGL (SIY) (SEQ ID NO: 17) peptide, anti-TCRβ-AF700 (H57-597), anti-CD8-Pacific Blue (53-6.7), anti-CD4-Pacific Orange (RM4-5) (all antibodies from BioLegend, San Diego, Calif.) and the Fixable Viability Dye eFluor 450 (eBioscience, San Diego, Calif.). Stained cells were analyzed using FACS Versa cytometer with FACSDiva software (BD Biosciences, San Jose, Calif.). Data analysis was conducted with FlowJo software (Tree Star, Ashland, Oreg.).

Figure 6A:
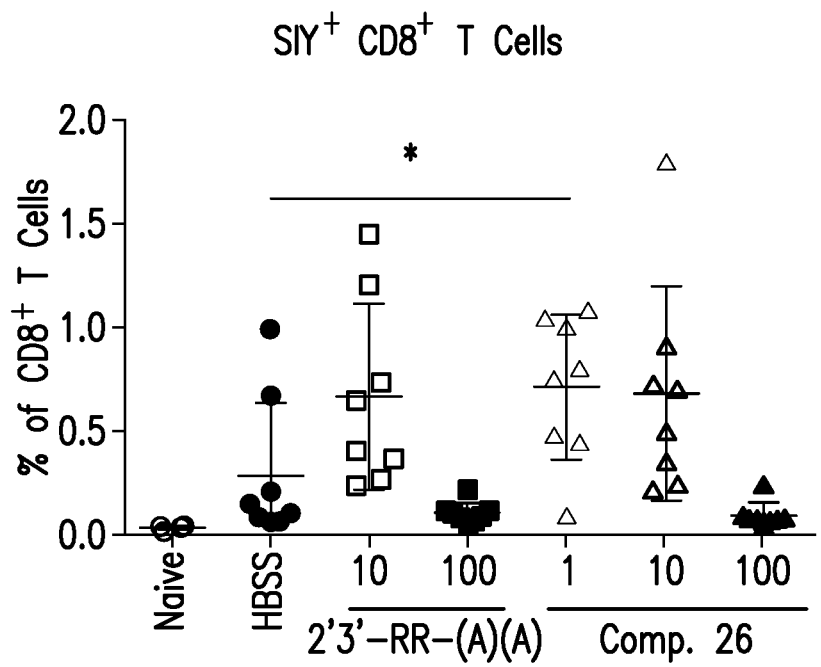
FIG. 6A-B depicts SIY⁺ CD8⁺ T-cells in PBMCs in a B16.SIY melanoma mouse model, measured in a FACS assay 7 days post third intra-tumoral injection of Compound 26 (6A) and Compound 35 (6B) at 1 µg, 10 µg or 100 µg and reference compound 2'3'-RR-(A)(A) at 10 µg or 100 µg.
Figure 6B:
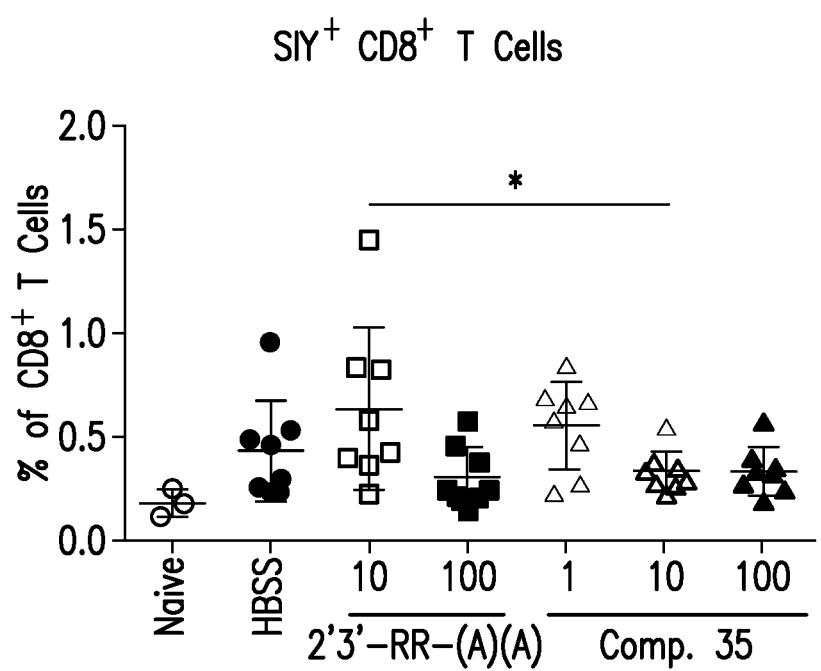

As shown in FIG. 6A, 2'3'-RR-(G)(2'F-A) (Comp. 26) elicits significantly higher T cell production of IFNγ in response to SIY peptide stimulation at the 1 µg dose, as compared to HBSS, and comparable T cell responses at 10 µg to the reference compound 2'3'-RR-(A)(A) ($*P<0.05$, student's t-test). As shown in FIG. 6B, 3'2'-RR-(2'F-G)(A) (Comp. 35) demonstrates measurable T cell responses at the 1 µg dose compared to naïve, unchallenged mice, although responses were lower than the reference compound 2'3'-RR-(A)(A) overall. These data demonstrate that the potent anti-tumor effects of these guanine-adenine mono-F-ML-CDN compounds are antigen-specific and T cell mediated.

Example 18: In Vivo Efficacy of Mono- or Di-F-ML-CDN Compounds 5, 10, 20, 49 and 50

Studies were also performed on a series of mono- and di-F-ML-CDN compounds to assess anti-tumor immune responses in comparison to the reference compound 2'3'-RR-(A)(A). Mice were treated with 2'3'-RR-(3'F-A)(2'F-A) (Example 2, Compound 5), 2'3'-RR-(3'βF-A)(2'F-A) (Example 3, Compound 10), 2'3'-RR-(3'F-A)(A) (Example 5, Compound 20), 2'3'-RR-(3'F-G)(2'F-A) (Example 12, Compound 49) or 2'3'-RR-(3'decanoyl-O-G)(2'F-A) (Example 6, Compound 50), where each compound was dosed at 0.1, 1, 10 and 100 µg in a total volume of 40 µL HBSS, and compared to 1 µg 2'3'-RR-(A)(A) in a total volume of 40 µL HBSS, or HBSS vehicle control. Treatments began when tumors reached a volume of approximately 100 mm³, on approximately day 9 post tumor implantation. The compounds were administered by a single subcutaneous injection into the center of the tumor (IT) using a 27-gauge needle. Tumors were measured twice weekly. Mice were euthanized on day 7 post IT injection and spleens were harvested and splenocytes prepared. Splenocytes ($2\times10^5$) were pre-incubated with anti-CD16/32 monoclonal antibody to block potential nonspecific binding, and labeled with PE-MHC class I pentamer (Proimmune) consisting of murine H-2Kb complexed to SIYRYYGL (SIY) (SEQ ID NO: 17) peptide, anti-TCRβ-AF700 (H57-597), anti-CD8-Pacific Blue (53-6.7), anti-CD4-Pacific Orange (RM4-5) (all antibodies from BioLegend) and the Fixable Viability Dye eFluor 450 (eBioscience). Stained cells were analyzed using FACS Versa cytometer with FACSDiva software (BD Biosciences). Data analysis was conducted with FlowJo software (Tree Star). Additionally, splenocystes were stimulated overnight in an IFNγ ELISPOT assay with media alone or with 1 µM SIYRYYGL (SIY) (SEQ ID NO: 17) peptide. IFN-γ ELISPOT plates were developed and quantified using a CTL plate reader and ImmunoSpot software.

Figure 7A:
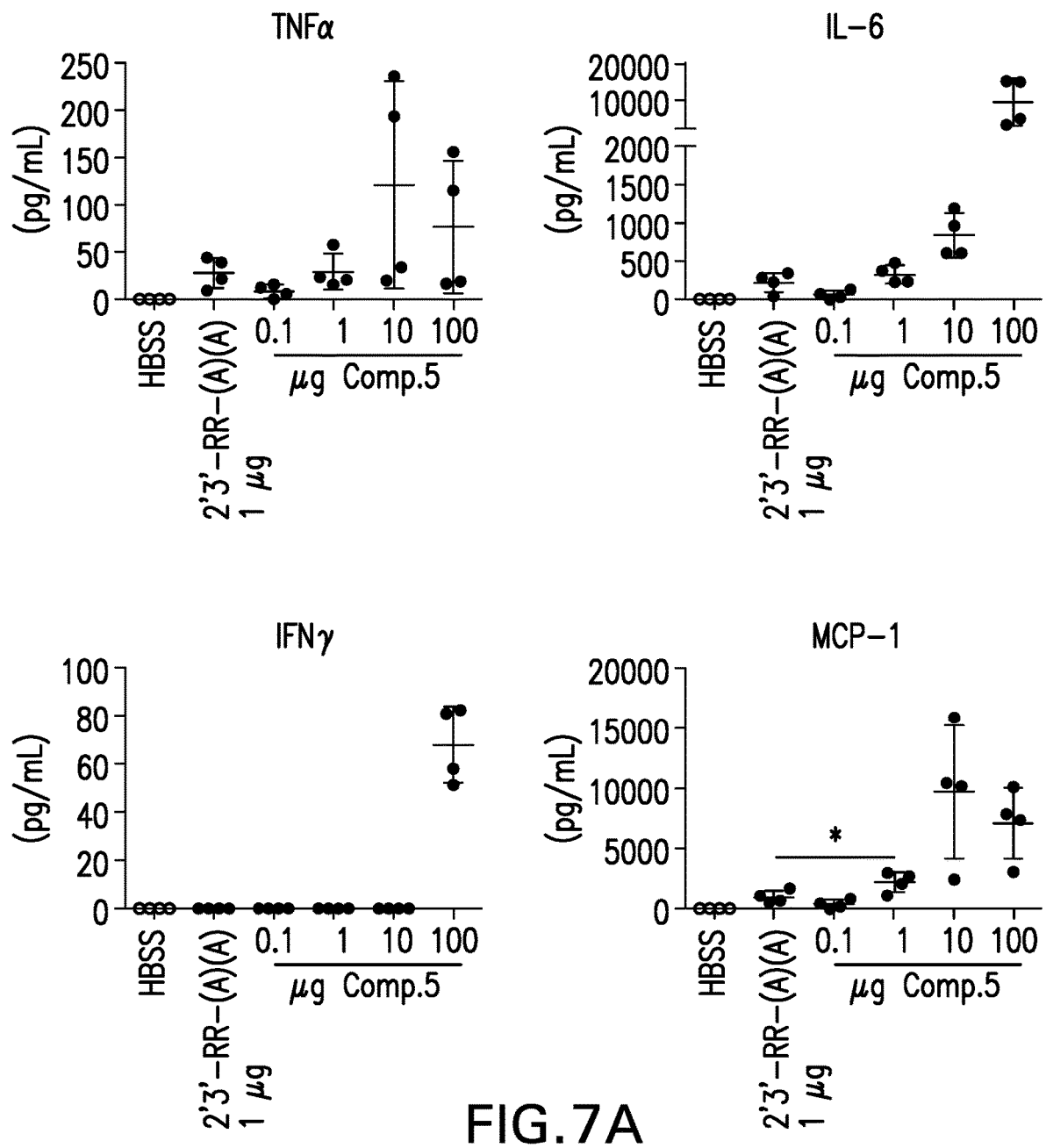
FIG. 7A-E depicts serum concentrations of pro-inflammatory cytokines TNF-α, IL-6, MCP-1, and IFN-γ in a B16.SIY melanoma mouse model, 6 hours post intra-tumoral injection of Compound 5 (7A), Compound 10 (7B) Compound 20 (7C), Compound 49 (7D) or Compound 50 (7E) at 0.1 µg, 1 µg, 10 µg or 100 µg and reference compound 2'3'-RR-(A)(A) at 1 µg.
Figure 7B:
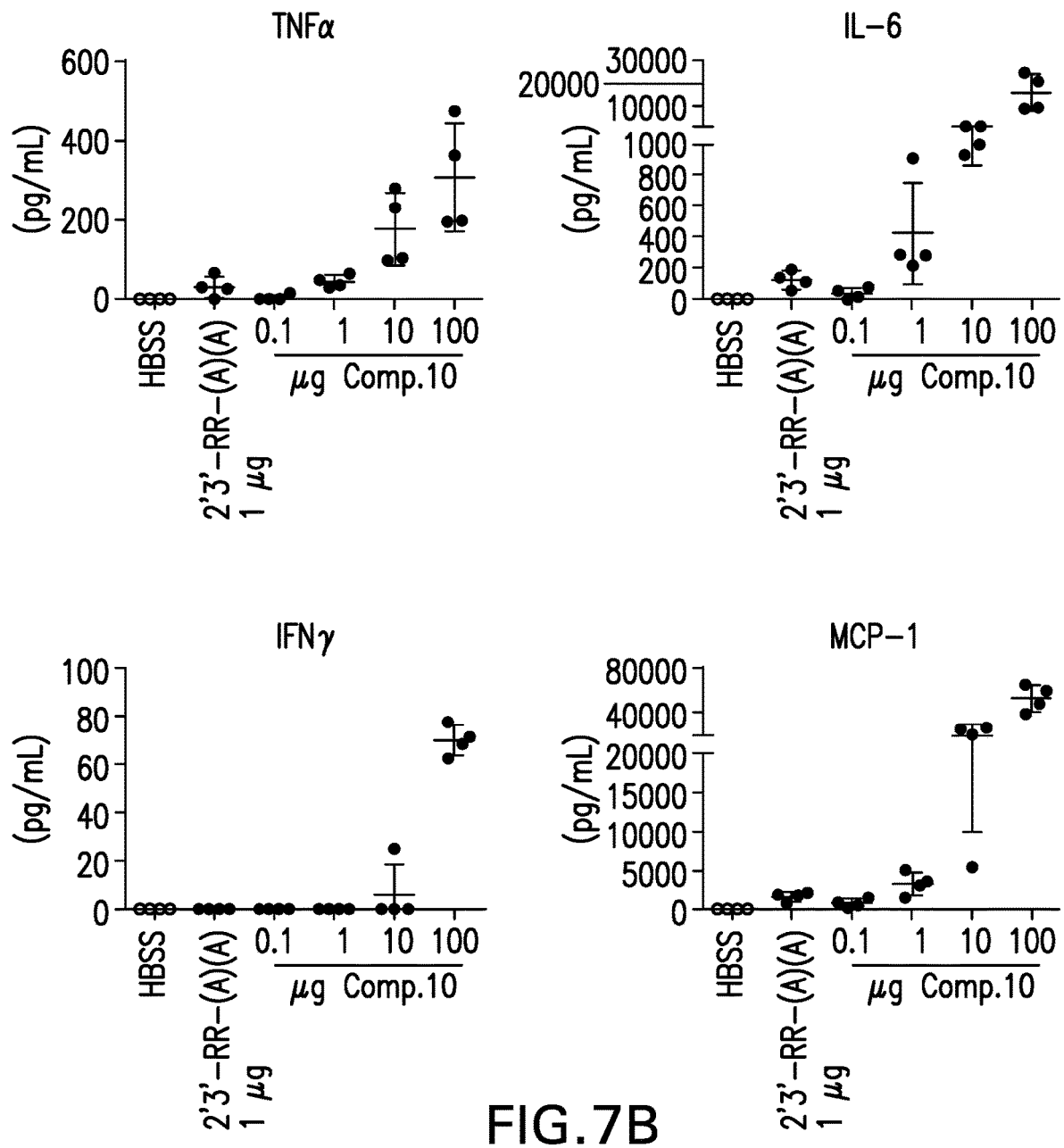
Figure 7C:
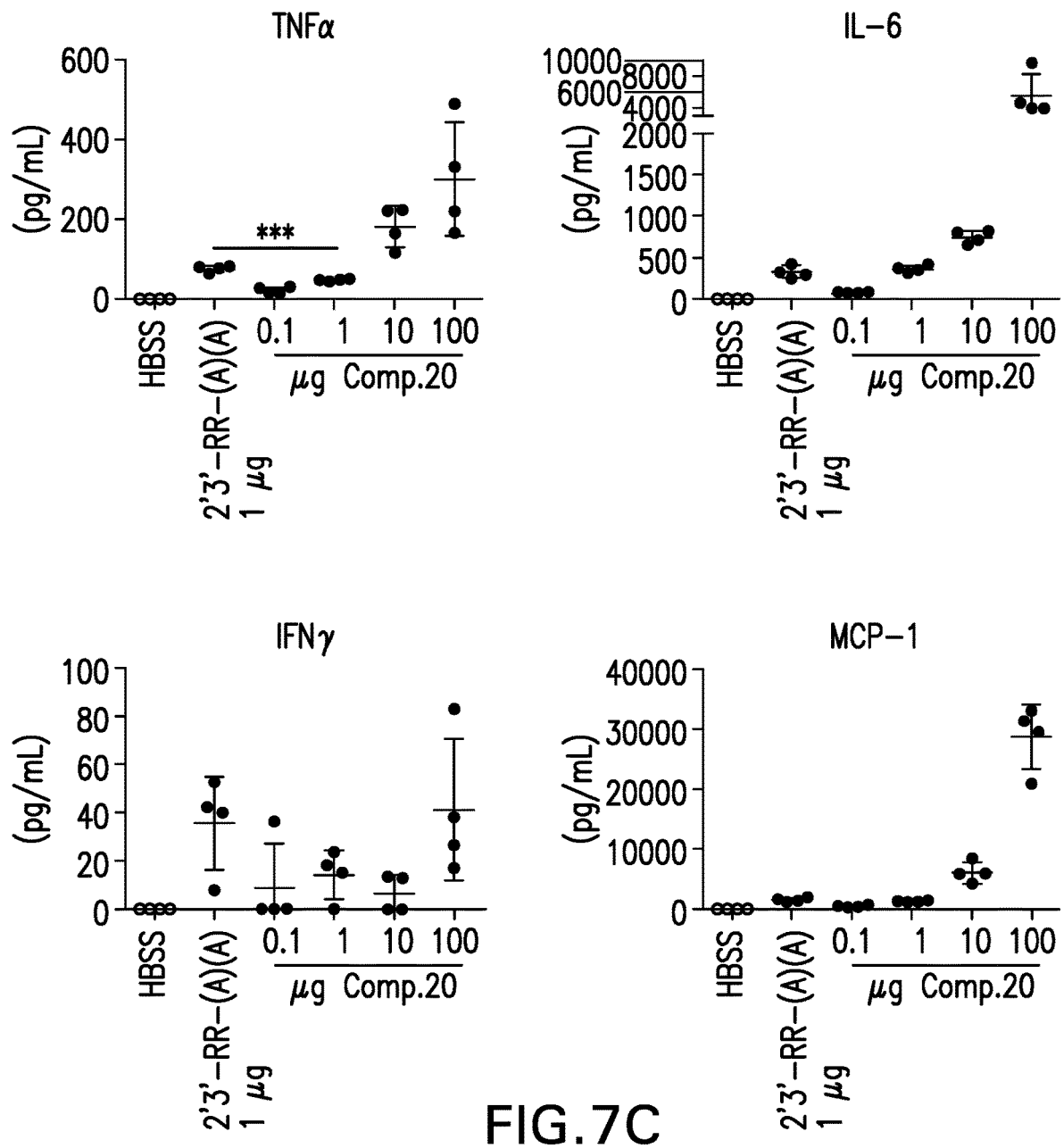
Figure 7D:
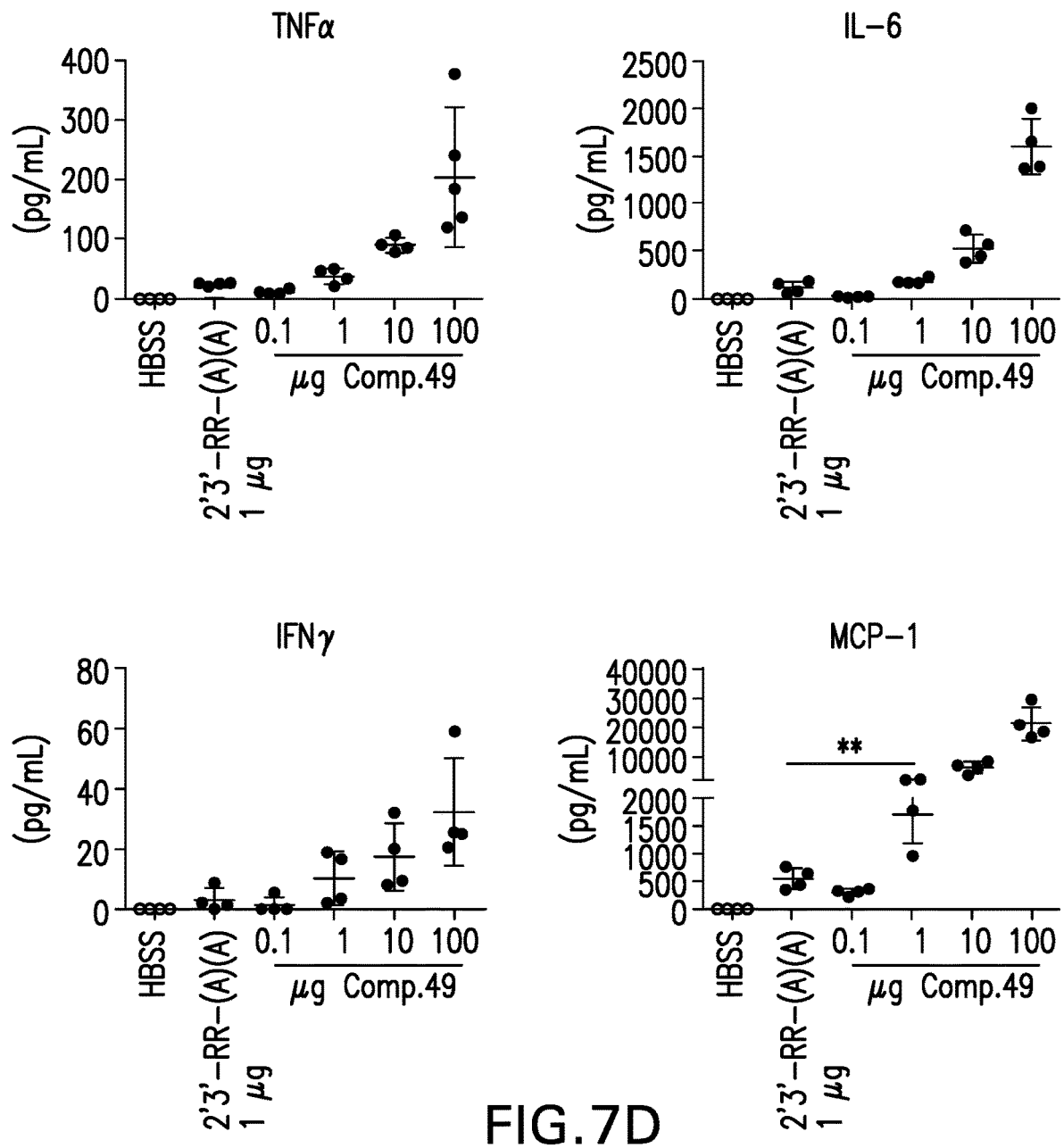
Figure 7E:
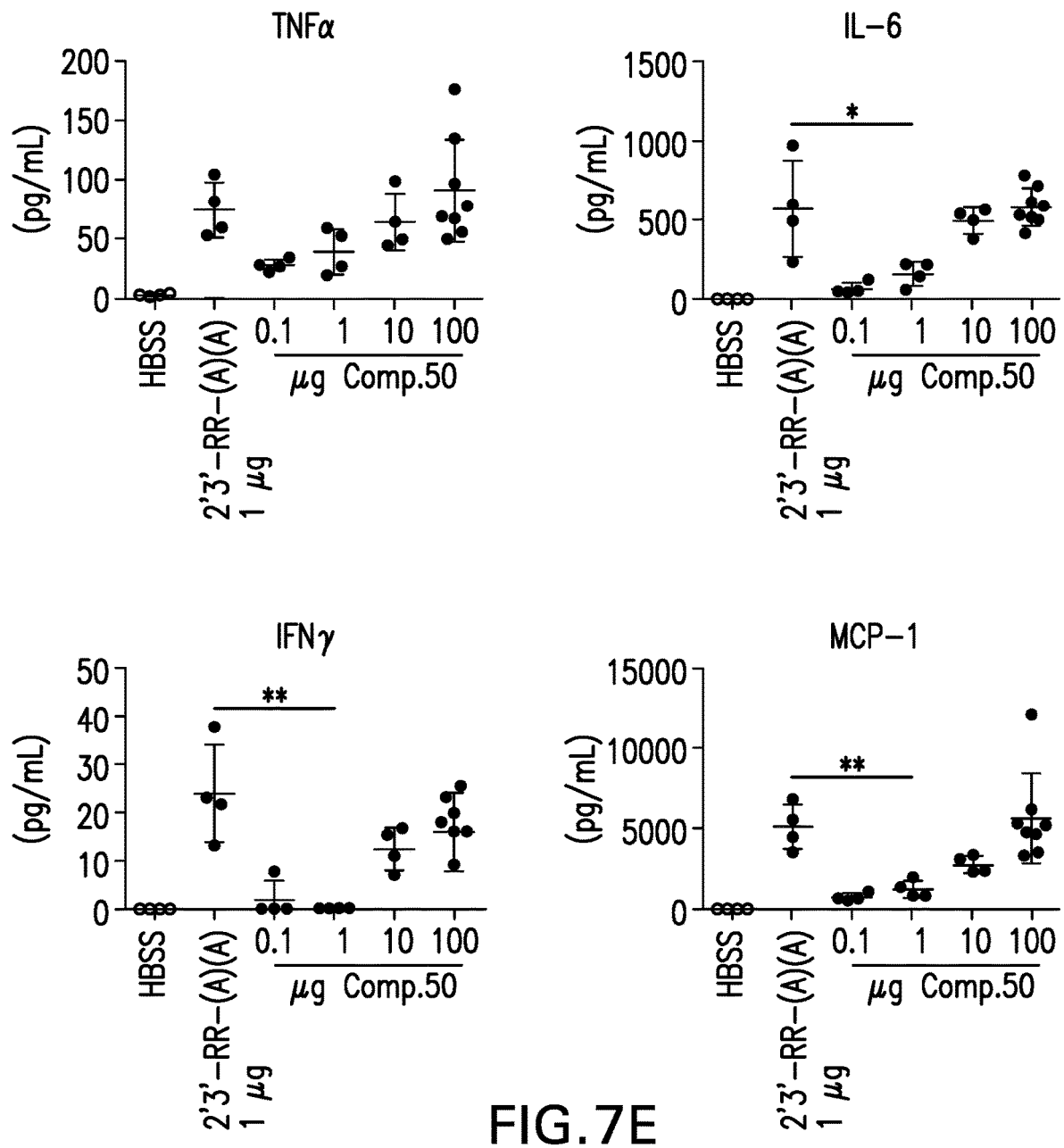

To assess the relative induction of systemic serum cytokines by the mono- and di-F-ML-CDN compounds as a measure of safety and tolerability, mice were bled six hours post-first IT injection and their serum was assessed by Mouse Inflammation Cytometric Bead Array (CBA, BD Biosciences). As shown in FIGS. 7A-D (7A—Comp. 5, 7B—Comp. 10, 7C—Comp. 20, 7D—Comp. 49), concentrations of pro-inflammatory cytokines (TNF-α, IL-6, MCP-1, and IFN-γ) at the 1 µg dose were comparable between 2'3'-RR-(A)(A) and the mono- and di-F-ML-CDN compounds 5, 10, 20 and 49. As shown in FIG. 7E, Compound 50 demonstrated significantly lower systemic cytokines than 2'3'-RR-(A)(A) ($*P<0.05$, $P<0.01$, $*P<0.001$, student's t-test). These data demonstrate a comparable safety profile for Compounds 5, 10, 20 and 49, as compared to reference compound 2'3'-RR-(A)(A), and a superior safety profile for Compound 50.

Figure 8:
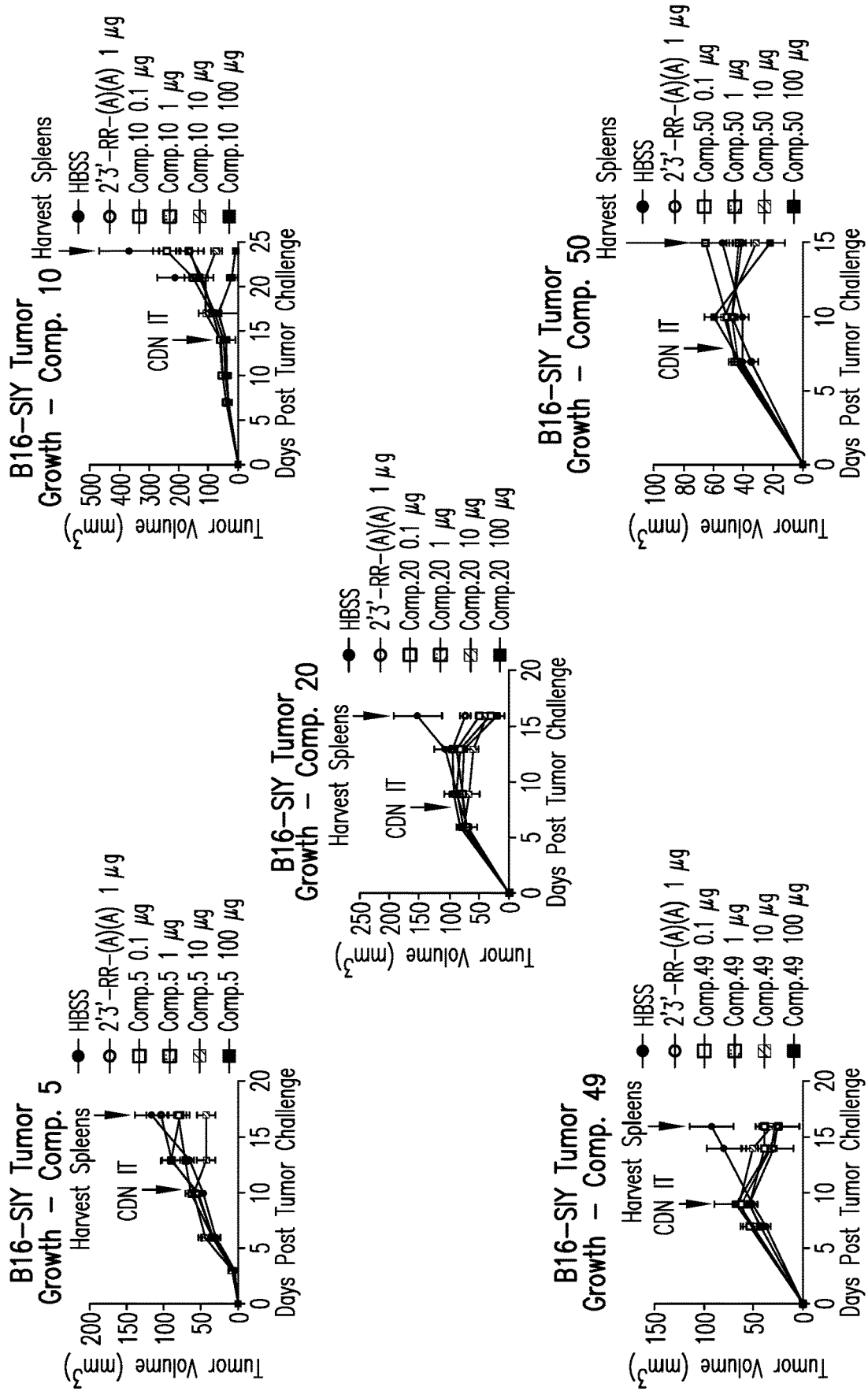
FIG. 8 depicts the tumor volume in a B16.SIY melanoma mouse model, following intra-tumoral injection of Compounds 5, 10, 20, 49 or 50 at 0.1 µg, 1 µg, 10 µg or 100 µg and reference compound 2'3'-RR-(A)(A) at 1 µg.
Figure 9A:
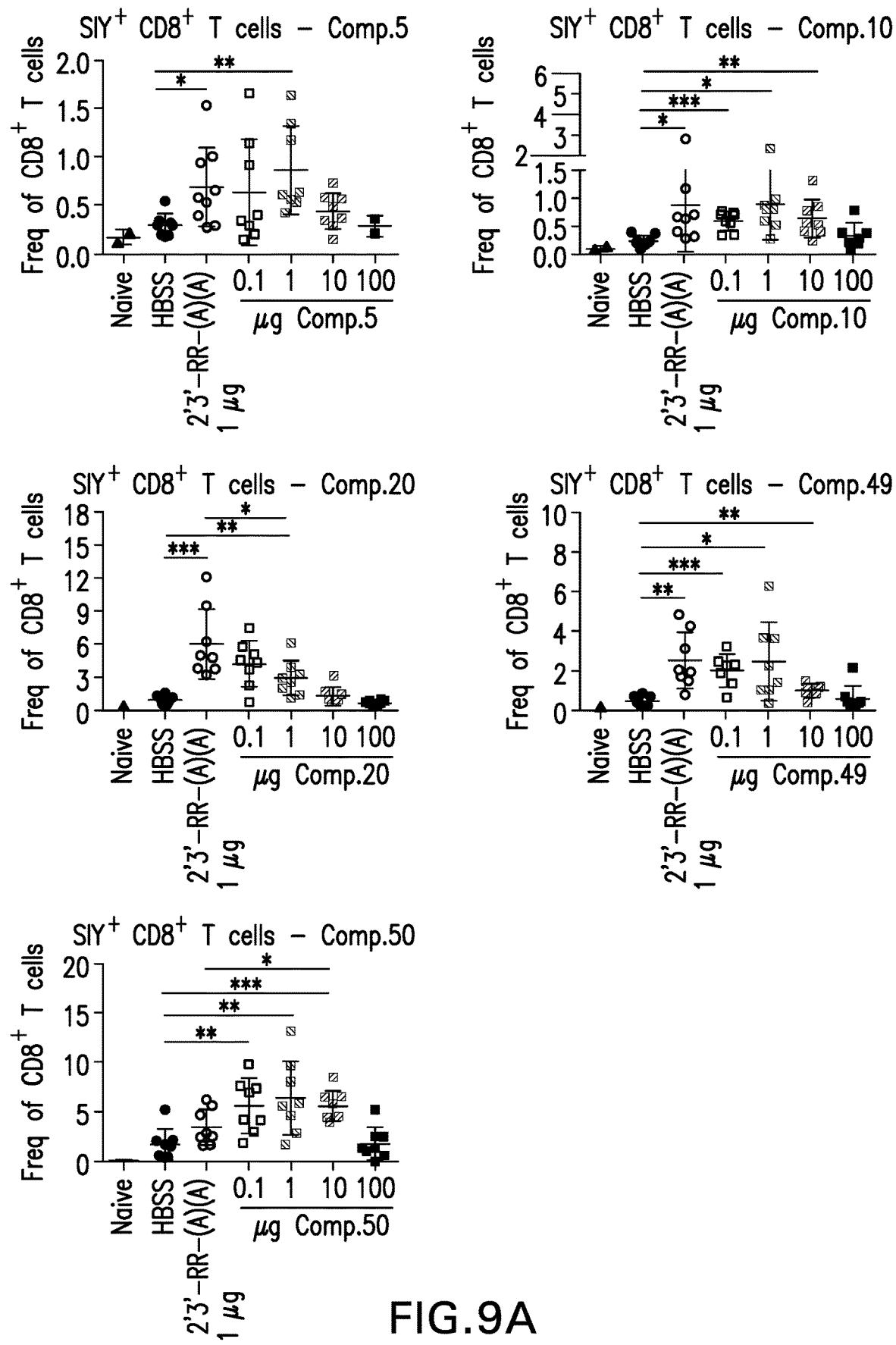
FIG. 9A-B depicts SIY⁺ CD8⁺ T-cells in splenocytes in a B16.SIY melanoma mouse model, following intra-tumoral injection of Compounds 5, 10, 20, 49 or 50 at 0.1 µg, 1 µg, 10 µg or 100 µg and reference compound 2'3'-RR-(A)(A) at 1 µg as measured by FACS (9A) or IFN-γ ELISPOT (9B).
Figure 9B:
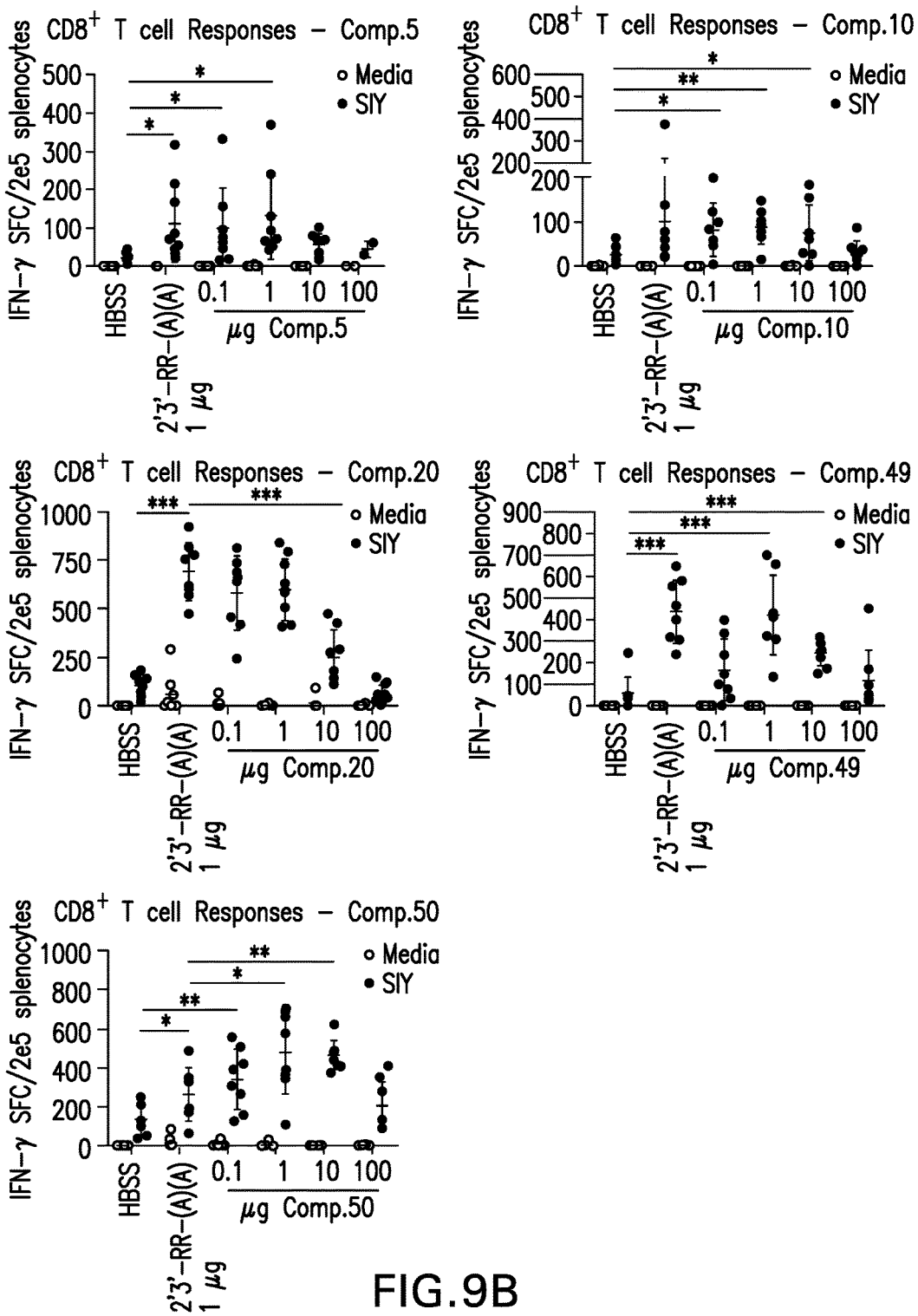

At the time of harvest, all compounds demonstrated measurable anti-tumor responses in a dose-dependent manner, compared to the 1 µg dose of the reference compound 2'3'-RR-(A)(A) and to HBSS control, with Compound 10 showing complete tumor inhibition at the 100 µg dose (FIG. 8). Immune responses to the SIY tumor antigen were measured by FACS pentamer staining of SIY-specific CD8+ T cells, as well as by IFNγ production in response to SIY peptide stimulation by ELISPOT. As shown in FIG. 9A, Compounds 5, 10, 20 and 49 all demonstrate significantly higher frequencies of SIY+ CD8+ T cells than HBSS control, and except for Compound 20, all demonstrate comparable responses at the 1 µg dose to 2'3'-RR-(A)(A). Further, Compound 50 demonstrated significantly higher T cell responses at the 10 µg dose compared to the reference compound (*P<0.05, P<0.01, *P<0.001, student's t-test). As a measure of antigen specific T cell functionality, these T cells were able to secrete IFNγ in response to SIY peptide stimulation in the ELISPOT assay in a manner that mirrored the trends for the FACS assay (FIG. 9B). These data demonstrate the ability of these mono- and di-F-ML-CDN compounds to elicit functional T cell-mediated anti-tumor immunity, in an antigen-specific manner.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound of Formula IB-g:

Formula IB-g

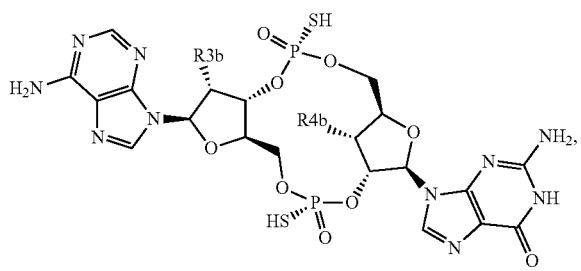

wherein R3b is —F and R4b is —OH or —O—C(=O)—C$_{1-14}$ alkyl, or a pharmaceutically acceptable salt, pharmaceutically acceptable solvate or pharmaceutically acceptable hydrate thereof.

2. The compound according to claim 1, wherein the compound is 2'3'-RR-(G)(2'F-A) having the structure:

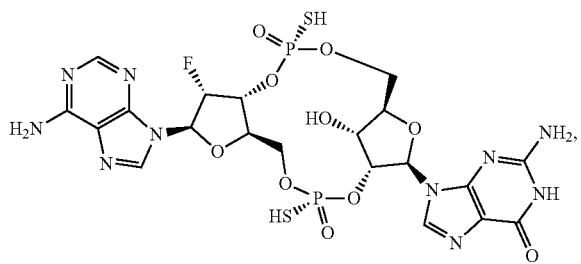 [SMILES: Nc1nc2c(ncn2[C@@H]2O[C@@H]3CO[P@@](=O)(S)O[C@H]4[C@@H](F)[C@H](n5cnc6c(N)ncnc65)O[C@@H]4CO[P@@](=O)(S)O[C@@H]2[C@@H]3O)c(=O)[nH]1]

or a pharmaceutically acceptable salt, pharmaceutically acceptable solvate or pharmaceutically acceptable hydrate thereof.

3. A composition comprising one or more compounds according to claim 1 and a pharmaceutically acceptable excipient.

4. A composition comprising one or more compounds according to claim 1 and a delivery vehicle which enhances cellular uptake and/or stability of the compound.

5. The composition according to claim 4, wherein the delivery vehicle comprises one or more agents selected from the group consisting of lipids, liposomes, interbilayer cross-linked multilamellar vesicles, biodegradeable poly(D,L-lactic-co-glycolic acid) [PLGA]-based or poly anhydride-based nanoparticles or microparticles, and nanoporous particle-supported lipid bilayers.

6. A composition comprising one or more compounds according to claim 1 and one or more agents selected from the group consisting of an immune checkpoint inhibitor; a Toll-like Receptor (TLR) agonist; a composition that mediates innate immune activation via TLRs, via (NOD)-like receptors (NLRs), via Retinoic acid inducible gene-based (RIG)-I-like receptors (RLRs), via C-type lectin receptors (CLRs), or via pathogen-associated molecular patterns ("PAMPs"); and a chemotherapeutic agent.

7. The composition according to claim 6, wherein the one or more agents is an immune checkpoint inhibitor or a histone deacetylase inhibitor.

8. The composition according to claim 3, further comprising one or more antigens selected for purposes of inducing an immune response against the antigen(s) when the composition is administered to an individual, optionally wherein the antigen is one or more recombinant protein antigens, wherein the recombinant protein antigen is a neoantigen, is related to an infectious disease, is related to a malignancy, or is related to an allergan.

9. A method for treating an individual suffering from cancer, comprising:
   administering to the individual an effective amount of the compound according to claim 1.

10. The method according to claim 9, wherein the administration is intravenous, subcutaneous, intramuscular, intradermal, oral, mucosal, vaginal, cervical, peri-tumoral, intratumoral, or directly into the tumor-draining lymph node(s).

11. A method of treating a disease in an individual, comprising: administering to the individual in need thereof i) an effective amount of the compound according to claim 1; and ii) an effective amount of one or more therapeutic antibodies that induce antibody-dependent cellular cytotoxicity, wherein the disease is selected from the group consisting of a cancer, acute rejection of an organ transplant, Type I diabetes mellitus, rheumatoid arthritis, psoriasis, Crohn's disease, restenosis and allergic asthma.

12. The compound according to claim 1, wherein the compound is 2'3'-RR-(3'decanoyl-O-G)(2'F-A) having the structure:

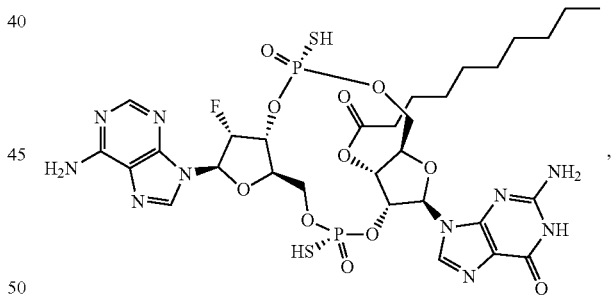

or a pharmaceutically acceptable salt, pharmaceutically acceptable solvate or pharmaceutically acceptable hydrate thereof.

* * * * *

SEQUENCE LISTING

```
<160> NUMBER OF SEQ ID NOS: 17

<210> SEQ ID NO 1
<211> LENGTH: 440
<212> TYPE: PRT
<213> ORGANISM: Artificial Sequence
<220> FEATURE:
<223> OTHER INFORMATION: Synthetic: heavy chain amino acid sequence of
      nivolumab

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80
```

```
Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 2
<211> LENGTH: 214
<212> TYPE: PRT
<213> ORGANISM: Artificial Sequence
<220> FEATURE:
<223> OTHER INFORMATION: Synthetic: light chain amino acid sequence of
      nivolumab

<400> SEQUENCE: 2
```

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
        210

<210> SEQ ID NO 3
<211> LENGTH: 447
<212> TYPE: PRT
<213> ORGANISM: Artificial Sequence
<220> FEATURE:
<223> OTHER INFORMATION: Synthetic: heavy chain amino acid sequences of
      pembrolizumab

<400> SEQUENCE: 3

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala

```
                130             135             140
Leu Gly Cys Leu Val Lys Asp Tyr Phe Pro Glu Pro Val Thr Val Ser
145             150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
                210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 4
<211> LENGTH: 218
<212> TYPE: PRT
<213> ORGANISM: Artificial Sequence
<220> FEATURE:
<223> OTHER INFORMATION: Synthetic: light chain amino acid sequence of
      pembrolizumab

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
                35                  40                  45
```

```
Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 5
<211> LENGTH: 118
<212> TYPE: PRT
<213> ORGANISM: Artificial Sequence
<220> FEATURE:
<223> OTHER INFORMATION: Synthetic: heavy chain amino acid sequence of
      MSB0010718C

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ile Met Met Trp Val Arg Gln Ala Pro Gly Lys Gly Leu Glu Trp Val
         35                  40                  45

Ser Ser Ile Tyr Pro Ser Gly Gly Ile Thr Phe Tyr Ala Asp Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Ile Lys Leu Gly Thr Val Thr Thr Val Asp Tyr Trp Gly Gln Gly Thr
            100                 105                 110

Leu Val Thr Val Ser Ser
        115

<210> SEQ ID NO 6
<211> LENGTH: 110
<212> TYPE: PRT
<213> ORGANISM: Artificial Sequence
<220> FEATURE:
<223> OTHER INFORMATION: Synthetic: light chain amino acid sequence of
      MSB0010718C

<400> SEQUENCE: 6
```

-continued

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
                100                 105                 110

<210> SEQ ID NO 7
<211> LENGTH: 368
<212> TYPE: PRT
<213> ORGANISM: Homo sapiens
<220> FEATURE:
<221> NAME/KEY: misc_feature
<222> LOCATION: (1)..(368)
<223> OTHER INFORMATION: Human cGAS

<400> SEQUENCE: 7

Gly Pro Asp Ala Ala Pro Gly Ala Ser Lys Leu Arg Ala Val Leu Glu
1               5                   10                  15

Lys Leu Lys Leu Ser Arg Asp Asp Ile Ser Thr Ala Ala Gly Met Val
                20                  25                  30

Lys Gly Val Val Asp His Leu Leu Leu Arg Leu Lys Cys Asp Ser Ala
            35                  40                  45

Phe Arg Gly Val Gly Leu Leu Asn Thr Gly Ser Tyr Tyr Glu His Val
    50                  55                  60

Lys Ile Ser Ala Pro Asn Glu Phe Asp Val Met Phe Lys Leu Glu Val
65                  70                  75                  80

Pro Arg Ile Gln Leu Glu Glu Tyr Ser Asn Thr Arg Ala Tyr Tyr Phe
                85                  90                  95

Val Lys Phe Lys Arg Asn Pro Lys Glu Asn Pro Leu Ser Gln Phe Leu
                100                 105                 110

Glu Gly Glu Ile Leu Ser Ala Ser Lys Met Leu Ser Lys Phe Arg Lys
            115                 120                 125

Ile Ile Lys Glu Glu Ile Asn Asp Ile Lys Asp Thr Asp Val Ile Met
    130                 135                 140

Lys Arg Lys Arg Gly Gly Ser Pro Ala Val Thr Leu Leu Ile Ser Glu
145                 150                 155                 160

Lys Ile Ser Val Asp Ile Thr Leu Ala Leu Glu Ser Lys Ser Ser Trp
                165                 170                 175

Pro Ala Ser Thr Gln Glu Gly Leu Arg Ile Gln Asn Trp Leu Ser Ala
                180                 185                 190

Lys Val Arg Lys Gln Leu Arg Leu Lys Pro Phe Tyr Leu Val Pro Lys
            195                 200                 205

His Ala Lys Glu Gly Asn Gly Phe Gln Glu Glu Thr Trp Arg Leu Ser
    210                 215                 220

Phe Ser His Ile Glu Lys Glu Ile Leu Asn Asn His Gly Lys Ser Lys
225                 230                 235                 240

Thr Cys Cys Glu Asn Lys Glu Glu Lys Cys Cys Arg Lys Asp Cys Leu

```
            245                 250                 255
Lys Leu Met Lys Tyr Leu Leu Glu Gln Leu Lys Glu Arg Phe Lys Asp
            260                 265                 270

Lys Lys His Leu Asp Lys Phe Ser Ser Tyr His Val Lys Thr Ala Phe
            275                 280                 285

Phe His Val Cys Thr Gln Asn Pro Gln Asp Ser Gln Trp Asp Arg Lys
            290                 295                 300

Asp Leu Gly Leu Cys Phe Asp Asn Cys Val Thr Tyr Phe Leu Gln Cys
305                 310                 315                 320

Leu Arg Thr Glu Lys Leu Glu Asn Tyr Phe Ile Pro Glu Phe Asn Leu
            325                 330                 335

Phe Ser Ser Asn Leu Ile Asp Lys Arg Ser Lys Glu Phe Leu Thr Lys
            340                 345                 350

Gln Ile Glu Tyr Glu Arg Asn Asn Glu Phe Pro Val Phe Asp Glu Phe
            355                 360                 365

<210> SEQ ID NO 8
<211> LENGTH: 362
<212> TYPE: PRT
<213> ORGANISM: Mus musculus
<220> FEATURE:
<221> NAME/KEY: misc_feature
<222> LOCATION: (1)..(362)
<223> OTHER INFORMATION: Mouse cGAS

<400> SEQUENCE: 8

Gly Pro Asp Lys Leu Lys Lys Val Leu Asp Lys Leu Arg Leu Lys Arg
1               5                   10                  15

Lys Asp Ile Ser Glu Ala Ala Glu Thr Val Asn Lys Val Val Glu Arg
            20                  25                  30

Leu Leu Arg Arg Met Gln Lys Arg Glu Ser Glu Phe Lys Gly Val Glu
        35                  40                  45

Gln Leu Asn Thr Gly Ser Tyr Tyr Glu His Val Lys Ile Ser Ala Pro
    50                  55                  60

Asn Glu Phe Asp Val Met Phe Lys Leu Glu Val Pro Arg Ile Glu Leu
65                  70                  75                  80

Gln Glu Tyr Tyr Glu Thr Gly Ala Phe Tyr Leu Val Lys Phe Lys Arg
                85                  90                  95

Ile Pro Arg Gly Asn Pro Leu Ser His Phe Leu Glu Gly Glu Val Leu
            100                 105                 110

Ser Ala Thr Lys Met Leu Ser Lys Phe Arg Lys Ile Ile Lys Glu Glu
        115                 120                 125

Val Lys Glu Ile Lys Asp Ile Asp Val Ser Val Glu Lys Glu Lys Pro
    130                 135                 140

Gly Ser Pro Ala Val Thr Leu Leu Ile Arg Asn Pro Glu Glu Ile Ser
145                 150                 155                 160

Val Asp Ile Ile Leu Ala Leu Glu Ser Lys Gly Ser Trp Pro Ile Ser
                165                 170                 175

Thr Lys Glu Gly Leu Pro Ile Gln Gly Trp Leu Gly Thr Lys Val Arg
            180                 185                 190
```

Thr Asn Leu Arg Arg Glu Pro Phe Tyr Leu Val Pro Lys Asn Ala Lys
    195                 200                 205

Asp Gly Asn Ser Phe Gln Gly Glu Thr Trp Arg Leu Ser Phe Ser His
    210                 215                 220

Thr Glu Lys Tyr Ile Leu Asn Asn His Gly Ile Glu Lys Thr Cys Cys
225                 230                 235                 240

Glu Ser Ser Gly Ala Lys Cys Cys Arg Lys Glu Cys Leu Lys Leu Met
            245                 250                 255

Lys Tyr Leu Leu Glu Gln Leu Lys Glu Phe Gln Glu Leu Asp Ala
        260                 265                 270

Phe Cys Ser Tyr His Val Lys Thr Ala Ile Phe His Met Trp Thr Gln
        275                 280                 285

Asp Pro Gln Asp Ser Gln Trp Asp Pro Arg Asn Leu Ser Ser Cys Phe
        290                 295                 300

Asp Lys Leu Leu Ala Phe Phe Leu Glu Cys Leu Arg Thr Glu Lys Leu
305                 310                 315                 320

Asp His Tyr Phe Ile Pro Lys Phe Asn Leu Phe Ser Gln Glu Leu Ile
                325                 330                 335

Asp Arg Lys Ser Lys Glu Phe Leu Ser Lys Lys Ile Glu Tyr Glu Arg
            340                 345                 350

Asn Asn Gly Phe Pro Ile Phe Asp Lys Leu
        355                 360

<210> SEQ ID NO 9
<211> LENGTH: 37
<212> TYPE: DNA
<213> ORGANISM: Artificial Sequence
<220> FEATURE:
<223> OTHER INFORMATION: Synthetic: forward primer

<400> SEQUENCE: 9
tacttccaat ccaatgcagc cccagctgag atctctg                                37

<210> SEQ ID NO 10
<211> LENGTH: 46
<212> TYPE: DNA
<213> ORGANISM: Artificial Sequence
<220> FEATURE:
<223> OTHER INFORMATION: Synthetic: reverse primer

<400> SEQUENCE: 10
ttatccactt ccaatgttat tattatcaag agaaatccgt gcggag                      46

<210> SEQ ID NO 11
<211> LENGTH: 19
<212> TYPE: DNA
<213> ORGANISM: Artificial Sequence
<220> FEATURE:
<223> OTHER INFORMATION: Synthetic: hSTING exon3F

<400> SEQUENCE: 11
gctgagacag gagctttgg                                                    19

```
<210> SEQ ID NO 12
<211> LENGTH: 19
<212> TYPE: DNA
<213> ORGANISM: Artificial Sequence
<220> FEATURE:
<223> OTHER INFORMATION: Synthetic: hSTING exon3R

<400> SEQUENCE: 12
agccagagag gttcaagga                                                   19

<210> SEQ ID NO 13
<211> LENGTH: 20
<212> TYPE: DNA
<213> ORGANISM: Artificial Sequence
<220> FEATURE:
<223> OTHER INFORMATION: Synthetic: hSTING exon6F

<400> SEQUENCE: 13
ggccaatgac ctgggtctca                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic: hSTING exon6R

<400> SEQUENCE: 14
cacccagaat agcatccagc                                                  20

<210> SEQ ID NO 15
<211> LENGTH: 21
<212> TYPE: DNA
<213> ORGANISM: Artificial Sequence
<220> FEATURE:
<223> OTHER INFORMATION: Synthetic: hSTING exon7F

<400> SEQUENCE: 15
tcagagttgg gtatcagagg c                                                21

<210> SEQ ID NO 16
<211> LENGTH: 21
<212> TYPE: DNA
<213> ORGANISM: Artificial Sequence
<220> FEATURE:
<223> OTHER INFORMATION: Synthetic: hSTING exon7R

<400> SEQUENCE: 16
atctggtgtg ctgggaagag g                                                21

<210> SEQ ID NO 17
<211> LENGTH: 8
<212> TYPE: PRT
<213> ORGANISM: Artificial Sequence
<220> FEATURE:
<223> OTHER INFORMATION: Synthetic: peptide

<400> SEQUENCE: 17

Ser Ile Tyr Arg Tyr Tyr Gly Leu
1               5
```